(12) United States Patent
Hsiao

(10) Patent No.: US 10,456,436 B2
(45) Date of Patent: Oct. 29, 2019

(54) USE OF HERBAL SAPONINS TO REGULATE GUT MICROFLORA

(71) Applicant: Wen Luan Wendy Hsiao, Hong Kong (HK)

(72) Inventor: Wen Luan Wendy Hsiao, Hong Kong (HK)

( * ) Notice: Subject to any disclaimer, the term of this patent is extended or adjusted under 35 U.S.C. 154(b) by 533 days.

(21) Appl. No.: 15/205,007

(22) Filed: Jul. 8, 2016

(65) Prior Publication Data

US 2016/0339070 A1   Nov. 24, 2016

Related U.S. Application Data

(63) Continuation-in-part of application No. 14/290,148, filed on May 29, 2014, now abandoned.

(51) Int. Cl.
| | |
|---|---|
| *A61K 36/424* | (2006.01) |
| *A61K 9/00* | (2006.01) |
| *A61K 31/7048* | (2006.01) |
| *A61K 31/704* | (2006.01) |
| *C12Q 1/689* | (2018.01) |
| *A61K 31/7052* | (2006.01) |
| *A61K 36/258* | (2006.01) |

(52) U.S. Cl.
CPC .......... *A61K 36/424* (2013.01); *A61K 9/0053* (2013.01); *A61K 31/704* (2013.01); *A61K 31/7048* (2013.01); *A61K 31/7052* (2013.01); *A61K 36/258* (2013.01); *C12Q 1/689* (2013.01)

(58) Field of Classification Search
CPC ................ A61K 36/424; A61K 36/258; A61K 2300/00; A61K 31/704; A61K 31/7048; A61K 9/0053; A61K 31/7052; C12Q 1/689
USPC .................................................. 424/758, 728
See application file for complete search history.

(56) References Cited

U.S. PATENT DOCUMENTS

| | | | | |
|---|---|---|---|---|
| 5,919,770 A  * | 7/1999 | Hideo | .................... | C07J 17/005 514/171 |
| 5,925,537 A  * | 7/1999 | Sung | ...................... | C07J 17/005 424/728 |
| 6,888,014 B2 * | 5/2005 | Huang | ................... | C07J 17/005 536/5 |
| 7,923,044 B2 * | 4/2011 | Bias | ...................... | A61K 35/744 424/195.15 |
| 2003/0087835 A1* | 5/2003 | Huang | ................... | C07J 17/005 514/26 |
| 2003/0175315 A1* | 9/2003 | Yoo | .......................... | A61K 8/06 424/400 |
| 2005/0197495 A1* | 9/2005 | Naidu | .................... | C07K 14/79 530/400 |
| 2006/0148733 A1* | 7/2006 | Zhang | .................. | A61K 31/704 514/33 |
| 2006/0172020 A1* | 8/2006 | Djang | .................... | A61K 31/05 424/725 |
| 2006/0293255 A1* | 12/2006 | Lin | ....................... | A61K 31/704 514/26 |
| 2008/0031978 A1* | 2/2008 | Chou | ..................... | A61K 36/16 424/728 |
| 2008/0261916 A1* | 10/2008 | Jaszberenyi | ............. | A21D 2/14 514/58 |
| 2009/0155388 A1* | 6/2009 | Olalde | ................. | A61K 31/555 424/702 |
| 2009/0169623 A1* | 7/2009 | Sene | ........................ | A61K 8/63 424/474 |
| 2010/0015109 A1* | 1/2010 | Bias | ..................... | A61K 35/744 424/93.44 |
| 2012/0190063 A1* | 7/2012 | An | .......................... | C12P 19/56 435/53 |

FOREIGN PATENT DOCUMENTS

| | | | |
|---|---|---|---|
| CN | 101392013 | * | 3/2009 |
| CN | 102894123 | * | 1/2013 |

OTHER PUBLICATIONS

Wu PK, Tai WCS, Choi CYR, Tsim KWK, Zhou H, Liu X, Jiang ZH, and Hsiao WLW.* Chemical and DNA authentication of taste variants of Gynostemma pentaphyllum herbal tea. Food Chemistry 128: 70-81, 2011.
Chen L, Tai WCS, and Hsiao WLW.* Dietary saponins from four popular herbal tea exert prebiotic-like effects on gut microbiota in C57BL/6 mice. J Functional Food17: 892-902, 2015.
Chen L, Tai WCS, Brar MS, Leung FCC , and Hsiao WLW.* Tumor grafting induces changes of gut microbiota in athymic nude mice in the presence and absence of medicinal Gynostemma saponins. PLOS One| DOI:10.1371/journal.pone.0126807 May 20, 2015.
Lei Chen, Manreetpal S Brar, Frederick CC Leung, WL Wendy Hsiao*.Triterpenoid herbal saponins enhance beneficial bacteria, decrease sulfate-reducing bacteria, modulate inflammatory intestinal microenvironment and exert cancer preventive effects in ApcMin/+ mice. Oncotarget. Apr. 21, 2016, doi:10.18632/oncotarget.8886, 2016.
William Chi Shing Tai, Wing Yan Wong, Magnolia Muk Lan Lee, Brandon Dow Chan, Cheng Lu and Wen Luan Wendy Hsiao*. Mechanistic study of the anti-cancer effect of Gypenosides in the ApcMin/+ mouse model using a proteomic approach. Proteomics DOI 10.1002/pmic.201500293, 2016.

* cited by examiner

*Primary Examiner* — Aaron J Kosar
(74) *Attorney, Agent, or Firm* — Wen Luan Wendy Hsiao

(57) ABSTRACT

The present invention relates to the use of a compound comprising plant based saponins for regulating and balancing gut microflora in a subject. The present invention also relates to the use of a compound comprising plant based saponins for exerting anti-cancer and anti-inflammatory effects by regulating and balancing the gut microbial ecosystem and providing a healthy epithelial microenvironment in the gut for a subject.

10 Claims, 119 Drawing Sheets
(18 of 119 Drawing Sheet(s) Filed in Color)
Specification includes a Sequence Listing.

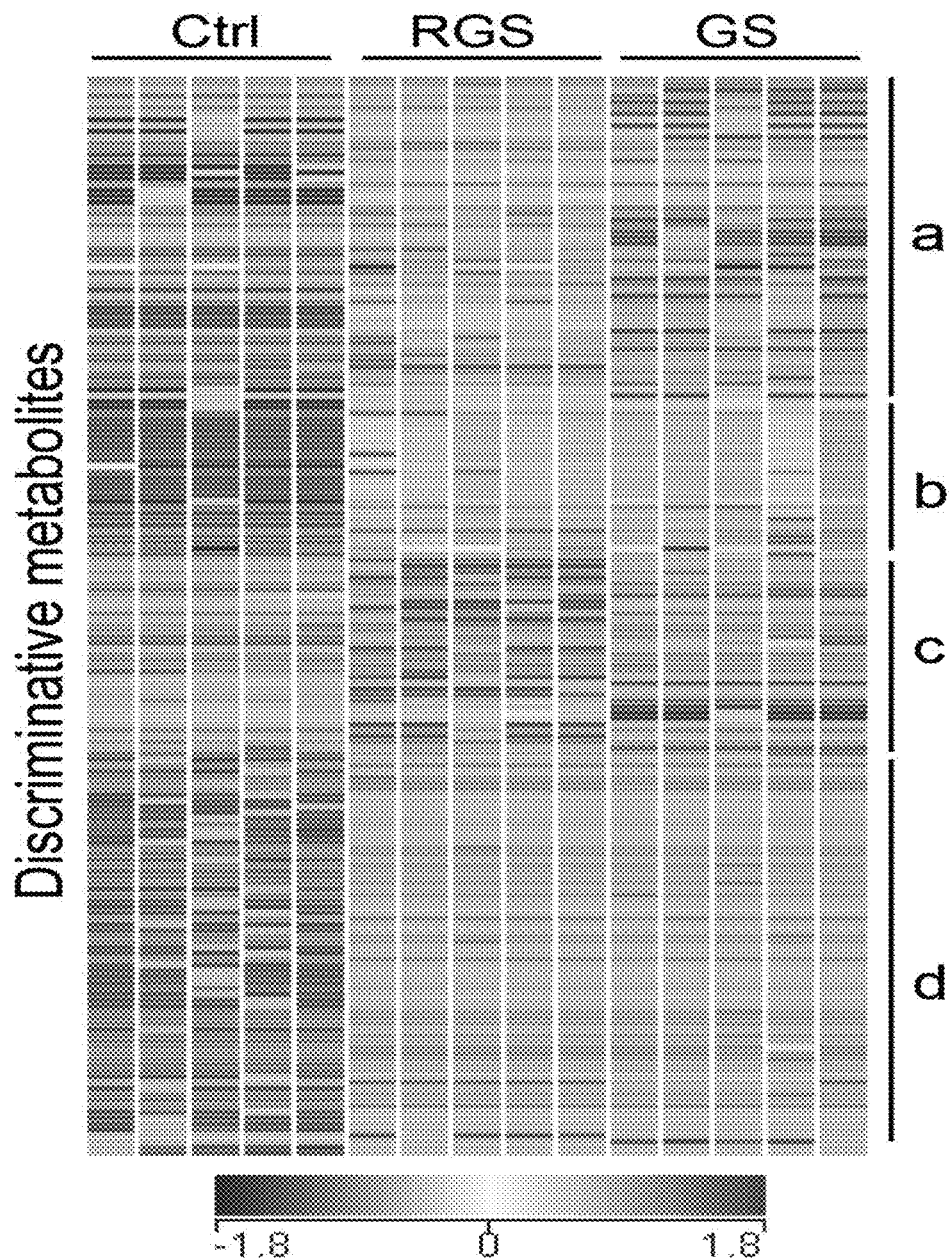

Changes in relative abundance of the main phyla of microbial communities in the gut

| Phylum | Normal | | | Xenograft | | |
|---|---|---|---|---|---|---|
| | Ctrl (%) | GpS (%) | Percent change | Ctrl (%) | GpS (%) | Percent change |
| Tenericutes | 2.30 ± 1.00 | 4.18 ± 1.88 | ↑ 81.81% | 1.66 ± 0.92 | 39.58 ± 18.38 | ↑ 2287.39% |
| TM7 | 0.019 ± 0.005 | 0.012 ± 0.009 | ↓ 37.67% | - | - | - |
| Proteobacteria | 1.98 ± 1.25 | 14.24 ± 6.08 | ↑ 618.50% | 1.68 ± 0.44 | 9.36 ± 3.15 | ↑ 458.29% |
| Firmicutes | 95.45 ± 2.16 | 81.30 ± 5.03 | ↓ 14.83% | 95.99 ± 1.32 | 49.20 ± 22.33 | ↓ 48.74% |
| Deferribacteres | - | - | - | 0.039 ± 0.031 | 0.022 ± 0.022 | ↓ 42.76% |
| Bacteroidetes | 0.11 ± 0.03 | 0.23 ± 0.12 | ↑ 111.57% | 0.43 ± 0.10 | 1.71 ± 0.84 | ↑ 301.93% |
| Actinobacteria | 0.025 ± 0.013 | 0.029 ± 0.009 | ↑ 14.43% | 0.005 ± 0.005 | 0.011 ± 0.009 | ↑ 137.65% |
| Acidobacteria | - | 0.003 ± 0.003 | - | - | - | - |

Fig. 11B

Unique fecal bacterial families found in the experimental groups

| Normal | vs | Xenograft |
|---|---|---|
| Enterococcaceae | | Deferribacteraceae |
| Streptococcaceae | | |
| Enterobacteriaceae | | |
| Pasteurellaceae | | |
| F16 | | |
| Unclassified RF39 | | |

| Normal no GpS | vs | Normal with GpS |
|---|---|---|
| Anaeroplasmataceae | | |
| Unclassified RF39 | | |

| Xenograft no GpS | vs | Xenograft with GpS |
|---|---|---|
| | | Pasteurellaceae |

Fig 13B

|  | Normal | | | | | | Xenograft | | | | | |
|  | Ctrl | | | GpS | | | Ctrl | | | GpS | | |
| OTU ID | Mouse 1 | Mouse 2 | Mouse 3 | Mouse 4 | Mouse 5 | Mouse 6 | Mouse 7 | Mouse 8 | Mouse 9 | Mouse 10 | Mouse 11 | Mouse 12 |
|---|---|---|---|---|---|---|---|---|---|---|---|---|
| 66 |  |  |  |  |  |  | 19 | 7 | 3 | 1 | 62 | 306 |
| 70 |  |  |  |  |  |  | 1 | 6 | 2 | 1 | 35 | 7 |
| 119 # |  |  |  | 64 | 4 | 2 | 6 | 8 | 9 | 1 | 247 | 304 |
| 121 | 3 | 2 |  | 9 | 28 | 2 | 1 | 7 |  | 1 | 24 | 19 |
| 237 |  |  |  |  |  |  |  |  |  |  | 5 | 2 |
| 274 |  |  |  |  |  |  | 7 | 1 |  |  |  | 12 |
| 281 # | 29 | 23 | 9 |  |  | 1 | 5 | 44 | 14 |  |  |  |
| 331 |  |  |  |  |  | 1 |  |  |  |  |  |  |
| 378 | 44 | 35 | 1 | 73 | 21 | 3 |  |  |  |  | 10 | 9 |
| 382 | 14 | 4 | 7 | 13 |  | 11 |  |  |  |  |  |  |
| 409 | 30 | 44 | 3 | 1 | 88 | 28 |  |  |  |  |  |  |
| 496 |  |  | 6 | 11 | 16 | 12 | 1 | 8 |  | 2 | 17 | 101 |
| 515 |  |  |  | 7 | 15 | 3 |  | 1 |  |  | 14 | 15 |
| 593 | 5 | 1 | 1 |  |  | 4 |  | 3 |  |  |  |  |
| 600 |  |  |  |  |  |  | 1 |  |  |  | 32 | 11 |

| OTU ID | Consensus Lineage |
|---|---|
| 66 | p__Proteobacteria;c__Epsilonproteobacteria;o__Campylobacterales;f__Helicobacteraceae;g__Helicobacter;s__Helicobactergammani |
| 70 | p__Firmicutes;c__Bacilli;o__Lactobacillales;f__Lactobacillaceae;g__Lactobacillus;s__Lactobacillusreuteri |
| 119 # | p__Bacteroidetes;c__Bacteroidia;o__Bacteroidales;f__Bacteroidaceae;g__Bacteroides;s__Bacteroidesacidifaciens |
| 121 | p__Tenericutes;c__Erysipelotrichi;o__Erysipelotrichales;f__Erysipelotrichaceae;g__;s__C11_K211 |
| 237 | p__Proteobacteria;c__Gammaproteobacteria;o__Pasteurellales;f__Pasteurellaceae;g__Actinobacillus;s__Actinobacilluscapsulatus |
| 274 | p__Deferribacteres;c__Deferribacteres;o__Deferribacterales;f__Deferribacteraceae;g__Mucispirillum;s__Mucispirillumschaedleri |
| 281 # | p__Tenericutes;c__Erysipelotrichi;o__Erysipelotrichales;f__Erysipelotrichaceae;g__Clostridium;s__Clostridiumcocleatum |
| 331 | p__Proteobacteria;c__Alphaproteobacteria;o__Rhizobiales;f__Bradyrhizobiaceae;g__Bradyrhizobium;s__Bradyrhizobiumelkanii |
| 378 | p__Proteobacteria;c__Gammaproteobacteria;o__Pasteurellales;f__Pasteurellaceae;g__Pasteurella;s__Pasteurellapneumotropica |
| 382 | p__Firmicutes;c__Clostridia;o__Clostridiales;f__Lachnospiraceae;g__Roseburia;s__Roseburiafaecis |
| 409 | p__Firmicutes;c__Bacilli;o__Lactobacillales;f__Streptococcaceae;g__Lactococcus;s__Lactococcusgarvieae |
| 496 | p__Tenericutes;c__Erysipelotrichi;o__Erysipelotrichales;f__Erysipelotrichaceae;g__;s__Pei061 |
| 515 | p__Firmicutes;c__Clostridia;o__Clostridiales;f__Ruminococcaceae;g__Anaerotruncus;s__Anaerotruncuscolihominis |
| 593 | p__Bacteroidetes;c__Bacteroidia;o__Bacteroidales;f__Bacteroidaceae;g__Bacteroides;s__Bacteroidesuniformis |
| 600 | p__Bacteroidetes;c__Bacteroidia;o__Bacteroidales;f__Porphyromonadaceae;g__Parabacteroides;s__Parabacteroidesdistasonis |

Fig. 14B

Changes in relative abundance of the main phyla of microbial communities in the feces

| Phylum | WT | | | Apc^Min/+ | | |
|---|---|---|---|---|---|---|
|  | Ctrl (%) | GpS (%) | Percent change | Ctrl (%) | GpS (%) | Percent change |
| Actinobacteria | 0.139 ± 0.019 | 0.414 ± 0.287 | ↑ 197.84% | 0.056 ± 0.012 ## | 0.073 ± 0.017 | ↑ 30.36% |
| Bacteroidetes | 0.73 ± 0.12 | 1.02 ± 0.18 | ↑ 39.73% | 0.53 ± 0.10 | 1.08 ± 0.27 | ↑ 103.77% |
| Cyanobacteria | 0.015 ± 0.007 | 0.024 ± 0.005 | ↑ 60.00% | 0.021 ± 0.008 | 0.02 ± 0.008 | ↓ 4.76% |
| Firmicutes | 39.42 ± 4.17 | 21.58 ± 3.36 | ↓ 45.26% ** | 40.16 ± 1.38 | 37.08 ± 8.20 | ↓ 7.76% |
| Proteobacteria | 44.95 ± 2.98 | 62.24 ± 3.44 | ↑ 38.46% ** | 50.50 ± 1.63 | 58.95 ± 8.68 | ↑ 16.73% |
| TM7 | 0.005 ± 0.005 | 0.001 ± 0.001 | ↓ 80.00% | 0.001 ± 0.001 | - | - |
| Tenericutes | 1.86 ± 0.20 | 2.29 ± 0.80 | ↑ 23.12% | 6.10 ± 0.99 # | 1.08 ± 0.21 | ↓ 82.30% ** |
| Verrucomicrobia | 12.89 ± 2.62 | 12.43 ± 4.95 | ↓ 3.57% | 2.63 ± 1.04 ## | 1.71 ± 0.65 | ↓ 34.98% |

Data are shown as mean ± SEM (n=5). **p<0.01, GpS versus Control; #p<0.05, ##p<0.01, Apc^Min/+ versus WT

Fig. 20D

▇;Other;Other;Other;Other;Other
▇;p__Actinobacteria;c__Actinobacteria;o__Actinomycetales;f__Corynebacteriaceae;g__Corynebacterium
▒;p__Actinobacteria;c__Actinobacteria;o__Actinomycetales;f__Propionibacteriaceae;g__Propionibacterium
▇;p__Actinobacteria;c__Actinobacteria;o__Bifidobacteriales;f__Bifidobacteriaceae;g__Bifidobacterium
▇;p__Actinobacteria;c__Actinobacteria;o__Coriobacteriales;f__;g__
 ;p__Actinobacteria;c__Actinobacteria;o__Coriobacteriales;f__Coriobacteriaceae;g__
 ;p__Actinobacteria;c__Actinobacteria;o__Coriobacteriales;f__Coriobacteriaceae;g__Adlercreutzia
▒;p__Actinobacteria;c__Actinobacteria;o__Coriobacteriales;f__Coriobacteriaceae;g__Collinsella
▒;p__Actinobacteria;c__Actinobacteria;o__Coriobacteriales;f__Coriobacteriaceae;g__Olsenella
▇;p__Bacteroidetes;c__Bacteroidia;o__Bacteroidales;f__;g__
▒;p__Bacteroidetes;c__Bacteroidia;o__Bacteroidales;f__Bacteroidaceae;g__Bacteroides
▒;p__Bacteroidetes;c__Bacteroidia;o__Bacteroidales;f__Porphyromonadaceae;g__
 ;p__Bacteroidetes;c__Bacteroidia;o__Bacteroidales;f__Porphyromonadaceae;g__Odoribacter
▒;p__Bacteroidetes;c__Bacteroidia;o__Bacteroidales;f__Porphyromonadaceae;g__Parabacteroides
 ;p__Bacteroidetes;c__Bacteroidia;o__Bacteroidales;f__Prevotellaceae;g__
 ;p__Bacteroidetes;c__Bacteroidia;o__Bacteroidales;f__Prevotellaceae;g__Prevotella
▒;p__Bacteroidetes;c__Bacteroidia;o__Bacteroidales;f__Rikenellaceae;g__
 ;p__Bacteroidetes;c__Bacteroidia;o__Bacteroidales;f__Rikenellaceae;g__Alistipes
 ;p__Cyanobacteria;c__4C0d-2;o__YS2;f__;g__
▇;p__Firmicutes;c__Bacilli;o__Bacillales;f__Staphylococcaceae;g__Staphylococcus
▒;p__Firmicutes;c__Bacilli;o__Lactobacillales;f__Lactobacillaceae;g__Lactobacillus
▒;p__Firmicutes;c__Bacilli;o__Lactobacillales;f__Streptococcaceae;g__Streptococcus
▇;p__Firmicutes;c__Bacilli;o__Turicibacterales;f__Turicibacteraceae;g__
▇;p__Firmicutes;c__Clostridia;o__Clostridiales;f__;g__
▒;p__Firmicutes;c__Clostridia;o__Clostridiales;f__Catabacteriaceae;g__
▇;p__Firmicutes;c__Clostridia;o__Clostridiales;f__Clostridiaceae;g__
▇;p__Firmicutes;c__Clostridia;o__Clostridiales;f__Clostridiaceae;g__Clostridium
▇;p__Firmicutes;c__Clostridia;o__Clostridiales;f__ClostridialesFamilyXI.IncertaeSedis;g__Sporanaerobacter
▇;p__Firmicutes;c__Clostridia;o__Clostridiales;f__ClostridialesFamilyXIII.IncertaeSedis;g__
▇;p__Firmicutes;c__Clostridia;o__Clostridiales;f__ClostridialesFamilyXIII.IncertaeSedis;g__Eubacterium
▇;p__Firmicutes;c__Clostridia;o__Clostridiales;f__Dehalobacteriaceae;g__Dehalobacterium
▒;p__Firmicutes;c__Clostridia;o__Clostridiales;f__Eubacteriaceae;g__Anaerofustis
▇;p__Firmicutes;c__Clostridia;o__Clostridiales;f__Lachnospiraceae;g__
▇;p__Firmicutes;c__Clostridia;o__Clostridiales;f__Lachnospiraceae;g__Blautia
 ;p__Firmicutes;c__Clostridia;o__Clostridiales;f__Lachnospiraceae;g__Clostridium
 ;p__Firmicutes;c__Clostridia;o__Clostridiales;f__Lachnospiraceae;g__Coprococcus
 ;p__Firmicutes;c__Clostridia;o__Clostridiales;f__Lachnospiraceae;g__Lachnobacterium
▒;p__Firmicutes;c__Clostridia;o__Clostridiales;f__Lachnospiraceae;g__Lachnospira
▇;p__Firmicutes;c__Clostridia;o__Clostridiales;f__Lachnospiraceae;g__Roseburia
▒;p__Firmicutes;c__Clostridia;o__Clostridiales;f__Lachnospiraceae;g__Ruminococcus
▒;p__Firmicutes;c__Clostridia;o__Clostridiales;f__Peptococcaceae;g__

Fig. 21 (continue)

p__Firmicutes;c__Clostridia;o__Clostridiales;f__Ruminococcaceae;g__
p__Firmicutes;c__Clostridia;o__Clostridiales;f__Ruminococcaceae;g__Clostridium
p__Firmicutes;c__Clostridia;o__Clostridiales;f__Ruminococcaceae;g__Eubacterium
p__Firmicutes;c__Clostridia;o__Clostridiales;f__Ruminococcaceae;g__Oscillospira
p__Firmicutes;c__Clostridia;o__Clostridiales;f__Ruminococcaceae;g__Ruminococcus
p__Proteobacteria;c__Alphaproteobacteria;o__;f__;g__
p__Proteobacteria;c__Alphaproteobacteria;o__Caulobacterales;f__Caulobacteraceae;g__
p__Proteobacteria;c__Alphaproteobacteria;o__Caulobacterales;f__Caulobacteraceae;g__Brevundimonas
p__Proteobacteria;c__Alphaproteobacteria;o__Rhizobiales;f__Bradyrhizobiaceae;g__Afipia
p__Proteobacteria;c__Alphaproteobacteria;o__Rhizobiales;f__Bradyrhizobiaceae;g__Bradyrhizobium
p__Proteobacteria;c__Alphaproteobacteria;o__Rhizobiales;f__Methylobacteriaceae;g__Methylobacterium
p__Proteobacteria;c__Alphaproteobacteria;o__Rhizobiales;f__Phyllobacteriaceae;g__
p__Proteobacteria;c__Alphaproteobacteria;o__Rhizobiales;f__Phyllobacteriaceae;g__Phyllobacterium
p__Proteobacteria;c__Alphaproteobacteria;o__Rhodobacterales;f__Rhodobacteraceae;g__Rhodobacter
p__Proteobacteria;c__Alphaproteobacteria;o__Sphingomonadales;f__Sphingomonadaceae;g__Novosphingobium
p__Proteobacteria;c__Betaproteobacteria;o__;f__;g__
p__Proteobacteria;c__Betaproteobacteria;o__Burkholderiales;f__Alcaligenaceae;g__
p__Proteobacteria;c__Betaproteobacteria;o__Burkholderiales;f__Burkholderiaceae;g__Burkholderia
p__Proteobacteria;c__Deltaproteobacteria;o__Desulfovibrionales;f__Desulfovibrionaceae;g__
p__Proteobacteria;c__Deltaproteobacteria;o__Desulfovibrionales;f__Desulfovibrionaceae;g__Bilophila
p__Proteobacteria;c__Deltaproteobacteria;o__Desulfovibrionales;f__Desulfovibrionaceae;g__Desulfovibrio
p__Proteobacteria;c__Deltaproteobacteria;o__Desulfovibrionales;f__Desulfovibrionaceae;g__LE30
p__Proteobacteria;c__Epsilonproteobacteria;o__Campylobacterales;f__Helicobacteraceae;g__Helicobacter
p__Proteobacteria;c__Gammaproteobacteria;o__Chromatiales;f__Sinobacteraceae;g__
p__Proteobacteria;c__Gammaproteobacteria;o__Enterobacteriales;f__Enterobacteriaceae;g__
p__Proteobacteria;c__Gammaproteobacteria;o__Enterobacteriales;f__Enterobacteriaceae;g__Enterobacter
p__Proteobacteria;c__Gammaproteobacteria;o__Enterobacteriales;f__Enterobacteriaceae;g__Escherichia
p__Proteobacteria;c__Gammaproteobacteria;o__Enterobacteriales;f__Enterobacteriaceae;g__Salmonella
p__Proteobacteria;c__Gammaproteobacteria;o__Pasteurellales;f__Pasteurellaceae;g__
p__Proteobacteria;c__Gammaproteobacteria;o__Pseudomonadales;f__Moraxellaceae;g__
p__Proteobacteria;c__Gammaproteobacteria;o__Pseudomonadales;f__Moraxellaceae;g__Acinetobacter
p__Proteobacteria;c__Gammaproteobacteria;o__Pseudomonadales;f__Pseudomonadaceae;g__Pseudomonas
p__TM7;c__TM7-3;o__CW040;f__F16;g__
p__Tenericutes;c__Erysipelotrichi;o__Erysipelotrichales;f__Erysipelotrichaceae;g__
p__Tenericutes;c__Erysipelotrichi;o__Erysipelotrichales;f__Erysipelotrichaceae;g__Allobaculum
p__Tenericutes;c__Erysipelotrichi;o__Erysipelotrichales;f__Erysipelotrichaceae;g__Clostridium
p__Tenericutes;c__Erysipelotrichi;o__Erysipelotrichales;f__Erysipelotrichaceae;g__Coprobacillus
p__Tenericutes;c__Mollicutes;o__Anaeroplasmatales;f__Anaeroplasmataceae;g__Anaeroplasma
p__Tenericutes;c__Mollicutes;o__RF39;f__;g__
p__Verrucomicrobia;c__Verrucomicrobiae;o__Verrucomicrobiales;f__Verrucomicrobiaceae;g__Akkermansia
p__Verrucomicrobia;c__Verrucomicrobiae;o__Verrucomicrobiales;f__Verrucomicrobiaceae;g__Haloferula

Fig. 21 (contine)

| | A | B | C | D | E | F | G | H |
|---|---|---|---|---|---|---|---|---|
| 1 | Pos | Pos | Neg | Neg | GCSF | GM-CSF | IL-2 | IL-3 |
| 2 | Pos | Pos | Neg | Neg | GCSF | GM-CSF | IL-2 | IL-3 |
| 3 | IL-4 | IL-6 | IL-6 | IL-9 | IL-10 | IL-12 p40p70 | IL-12p70 | IL-13 |
| 4 | IL-4 | IL-6 | IL-6 | IL-9 | IL-10 | IL-12 p40p70 | IL-12p70 | IL-13 |
| 5 | IL-17 | IFN-γ | MCP-1 | MCP-3 | RANTES | SCF | sTNFRI | TNF-α |
| 6 | IL-17 | IFN-γ | MCP-1 | MCP-3 | RANTES | SCF | sTNFRI | TNF-α |
| 7 | Thrombopoietin | VEGF | Blank | Blank | Blank | Blank | Blank | Pos |
| 8 | Thrombopoietin | VEGF | Blank | Blank | Blank | Blank | Blank | Pos |

Fig. 25A

US 10,456,436 B2

USE OF HERBAL SAPONINS TO REGULATE GUT MICROFLORA

CROSS-REFERENCE TO RELATED APPLICATIONS

This application is a continuation-in-part application of U.S. Non-Provisional patent application Ser. No. 14/290,148 filed on May 29, 2014 which claims the benefit of U.S. Provisional Application Ser. No. 61/899,507 filed on Nov. 4, 2013. Foregoing applications are hereby incorporated by reference in their entirety.

FIELD OF INVENTION

The present invention relates to the use of a plant based compound in the regulation of gut microflora in a host animal. The present invention also relates to the use of a plant based compound to exert anti-cancer and anti-inflammatory effects by regulating and balancing the gut microbial ecosystem of a host animal.

BACKGROUND OF THE INVENTION

Normal gut microbes make significant contributions to the overall health of their host including protection against harmful microorganisms and stimulation of the immune system. Their importance can be traced back to 400 B.C., as the ancient Greek physician Hippocrates wrote, "death sits in the bowels" and "bad digestion is the root of all evil". The intestinal tract is the primary site of interaction between the host immune system and the microbial ecosystem. The microbiome contains at least 100-fold more genes than the complete human genome, and the composition of gut microflora can likely be altered due to the plasticity of the microbiome. In healthy individuals, alterations in the microbiome composition have been linked to dietary patterns, ageing, environment and host genotype, etc. Besides the genomic influence, the host's dietary and drug uptake can also alter the composition of microflora. The fat or carbohydrate-restricted low calorie diet made obese people lose weight and result in an increase in Bacteroidetes. Conversely, the microbes can influence the energy harvesting from diet. Furthermore, the gut microbiota can also affect the bioavailability and bioactivity of ingested products, including functional foods and traditional Chinese medicine (TCM). Recent findings have revealed that the gut microflora play an even greater role in modulating human metabolic phenotypes and individuals' drug responses than previously believed. For example in Ley R E, Turnbaugh P J, Klein S, Gordon J I (2006). Microbial ecology: human gut microbes associated with obesity. Nature 444: 1022-1023 and Nicholson J K, Holmes E, Wilson I D (2005). Gut microorganisms, mammalian metabolism and personalized health care. Nat Rev Microbiol 3: 431-438, the host's dietary and drug uptake can alter the microbial composition. Conversely, microbes can influence the bioavailability and bioactivity of ingested products, including functional foods and herbal medicines. For example, recent findings in Ley R E, Turnbaugh P J, Klein S, Gordon J I (2006). Microbial ecology: human gut microbes associated with obesity. Nature 444: 1022-1023 and Ley R E, Turnbaugh P J, Klein S, Gordon J I (2006). Microbial ecology: human gut microbes associated with obesity. Nature 444: 1022-1023 indicated that the composition of two predominant gut bacterial phylum, Firmicutes and Bacteroidetes, show tight association with obesity of human and mice.

Another recent report, namely, Holmes E, Loo R L, Stamler J, Bictash M, Yap I K, Chan Q et al., (2008). Human metabolic phenotype diversity and its association with diet and blood pressure. Nature 453: 396-400, on the metabolic phenotyping of urine specimens of 4,630 participants from China, Japan, UK and USA indicated that gut microbial activities contribute to the ethnic diversity and its association with diet and blood pressure. Studies also showed that gut microbiota can alter bioavailability of intake natural products. For example, in Akao T, Kawabata K, Yanagisawa E, Ishihara K, Mizuhara Y, Wakui Y et al., (2000). Baicalin, the predominant flavone glucuronide of scutellariae radix, is absorbed from the rat gastrointestinal tract as the aglycone and restored to its original form. The Journal of pharmacy and pharmacology 52: 1563-1568, the case of the flavones baicalin isolated from scutellariae radix, the ingested baicalin is first hydrolyzed by the gut microbacteria to form the aglycone, followed by absorption and subsequently conjugated back to baicalin. Another example in Wang Y, Tang H, Nicholson J K, Hylands P J, Sampson J, Holmes E (2005). A metabonomic strategy for the detection of the metabolic effects of chamomile (Matricaria recutita L.) ingestion. Journal of agricultural and food chemistry 53: 191-196, showed that functional food chamomile tea altered the metabolites and bacterial composition.

Metabolic activation of ginseng saponins and ginsenosides by intestinal bacteria has also been investigated extensively. Other natural products isolated from TCM have also been proven to be metabolized by gut microbes to form active drugs, such as glycyrrhizin, paeoniflorin, baicalin, puerarin and daidzin. Nevertheless, studies have been confined to the metabolites of the TCM, and no systematic study of the alteration of the microflora under the influence of ingested herbal medicines.

It is possible that TCM with a longer residence time in the intestinal tract may have a great chance to affect the gut microbial ecosystem. Saponins are the natural triterpenoids found in many herbal and edible plants. Saponins have the following traits underlying poor membrane permeability and result in poor intestinal absorption, relative high molecular mass (>500 Da), high hydrogen-bonding capacity (>12) and high molecular flexibility (>10). These non-absorbable saponins are too difficult to be absorbed through the intestinal wall and able to interact with gut microflora for a longer time. Saponins are commonly found in a large number of natural sources and particularly abundant in many herbal and edible plants. They are a group of amphiphilic glycosides containing one or more sugar chains bound to a nonpolar triterpene (FIG. 1A) or steroid aglycone (FIG. 1B) skeleton.

Citation or identification of any reference in this section or any other section of this application shall not be construed as an admission that such reference is available as prior art for the present application.

SUMMARY OF INVENTION

In accordance with a first aspect of the present invention, there is provided a use of a composition comprising saponins extracted from plants for improving gut microbial ecosystem of a subject.

In an embodiment of the first aspect, the plants comprising Gynostemma pentaphyllum (Gp), Panax pseudoginseng, Panax notoginseng and Panax ginseng.

In an embodiment of the first aspect, the Panax ginseng is processed to comprise red ginseng.

In an embodiment of the first aspect, the *Panax ginseng* is processed by steaming.

In an embodiment of the first aspect, the plants further comprising *Radix Notoginseng* of *Panax pseudoginseng*, *Radix Notoginseng* of *Panax notoginseng* and *Radix Ginseng* of *Panax ginseng*.

In an embodiment of the first aspect, the saponins are of a range of concentration of about 500 mg/kg to 750 mg/kg in the composition.

In an embodiment of the first aspect, the improvement to the gut microbial ecosystem comprising regulating and balancing the gut microbial ecosystem by increasing symbionts in the gut ecosystem of said subject.

In an embodiment of the first aspect, said subject is a human.

In an embodiment of the first aspect, the composition is used as prebiotics for improving the gut microbial ecosystem of a subject.

In an embodiment of the first aspect, the improvement of the gut microbial ecosystem of a subject results in an inhibitory effect on tumor growth in said subject.

In a second aspect of the present invention, there is provided a method of inducing prebiotic condition in digestive organs of a subject by administering to said subject a composition comprising saponins extracted from *Gynostemma pentaphyllum*.

In an embodiment of the second aspect, said digestive organs comprising the gut, intestines and digestive track of said subject.

In an embodiment of the second aspect, said composition is administered orally to said subject.

In an embodiment of the second aspect, approximately HED 40 mg of the saponins per kg of the subject is administered.

In an embodiment of the second aspect, said subject is a mammal.

In an embodiment of the second aspect, said subject is human.

In a third aspect of the present invention, there is provided a use of a composition comprising saponins extracted from *Gynostemma pentaphyllum* as prebiotics in a subject in need thereof.

In an embodiment of the third aspect, said subject in need thereof is a mammal.

In an embodiment of the third aspect, said composition is used by oral consumption.

In an embodiment of the third aspect, said composition enhance beneficial commensal bacteria in the subject in need thereof.

In an embodiment of the third aspect, said composition reduce sulfate-reducing bacteria in the subject in need thereof.

In an embodiment of the third aspect, said composition suppress pro-inflammatory cytokines and signaling molecules in digestive organs of the subject in need thereof.

In an embodiment of the third aspect, said composition suppress pro-oncogenic cytokines and signaling molecules in digestive organs of the subject in need thereof.

In a fourth aspect of the present invention, there is provided a method of preventing colorectal cancer comprising administering to a subject a composition comprising saponins extracted from *Gynostemma pentaphyllum*.

In an embodiment of the fourth aspect, said composition is administered orally to said subject.

In an embodiment of the fourth aspect, approximately HED 40 mg of the saponins per kg of the subject is administered.

In an embodiment of the fourth aspect, said subject is a mammal.

In an embodiment of the fourth aspect, said subject is human.

Other aspects and advantages of the invention will become apparent to those skilled in the art from the following description of the drawings, which are given by way of example only to illustrate the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 6G shows the results of heatmap analysis of discriminative metabolites in fecal samples from control mice, red *ginseng* and *ginseng* saponins treated mice.

FIG. 11B shows changes in relative abundance of the main phyla of microbial communities in the gut.

FIG. 13B shows the unique families between normal and xenograft nude mice; normal nude mice with or without GpS treatment; xenograft nude mice with or without GpS treatment (n=3 per group).

FIG. 14A shows the OTU heatmap of identified bacterial species; FIG. 14B shows the corresponding OTU IDs of FIG. 14A with the respective identified bacterial species.

The effect of herbal saponins on common commensal bacteria in the faecal samples of mice are shown in FIG. 18A (*Bacteroides*)

The comparison of microbial composition between the control and GpS-treated WT and Apc$^{Min/+}$ mice are shown in FIG. 20A and FIG. 20B. FIG. 20C-FIG. 20E show 16S pyrosequencing analysis on the fecal genomic DNA samples from the WT and Apc$^{Min/+}$ mice with or without GpS treatment for 8 weeks (n=5/group). FIG. 20C is PCoA plots of all samples from different treatment groups. The data are analyzed using QIIME software with the workflow script. PCoA plots are then generated using the unweighted UniFrac distance metric. FIG. 20D shows changes in the relative abundance of the main phyla of microbial communities in the feces. Beta diversity is calculated by QIIME software. FIG. 20E Bacteroidetes/Firmicutes ratio of WT and Apc$^{Min/+}$ mice treated and untreated with GpS. Data is presented as the mean±SEM (*P<0.05, GpS versus control).

FIG. 22A is the taxonomic representations of the fecal microbiome. The differentially abundant taxa are presented with different colors using LEfSe method. The taxa from the untreated and GpS-treated Apc$^{Min/+}$ mice are colored in red and green, respectively. The taxa with non-significant changes are colored in yellow. Each circle's diameter represents the taxon abundance. FIG. 22B shows the histogram of the LDA scores of fecal 16S rRNA gene sequences of the untreated controls (dark color) and GpS-treated Apc$^{Min/+}$ mice (light color). LDA scores characterized the magnitude of differential abundance in the microbial taxa between compared samples. FIG. 22C shows the relative abundance of differentially abundant genera. Data is presented as the mean±SEM (*P<0.05, P<0.01, *P<0.001, GpS versus control); n=5/group. FIG. 22D shows the fold change of dissimilatory (bi)sulfite reductase (dsrA) gene in fecal genomic DNA samples obtained from mice treated with GpS for 8 weeks. The DNA subjected to qRT-PCR is the same as the one applied to pyrosequencing. FIG. 22E shows relative expression of dsrA gene over 8 weeks. qRT-PCR is used to determine the level of dsrA gene and normalized to that of the total fecal bacteria, and expressed as fold change of the WT control group in FIG. 22D or fold change over the 0 w sample (before treatment) of each mouse shown in FIG. 22E. FIG. 22F shows the relative abundance of Deltaproteobacteria. Data is presented as the mean±SEM (**P<0.01 GpS versus control samples; #P<0.05 versus 0 w samples); n=6/group.

FIG. 23A is the H&E staining. FIG. 23B is MC staining of Paneth cells. FIG. 23C is Alcian blue staining of goblet cells. Hematoxylin and eosin (H&E) staining are used to visualize the formalin-fixed sections of small intestine. MC staining of lysozyme is applied to identify the Paneth cells in the small intestine, and the dark brown (arrows) at the bottom of the intestinal crypts indicates the presence of Paneth cells. Alcian blue staining is used to identify the goblet cells, and the blue staining (arrows) indicates the presence of the goblet cells. FIG. 23D shows the relative mRNA expression of Paneth cells related antimicrobial peptide and FIG. 23E shows the mRNA expression of goblet cells related mucins. Data is evaluated by qRT-PCR in the intestinal mucosal samples. Data is normalized to the expression of reference gene, and expressed as fold change of the WT control group. Data is presented as the mean±SEM (*P<0.05, GpS versus control samples; ##P<0.01, ###P<0.001, Apc$^{Min/+}$ versus WT control samples); n=6/group. FIG. 23F is IHC staining of E-cadherin and N-cadherin. Positive expression is indicated by the brown color staining. Nuclear is stained and appeared in blue color that is done by hematoxylin staining.

FIG. 24A is western blot analysis: mucosa from the small intestine and colon are collected after 8 weeks of treatment. Mucosal protein lysates are analyzed by western blotting with specified indicated antibody. GAPDH is used as a loading control. Each lane represents sample obtained from individual mouse (n=3/group). FIG. 24B is IHC staining of STAT3 and FIG. 24C is MC staining of beta-catenin in the small intestine and colon. Arrows indicate the STAT3 nuclear translocation.

FIG. 25A-D shows the effect of GpS on the mucosal cytokine profiles. Mucosal lysates from five selected mice per group are pooled together, and analyzed using the cytokine array kit. FIG. 25A shows the location of detected cytokines in the membrane. FIG. 25B shows representative cytokine array blots showing differential expressed cytokines. FIG. 25C shows densitometric analysis of the altered cytokines upon GpS treatment. Data is normalized to the positive control and presented as fold changes relative to the controls. Results are representative of two independent experiments with duplicate in each membrane. Data is presented as the mean±SEM (*P<0.05, **P<0.01, GpS versus control group). MCP: monocyte chemoattractant protein; sTNFRI: soluble tumor necrosis factor receptor I. FIG. 25D is IHC staining of IL-4 in the small intestine and colon. Arrows indicate the representative staining of the positive cells.

FIG. 26A shows the relative mRNA expression of M1 and M2 macrophage markers. qRT-PCR analysis of mRNA extracted from the mucosal lysates of experimental mice are performed with specific primers. Data is normalized to the expression of reference gene, and expressed as fold change of the untreated group. FIG. 26B shows the relative mRNA expression of macrophage polarization related cytokines and FIG. 26C shows the relative expression of inflammation related molecules. Data is normalized to the expression of reference gene, and expressed as fold change relative to the WT control group. Data is presented as the mean±SEM (*$P<0.05$, **$P<0.01$ GpS versus control samples; #$P<0.05$, ##$P<0.01$, ####$P<0.001$, $Apc^{Min/+}$ versus WT control samples); n=6/group. FIG. 26D is IHC staining of iNOS and Arginase I. Arrows indicate the representative staining of the positive cells.

DETAILED DESCRIPTION OF THE PREFERRED EMBODIMENTS

Figure 1A:
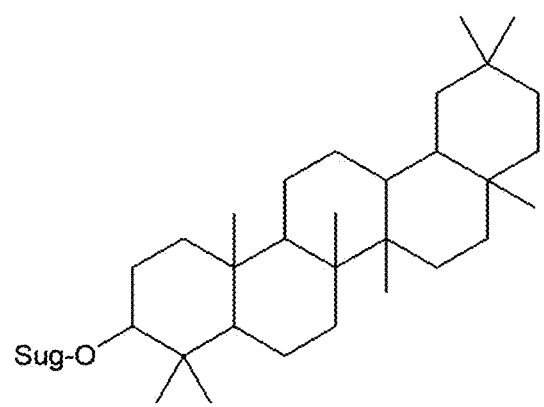
FIG. 1 shows the chemical structures of common saponins including (FIG. 1A) triterpenoid saponins and (FIG. 1B) steroid saponins.
Figure 1B:
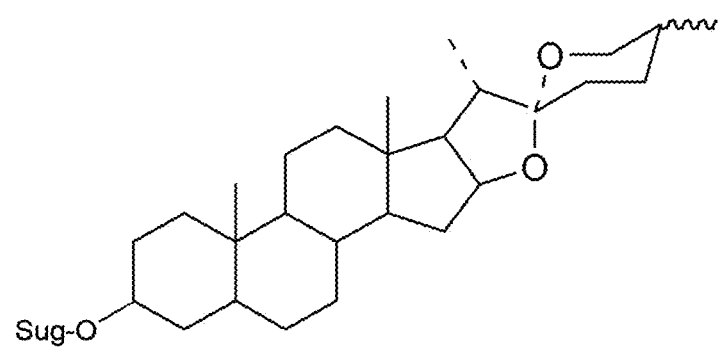

The present invention is not to be limited in scope by any of the specific embodiments described herein. The following embodiments are presented for exemplification only.

The present invention relates to a composition comprising saponins extracted from plants for improving gut ecosystem of a subject. In particular, the present invention relates to the use of saponins from *Gynostemma pentaphyllum* (Gp), *Radix Notoginseng* of *Panax pseudoginseng* (or *Panax notoginseng*), *Radix Ginseng* of *Panax ginseng* and red *ginseng* (steamed *Panax ginseng*) in regulating and balancing the gut microbial ecosystem by increasing symbionts. The present invention also has possible application in treatment with saponins from *Gynostemma pentaphyllum* (Gp) to exert anti-cancer effects by regulating and balancing the gut microbial ecosystem for the host animal.

Saponins from *Gynostemma pentaphyllum* (Gp), *Radix Notoginseng*, *Radix Ginseng* and Red *Ginseng* (Steamed *Panax ginseng*) and the Effects on Gut Microflora Saponins from four famous plant based or herbal Chinese medicines are involved in this example of the present invention, including *Gynostemma pentaphyllum* (Gp), *Radix Notoginseng* of *Panax pseudoginseng* (or *Panax notoginseng*), *Radix Ginseng* of *Panax ginseng* and red *ginseng* (steamed *Panax ginseng*). Triterpenoid saponins are the major compounds in these herbal medicines and are considered to be the main bioactive components responsible for a variety of pharmacological activities.

Materials and Methods

The chemical figure printings of the four plant based saponins (from *Gynostemma pentaphyllum* (Gp), *Radix Notoginseng*, *Radix ginseng* and red *ginseng* (steamed *Panax ginseng*)) were performed according to Wu P K, Tai C S, Choi C Y, Tsim W K, Zhou H, Liu X et al., (2011) Chemical and DNA authentication of taste variants of *Gynostemma pentaphyllum* herbal tea. *Food Chemistry* 128: 70-80.

Animals and Treatments

Animal welfare and experimental procedures were performed strictly in accordance with the care and use of laboratory animals. All procedures were approved by the University Ethics Review Committee for animal research. The C57BL/6 mice (8 weeks old) were purchased from Chinese University of Hong Kong, on a 12-h light/dark cycle and with free access to food and water. Total saponins of *Gynostemma pentaphyllum* (GpS), *Radix Notoginseng* (NGS), *Radix ginseng* (GS) and red *ginseng* (RGS) were dissolved in milli-Q $H_2O$ at 50 mg/ml respectively and then filtered (0.2 µm). Single dose of these four different saponins at 500 mg/kg or milli-Q $H_2O$ control was given to different treatment groups of mice daily by gavage, started the second day after the first fecal samples collection. For experimental animal, fecal samples were collected (8:00-10:00 a.m.) at day 0 (before treatment), and 5 days, 10 days and 15 days after treatment. All fecal samples were immediately stored at −20° C. and kept for later DNA extraction.

Bacterial Genomic DNA Extraction from Fecal Samples

Total genomic DNA was isolated from fecal samples as described with slight modification as in the previous study. 0.1 g of fecal samples were vortexed in 4 ml sterile PBS (pH 7.4) for 5 minutes, then centrifuged at 40×g for 8 minutes to collect the upper phase containing the bacteria. After repeating this procedure once, the supernatant was centrifuged at 2000×g for 8 minutes. The supernatant was discarded and the bacterial pellets were then washed twice with PBS. The bacterial pellets were used for DNA extraction as described. The DNA concentration was determined by NanoDrop 1000 spectrophotometry.

ERIC (Enterobacterial Repetitive Intergenic Consensus)-PCR

ERIC sequences are non-coding, highly conserved intergenic repeated sequences that reside in the genome of various bacterial species in addition to enterobacteria as it was first discovered. ERIC-PCR was used to profile the gut microbiome using fecal genomic DNA as the template and a pair of ERIC specific primer sequences: ERIC 1R (SEQ ID: 1) (5'-ATGTAAGCTCCTGGGGATTCAC-3') and ERIC 2 (SEQ ID: 2) (5'-AAGTAAGTGACTGGGGT-GAGCG-3'). A 25 µl reaction mixture containing 5 ti 5×PCR reaction buffer, 200 µM dNTP, 2.5 mM $Mg^{2+}$, 0.4 µM primers, 1 unit Hotstart Taq polymerase, and 50 ng fecal genomic DNA. PCR was performed under the following conditions: an initial denaturation at 94° C. for 5 minutes, followed by 35 cycles of denaturing at 95° C. for 50 seconds, annealing at 49° C. for 30 seconds, 46° C. for 30 seconds, and extension at 72° C. for 3 minutes; and then a final extension at 72° C. for 9 minutes. 10 μl of each PCR product was loaded into a 2% (w/v) agarose gel containing 0.5 μg/ml ethidium bromide and run for 40 minutes at 100 V in 1×TAE buffer. A DNA ladder (0.1-10.0 kb) was used as DNA marker (NEB, N3200). Agarose gels were photographed using a Gel Doc™ XR+ System.

Data Analysis of ERIC-PCR Fingerprints

Partial least squares discriminant analysis (PLS-DA) was performed to visualize the dynamic changes of microflora composition before and after treatment. Based on the distance and the intensity of each DNA bands (lane %), the banding patterns of ERIC-PCR products separated on the gel were digitized by Image Lab 3.0 system (Bio-Rad) and performed PLS-DA analysis using SIMCA-P 12.0 tool. Sorenson's pairwise similarity coefficient (Cs) was used to perform a paired comparison on the microflora profiles before and after treatment. Two identical profiles create a Cs value of 100%, whereas two completely different profiles (no common bands) result in a Cs value of 0%. Cs (%)= $(2 \times j)/(a+b) \times 100\%$, where a is the number of total bands in the ERIC-PCR pattern for one sample, b is the number for the other, and j is the number of the common bands shared by the two samples. Shannon-Weiner diversity index, also called H' index, refers to the community richness, was used to describe the microflora distribution of PCR bands in our study, although each ERIC-PCR band does not have to stand for one individual bacterial species. $H'=\Sigma-(Pi*\ln Pi)$, where pi refers to the relative abundance of each band in the lane of the fingerprint (lane %).

Identification of Bacterial Species Using 16S rRNAPCR

The abundance of specific bacteria was measured by qPCR using Applied Biosystems ViiA™ 7 PCR system (Carlsbad, Calif., USA) with taxon-specific 16S rRNA gene primers (Invitrogen, Carlsbad, Calif., USA). A universal primer set was used to detect the 16S rRNA gene of total bacteria, and used to calculate the relative abundance of specific bacteria group. The sequences of the primers used were listed in Table 1. Briefly, the qPCR was carried out using Power SYBR® Green PCR Maser Mix (Applied Biosystems Inc.) with 5 ng faecal genomic DNA and 200 nM of each primer. The amplification conditions were as follow: 95° C. for 10 min, followed by 40 cycles of 95° C. for 15 s and 60° C. for 1 min. Using the same batch of genomic DNA from each faecal sample, qPCR was performed to determine the amount of the following bacteria: Firmicutes, Bacteroidetes, *Bacteroides, Lactobacillus, Bifidobacterium, Clostridium* Cluster IV and *Faecalibacterium prausnitzii*. Ten samples were used for each experimental group. The comparative Ct method ($2^{\Delta\Delta Ct}$ method) was applied to determine the relative change of specific bacteria in the faeces of individual mouse before (D0) and after treatment. $\Delta\Delta Ct = (Ct_{treatment\_specific\ bacteria} - Ct_{treatment\_total\ bacteria}) - (Ct_{D0\_specific\ bacteria} - Ct_{D0\_total\ bacteria})$.

TABLE 1

16S rRNA PCR Primers

| SEQ ID No. | Target group | Primer | Sequence (5' to 3') | Reference |
|---|---|---|---|---|
| 3 | Total bacteria | UniF340 | ACTCCTACGGGAGGCAGCAGT | (Croswell, Amir, Teggatz, Barman, & Salzman, 2009) |
| 4 | | UniR514 | ATTACCGCGGCTGCTGGC | |
| 5 | Firtnicutes | 928F-Firm a | TGAAACTYAAAGGAATTGACG | (Bacchetti De Gregoris, Aldred, Clare, & Burgess, 2011) |
| 6 | | 928F-Firm b | TGAAACCYAAAGGAATTGACG | |
| 7 | | 1040FirmR | ACCATGCACCACCTGTC | |
| 8 | Bacteroidetes | 798cfbF a | CAAACAGGATTAGATACCCT | (Bacchetti De Gregoris, et al., 2011) |
| 9 | | 798cfbF b | CGAACAGGATTAGATACCCT | |
| 10 | | cfb967R | GGTAAGGTTCCTCGCGTAT | |
| 11 | Bacteroides | BactF296 | GAGAGGAAGGTCCCCCAC | (Guo, et al., 2008) |
| 12 | | BactR412 | CGCTACTTGGCTGGTTCAG | |
| 13 | Lactobacillus | LabF362 | AGCAGTAGGGAATCTTCCA | (Penders, et al., 2006) |
| 14 | | LabR677 | CACCGCTACACATGGAG | |
| 15 | Bifidobacterium | BifF | GCGTGCTTAACACATGCAAGTC | (Penders, et al., 2006) |
| 16 | | BifR | CACCCGTTTCCAGGAGCTATT | |
| 17 | Clostridium Cluster IV | Clep866mFa | TTAACACAATAAGTAATCCACCTGG | (Ramirez-Farias, et al., 2009) |
| 18 | | Clep866mFb | TTAACACAATAAGTTATCCACCTGG | |
| 19 | | Clep1240mR | ACCTTCCTCCGTTTTGTCAAC | |
| 20 | Faecalibacterium prausnitzii | Fprau223F | GATGGCCTCGCGTCCGATTAG | (Bartosch, Fite, Macfarlane, & McMurdo, 2004) |
| 21 | | Fprau420R | CCGAAGACCTTCTTCCTCC | |

Bacchetti De Gregoris, T., Aldred, N., Clare, A. S., & Burgess, J. G (2011) Improvement of phylum- and class-specific primers for real-time PCR quantification of bacterial taxa. *J Microbiol Methods*, 86, 351-356.

Bartosch, S., Fite, A., Macfarlane, G T., & McMurdo, M. E. (2004). Characterization of bacterial communities in feces from healthy elderly volunteers and hospitalized elderly patients by using real-time PCR and effects of antibiotic treatment on the fecal microbiota. *Appl Environ Microbiol*, 70, 3575-3581.

Croswell, A., Amir, E., Teggatz, P., Barman, M., & Salzman, N. H. (2009). Prolonged impact of antibiotics on intestinal microbial ecology and susceptibility to enteric *Salmonella* infection. *Infect Immun*, 77, 2741-2753.

Guo, X., Xia, X., Tang, R., Zhou, J., Zhao, H., & Wang, K. (2008). Development of a real-time PCR method for Firmicutes and Bacteroidetes in faeces and its application to quantify intestinal population of obese and lean pigs. *Lett Appl Microbiol*, 47, 367-373.

Penders, J., Thijs, C., Vink, C., Stelma, F. F., Snijders, B., Kummeling, I., van den Brandt, P. A., & Stobberingh, E. E. (2006). Factors influencing the composition of the intestinal microbiota in early infancy. *Pediatrics*, 118, 511-521.

Ramirez-Farias, C., Slezak, K., Fuller, Z., Duncan, A., Holtrop, G, & Louis, P. (2009). Effect of inulin on the human gut microbiota: stimulation of *Bifidobacterium adolescentis* and *Faecalibacterium prausnitzii*. *Br J Nutr*, 101, 541-550.

Metabonomic Study

A metabolomic study on the fecal samples collected from different plant based saponins treated mice was performed by using ultra high-performance liquid chromatography (UHPLC) coupled with quadrupole time-of-flight (Q-TOF) mass spectrometry. The Mass Profiler Professional (MPP) B.02.00 software was used to analyze the metabolomic data. The metabolites of fecal samples were extracted with methanol. The volume of 100% methanol in the extraction was 250 μl per 0.1 g of feces. Fecal samples were homogenized in methanol, followed by vortexing and incubating for 15 min at room temperature and then centrifuged at maximum speed (~20000 g) for 15 min. The supernatant was transferred and filtered (0.22 um Hydrophilic PVDF, Millipore). The metabolite extracts were frozen at −20° C. until analysis. The chromatography was performed on Agilent 1290 Infinity UHPLC equipped with G4220A binary pump, G4226A automatic sample injector and G4212A Diode Array Detector (Agilent Technologies, Santa Clara, Calif., USA). The separation was conducted with an ACQUITY UPLC BEH C8 column, 2.1×100 mm i.d., 1.7 μm (Waters Corp., Milford, Mass., USA). A mobile phase consisted of 0.1% acetic acid and 5 mM ammonium acetate in milli-Q water (A) and acetonitrile (B) was used for separation. The system was programmed with the following gradients: 0-0.25 min, 10% B; 0.25-5 min, 10-75% B; 5-22 min, 75-99% B; 22-27 min, 99% B. The flow rate was kept constant at 0.4 ml/min at 45° C. for a total run time of 30 min. The volume of sample injection was 8 μl. An Agilent 6540 Ultra High Definition (UHD) Accurate-Mass Q-TOF mass spectrometer (Agilent Technologies, Santa Clara, Calif., USA) was coupled to the UHPLC system described above via an electrospray ionization (ESI) ion source with Jet-Stream technology for the comprehensive LC/MS analysis of fecal samples. The ESI-MS spectra were acquired in the positive and negative ion modes. Ultra-high-purity nitrogen was used as collision gas in product ion scanning experiments. The capillary voltage was set at 4.5 kV. The drying gas and sheath gas were delivered at flow rate of 8 L/min and temperatures were 300° C. and 350° C., respectively. The pressure of nebulizer gas was 35 psi. The fragmentor voltage is 135 V. The mass analyzer was scanning from 80 to 1700 (m/z). Data were collected at a spectral acquisition rate of 2 Hz. MassHunter Qualitative Analysis was used to create the Molecular feature extraction (MFE) method for the metabolomics data. MassHunter DA Reprocessor was then used to automate MFE on all of the samples in a single batch processing. The molecular features for each sample data file were exported as a CEF file and imported into MPP software. Principal Component Analysis (PCA) was used to find differences between samples and weigh relative contributions of compounds to the separation of the groups by MPP. A series of differential metabolites were obtained and heatmap was generated based on statistical analysis (Oneway ANOVA, $p<0.05$) by MPP.

Statistical Analysis

The data obtained from two independent experiments, a total of ten mice per group were analyzed and presented as mean±SEM. Statistical comparisons were performed using repeated measures ANOVA followed by Dunnett's post test with the GraphPad Prism version 5.00 (GraphPad Software, San Diego, Calif., USA) at P values of <0.001(*), <0.01 () or <0.05(*).

Results

Chemical Profiles of Four Plant Based Saponins

ERIC-PCR Fingerprint of Fecal Microflora in Plant Based Saponins Treated Mice

Figure 2A:
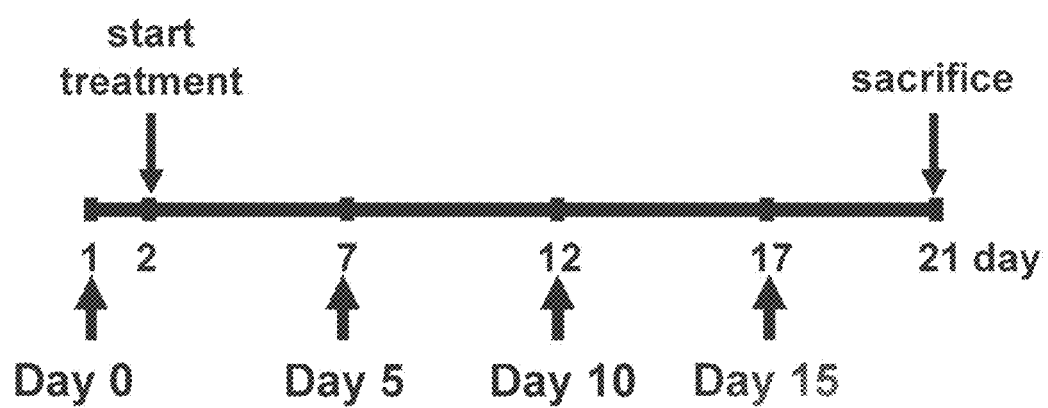
FIG. 2A shows a schematic diagram illustrating the experimental design.
Figure 2B:
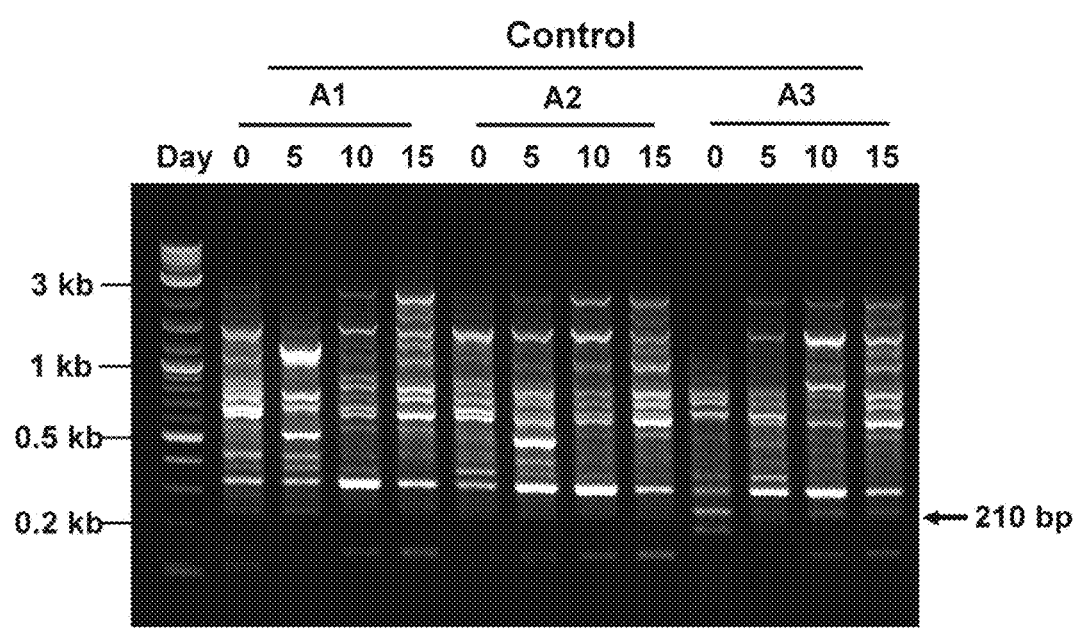
FIG. 2B shows the ERIC-PCR fingerprints of the control group. ERIC-PCR data of faecal samples from three representative mice group (A1-A3) obtained at Day 0, 5, 10 and 15 are shown in the gel image. A total of ten mice are used for each group.
Figure 2C:
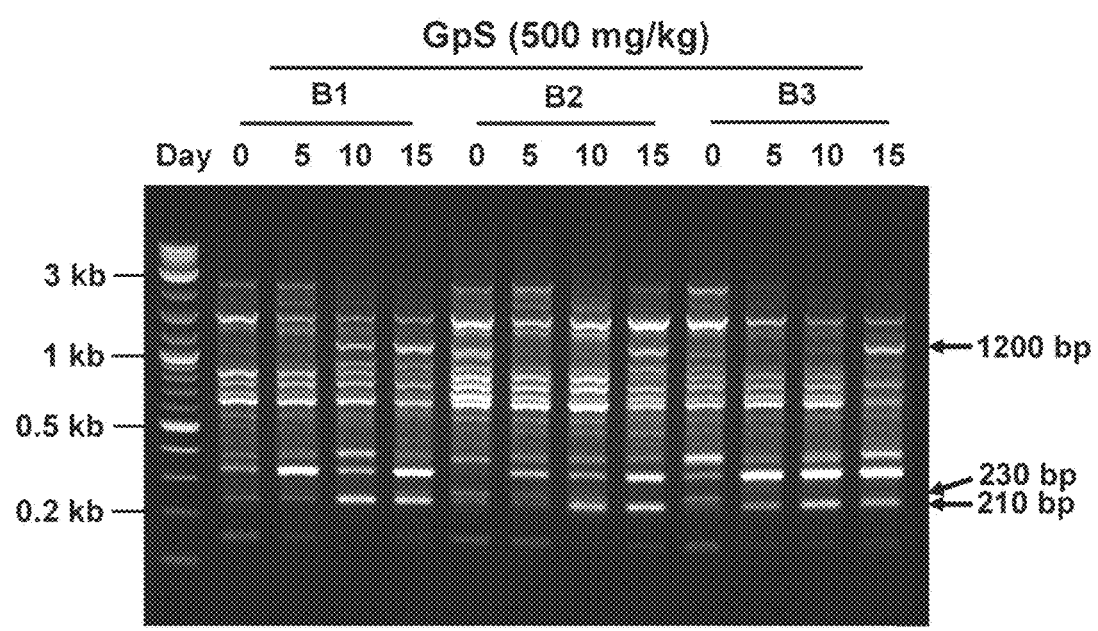
FIG. 2C shows the ERIC-PCR fingerprints of the Gp saponins (GpS) treatment group. ERIC-PCR data of faecal samples from three representative mice group (B1-B3) obtained at Day 0, 5, 10 and 15 are shown in the gel image. A total of ten mice were used for each group.
Figure 2D:
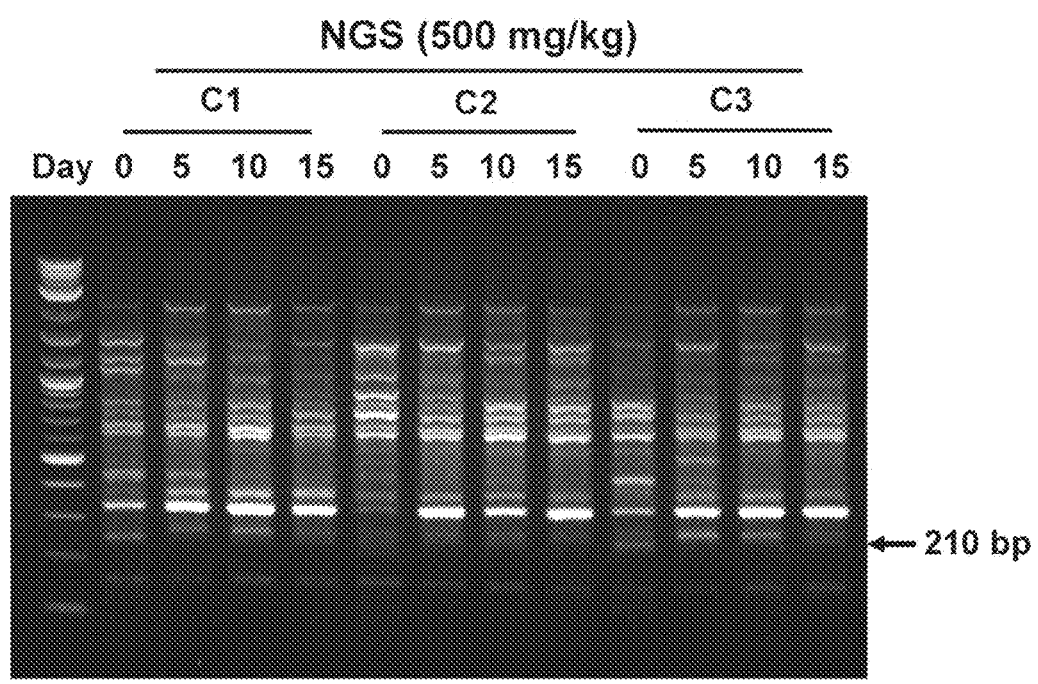
FIG. 2D shows the ERIC-PCR fingerprints of the *Notoginseng* saponins (NGS) treatment group. ERIC-PCR data of faecal samples from three representative mice group (C1-C3) obtained at Day 0, 5, 10 and 15 are shown in the gel image. A total of ten mice were used for each group.
Figure 2E:
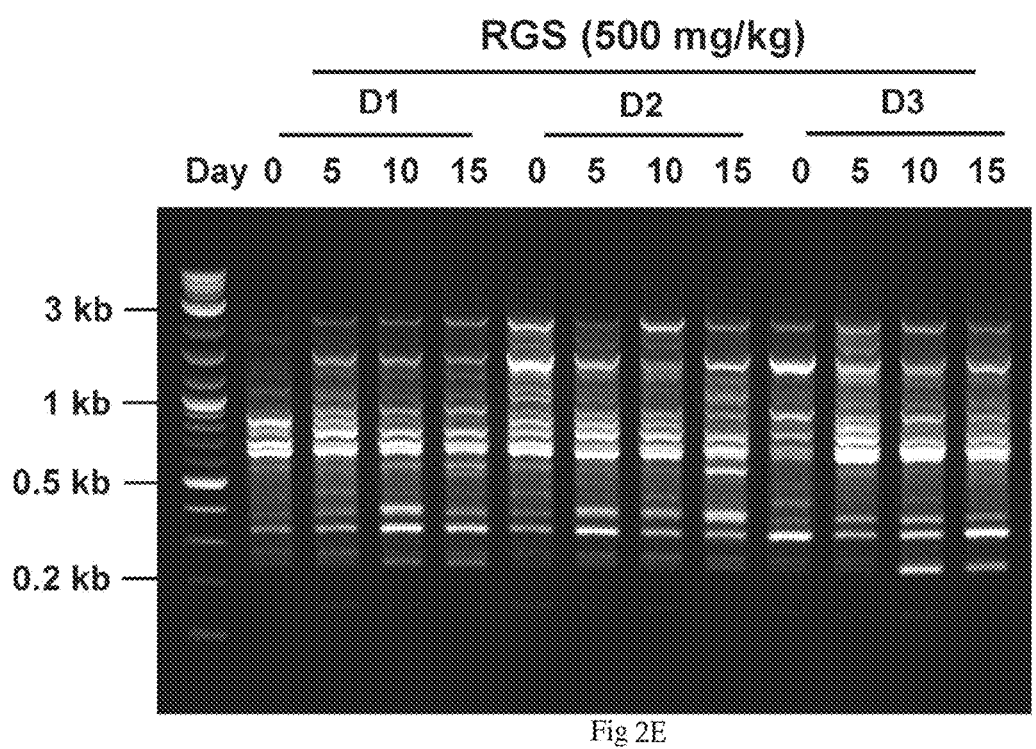
FIG. 2E shows the ERIC-PCR fingerprints of the red *ginseng* saponins (RGS) treatment group. ERIC-PCR data of faecal samples from three representative mice group (D1-D3) obtained at Day 0, 5, 10 and 15 are shown in the gel image A total of ten mice were used for each group.
Figure 2F:
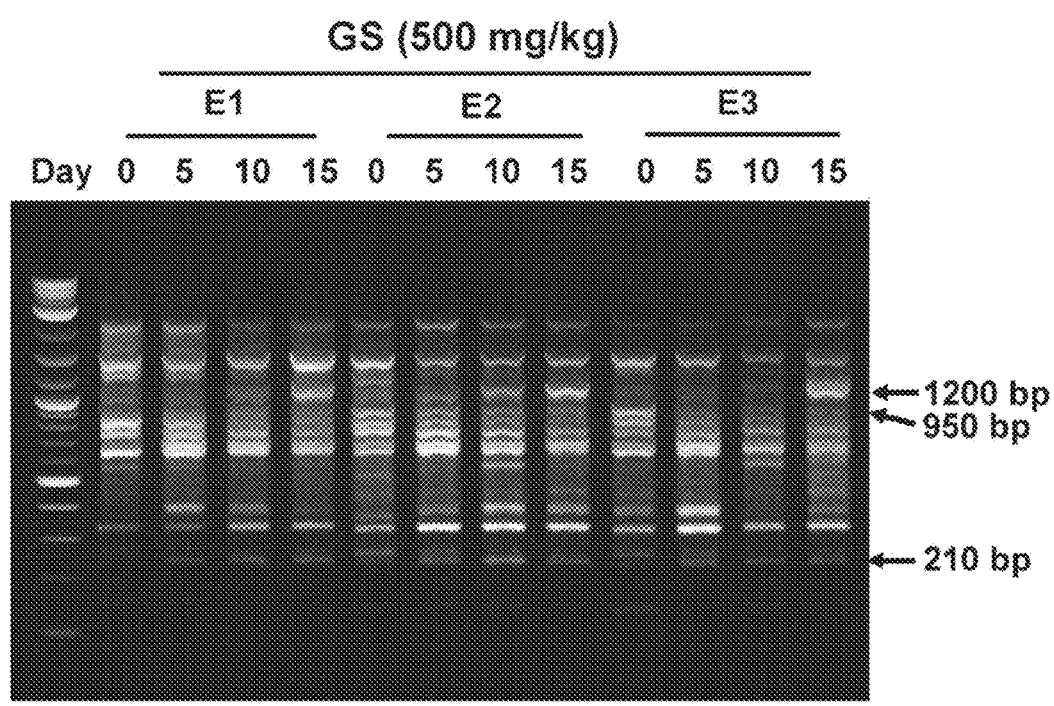
FIG. 2F shows the ERIC-PCR fingerprints of the *ginseng* saponins (GS) treatment group. ERIC-PCR data of faecal samples from three representative mice group (E1-E3) obtained at Day 0, 5, 10 and 15 are shown in the gel image. A total of ten mice were used for each group.
Figure 2G:
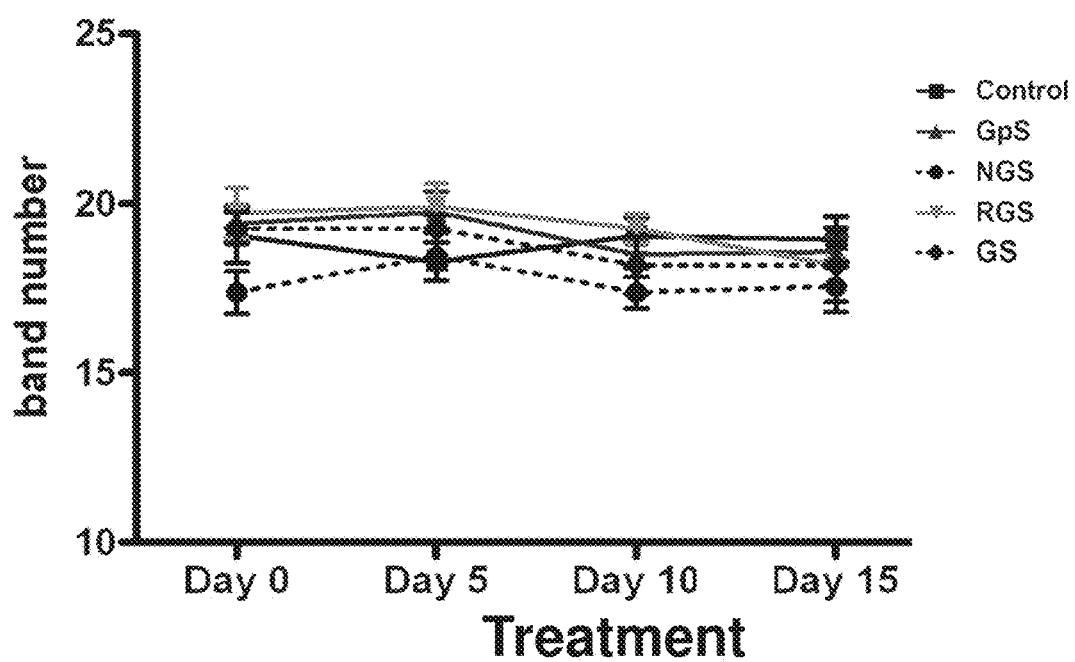
FIG. 2G shows the band numbers of the different treatment groups.
Figure 2H:
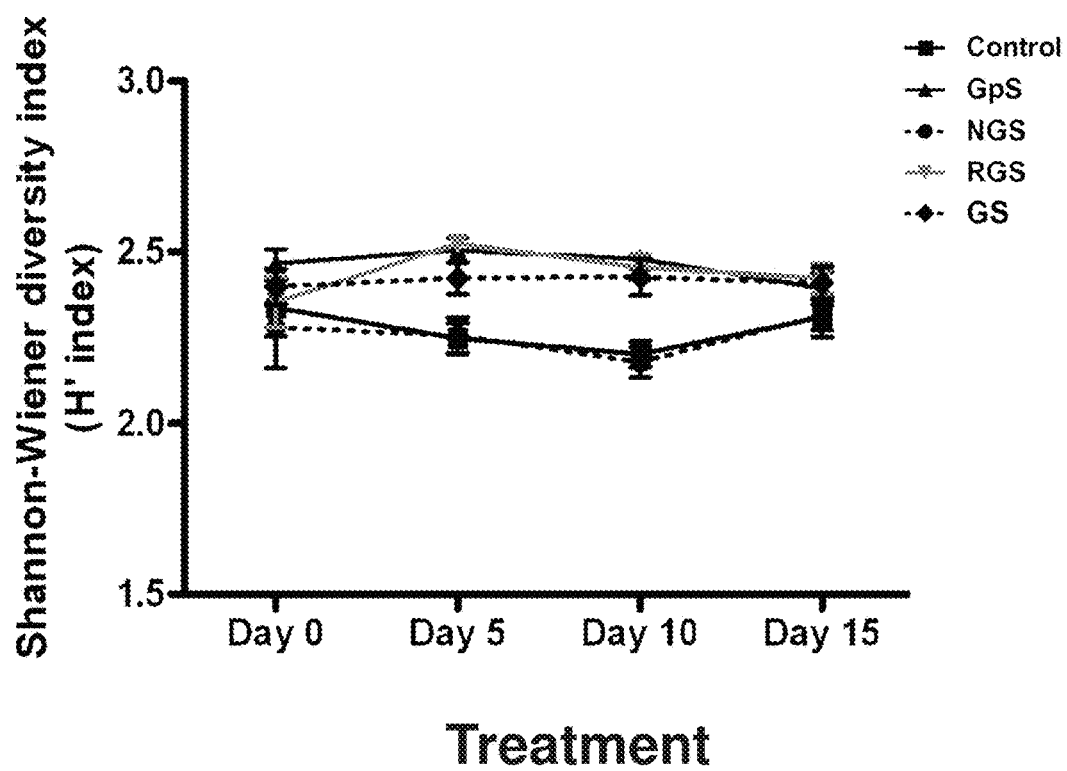
FIG. 2H shows the Shannon-Wiener diversity index (H' index) of the different treatment groups.
Figure 2I:
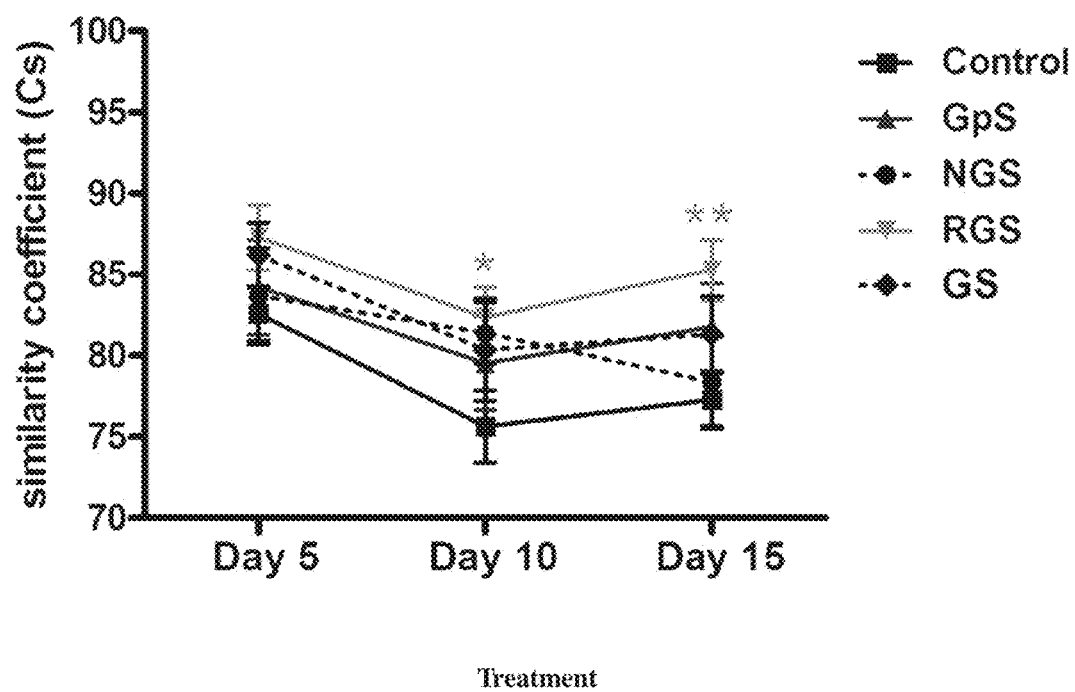
FIG. 2I shows the Sorenson's pairwise similarity coefficient (Cs) of the different treatment groups.

To investigate how plant based saponins would affect the gut microflora composition in the normal mice, fecal samples were collected from the five groups including control group and four different plant based saponins treatment groups at Day 0, Day 5, Day 10 and Day 15 as described (see FIG. 2A-2F). Genomic DNA isolated from the fecal samples was analyzed by ERIC-PCR. Among all the treated mice, the fecal microbial fingerprints showed an average of 19 fragments per sample, ranging from approximately 100 to 3000 bp with various intensities (FIG. 2B-2F). There were no significant differences in the numbers of ERIC-PCR fragments among different treatment groups (FIG. 2G) as well as the Shannon-Wiener diversity index (FIG. 2H). On the other hand, the similarities between samples were evaluated by calculating Sorenson's pairwise similarity coefficient (Cs). For individual mice, the microbial profiles of Day 5, Day 10 and Day 15 samples were compared to their Day 0 status (before treatment). Two identical profiles and two completely different profiles create Cs value of 100% and 0%, respectively. Compared to the control group, the samples collected on different days from the same mouse showed a better consistency in plant based saponins treated groups. The fecal microbial composition showed a higher Cs ranging from 76% to 97% in mice with red *ginseng* saponins treatment, followed by *ginseng* (65%-95%) and *Gynostemma pentaphyllum* saponins (62%-95%). However, the similarity coefficient in the mice with the treatment of *notoginseng* saponins was closer to the control mice at Day 15 (FIG. 2I).

Plant Based Saponins Altered the Fecal Microbial Composition

The PLS-DA plots, based on the ERIC-PCR banding patterns, displayed a clear alteration of microflora profiles in the plant based saponins treatment groups in contrast to the control group. The fecal microflora composition was fixed in a relatively stable pattern after plant based saponins treatment at different time points. The fecal microflora communities in plant based saponins treated mice clustered in an area that remained distinct from that of controls (FIG. 3A-3D). However, there was some overlapping between the samples from control and *notoginseng* saponins treated mice. When comparing the fecal microbial composition before and after treatment, the cluster of samples from red *ginseng* saponins treated mice was quite close to Day 0 status (before treatment). This finding was consistent with the highest Cs value in red *ginseng* saponins treatment group. Interestingly, among the four plant based saponins, red *ginseng* and *ginseng* saponins yielded relatively similar patterns of microbial composition.

Fecal Microflora Showed Differential Response to Different Plant Based Saponins

We then further identified the differential ERIC-PCR fragments between saponins treated mice and controls. As shown in FIG. 4A-4D (arrows indicated 210 bp fragments in the fingerprints in FIG. 2B-2F), Gp and *ginseng* saponins can increase the intensity of the 1200 bp fragment. Additionally, *ginseng* saponins can decrease the intensity of the 950 bp fragment, while Gp saponins can reduce the 230 bp band. Furthermore, the intensity of 210 bp fragment was significantly down-regulated in controls, whereas the three plant based saponins, Gp, red *ginseng* and *ginseng* saponins, can enhance this band after treatment. All these discriminative ERIC-PCR fragments further revealed the differential response of the gut microbiota to the treatment of different plant based saponins, and can be the main contributors to the distinct ERIC-PCR profiles among different treatment groups.

Figure 5A:
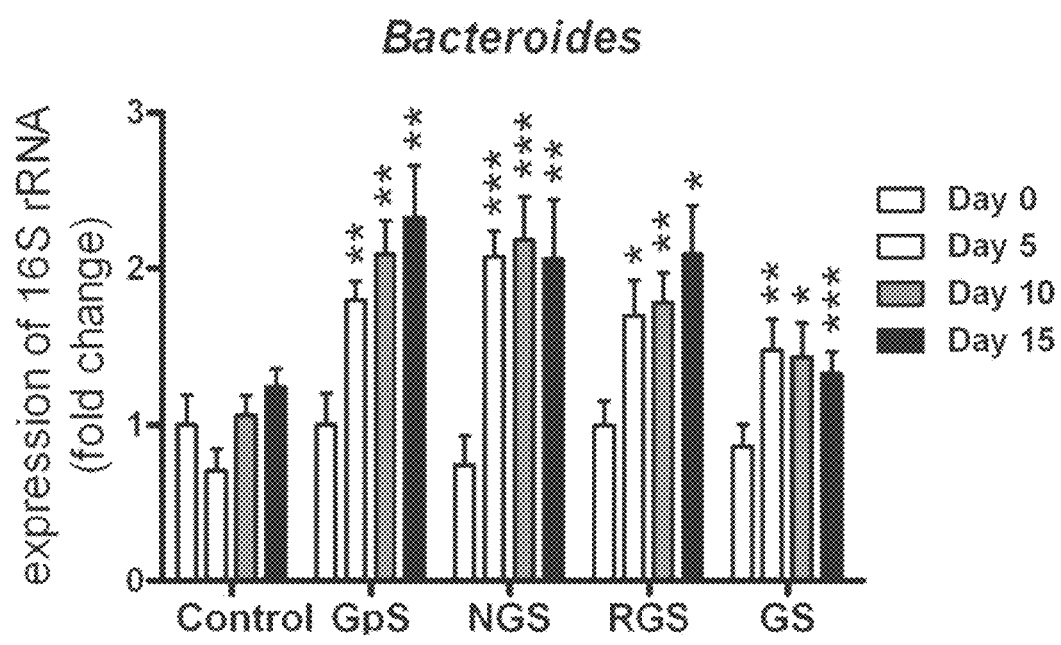
FIG. 5A shows the effect of different plant based saponins including Gp, *notoginseng*, red *ginseng* and *ginseng* saponins and control on *Bacteroides* as determined by 16S rRNA PCR.
Figure 5B:
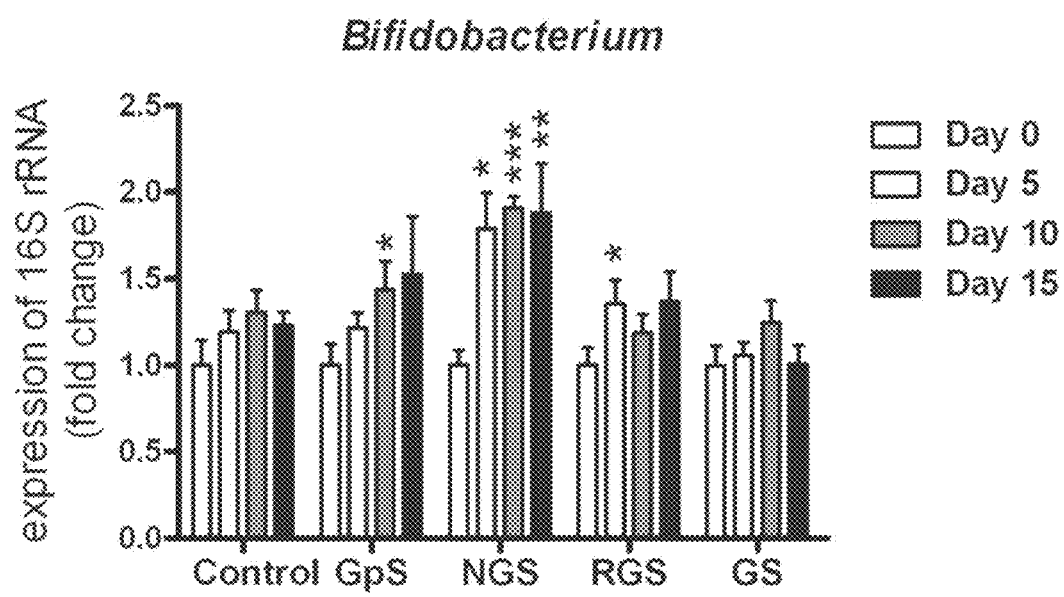
FIG. 5B shows the effect of different plant based saponins including Gp, *notoginseng*, red *ginseng* and *ginseng* saponins and control on *Bifidobacterium* as determined by 16S rRNA PCR.
Figure 5C:
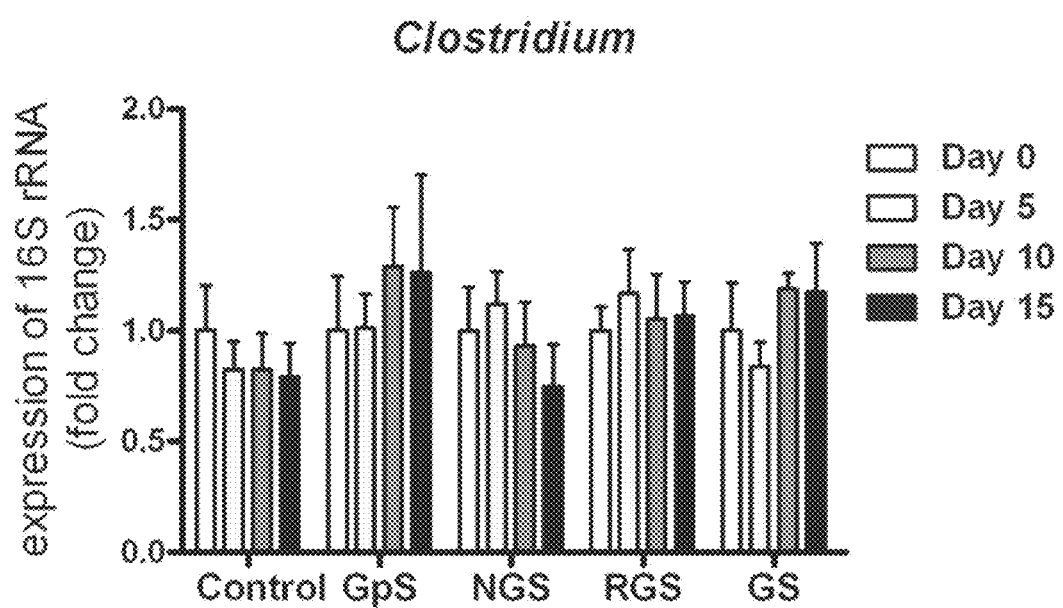
FIG. 5C shows the effect of different plant based saponins including Gp, *notoginseng*, red *ginseng* and *ginseng* saponins and control on *Clostridium* as determined by 16S rRNA PCR.
Figure 5D:
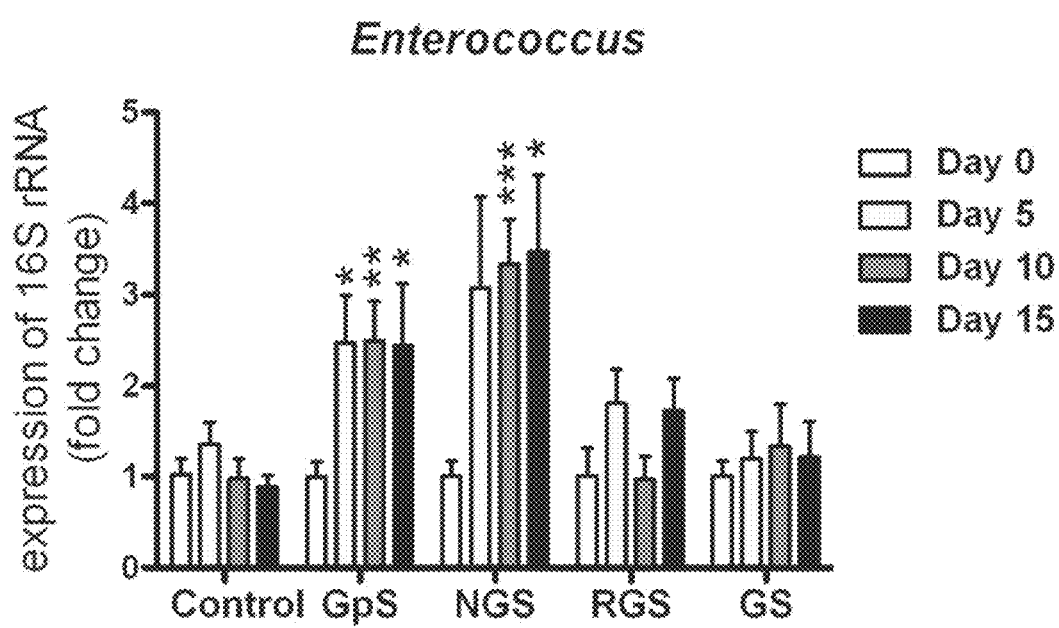
FIG. 5D shows the effect of different plant based saponins including Gp, *notoginseng*, red *ginseng* and *ginseng* saponins and control on *Enterococcus* as determined by 16S rRNA PCR.
Figure 5E:
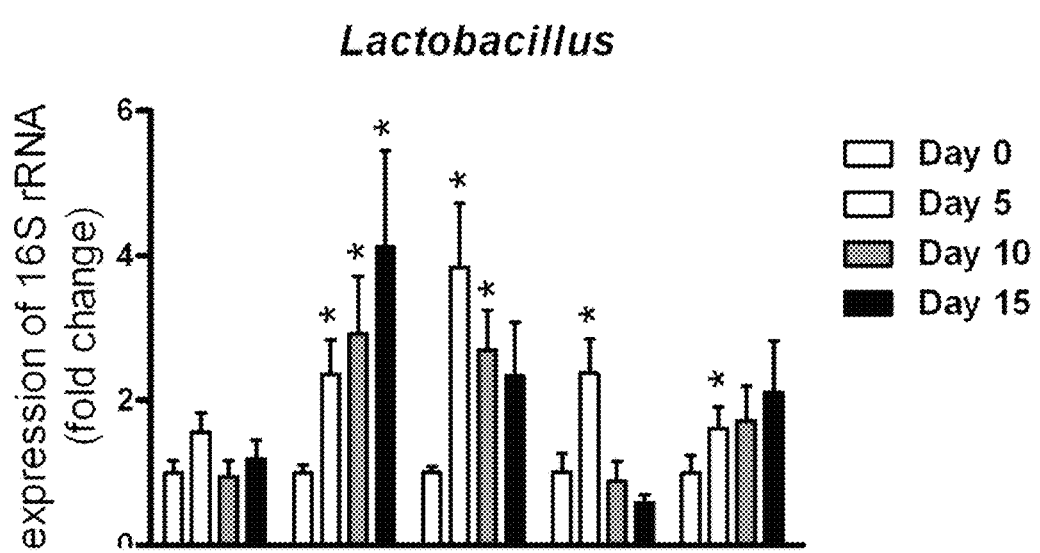
FIG. 5E shows the effect of different plant based saponins including Gp, *notoginseng*, red *ginseng* and *ginseng* saponins and control on *Lactobacillus* as determined by 16S rRNA PCR.

Plant Based Saponins Differentially Affect the Relative Abundance of Bacteroidetes and Firmicutes in Faecal Microbiota We also investigated the major bacterial genera in the feces of plant based saponins treated mice by 16S rRNA PCR. There are two dominant bacterial phyla in the gut ecosystem, Gram-positive Firmicutes (most notably *Clostridium* spp., *Enterococcus* spp. and *Lactobacillus* spp.) and Gram-negative Bacteroidetes (*Bacteroides* spp.). Using PCR primer sets of the 16S rRNA specific for the above bacteria genera as well as *Bifidobacterium* spp., we found that these four plant based saponins all can significantly enhance the level of *Bacteroides* (FIG. 5A); Gp and *notoginseng* saponins showed much more effect on the increase of *Bifidobacterium, Lactobacillus*, as well as *Enterococcus*, and no obvious changes in the level of *Clostridium* in all of the treatment groups (FIG. 5B-5E).

Plant Based Saponins Altered the Fecal Metabolites

Figure 6A:
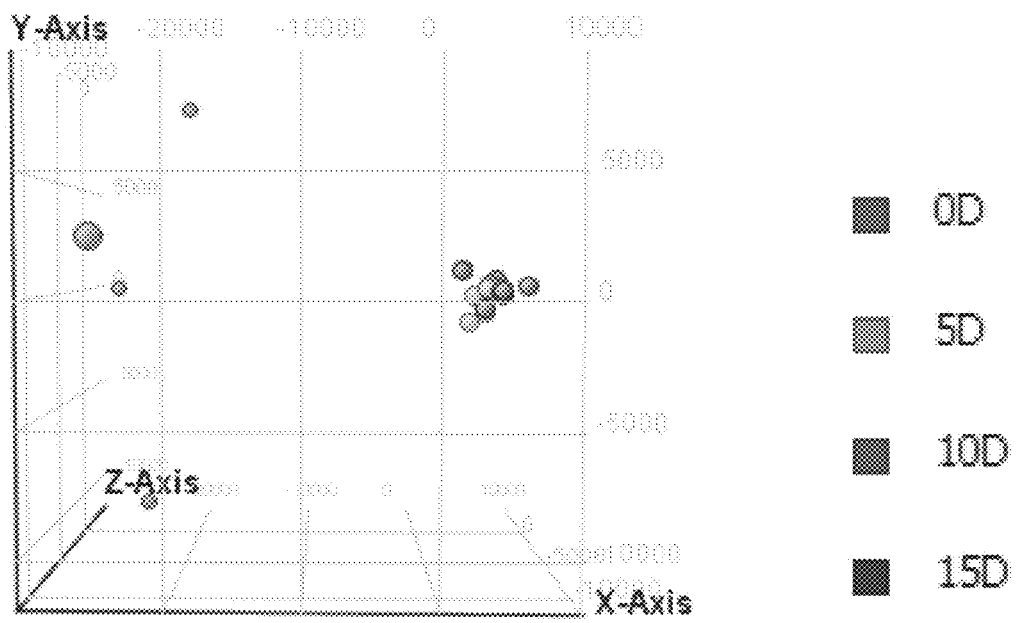
FIG. 6A-6E show the 3D score plot of principal component analysis (PCA) of MS data showing the comparison of fecal metabolic profiles among different treatment groups in ESI positive mode.
Figure 6B:
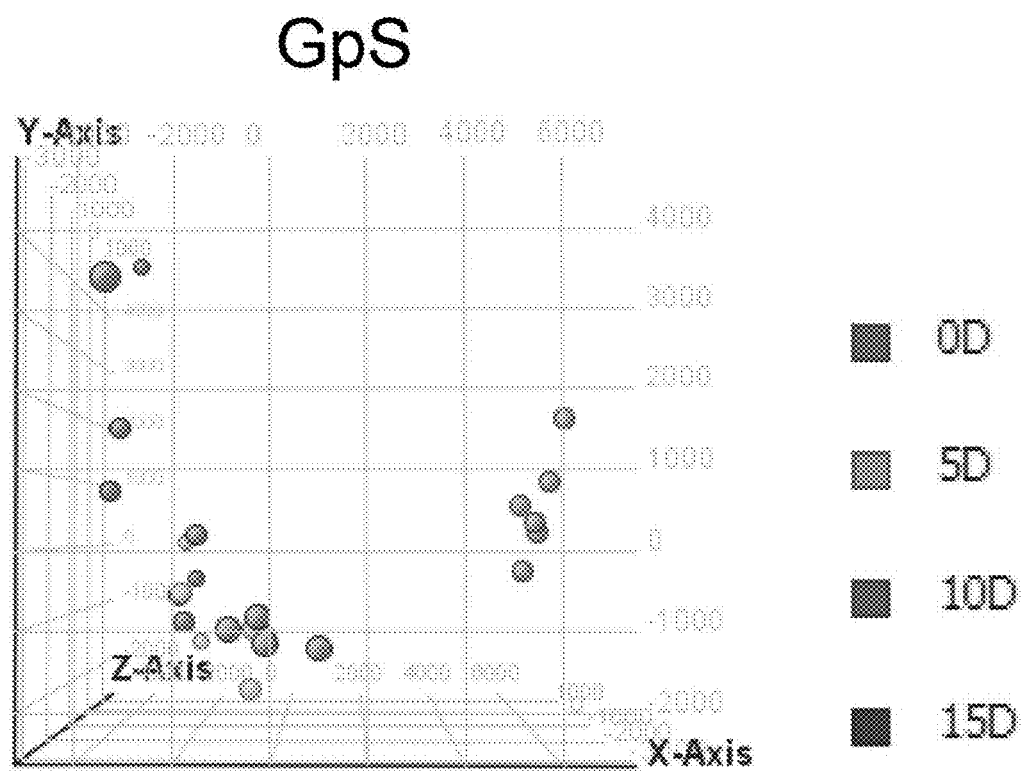
Figure 6C:
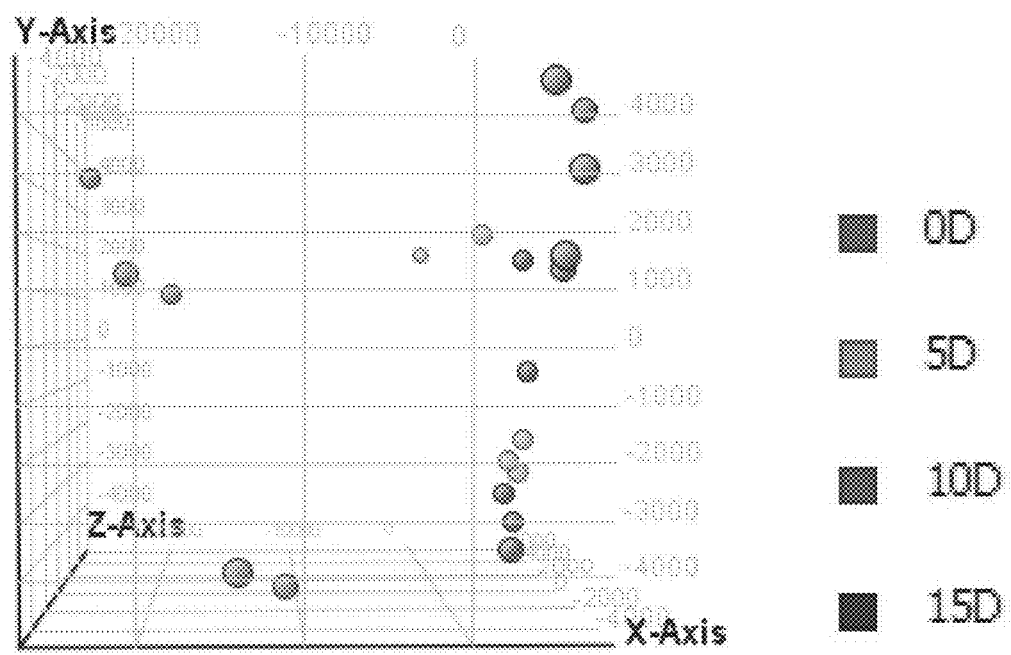
Figure 6D:
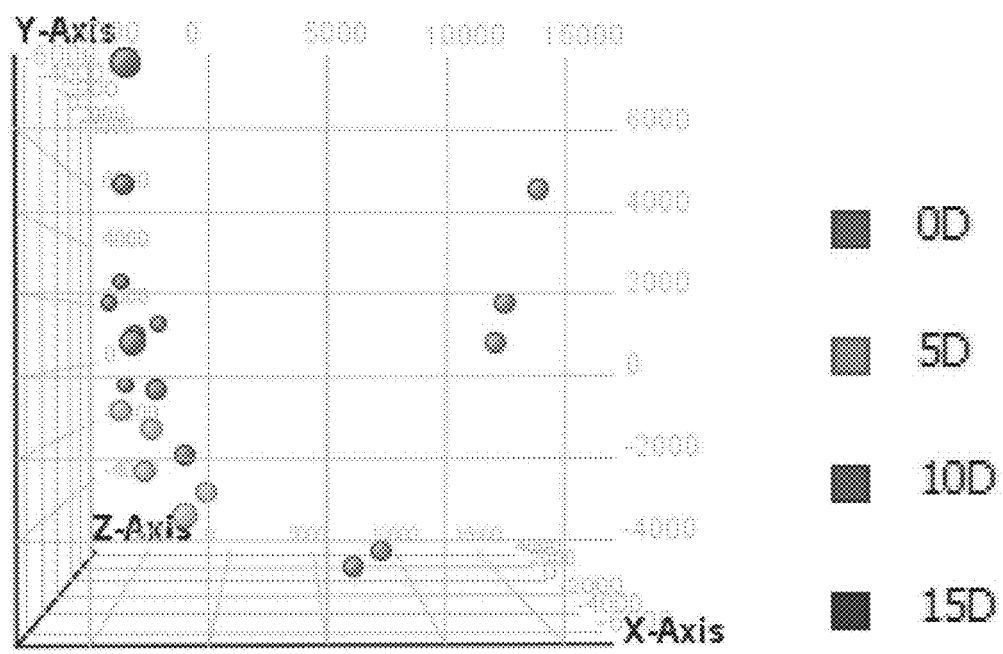
Figure 6E:
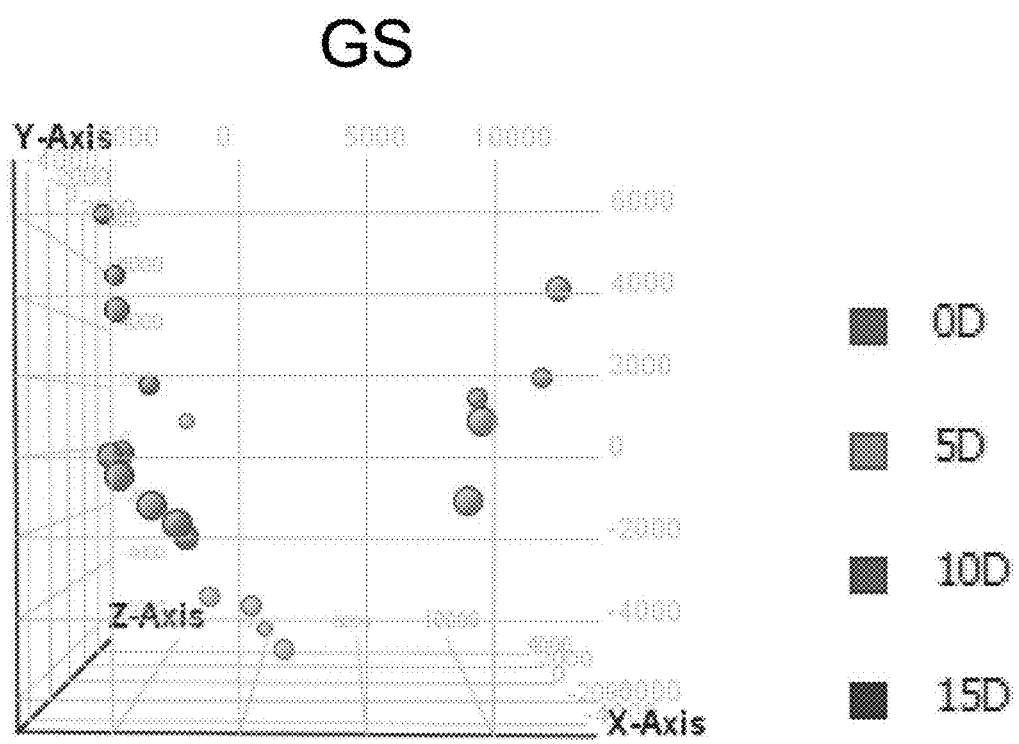
Figure 6F:
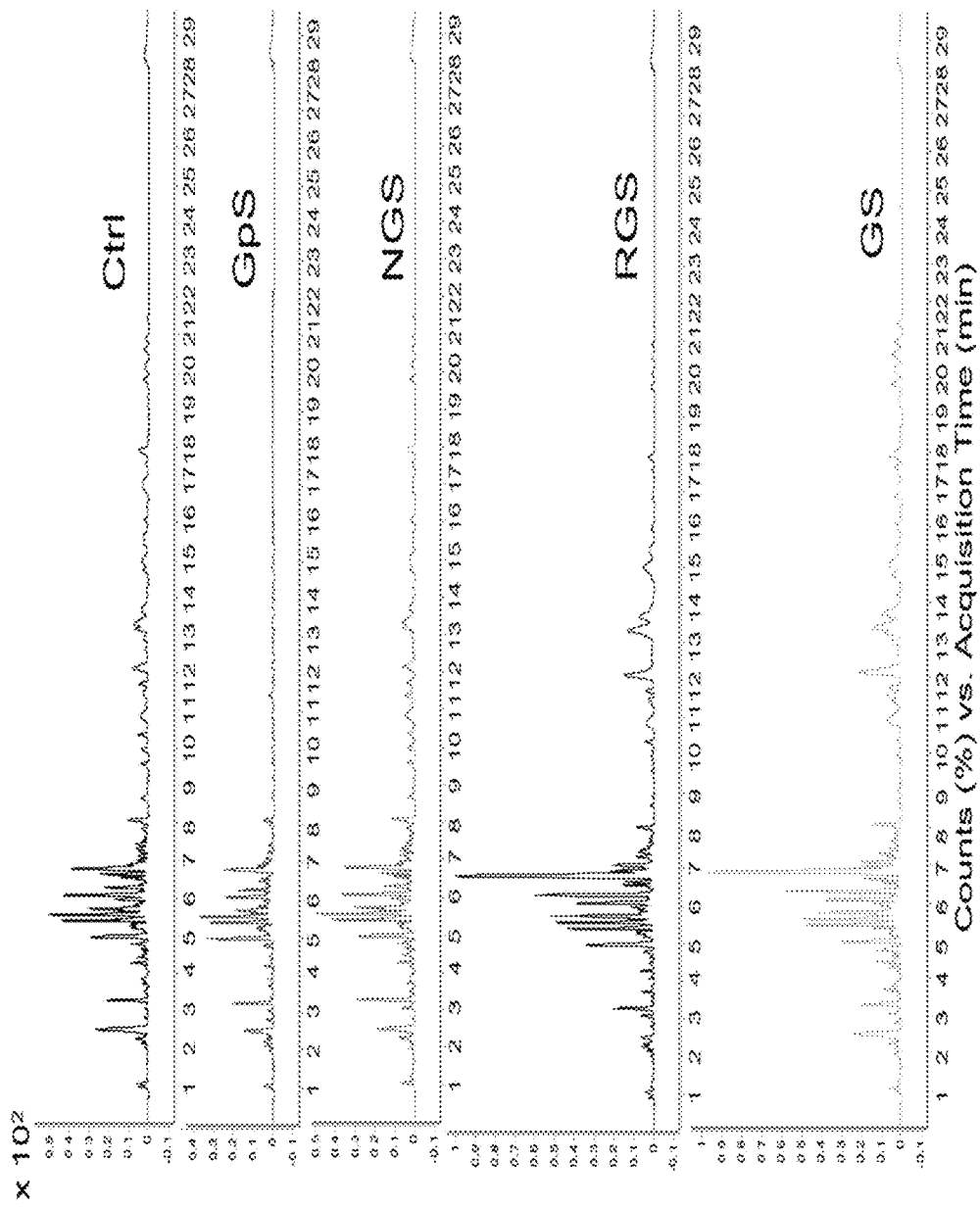
FIG. 6F shows the representative chromatograms of the fecal metabolites among different treatment groups.

To investigate the effect of plant based saponins on the fecal metabolites, an ultrahigh-performance liquid chromatography coupled with Q-TOF mass spectrometry was performed to obtain the fecal metabolic profiles. The acquired data were subjected to principal component analysis by using MPP software. As shown in FIG. 6A-6E, fecal metabolites from control mice at Day 5, Day 10 and Day 15 clustered together. However, plant based saponins-treated mice showed a shift in a time-dependent manner. By comparing base peak chromatogram (FIG. 6F), it seemed that the fecal metabolic profile of *notoginseng* saponins-treated mice was closest to that of the control mice at Day 15, which was consistent with the comparative results of fecal microbiota among different treatment groups. On the other hand, we found red *ginseng* saponins and *ginseng* saponins dramatically altered the fecal metabolites. In contrast to Gp saponins and *notoginseng* saponins, the metabolomic profiles of red *ginseng* and *ginseng* saponins showed a relatively similar pattern although the differences can also be found within the two groups. Then we generated a heatmap (FIG. 6G) by MPP software to further reveal the general pattern of discriminative metabolites between these two groups. Compared to the control group, roughly half of the discriminative metabolites (b & d) showed similar changes in red *ginseng* and *ginseng* saponins treatment groups. Meanwhile, some metabolites showed different degrees of alteration (a) or an opposite alteration (c).

Discussion

Most current drug development is focused on identifying a novel candidate against a specific target, for example, a receptor or an enzyme. However, gut microbial ecosystem has long been underestimated. The gut microbiota is now proposed to be a potential therapeutic strategy, as well as a big treasury for drug development. Traditional Chinese Medicine is believed to modulate homeostasis by balancing Yin and Yang. It is possible that TCM can also restore the balance of the gut microbial system, thus achieving homeostasis and producing therapeutic effects in the host. However, the research on the effect of plant based medicines on gut microflora is very limited, and their mediated interactions between host and microflora have been seldom investigated.

Recent findings have already revealed that saponins can be hydrolysed by intestinal flora. After absorption, the deglycosylated metabolites (aglycones) undergo phase I and/or II metabolism. But how would gut microflora respond to the treatment of plant based saponins? We hypothesize that plant based saponins may change the composition of gut microflora, which in turn alter the metabolites through host-microbe interactions. As the first step towards understanding the role of the microflora in host drug responses, we try to understand the association between gut microflora and plant based saponins.

The chemical profiles, microbial profiles and metabolic profiles in plant based saponins treated mice have been investigated in this example. *Ginseng* (*Panax ginseng* C. A. Meyer, Araliaceae) is a commonly used herbal medicine in many Asian countries. It is also used as a popular dietary supplement in recent years. There are two kinds of commercial *ginseng* products, including *ginseng* and red *ginseng*. Red *ginseng* is produced by steaming raw *ginseng*. *Ginseng* saponins, also termed as ginsenosides, are considered as the main bioactive components of *ginseng*. The pharmacological effects of these ginsenosides have been attributed to the biotransformation mediated by human intestinal bacteria. It has been recognized that red *ginseng* demonstrates more effective in pharmacological activities than *ginseng* in some notable respects. The differences in the bioactivities of *ginseng* and red *ginseng* may due to the changes of chemical constituents that occurred during the steam-processing. With the process of steaming or heating, the polar *ginseng* saponins were decreased, whereas the less polar *ginseng* saponins were increased. On the other hand, as the first example of *ginseng* saponins that found outside of the Araliaceae family, *Gynostemma pentaphyllum* contains more than 100 different gypenosides. Gypenosides are structurally identical to known ginsenosides, such as Rd, Rb1, Rb3, F2, Rc, Rg3, as well as malonylginsenosides Rb1 and Rd, make up around 25% of the total gynosaponins in Gp. The saponins isolated from *notoginseng* include notoginsenosides, ginsenosides and gypenosides. Among these saponins, ginsenoside Rg1, Rb1, Rd, and notoginsenoside R1 are considered to be the main constituents in *Radix Notoginseng*. The differential response of fecal microflora to these four different plant based saponins can be attributed to their different chemical constitutes. Among the four plant based saponins, red *ginseng* and *ginseng* saponins treated mice presented relatively similar profiles of microbial composition but still with distinguished changes in a time dependent manner. It is reasonable to suppose that this phenomenon may be associated with the similarities and differences in the chemical profiles between red *ginseng* and *ginseng*. The fecal metabolic profiles were also similar in red *ginseng* and *ginseng* saponins treated mice. On the other hand, the fecal microflora composition as well as the fecal metabolites in *notoginseng* saponins treated mice was closer to the control mice than other plant based saponins treated mice. All these findings can be a result of different ingested saponins-caused different microbial alteration followed by corresponding changes in the fecal metabolites.

Accumulating evidence indicates that the gut microflora play an important role in the development of obesity, diabetes, cancer, chronic liver disease and inflammatory bowel disease, etc. Among these diseases, the association between the gut microbiota and metabolic disorders has been well studied. Abnormal microbial composition has been identified as a key regulator in metabolic disorders. For examples, a shift in the ratio between Firmicutes and Bacteroidetes has been linked to obesity. It is reasonable to suggest that some diseases will affect the composition of the gut microbiota and regulation in the microbiota can contribute to the treatment of disease. Interestingly, we found that the level of *Bacteroides*, a major genus within the phylum Bacteroidetes, can be increased by the treatment of plant based saponins, including Gp, *notoginseng*, red *ginseng* and *ginseng* saponins. Although this finding was observed in the normal mice, it still provided a hint that plant based saponins can play a role in modulating the gut microbiota in the diseases with a shift ratio of Firmicutes and Bacteroidetes. Current strategies for manipulating the microbiota mainly include probiotics, prebiotics and synbiotics (a combination of probiotics and prebiotics). Some functional food and herbal medicines may also have the similar effects. Here, we found Gp and *notoginseng* saponins showed much more effect on the beneficial bacteria, including *Bifidobacterium* pp. and *Lactobacillus* pp. Prebiotics are known as non-digestible food ingredients that can enhance the growth or activity of beneficial microbes, such as oligofructose and inulin. It seemed that the two plant based saponins, Gp and *notoginseng* saponins, can also function as prebiotics, which will stimulate the growth of helpful bacteria and be conducive to good health. As is known, compound K is more effective than ginsenoside Rb1 in certain aspects such as anti-tumor, anti-inflammatory, and anti-allergic activities. The populations of *Bacteroides* and *Bifidobacterium* have been suggested to potently metabolize ginsenoside Rb1 to compound K. Gut microbial variations play an important role in drug metabolism, efficacy and toxicity in the host and gut microbiota have already been suggested to be taken into consideration in personalized health care in future. Different microbial composition may cause different drug response. Modulation of the gut microbiota may increase the capacity of drug metabolism.

Saponins from *Gynostemma pentaphyllum* (Gp) and the Effects on Tumor

*Gynostemma pentaphyllum* (Gp) is consumed as an herbal tea as well as folk medicine that was well documented in the Compendium of Materia Medica in China dated back to 16th Century for treating various symptoms, including cancer. The main active components in Gp are triterpenoid saponins named gypenosides. Our current finding demonstrated that treatment with Gp total saponins (GpS) exerts anti-cancer effects in xenograft nude mice. In this example, the gut microbial compositions between the normal and the tumor-bearing nude mice are compared, and then how GpS treatment would shape the composition of the gut microflora in both healthy and tumor-bearing animals are investigated.

Materials and Methods

Animals and Treatments

Animal welfare and experimental procedures were performed strictly in accordance with the care and use of laboratory animals. All procedures were approved by the University Ethics Review Committee for animal research. The athymic nude mice (BALB/c-nu/nu) were purchased from Chinese University of Hong Kong and maintained in IVC cages, on a 12-h light/dark cycle. Xenograft was done by injecting 106 R6/GFP-Ras transformed cells into the right flank of each 7-8 weeks old mice. The Rat6/GFP-Ras cell line is a transformed clonal cell line established from a transformed focus derived from R6 rat fibroblast cultures transfected by a GFP-tagged ras oncogene vector in our laboratory. The total saponins (GpS), extracted from the aerial parts of *Gynostemma pentaphyllum*, was purchased from the Hauduo Natural Products (Guangzhou, China). Authentication and chemical profiling of each batch were monitored for qualitative control according to Wu P K, Tai C S, Choi C Y, Tsim W K, Zhou H, Liu X et al., (2011). Chemical and DNA authentication of taste variants of *Gynostemma pentaphyllum* herbal tea. *Food Chemistry* 128: 70-80 (see FIG. 15). GpS was dissolved in 0.5% carboxymethyl cellulose (CMC) at 50 mg/ml. Single dose of GpS at 750 mg/kg or solvent control was given daily by gavage, started the second day after the implant of GFP-Ras cells. For the antibiotic intervention experiment, mice were pretreated with antibiotic (Penicillin/Streptomycin, 10 mg/ml; GIBCO 15140) or saline (control) by gavage (twice/day, total 700 µl/mouse/day) for 5 days, followed by implantation of 106 GFP-Ras transformed cells as described above.

Fecal Samples Collection

For experimental animals, fecal samples were collected (8:00-10:00 a.m.) at day 0 (before xenograft), and 5 days and 10 days after GpS treatment. For the antibiotic intervention, fecal samples were collected one day before and 5 days after antibiotic intervention, then 5 days and 10 days after GpS treatment. All fecal samples were immediately stored at −20° C. and kept for later DNA extraction.

Bacterial Genomic DNA Extraction from Fecal Samples

Total genomic DNA was isolated from fecal samples as described in Kong J, Li X B, Wu C F (2006). A molecular Biological Method for Screening and Evaluating the Traditional Chinese Medicine Used in Pi-deficiency Therapy Involving Intestinal microflora. *Asian Journal of Traditional Medicines* 1: 1-6 and McCracken V J, Simpson J M, Mackie R I, Gaskins H R (2001). Molecular ecological analysis of dietary and antibiotic-induced alterations of the mouse intestinal microbiota. *The Journal of nutrition* 131: 1862-1870, with slight modification. 0.1 g of fecal samples were vortexed in 4 ml sterile PBS (pH7.4) for 5 min, then centrifuged at 40×g for 8 min to collect the upper phase containing the bacteria. After repeating this procedure once, the supernatant was centrifuged at 2000×g for 8 min. The supernatant was discarded and the bacterial pellets were then washed twice with PBS for DNA isolation. DNA concentration was determined by NanoDrop 1000 spectrophotometry.

ERIC (Enterobacterial Repetitive Intergenic Consensus)-PCR

ERIC sequences are non-coding, highly conserved intergenic repeated sequences that reside in the genome of various bacterial species in addition to enterobacteria. ERIC-PCR was used to profile the gut microbiome using fecal genomic DNA as the template and a pair of ERIC specific primer sequences: ERIC 1R (SEQ ID No. 1) (5'-ATGTAAGCTCCTGGGGATTCAC-3') and ERIC 2 (SEQ ID No. 2) (5'-AAGTAAGTGACTGGGGTGAGCG-3'). The PCR reaction was optimized and determined with orthogonal array design. A 25 µl reaction mixture containing 5 µl 5×PCR reaction buffer, 250 µM dNTP, 2 mM Mg2+, 0.4 µM primers, 1.5 unit Hotstart Taq polymerase, and 50 ng fecal genomic DNA. PCR was performed under the following conditions: 94'IC for 5 min, followed by 35 cycles of 95'IC for 50 seconds, 49'IC for 30 seconds, 46'IC for 30 seconds, and 72'IC for 3 min; and then a final extension at 72'IC for 9 min. 10 μl of each PCR product was loaded into a 2% (w/v) agarose gel containing 0.5 μg/ml ethidium bromide and run for 40 min at 100 V. A DNA ladder (0.1-10.0 kb) was used as DNA size marker (NEB, N3200). Agarose gels were photographed using a Gel Doc™ XR+ System.

Data Analysis of ERIC-PCR Fingerprints

Partial least squares discriminant analysis (PLS-DA) was performed to analyze the dynamic changes of microflora composition of experimental groups. Based on the distance and the intensity of each DNA bands, the banding patterns of ERIC-PCR products separated on the gel were digitized by Image Lab 3.0 system (Bio-Rad) and performed PLS-DA analysis using SIMCA-P 12.0 tool. The Correlation coefficient was calculated and used to assess the correlation between two samples using the CORREL function in Microsoft Office Excel 2003.

16S rRNA Pyrosequencing of Fecal DNA Samples

PCR was performed for each sample in a final reaction volume of 25 ul comprising 0.1-2 μl DNA, 300 nM of each primer (563F and 1064R of 16S rRNA gene), 2.5 μl of 10× Expand High Fidelity buffer (Roche), 200 μM PCR Grade Nucleotide Mix, and 2.6 units of Expand High Fidelity Enzyme mix (Roche) with the reaction volume adjusted using milli-Q H2O. The forward primer of each reaction had a unique 11-nt barcode to enable demultiplexing of reads post-sequencing. The PCR conditions were conducted with an initial denaturation at 94° C. for 2 min followed by 35 cycles of 94° C. for 15 s, 58° C. for 20 s, and 72° C. for 1 min. Finally, an elongation reaction for 7 min at 72° C. was performed followed by cooling at 4° C. until collection. Amplicon sizes were confirmed on 1% agarose gel and purified with PureLink Quick Gel Extraction Kit (Life Technologies). Amplicon libraries were quantified with Quant-iT PicoGreen dsDNA Assay Kit (Life Technologies) using FLUOstar OPTIMA F fluorometer (BMG Labtech GmbH, Offenburg, Germany) and visually assessed using the FlashGel System (Lonza Group Ltd., Basel, Switzerland). Emulsion-PCR and pyrosequencing using titanium chemistry on the GS Junior System (454 Life Sciences Corp., Branford, Conn., USA) was carried out as detailed by the manufacturer.

Denoising and Analysis of Pyrosequencing Data

Pyrosequencing data were processed and analyzed using the Quantitative Insights Into Microbial Ecology software (QIIME version 1.5.0), available at http://qiime.sourceforge.net/. Denoising of raw sequences was performed to reduce the amount of erroneous operational taxonomic units (OTUs). Sequences were removed if they were <200 or >1000 nucleotides, with quality score below 25, contained primer mismatches or uncorrectable barcodes, or had a homopolymer run or ambiguous bases in excess of 6. The denoised sequences were assigned to OTUs with a 97% identity threshold, and the most abundant sequence from each OTU was selected as a representative sequence showing up in that OTU. Taxonomy was assigned to OTUs by using the Basic Local Alignment Search Tool (BLAST) for each representative sequence. For tree-based analyses, PyNAST was used to align these representative sequences of each OTU, and FastTree algorithm was used to build a phylogenetic tree. The differences in overall community composition between compared samples were determined using the unweighted UniFrac metric. Linear discriminant analysis (LDA) effect size (LEfSe) method was used to evaluate the key phylotypes responsible for the observed differences between microbial communities. OTU network was generated by QIIME and visualized with Cytoscape. Shannon-Weiner diversity index (H') was used to evaluate the diversity of microbial communities. Venn diagram was used to figure out the unique and shared taxa between microbial communities.

Statistical Analysis

The data obtained are presented as means±SEM, and statistical comparisons were performed using one-way ANOVA followed by Student's t-test at P values of <0.01 (**) or <0.05(*).

Results

A Significant Shift in the Gut Microbiota of the Xenograft Animals

Figure 7A:
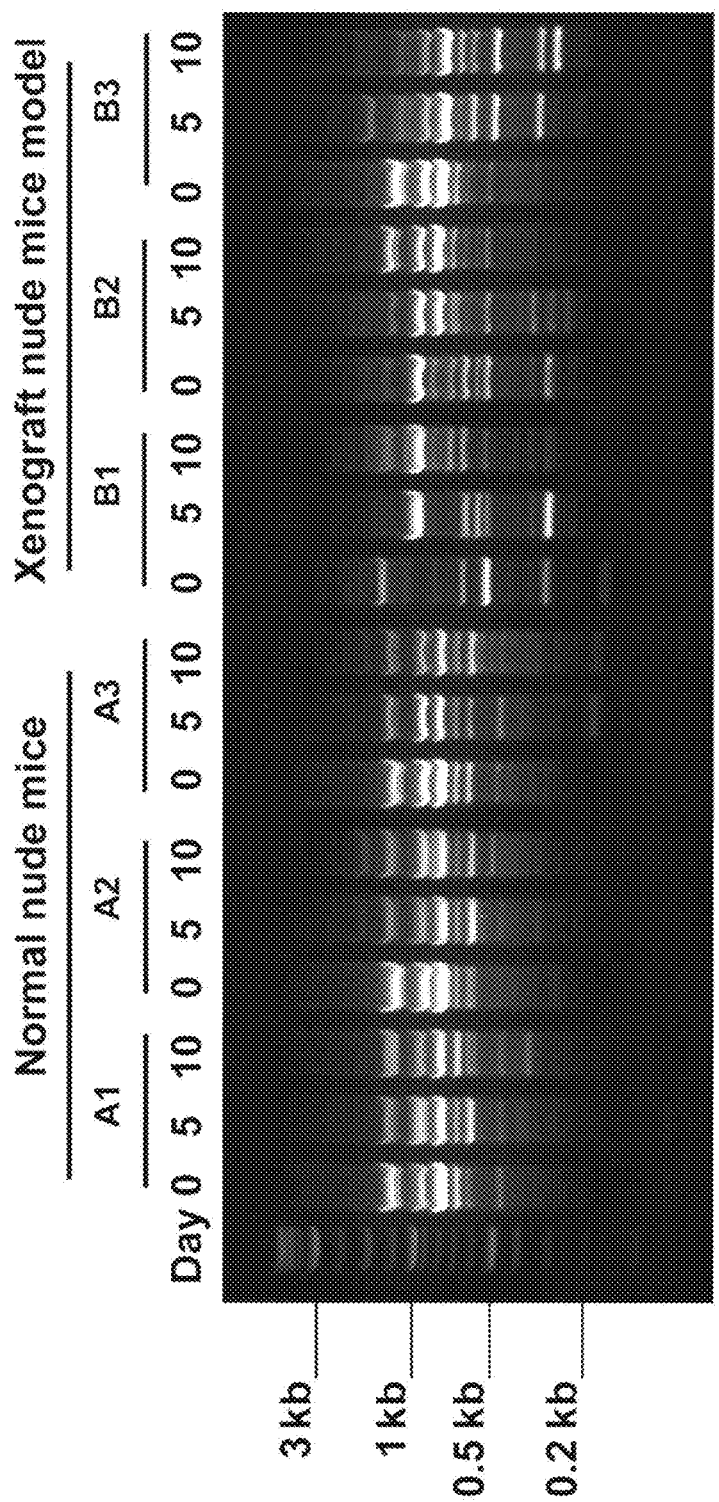
FIG. 7A shows the representative ERIC-PCR DNA fingerprints of the fecal microflora of individual normal and xenograft nude mice. Fecal samples were collected before xenograft (Day 0), and 5 & 10 days upon saline or tumor cells injection; A1-3: three control mice; B1-3: three xenograft nude mice.
Figure 7B:
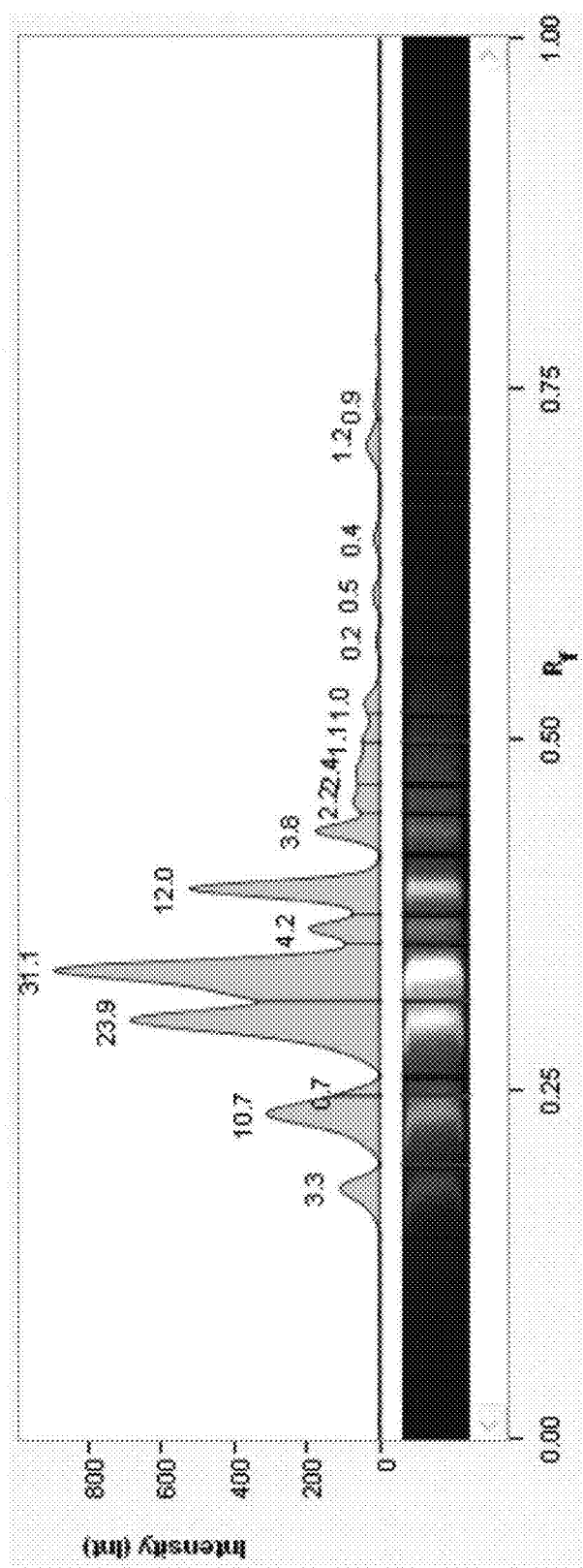
FIGS. 7B and 7C show the digitization of ERIC-PCR fingerprints.
Figure 7C:
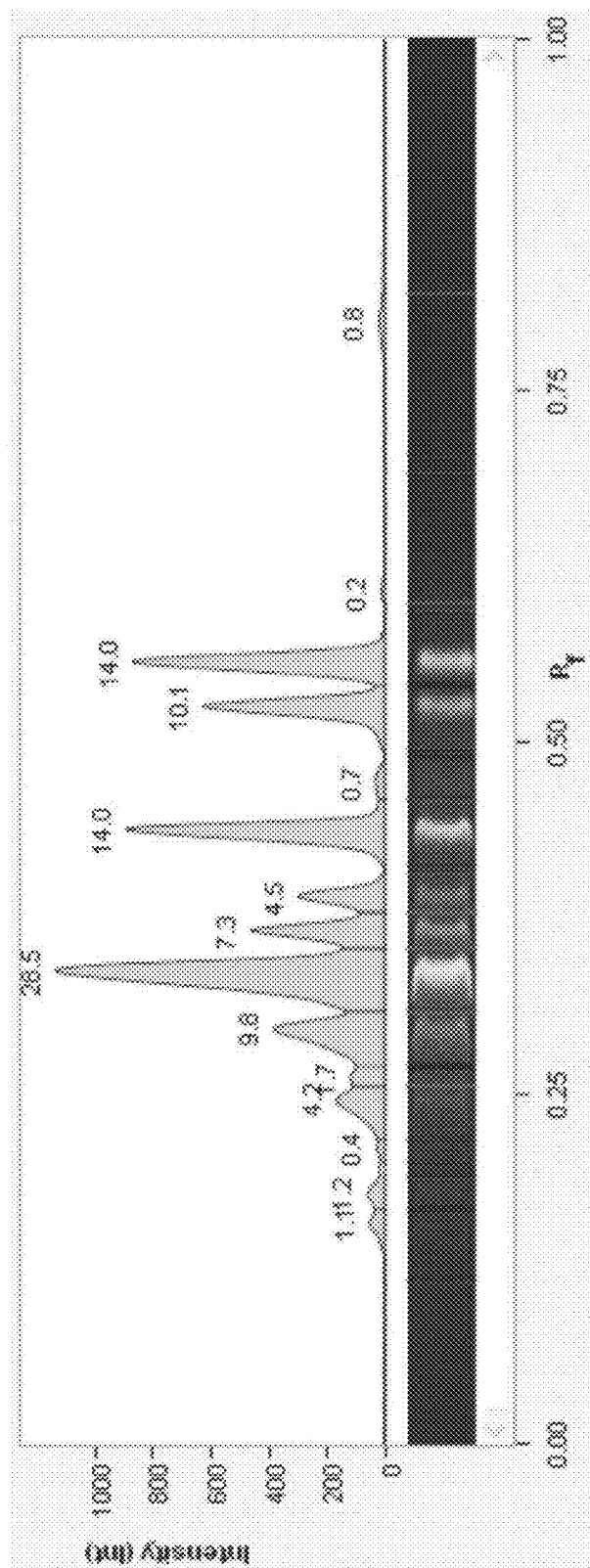
Figure 7D:
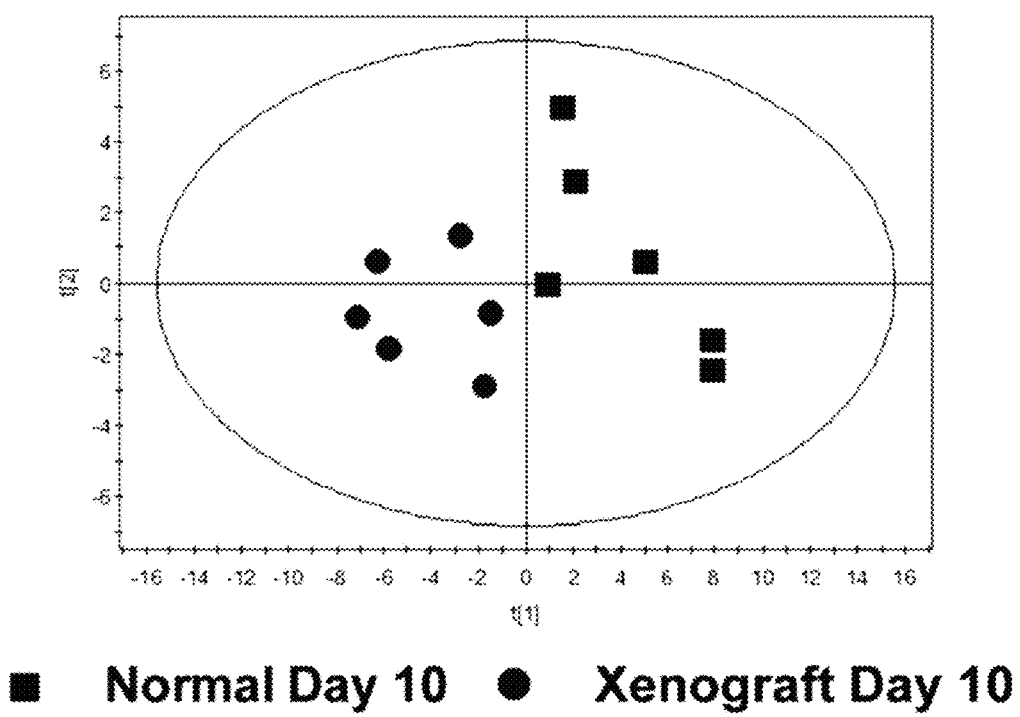
FIG. 7D shows the PLS-DA plot of ERIC-PCR data from fecal microflora of normal and xenograft nude mice at Day 10. Box: the normal nude mice; Dot: the xenograft nude mice.
Figure 7E:
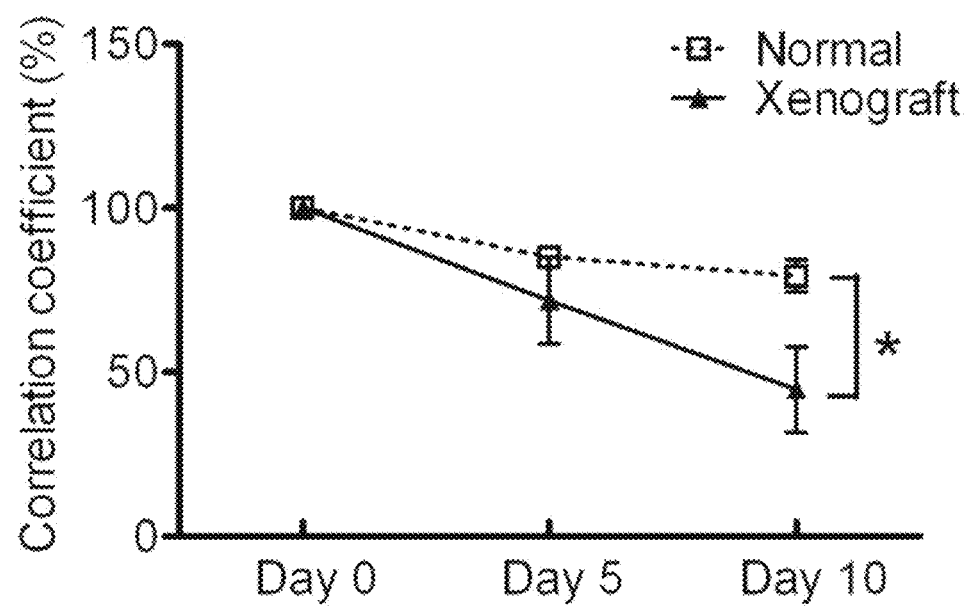
FIG. 7E shows the correlation coefficients of fecal microflora of normal and xenograft nude mice.

Microflora of healthy individual contains a balanced composition. In the diseased state of the host, there is a shift in the composition of the microflora, such as a reduction in the symbionts or an increase in the pathobionts. To investigate whether tumor xenograft would induce shift in gut microbiota, nude mice with and without xenograft were used as the animal models. Fecal samples were collected from the experimental animals for microbial DNA preparation and used for ERIC-PCR analysis of fecal microflora profile. As shown in FIG. 7A, similar banding patterns were observed among individual mice from the normal group throughout the experimental period, while obvious alterations in banding pattern were appeared among the xenograft-mice. The banding patterns were then digitized by Image Lab 3.0 system (Bio-Rad) and performed PLS-DA analysis (FIGS. 7B & 7C). The fecal microbiota of the normal and the tumor bearing mice were clearly separated in the PLS-DA plot (FIG. 7D) and in the correlation coefficient plot for divergent analysis (FIG. 7E). These findings suggest that the microflora likely maintained different patterns between normal and tumor-bearing mice. Tumor growth can induce the shift in the microflora composition.

GpS Inhibited Tumor Growth and Concurrently Regulated Microflora Composition

Figure 8A:
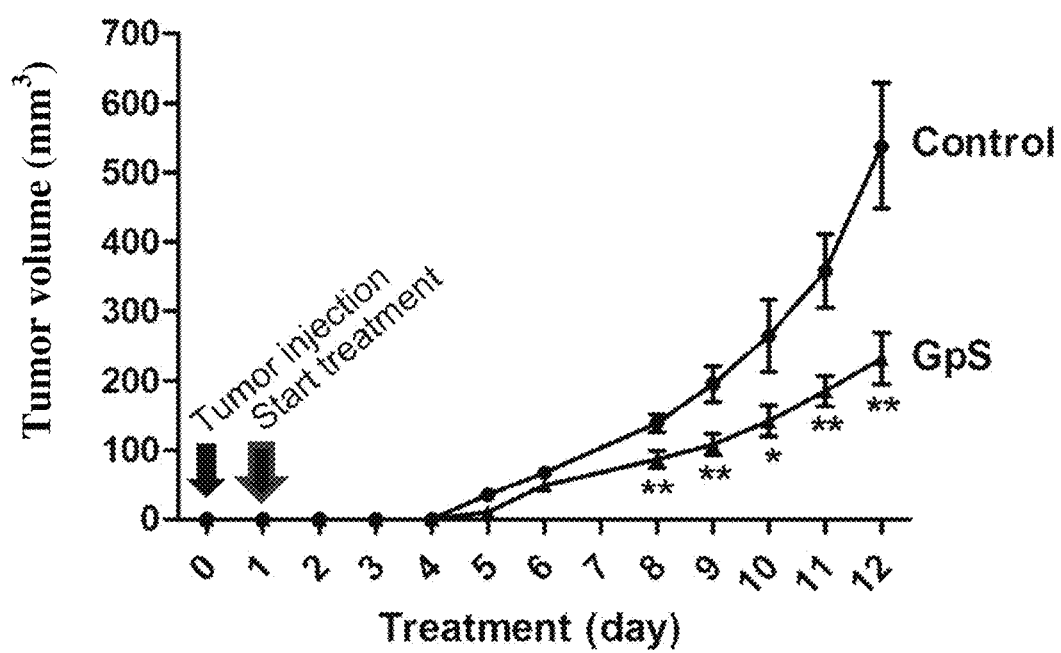
FIG. 8A shows the effect of GpS on tumor growth in nude mice showing the tumor volume.
Figure 8B:
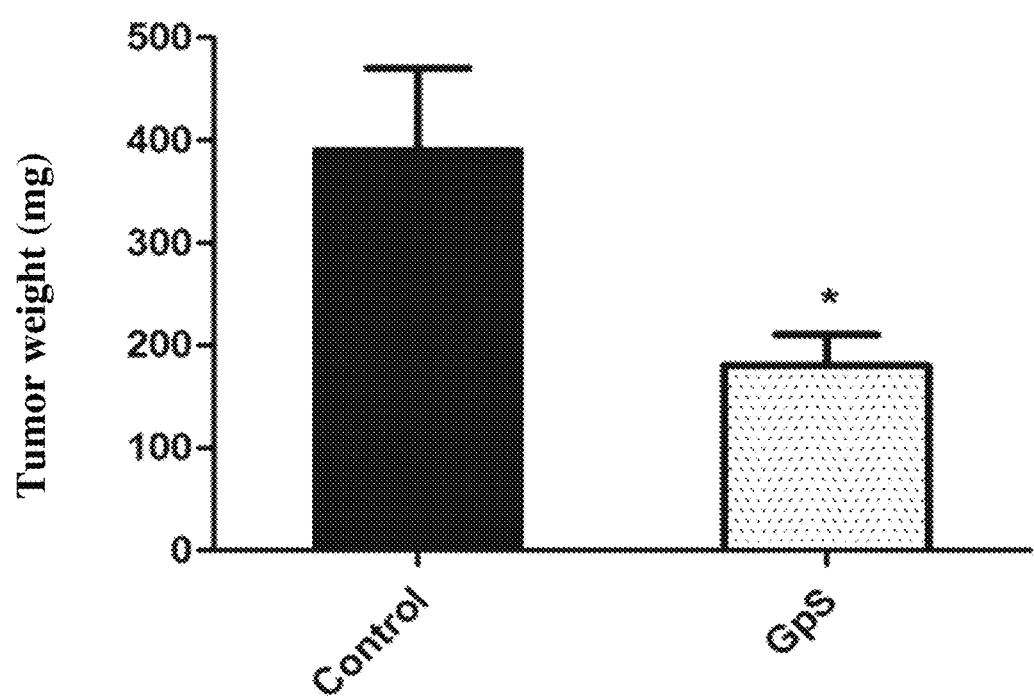
FIG. 8B shows the effect of GpS on tumor growth in nude mice showing the tumor weight.
Figure 8C:
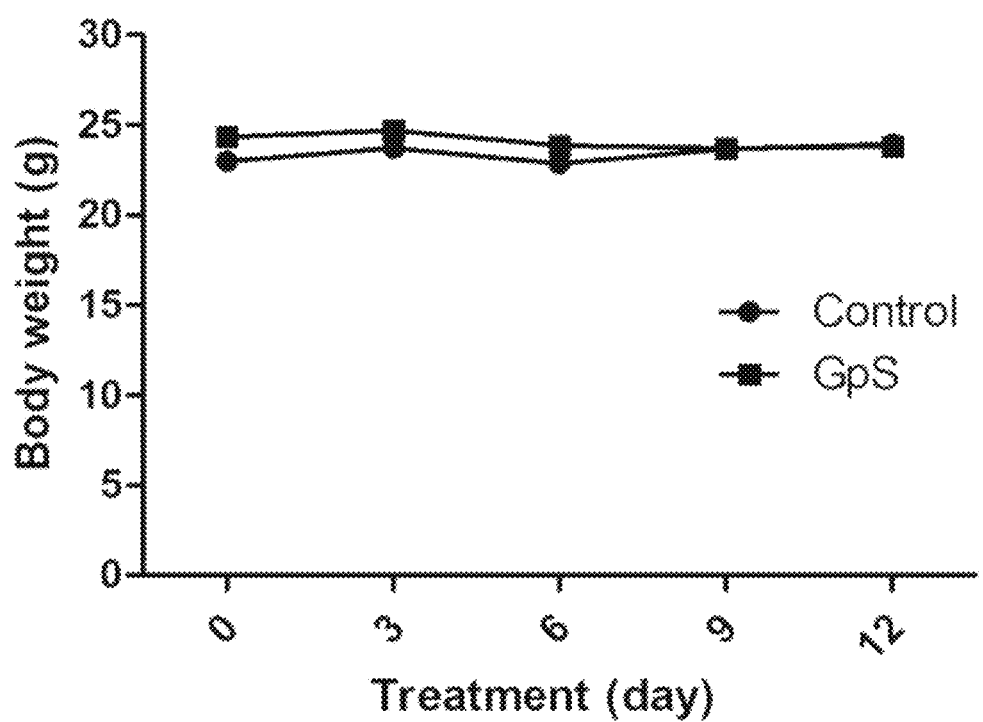
FIG. 8C shows the effect of GpS on tumor growth in nude mice showing the body weight.

To test the effect of GpS on tumor growth, GFP-Ras cells (106) were subcutaneously injected into the right flank of each 6-8 weeks old nude mice. Tumor was measured with an electronic caliper in a blinded manner daily and tumor volume is calculated using the formula, (length×width2)/2. The control mice were injected with same volume of PBS solution. Single daily dose of GpS at 750 mg/kg or vehicle (0.5% CMC) by gavage started the second day after the implant of GFP-Ras cells and carried out for 12 days. The tumor volume and tumor weight of GpS-treated group reduced by 60% and 50% compared to the untreated group (FIGS. 8A & 8B). No weight loss in the treatment group was observed (FIG. 8C).

Figure 9A:
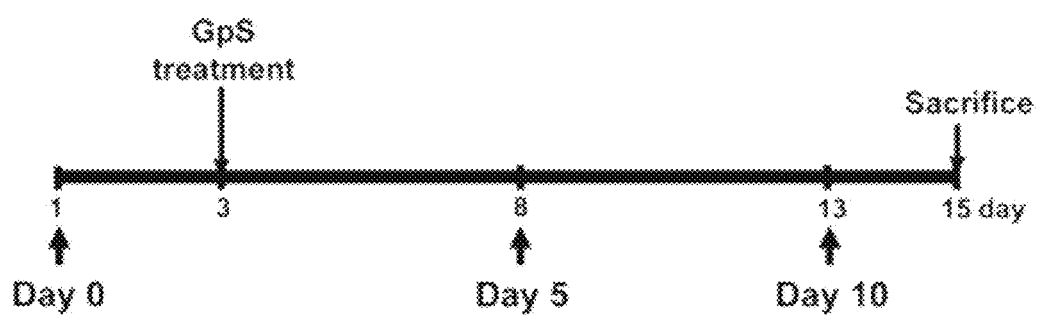
FIG. 9A shows a schematic diagram of experimental design for the effect of GpS on the composition of fecal microflora in normal nude mice.
Figure 9B:
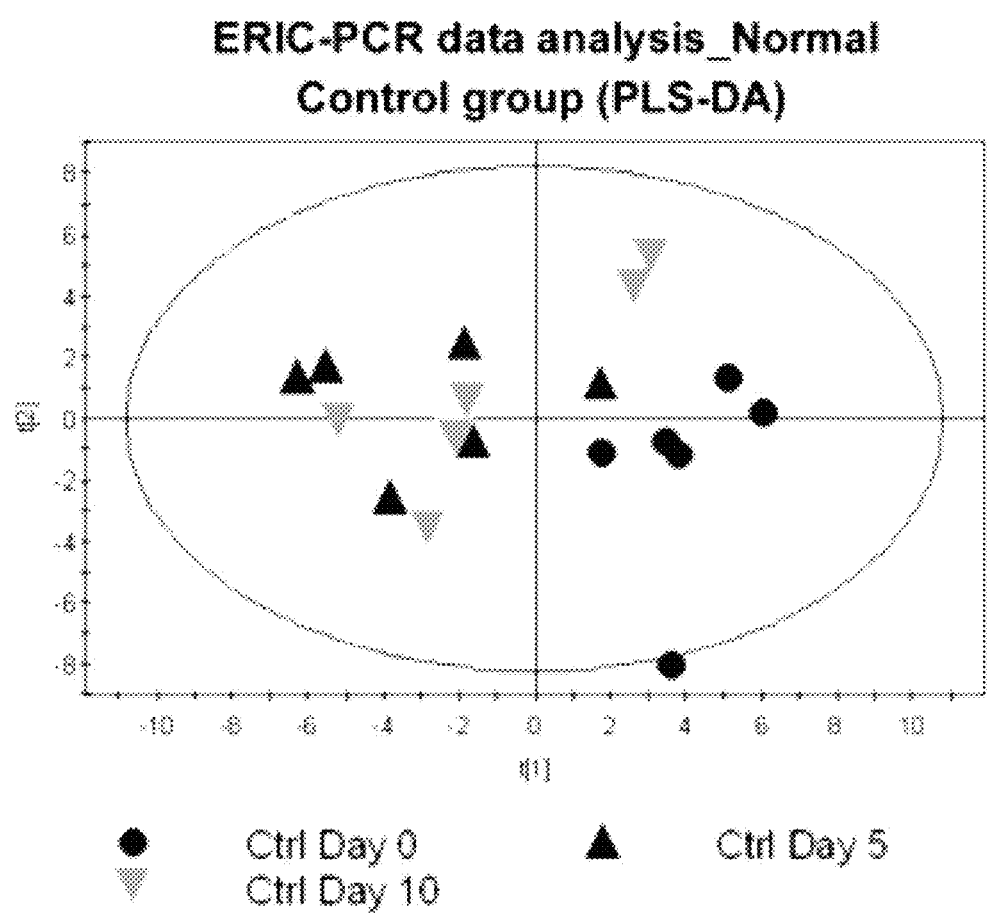
FIG. 9B shows the PLS-DA score plots of ERIC-PCR data of the control group in normal nude mice (n=6)
Figure 9C:
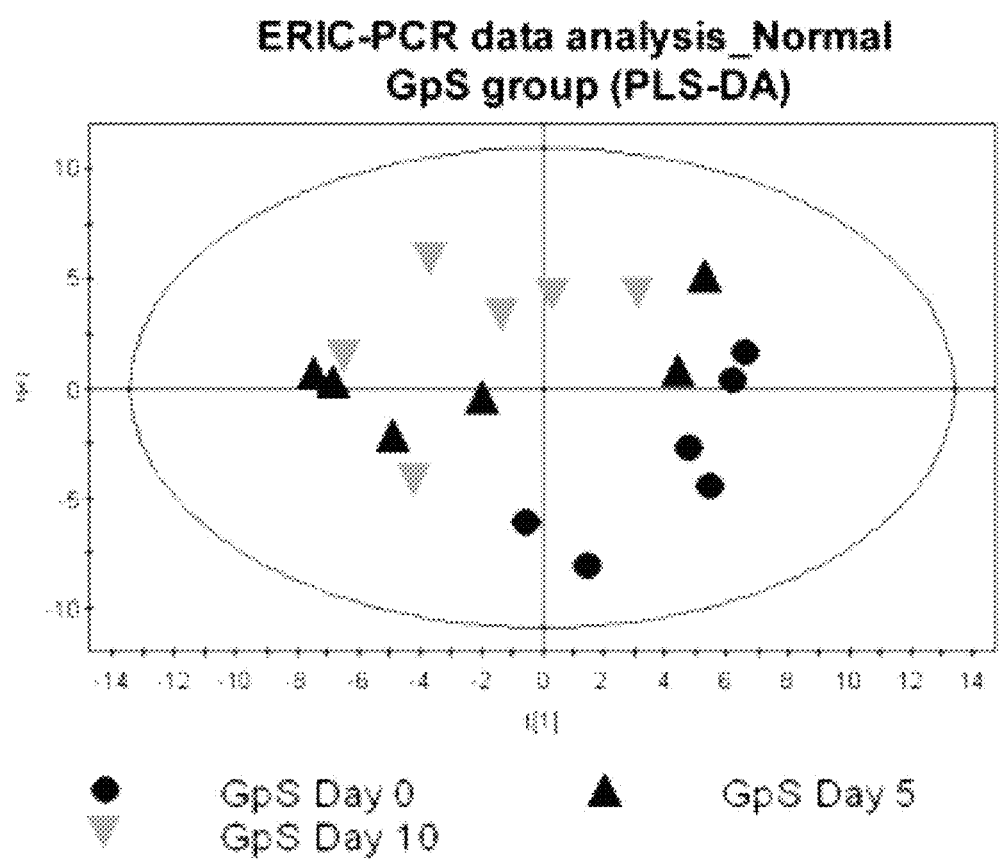
FIG. 9C shows the PLS-DA score plots of ERIC-PCR data of the GpS treatment group in normal nude mice (n=6)
Figure 9D:
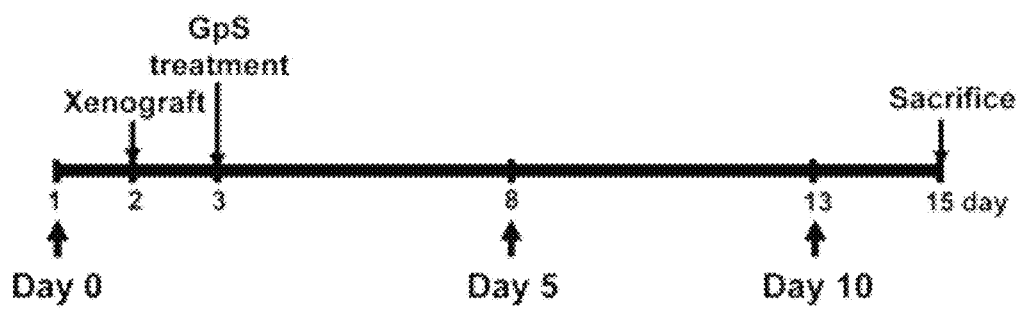
FIG. 9D shows a schematic diagram of experimental design for the effect of GpS on the composition of fecal microflora in xenograft nude mice.
Figure 9E:
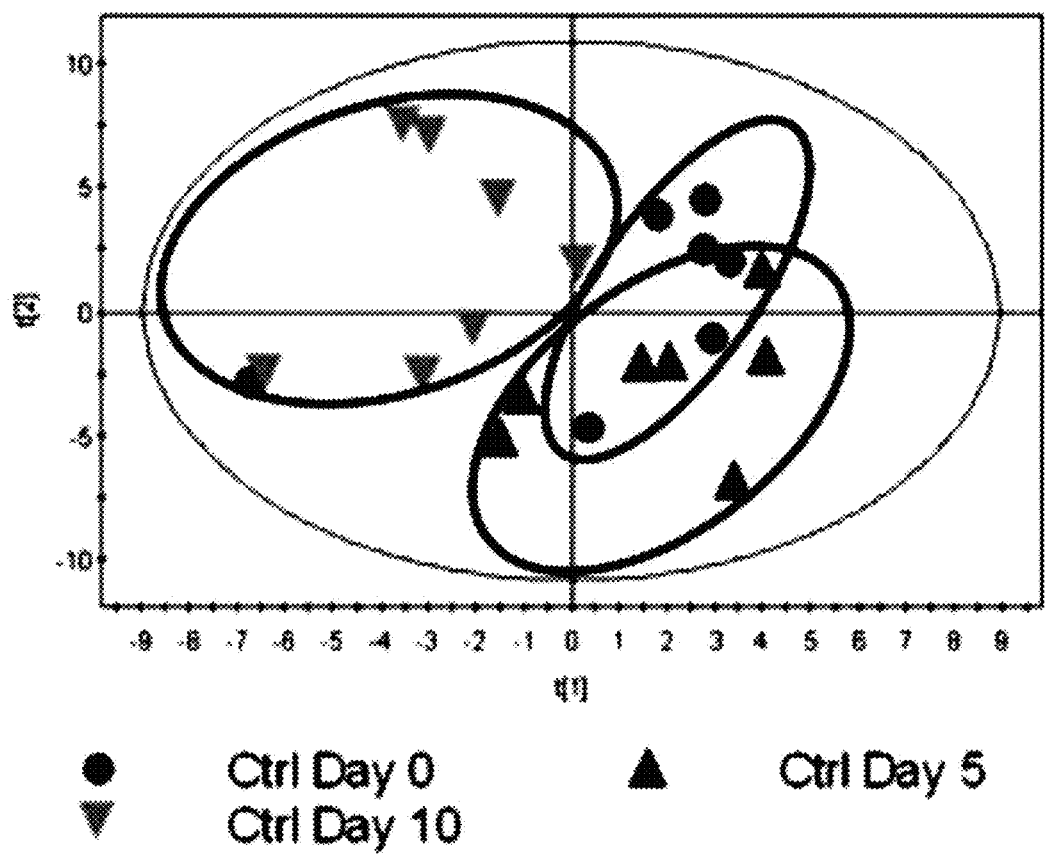
FIG. 9E shows a PLS-DA score plots of ERIC-PCR data of the control group in xenograft nude mice (n=7)
Figure 9F:
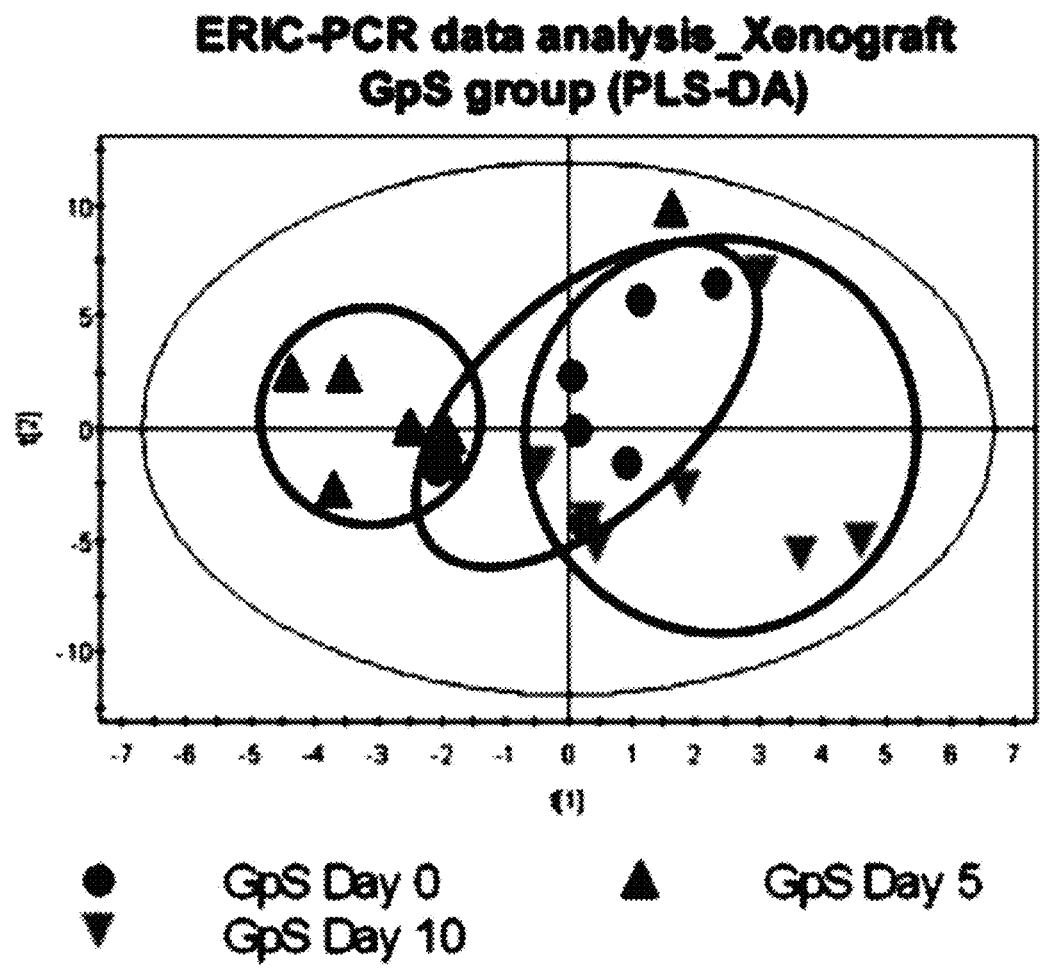
FIG. 9F shows a PLS-DA score plots of ERIC-PCR data of the GpS treatment group in xenograft nude mice (n=7)
Figure 9G:
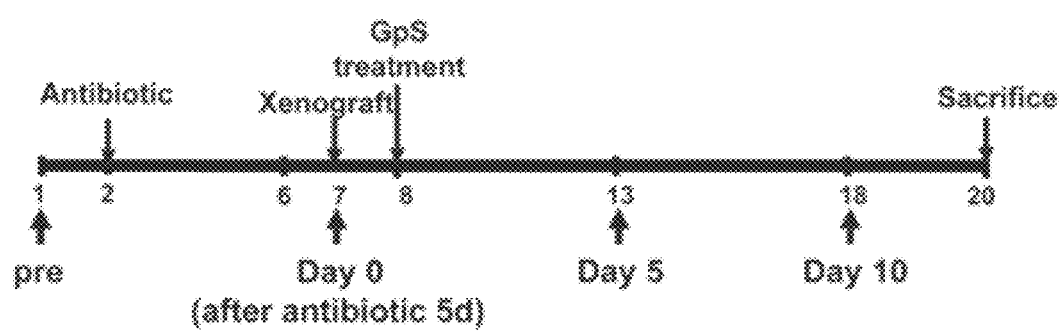
FIG. 9G shows a schematic diagram of experimental design for comparing composition of fecal microflora between the control and GpS groups in xenograft nude mice with antibiotic intervention.
Figure 9H:
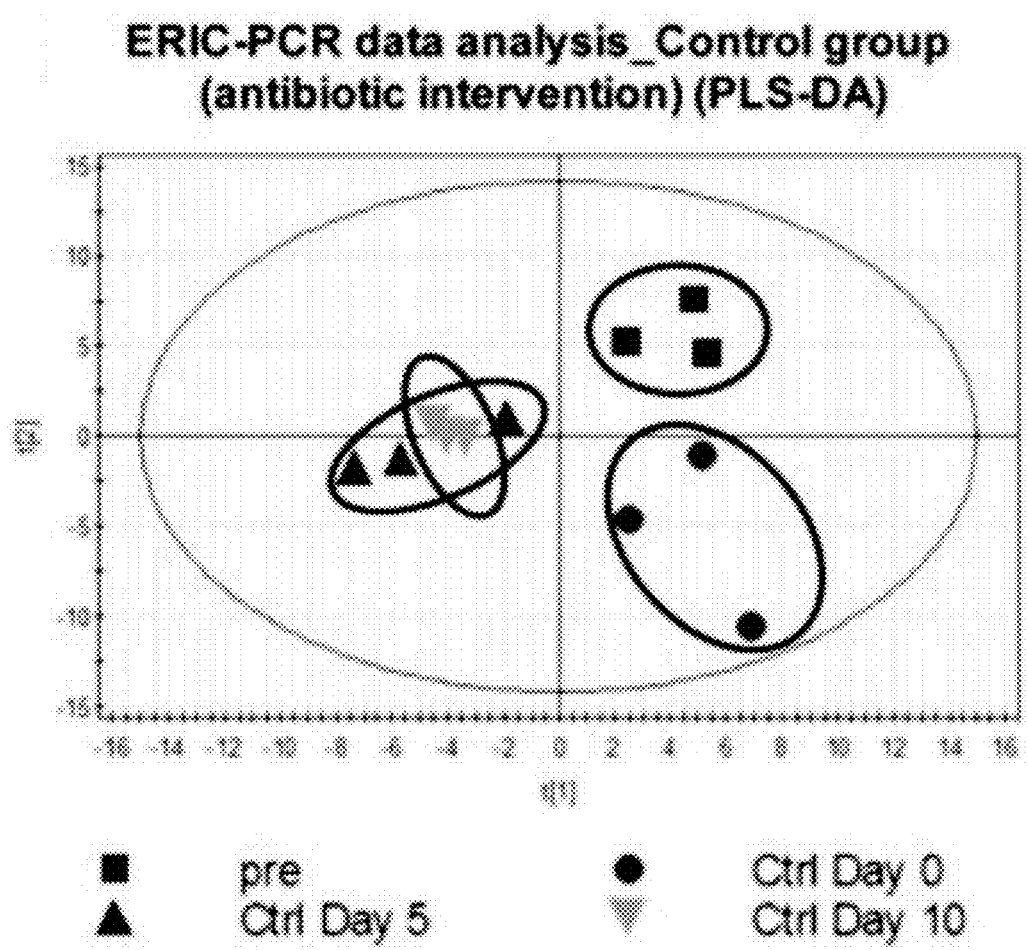
FIG. 9H shows the PLS-DA score plots of ERIC-PCR data of the control group in xenograft nude mice with antibiotic intervention (n=3)

To investigate how GpS would modulate the gut microflora in the normal and xenograft nude mice, fecal samples were collected from four experimental groups, i.e. the normal group with and without GpS treatment; and the xenograft group with and without GpS treatment at Day 0, Day 5 and Day 10 as described in the treatment schemes (FIGS. 9A & 9D). Genomic DNA isolated from the fecal samples were analyzed by ERIC-PCR. The PLS-DA plots, based on the ERIC-PCR banding patterns, displayed a rather random modification of microbiota between Day 0 vs Day 5/10 time points in both GpS-treated or control normal mice (FIGS. 9B & 9C). In the xenograft mice, on the other hand, fecal microbiota from Day 0, Day 5 and Day 10 groups seems to clustering together within each group, yet drifting apart from Day 0 time point (FIG. 9E). Interestingly, upon GpS treatment, the microbiota community of Day 10 group was drifting back to the non-tumor stage and aligned mostly with Day 0 microbiota (FIG. 9F), which was not observed in the non-treatment groups (FIG. 9E). Such shift of microbiota composition induced by GpS was also observed in xenograft nude mice treated with antibiotic prior to tumor injection and GpS treatment (FIG. 9H vs 9I). Pretreatment with antibiotic helped to synchronize, but did not alter the gut microflora in the experimental mice.

16S Pyrosequencing Further Revealed the Different Microbial Communities Between the Normal and Xenograft Nude Mice To obtain more comprehensive information of the gut microbial communities in nude mice, we performed 16S rRNA pyrosequencing on the fecal DNA obtained from the Day 10 time point of normal and xenograft nude mice, with and without GpS treatment described in the experiment showed in FIG. 9A-9I (3 fecal samples per group, a total of 12 samples). A total of 147128 reads that passed quality control were produced in this study, with an average of 12261 sequences per sample. 399 distinct operational taxonomic units (OTUs) were determined after denoising using QIIME method according to Caporaso J G, Kuczynski J, Stombaugh J, Bittinger K, Bushman F D, Costello E K et al., (2010). QIIME allows analysis of high-throughput community sequencing data. *Nature methods* 7: 335-336.

Figure 10A:
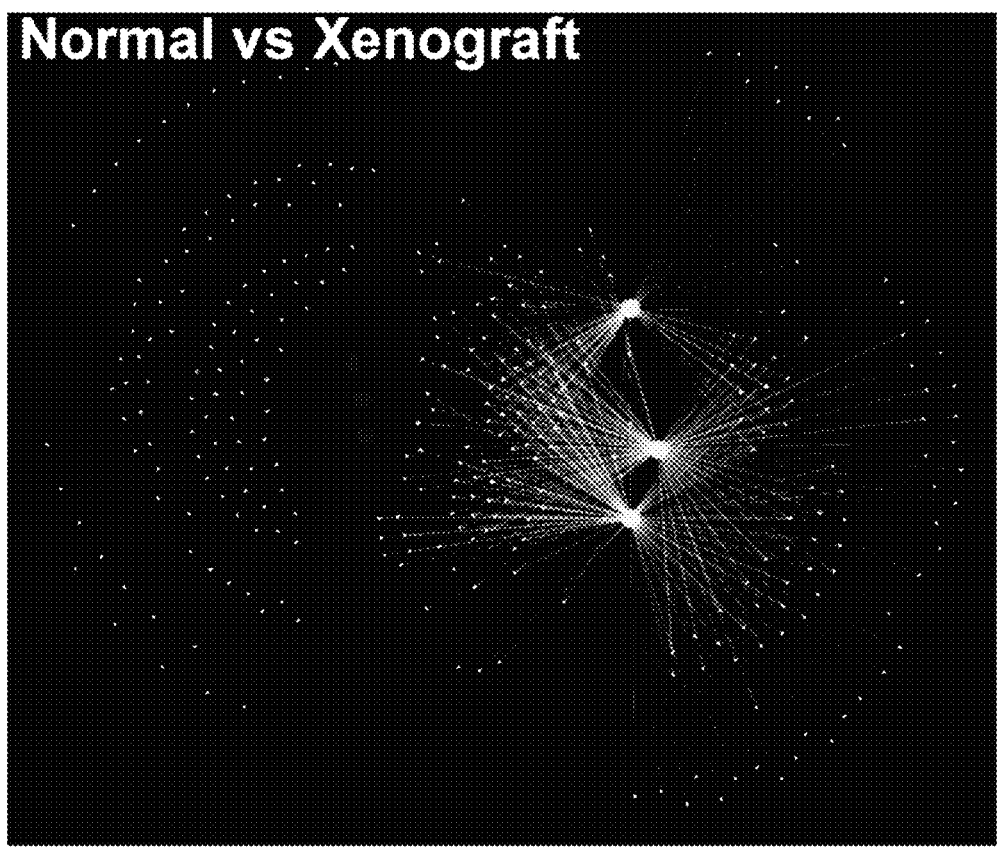
FIG. 10A shows the OTU network of fecal samples from normal and xenograft nude mice.
Figure 10B:
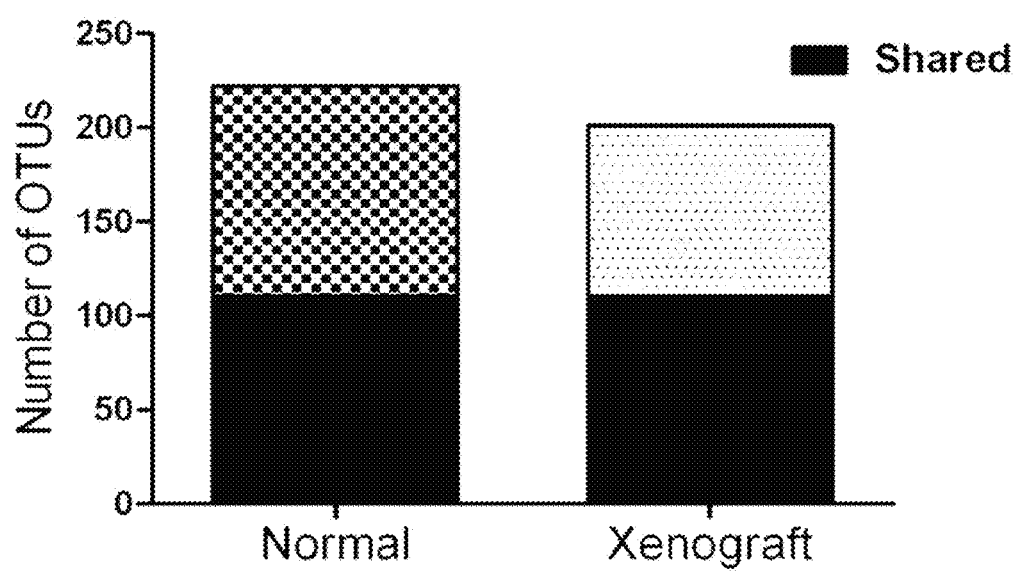
FIG. 10B shows the numbers of shared and unique OTUs of normal and xenograft nude mice.
Figure 10C:
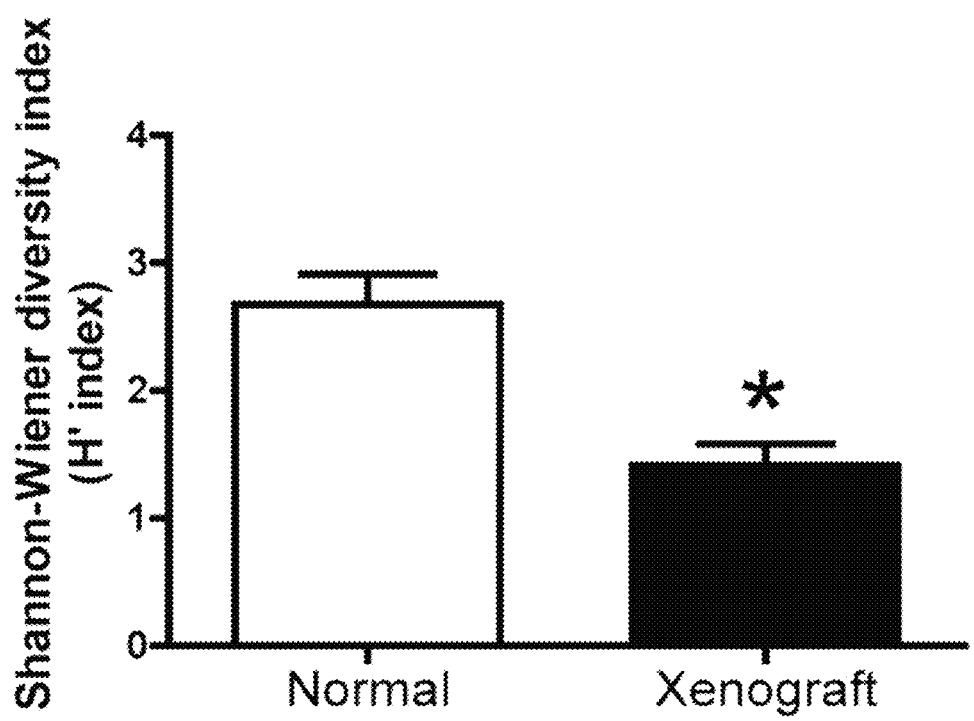
FIG. 10C shows the diversity of fecal microflora in normal and xenograft nude mice by Shannon-Wiener diversity index (H').

Denoised OTUs derived from the normal and xenograft mice were first collected and OTU network analysis was performed to generate an image of overall clustering of the test samples. As discussed in the previous session, tumor progression is likely to cause the separation in fecal microbiome between normal and xenograft nude mice. Similar finding was also observed in the OTU network analysis (FIG. 10A). By comparing the number of OTUs in nude mice with or without xenografted tumors, we found only 110 OTUs were shared. 112 and 91 unique OTUs can be found in normal and xenograft nude mice, respectively (FIG. 10B). In contrast to normal nude mice, reduced microbial diversity was found in xenograft nude mice based on the calculated Shannon-Weiner diversity index (FIG. 10C).

Figure 10D:
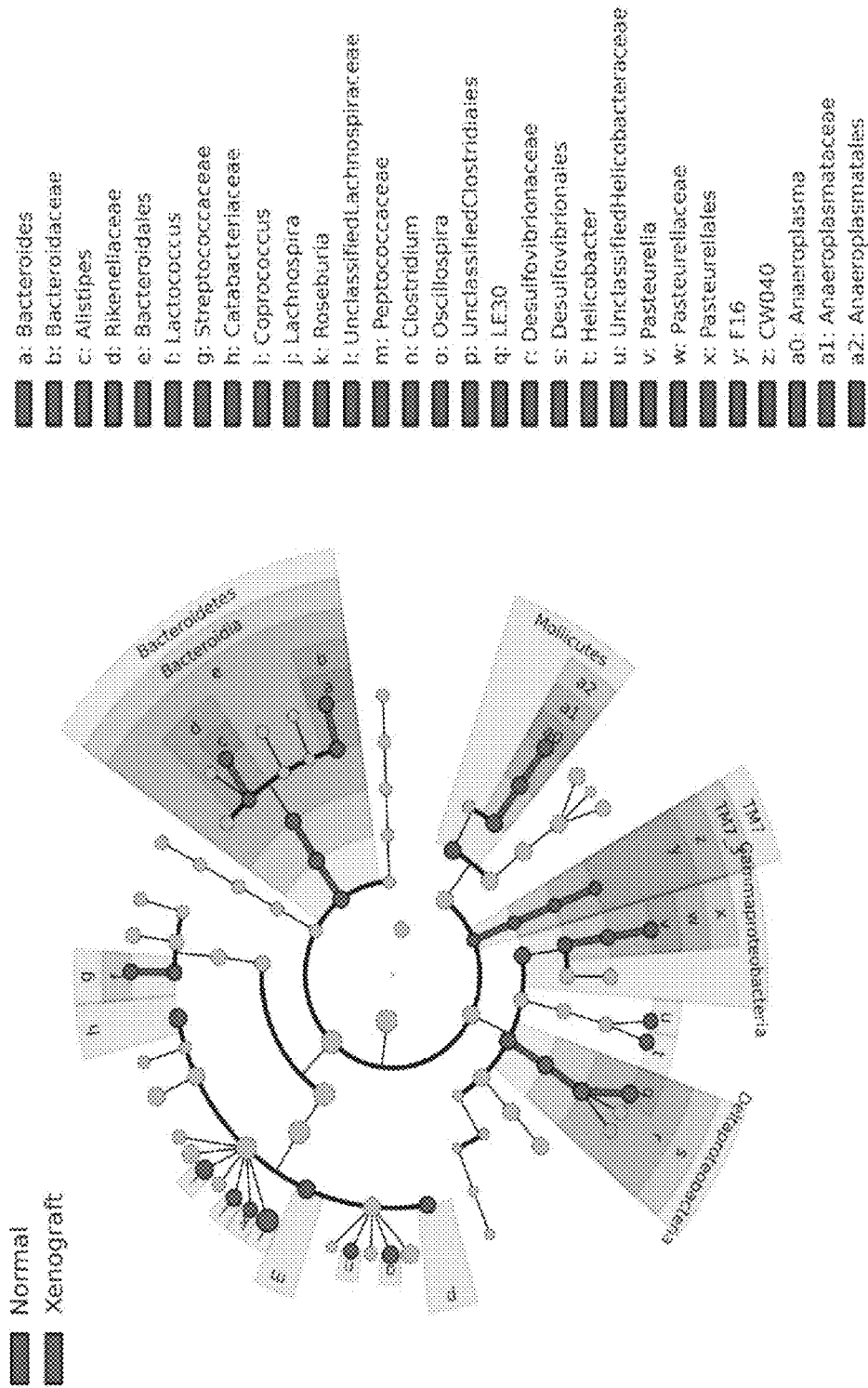
FIG. 10D shows the taxonomic representations of fecal microbiome of normal and xenograft nude mice; the differentially abundant taxa are presented with designated colors using LEfSe method. The taxa from nonxenograft and xenograft mice are colored in red and green, respectively. The taxa with nonsignificant changes between the nonxenograft and xenograft mice are colored in yellow. Diameter of the circle represents the taxon abundance.
Figure 10E:
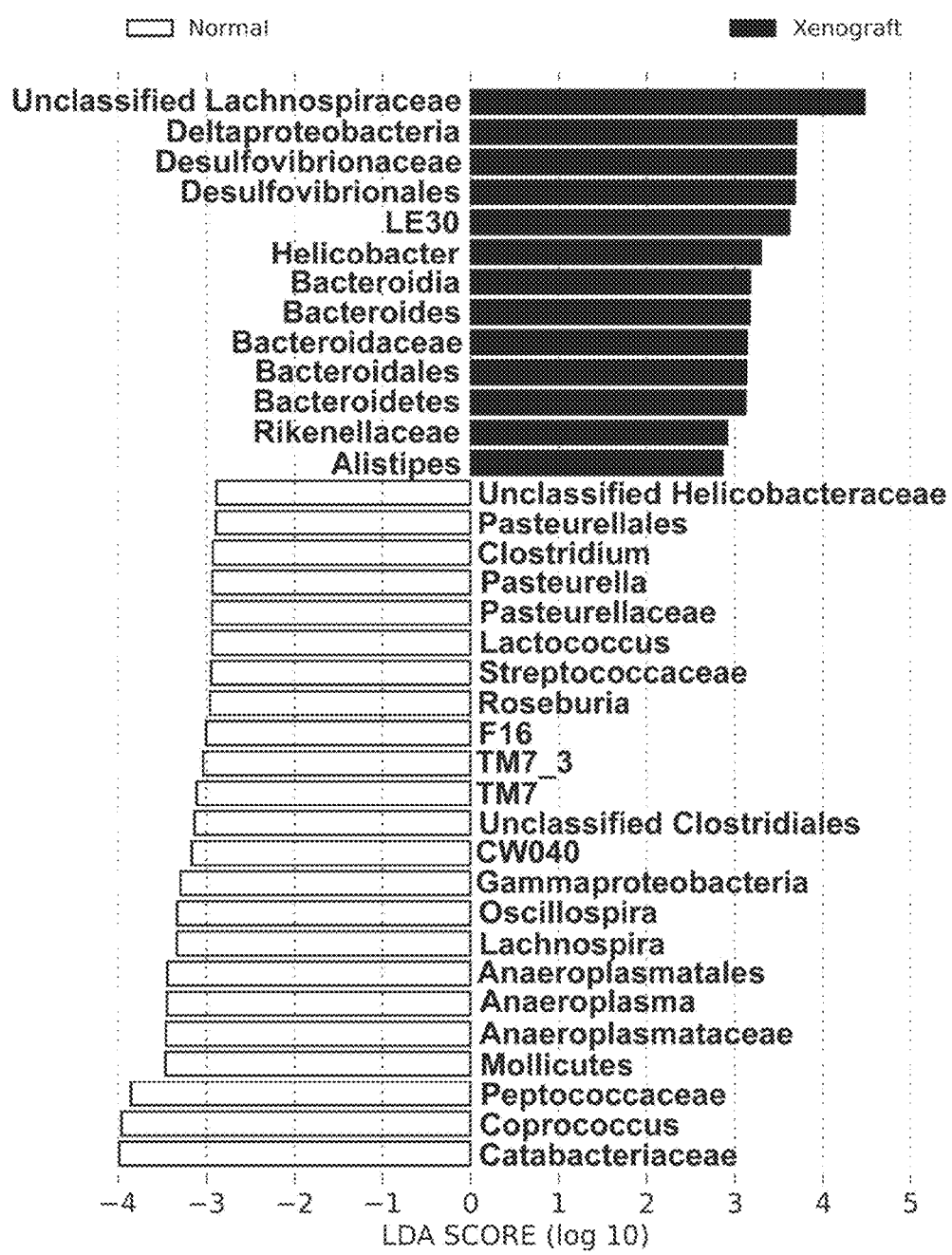
FIG. 10E shows the histogram of the LDA scores of fecal 16S rRNA sequences of normal (white) and xenograft (black) mice.
Figure 10F:
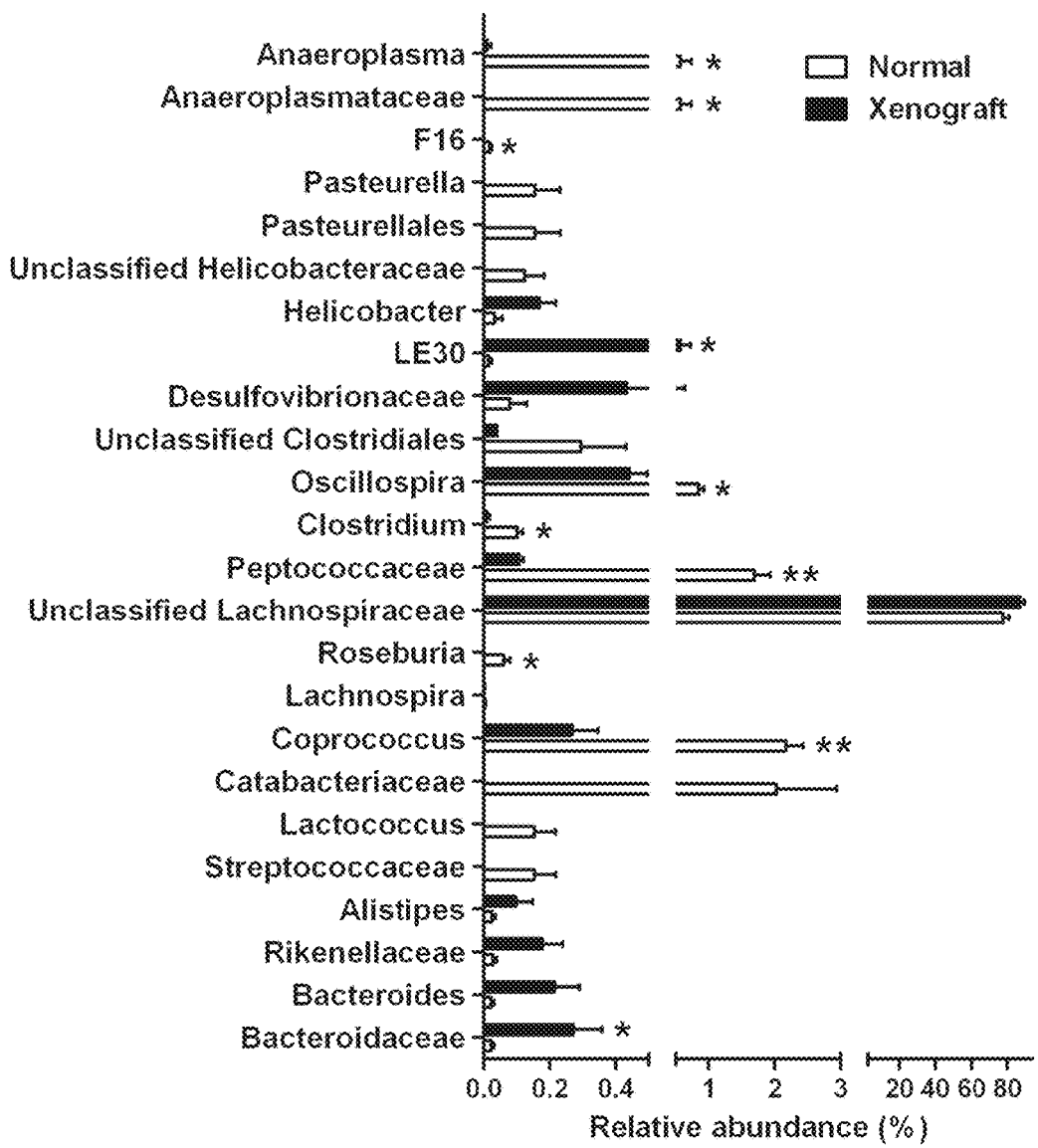
FIG. 10F shows the relative abundance of differentially abundant families and genera between normal and xenograft mice; Nonxenograft (normal) nude mice, n=3; Xenograft nude mice, n=3. Data are presented as the mean±SEM (*P<0.05, **P<0.01, nonxenograft versus xenograft group).

The 16S pyrosequencing data was then analysed using the Linear discriminant analysis (LDA) effect size (LEfSe) method to identify the key phylotypes responsible for the differences in fecal microbial communities between the normal and the xenograft nude mice. As shown in FIG. 10D, the taxonomic distribution of fecal microbiota between the normal and the tumor-bearing animals varied significantly at all taxonomic levels. At the phylum level, the most differentially abundant bacterial taxon in the feces of normal mice was TM7, whereas xenograft mice were overrepresented by Bacteroidetes (FIG. 10D-10F). Data showed that tumor-bearing nude mice harbored a fecal microbiota relatively enriched in Deltaproteobacteria but depleted in Gammaproteobacteria, both taxa are under Gram-Proteobacteria. Mollicutes, which is under the phylum of Tenericutes, was also underrepresented in xenograft nude mice (FIG. 10D). The histogram of the linear discriminant analysis (LDA) score (FIG. 10E) and the relative abundance score (FIG. 10F) showed the statistically and biologically differential clades appeared in the normal and xenograft nude mice. It is of worthy mentioned that although Firmicutes was not identified as the differentially abundant phylum, the clades under this phylum, such as Catabacteriaceae, Peptococcaceae, *Coprococcus* were particularly enriched in normal, but not in the xenograft mice (FIG. 10F).

Figure 11A:
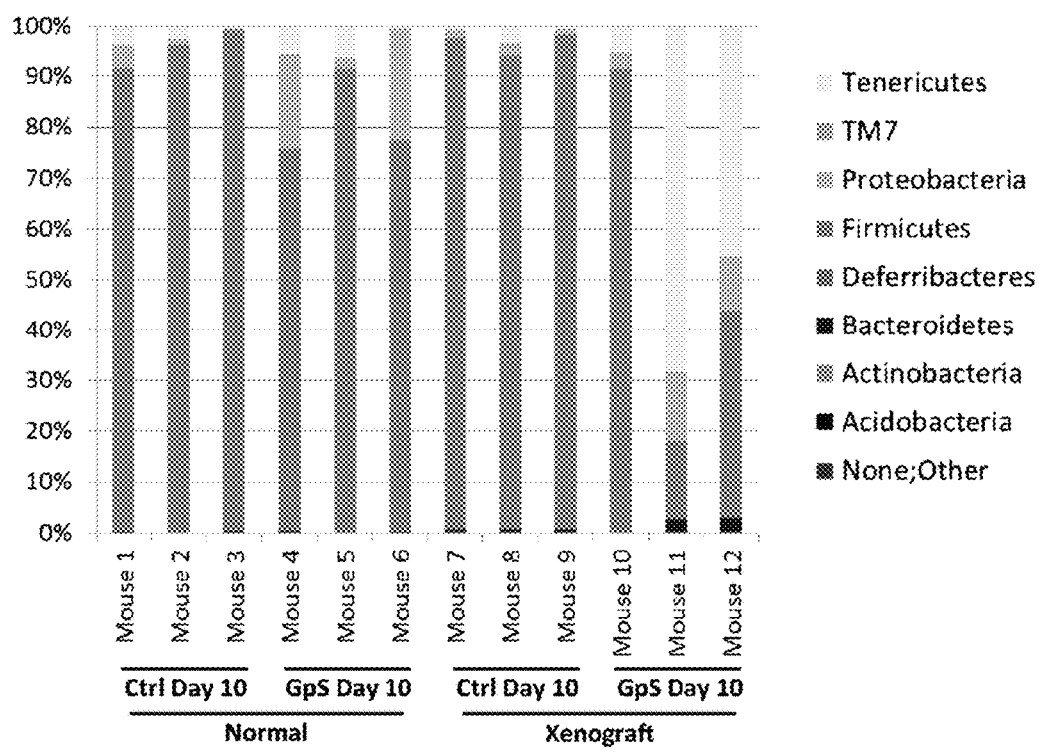
FIG. 11A shows a bar chart of relative abundance of bacterial phyla in nude mice with or without GpS treatment.

GpS Treatment Significantly Altered Fecal Microbiota of Normal and Xenograft Nude Mice The 16S pyrosequencing data demonstrated that GpS treatment caused alteration of the relative abundance of dominant taxa in fecal microbiota both at the phylum (FIGS. 11A & 11B). However, the alteration induced by GpS is more prominent in the xenograft than the normal mice. Within the three prominent phyla, mice treated with GpS, compared to the untreated, exhibited relatively lower abundance of Firmicutes (from 95.45 down to 81.30%), and higher abundance of Tenericutes (from 2.3 to 4.18%), Proteobacteria (from 1.98 to 14.24%) as well as Bacteroidetes (0.11 to 0.23%) (FIG. 11B). In the xenograft mice, GpS treatment markedly reduced the Firmicutes (from 95.99% down to 49.2%), in the meantime, it increased substantially the relative abundance of Tenericutes (from 1.66% to 39.58%) and Proteobacteria (from 1.68 to 9.36%) (FIG. 11B). Although the Bacteroidetes levels are relatively low abundance, we observed a 3-fold higher relative abundance of Bacteroidetes in GpS treated xenograft nude mice than that in controls (FIG. 11B).

Figure 12A:
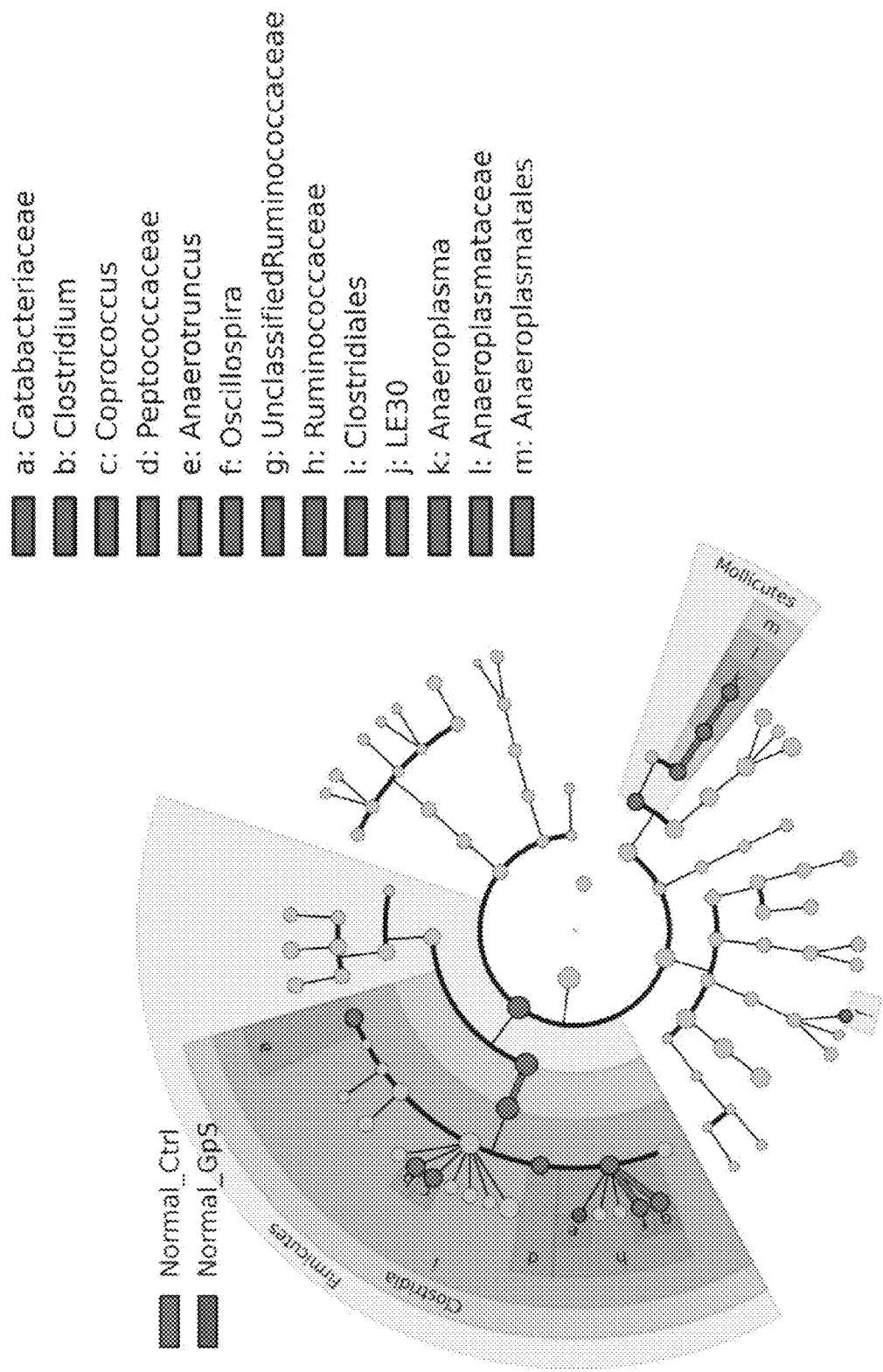
FIG. 12A shows the taxonomic representations of fecal microbiome of normal (nonxenograft) nude mice with or without GpS treatment.
Figure 12B:
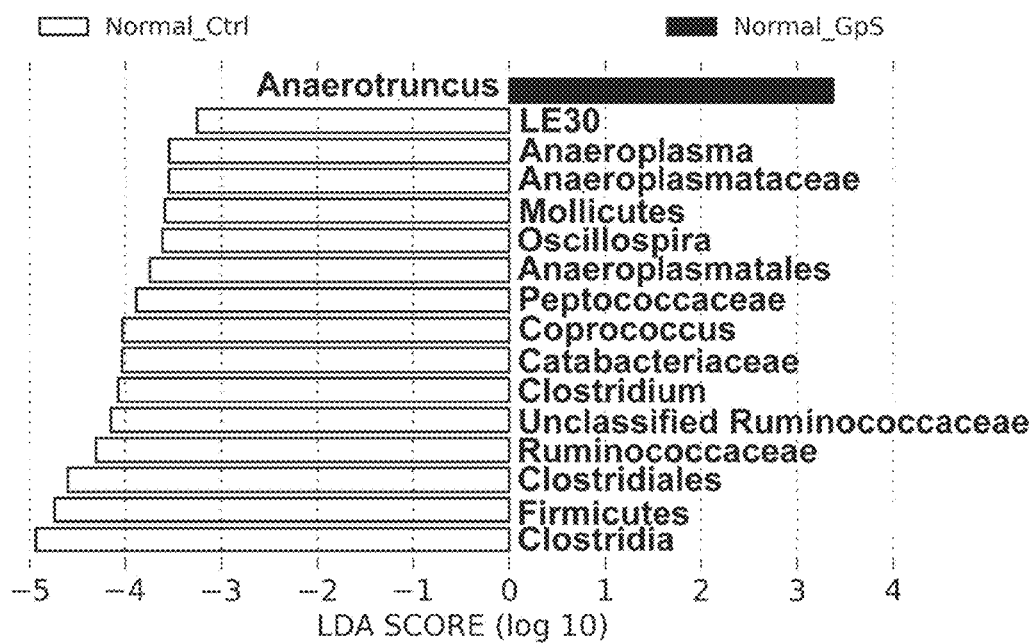
FIG. 12B shows the histogram of the LDA scores for differentially abundant clades. White: samples from controls; Black: samples from normal nude mice with 10 days of GpS treatment.
Figure 12C:
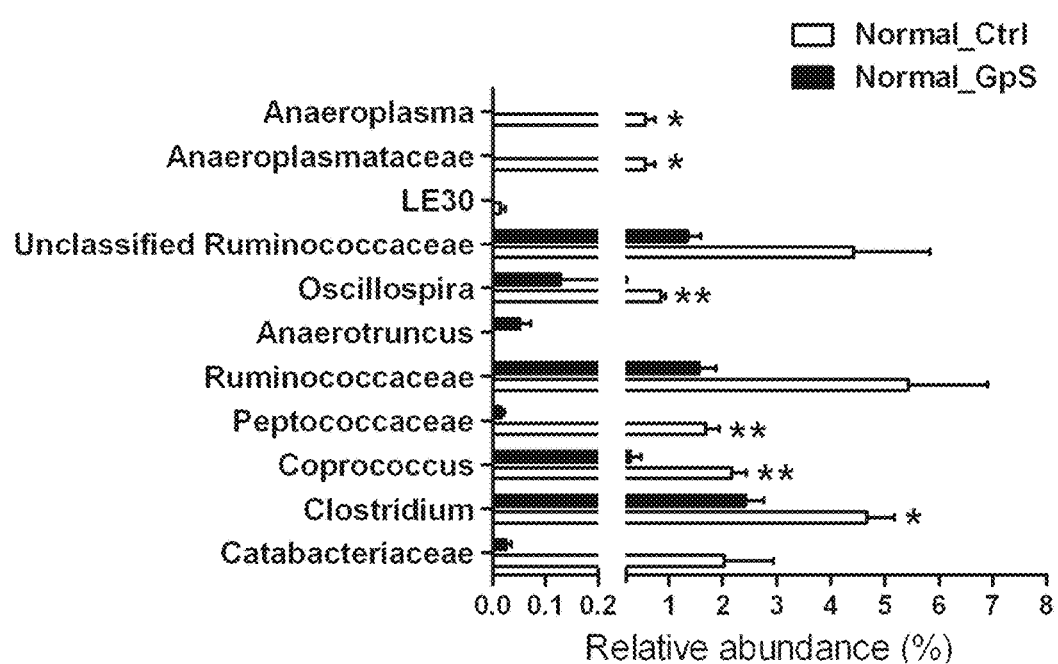
FIG. 12C shows the relative abundance of differentially abundant families and genera in normal nude mice with or without GpS treatment (Control group, n=3; GpS group, n=3)

We further analyzed the differential microbial phylogenic structures of normal and xenograft nude mice responding to GpS treatment by LEfSe tool. The taxonomic representations of the analysis are displayed as cladograms in FIG. 12A-12F. In normal nude mice, two classes were identified as the differentially abundant bacterial taxa, including Clostridia and Mollicutes (FIG. 12A). Clostridia was identified with a very high LDA score (approximately five orders of magnitude, FIG. 12B), reflecting marked abundance in normal mice (mean 94.98%) and consistently relatively low abundance in GpS-treated mice (mean 80.33%). Within Clostridia, the families such as Catabacteriaceae, Peptococcaceae and Ruminococcaceae and the genus, such as *Clostridium, Coprococcus*, Oscillospira were all found enriched in normal mice relative to the GpS-treated mice. In addition, the lineages of Mollicutes, the class under Tenericutes, including Anaeroplasmatales, Anaeroplasmataceae and *Anaeroplasma* were all the differentially abundant clades in the normal group (FIG. 12A). Based on the relative abundance score (%), Anaerotruncus, the genus under Clostridia, was the only differentially abundant taxon detected in the treated mice, while all other families and genera were all significantly lower in relative abundance compared to untreated mice (FIG. 12C).

Figure 12D:
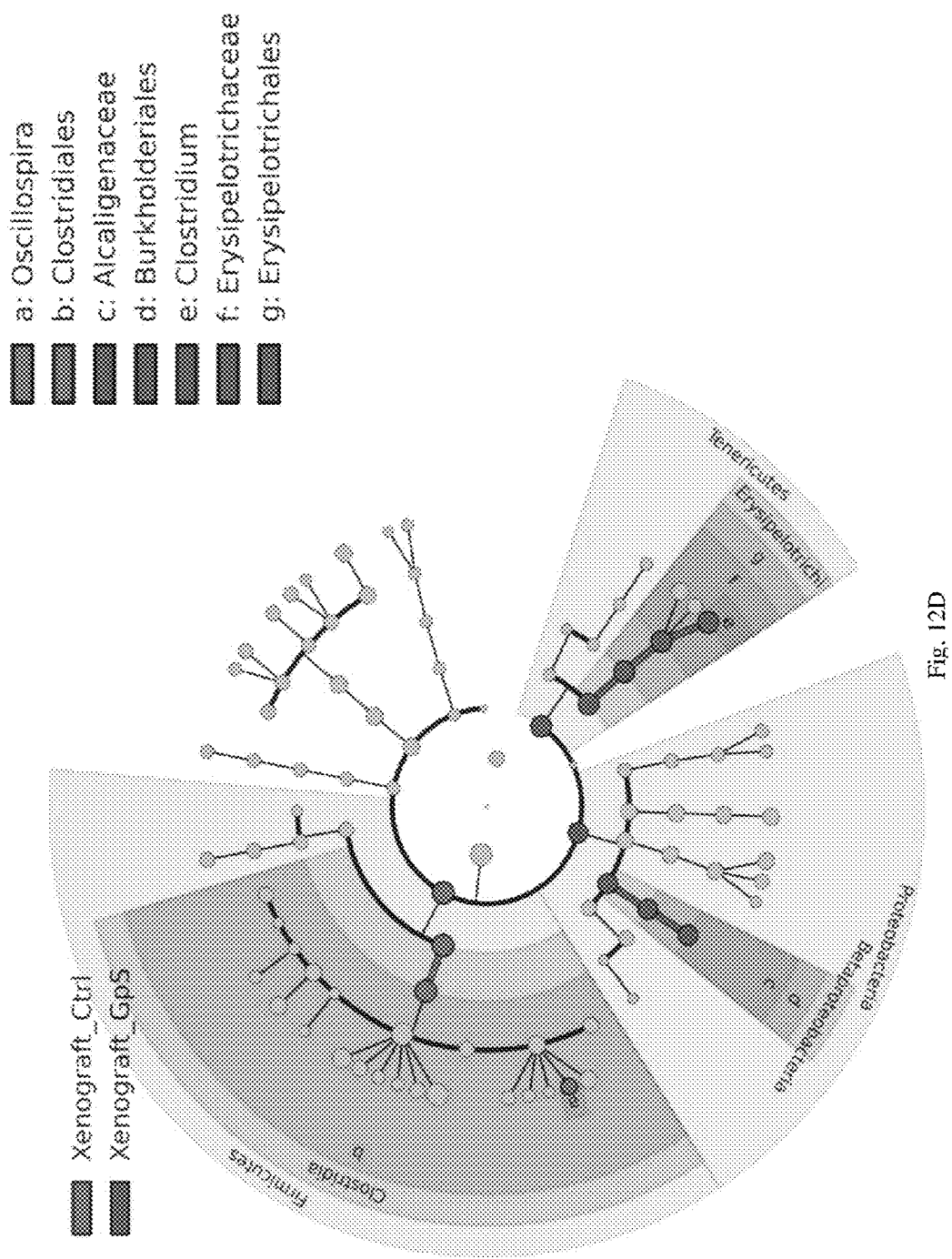
FIG. 12D shows the taxonomic representations of fecal microbiome of xenograft nude mice with or without GpS treatment.
Figure 12E:
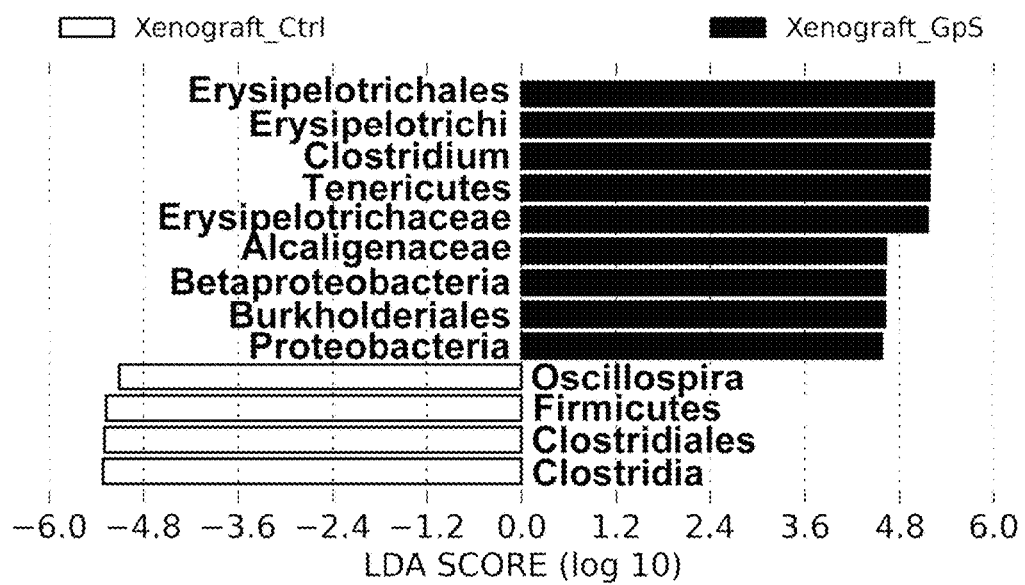
FIG. 12E shows the histogram of the LDA scores for differentially abundant taxa. White: samples from controls; Black: samples from xenograft nude mice with 10 days of GpS treatment.
Figure 12F:
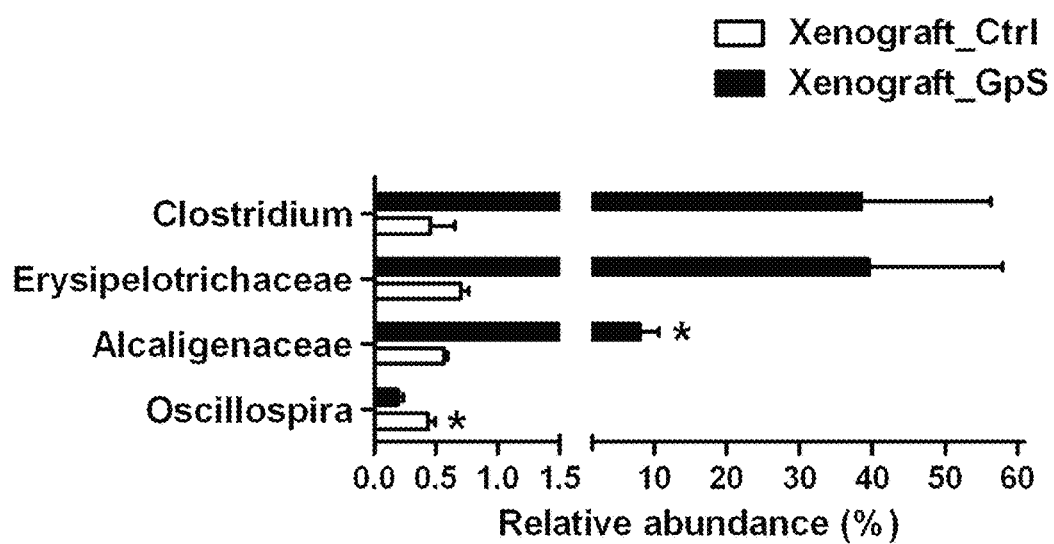
FIG. 12F shows the relative abundance of differentially abundant families and genera in xenograft nude mice with or without GpS treatment (Control group, n=3; GpS group, n=3).

In the xenograft nude mice, the three dominant phyla: Firmicutes, Proteobacteria and Tenericutes showed differential responses to GpS treatment. The major components contributing to these three distinguished phyla were the following classes: Clostridia (uncer Firmicutes) (95.84% vs. 49.08%), Betaproteobacteria (under Proteobacteria) (0.81% vs. 8.01%) and Erysipelotrichi (under Tenercutes) (1.65% vs. 39.58%) between the control and the GpS-treated mice (FIG. 12D). Differences of bacterial community structure between the control and the treatment mice were also demonstrated in the phylogenetic structure within individual lineages. In the GpS-treated xenograft mice, there were two notable lineages showing relatively high abundance with the greatest differences compared to the controls. One was the Proteobacteria-Betaproteobacteria-Burkholderiales-Alicaligenaceae lineage. The other was Tenercutes-Erysipelotrichi-Erysipelotrichales-*Clostridium* lineage (FIG. 12D). At the family level of these two particular lineages, we found that Alcaligenaceae (0.81% vs. 8.01%) and Erysipelotrichaceae (1.65% vs. 39.58%) were the main differentially abundant clades in the GpS-treated mice. At genus level, *Clostridium* presented greatest variations with over five orders of magnitude difference in abundance between the two groups (FIG. 12E). It constituted less than 0.5% of total bacteria in controls, however, it was much more prevalent in the GpS-treated mice (mean 38.48%).

Figure 13A:
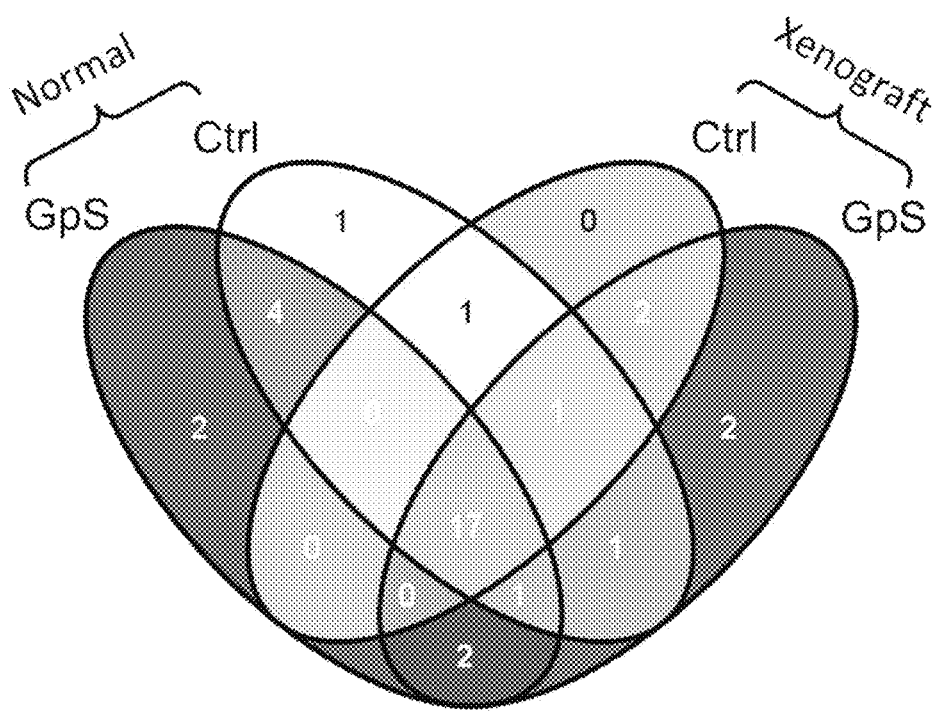
FIG. 13A shows the Venn diagram showing the number of unique and shared bacterial families between normal and xenograft nude mice with or without GpS treatment.
Figure 14C:
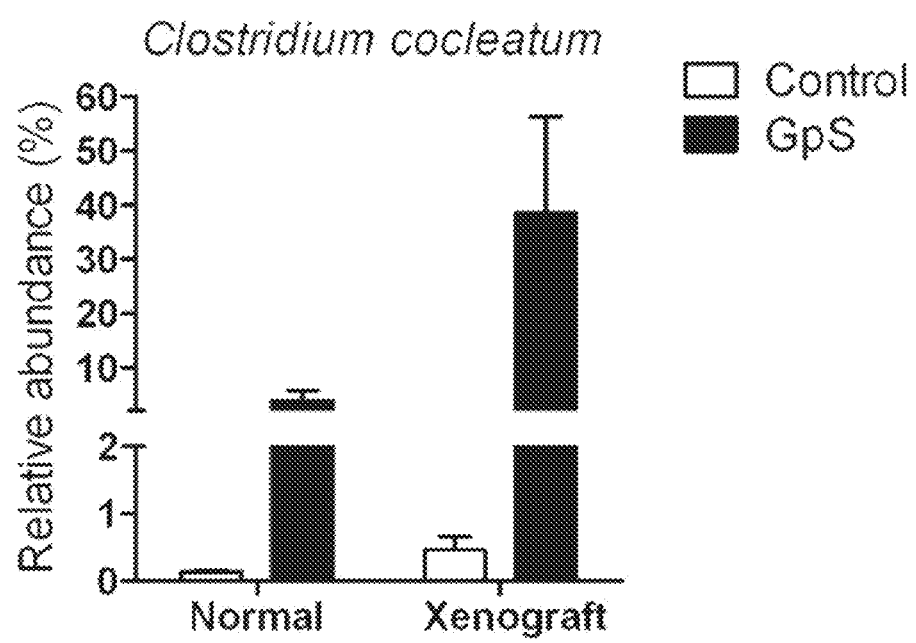
FIG. 14C shows the relative abundance of *Clostridium cocleatum* in normal and xenograft nude mice with or without GpS treatment. Data are presented as mean±SEM (n=3 per group)
Figure 14D:
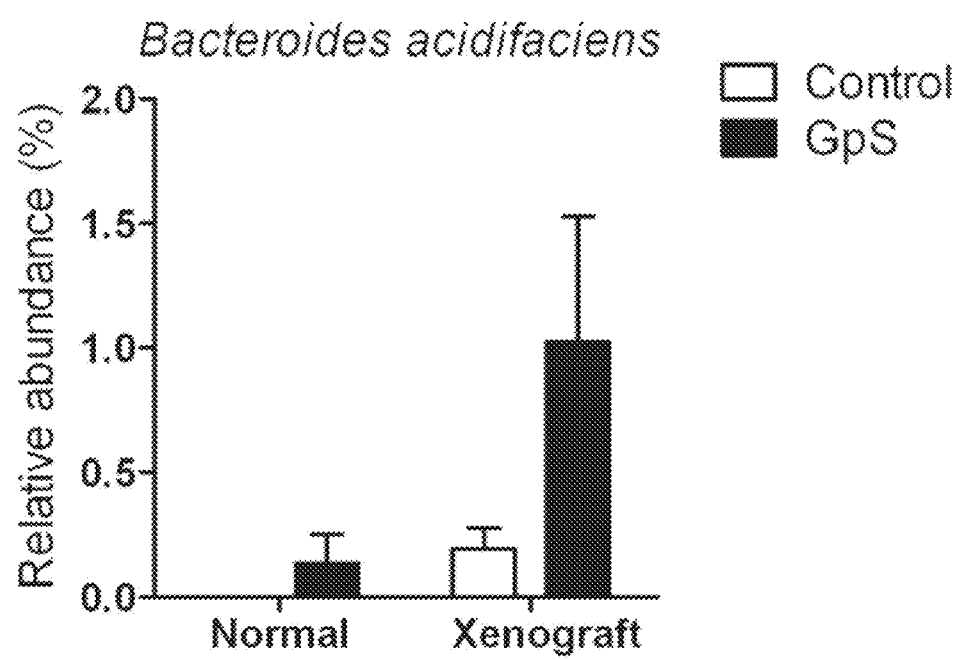
FIG. 14D shows the relative abundance of *Bacteroides acidifaciens* in normal and xenograft nude mice with or without GpS treatment. Data are presented as mean±SEM (n=3 per group).

Identification of the Unique Bacterial Families Associated with Different Treatment Groups To identify taxa that are unique to different treatment groups, we compared the unique and shared bacterial families by Venn Diagram. As shown in FIG. 13A, there were 7 and 2 unique bacterial families found in the normal and xenograft mice, respectively, while 19 bacterial families were overlapped between the two groups. When compared the microbial communities in the normal nude mice with or without GpS treatment, we found 22 bacterial families were shared, whereas control and GpS-treated groups each exclusively harbored 4 different families. On the other hand, in xenograft nude mice, 20 bacterial families were detected in both controls and GpS-treated mice. Only one unique bacterial family was found in controls while six unique families were found in the GpS-treated xenograft mice. These unique bacterial families with a mean relative abundance>0.01% were listed in FIG. 13B. Deferribacteraceae (under Deferribacteres) was only detected in xenograft nude mice, while Enterococcaceae, and Streptococcaceae under Firmicutes, Enterobacteriaceae and Pasteurellaceae under Proteobacteria, and two unclassified F16 and RF39 were unique to normal individuals. Comparing the normal nude mice with or without GpS treatment, we found the unclassified RF39 and Anaeroplasmataceae (under Proteobacteria) were absent from the GpS-treated individuals. Another interesting finding was that Pasteurellaceae, which was depleted in xenograft nude mice, was presented in the GpS-treated tumor bearing mice.

Identification of Bacterial Species Altered Upon GpS Treatment

Based on the consensus lineage map of OTUs generated by QIIME software, most of the bacteria identification can be down to the genus level, while few can be identified to the species level. For example, one OTU is related to *Clostridium cocleatum*, and another OTU is related to *Bacteroides acidifaciens*. Both species showed an increasing trend after GpS treatment in both normal and xenograft nude mice. Compared to the un-treated control, *Clostridium cocleatum* increased more than 28 fold (in relative abundance) in GpS-treated normal mice. In the xenograft groups, an 80 fold increment of relative abundance of *Clostridium cocleatum* in response to GpS treatment. The relative abundance of *Bacteroides acidifaciens* increased by 5 fold compared to the un-treatment controls (FIG. 14A-14D). The striking increase of *Clostridium cocleatum* appeared to be an important driver of fecal bacterial community structure in GpS-treated tumor bearing mice.

Figure 15:
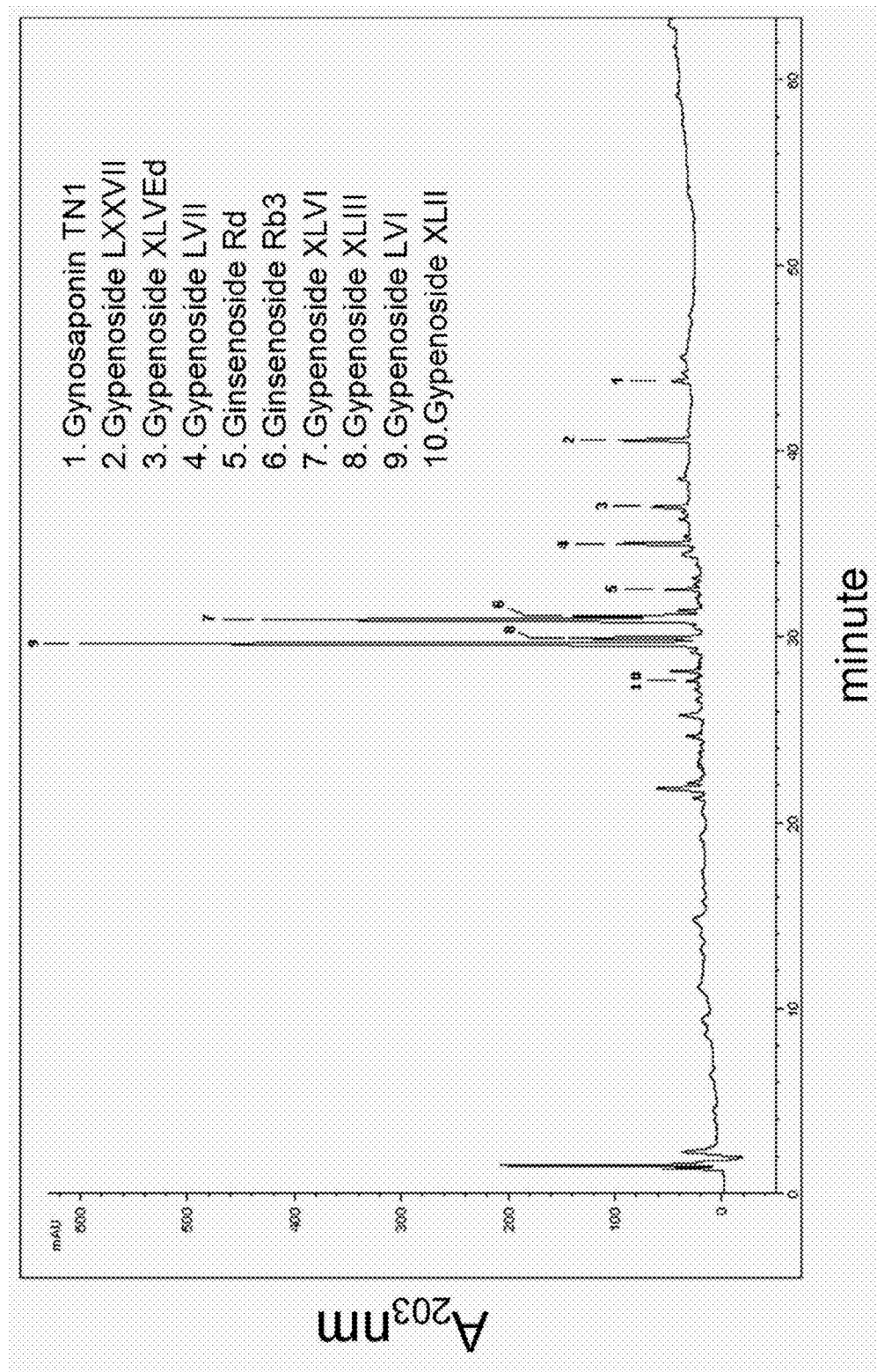
FIG. 15 shows the quality control of GpS.

FIG. 15 shows the UPLC chemical profile of GpS along with 10 single gypenosides as the standards.

Discussion

The gut microflora are believed to shape intestinal immune response during health and disease. Host immune regulation in turn is also vital in shaping a normal microbiota; disturbance of host regulation creates a dysbiotic microbiota, which is characterized by an imbalanced microflora community. In addition, it is evidence that different dietary compounds would interact and affect the regional or temporal composition of the gut microbiota. Gp herbal tea, similar to the green tea, can be consumed as regular tea, it also has various medicinal functions including anti-cancer effect. The questions addressed in this example are two-fold: 1) How would gut microbiota response to dietary/medicinal saponins under healthy and diseased states? 2) As our data indicated, Gp sapoinins treatment can significantly reduce the size of xenograft tumor. Could there be a link between the tumor growth and the composition of gut microbiota? To address the questions, we employed ERIC-PCR and 16S pyrosequencing methods to systematically monitor the structural dynamics of fecal microbial communities in nude mice subjected to different treatments. PLS-DA plots of ERIC-PCR data revealed an observed correlation between changes in microbial composition and the disease phenotype. Pyrosequencing based LEfSe analysis, based on the pyrosequencing data, demonstrated that tumor xenograft can markedly modify gut microflora at various phylogenic levels. Normal nude mice are enriched with Firmicutes while xenograft mice are enriched with Bacteroidetes has identified key bacterial alterations between normal and xenograft nude mice, which may provide possible biomarkers used for detecting or monitoring cancer development. Meanwhile, we found a decline in microbial diversity occurred in tumor-bearing nude mice, which may be a byproduct of the cancer process. Likewise, the reduced microbial diversity can also be found in other diseases, such as inflammatory bowel disease and obesity. Our results hint at potential and plausible features of a cancer-induced dysbiotic microbiota. It is possible that tumor progression leads to dysregulation of the immune system, accounting for the alteration in microbiota.

Figure 9I:
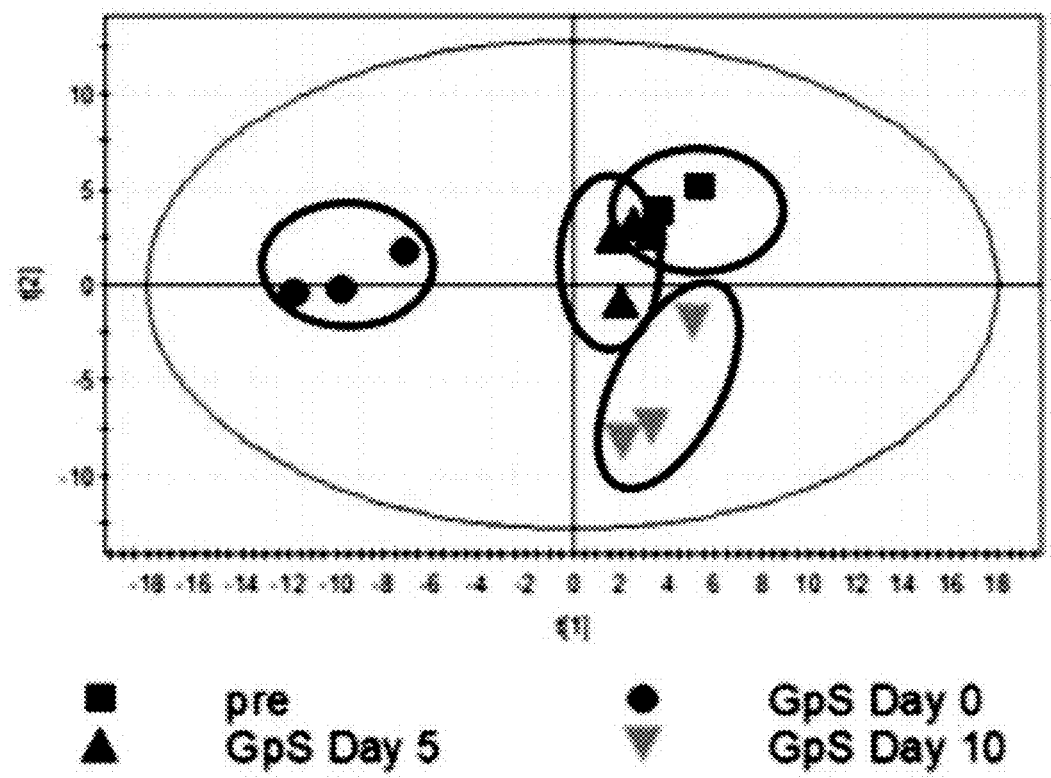
FIG. 9I shows the PLS-DA score plots of ERIC-PCR data of the GpS treatment group in xenograft nude mice with antibiotic intervention (n=3).

As is known, ERIC-PCR is initially used to detect species under Enterobacteriaceae and Vibrionaceae families, including few top organisms such as *Escherichia coli, Salmonella enterica, Yersinia pestis* and *Vibrio cholera*. Later, Eric sequences are also found in the genome of various bacterial species as described in Delihas N (2007). Enterobacterial small mobile sequences carry open reading frames and are found intragenically—evolutionary implications for formation of new peptides. *Gene regulation and systems biology* 1: 191-205; Wang L, Jin Y, Zhao L, Pang X, Zhang X (2009). ERIC-PCR-based strain-specific detection of phenol-degrading bacteria in activated sludge of wastewater treatment systems. *Letters in applied microbiology* 49: 522-528 and Wilson L A, Sharp P M (2006). Enterobacterial repetitive intergenic consensus (ERIC) sequences in *Escherichia coli*: Evolution and implications for ERIC-PCR. *Molecular biology and evolution* 23: 1156-1168. To these microbial communities identified by ERIC-PCR, two interesting aspects were revealed. Firstly, tumor xenograft were able to alter the gut microbiota with a rather short period of time (FIG. 7A-7E). Secondly, GpS treatment can modulate the dysbiosis in tumor-bearing status and restore the microflora composition back to the non-tumor situation on the day of tumor cell injection (FIGS. 9F and 9I). Such shift was also observed in xenograft nude mice pretreated with antibiotic prior to tumor injection and GpS treatment (FIG. 9H vs 9I), but not observed in the normal mice obtained same GpS treatment. Whether this alteration of gut microbiota was a refection of regression of the tumor or a direct effect of GpS treatment is of interest for further investigation. During tumor progression, GpS treatment was likely to achieve balance of the microbial ecosystem by counteracting the alterations of these ERIC-PCR detected bacteria, such as Enterobacteriaceae family, which was also significantly more abundant in other disease model like colitis-susceptible Il10−/− mice.

Subsequently, the fecal microbial communities were assessed and compared by 16S pyrosequencing to obtain a more comprehensive microbiota profile. At phylum level, Tenericutes, Proteobacteria and Bacteroidetes were more abundant in GpS-treated nude mice than in controls, whereas Firmicutes showed the opposite pattern, especially in tumor-bearing nude mice. A shift in the ratio between Firmicutes and Bacteroidetes has been reported in many other studies. It has been linked to many diseases, such as obesity. Based on the analysis of pyrosequencing data, we found that Bacteroidetes/Firmicutes ratio showed an increased trend after 10 days of GpS treatment in nude mice with xenografted tumors. On the other hand, we found GpS treatment can increase the relative abundance of Proteobacteria which are the major group of Gram-negative bacteria in the gut. The lipopolysaccharide (LPS) in the outer layer of the bacteria. LPS has been recognized in Goto S, Sakai S, Kera J, Suma Y, Soma G I, Takeuchi S (1996). Intradermal administration of lipopolysaccharide in treatment of human cancer. *Cancer Immunol Immunother* 42: 255-261 as a treatment for cancer by stimulating immune system. In our case, the increased Proteobacteria in GpS-treated mice may potentially enhance the secretion of LPS thus activate an immune response against tumors.

Pyrosequencing analysis also identified few species of bacteria upon GpS treatment. *Clostridium cocleatum* and *Bacteroides acidifaciens* were the two species showing increased trend in both normal and xenograft mice treated with GpS (FIGS. 14C & 14D), which have several well-documented beneficial effects. For example, study in Boureau H, Decre D, Carlier J P, Guichet C, Bourlioux P (1993). Identification of a *Clostridium cocleatum* strain involved in an anti-*Clostridium difficile* barrier effect and determination of its mucin-degrading enzymes. *Research in microbiology* 144: 405-410 indicated that strain of *C. cocleatum* can exert a protective barrier effect against the colonization the pathogenic *Clostridium difficile* in the gut and displayed multiple glucosidase activities that can involve in degrading the oligosaccharide chains of mucin in the digestive tract. *C. cocleatum* was significantly reduced in irritable bowel syndrome patients. In addition, *C. cocleatum* plays a role in the conversion of diglucoside, and have the de-glycosylation activity. *Clostridium* bacteria occupy a major fraction of mammalian gut microbiota and are responsible for promoting anti-inflammatory immune responses. It is concluded that *C. cocleatum*, which exhibited a striking increase in GpS-treated xenograft nude mice, contributed most to differentiate the microbial structures from the controls. Aside from the well-documented beneficial effects discussed above, *C. cocleatum* may take part in the metabolism of Gp saponins through glucosidase activities and have a role similar to symbionts.

*Bacteroides acidifaciens* was first isolated from the cecum of mice. *B. acidifaciens* and its closed relative, *B. uniformis* were found to be associated with the degradation of the isoflavone in human feces. Recent study in Yanagibashi T, Hosono A, Oyama A, Tsuda M, Suzuki A, Hachimura S et al., (2012). IgA production in the large intestine is modulated by a different mechanism than in the small intestine: *Bacteroides acidifaciens* promotes IgA production in the large intestine by inducing germinal center formation and increasing the number of IgA(+) B cells. *Immunobiology* demonstrated that *B. acidifaciens* promoted IgA production. It is reasonable to assume that the beneficial effects of *Clostridium cocleatum* and *Bacteroides acidifaciens* be potentially conducive to the anti-cancer effect of GpS. It is intriguing that the changes in gut microbiota observed in GpS-treated xenograft nude mice were more apparent than that in GpS-treated normal individuals. It seemed that the therapeutic effect of GpS was enhanced in some pathological conditions. One possible reason for this was that some pathological conditions generated a disturbed microbial system and GpS treatment can reverse this imbalance. The increase in these beneficial bacteria induced by GpS treatment, can function as symbionts and contribute to rebalancing the microbial ecosystem and exerting an inhibitory effect on tumor growth.

In conclusion, the present invention demonstrates how dietary saponins can exert regulating and balancing effects on the gut microbial ecosystem. The results indicated that tumor growth can impact on dynamics of the gut microbial ecosystem. At the same time, we also demonstrated that GpS treatment can alter the gut microflora composition, in particular boosting beneficial bacteria and then contributing to restore the dysbiosis back to eubiosis state.

Remarkably few studies have examined the influence of herbal saponins on the composition of the gut microbial community; hence there is a serious gap in the understanding of the saponins-microbe interactions. In a further embodiment of the present invention, the inventors demonstrate the impact of four sources of herbal saponins on the composition of the gut microbiota. The saponins of the present invention are the major active constituents of the four commonly used dietary herbal tea: ginseng (GS), red ginseng (RGS), *notoginseng* (NGS) and jiaogulan (Gp).

Methods and Materials

Sources of Herbal Saponins

GS, RGS and NGS with 80% purity were purchased from Hongjiu Biotech Company Ltd., Dalian, China. Standardization of the saponins was performed by ultra high-performance liquid chromatography (UPLC)-mass spectrometry (MS) using 19 known ginsenosides as standard markers. The authentication and chemical profiling of GpS were performed.

Animals and Treatments

Figure 16A:
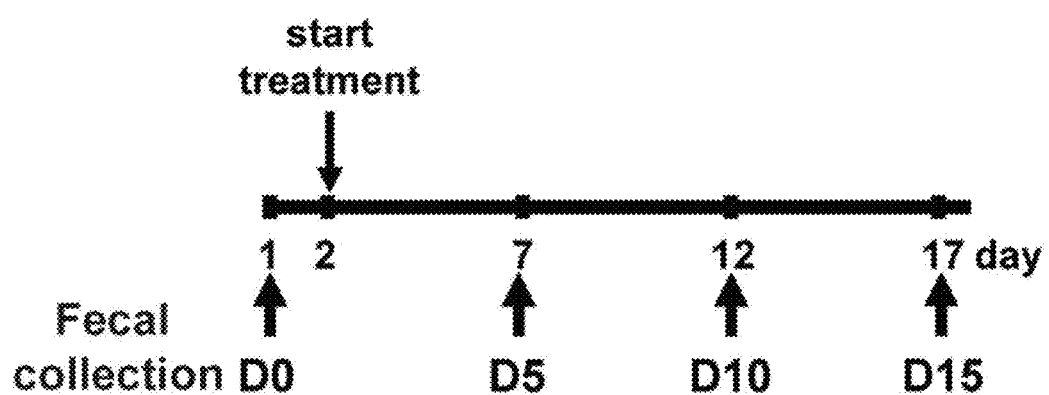
FIG. 16A shows treatment scheme of a time course study of the faecal microbiota of mice from different herbal saponins treatment groups.

The animal welfare and experimental procedures were performed strictly in accordance with the procedures approved by the University Ethics Review Committee of Hong Kong Baptist University for the care and use of laboratory animals. The C57BL/6 mice were purchased from the Chinese University of Hong Kong, and kept on a 12-h light/12-h dark cycle, 20-22° C. temperature and 40-60% humidity with free access to food and water. Mice were fed with a standard diet (PicoLab® Rodent Diet 20-5053, LabDiet, St. Louis, Mo., USA). Saponins were dissolved in Milli-Q $H_2O$ at 50 mg/ml and then sterilized with 0.2 μm filter. Young male mice (8 week old) were randomly divided into five experimental groups. Mice in all groups were given daily single dose of herbal saponins (GS, RGS, NGS, and GpS) at 500 mg/kg or Milli-Q $H_2O$ by gavage for 15 consecutive days. Mice were not fasted before drug treatment. In order to minimize the influence of food intake, the daily food intakes of the mice were monitored using a comprehensive laboratory animal monitoring system (CLAMS; Columbus Instruments, Columbus, Ohio, USA). The lowest level of food intake was pinpointed in the afternoon hours, thus the inventors set the timing of daily drug feeding around 15:00. Two independent experiments were performed with five mice per group for each experiment (total 50 mice, 10 mice per group in total). Animal faeces were collected from each individual mouse for two consecutive hours from 8:00 to 10:00 AM at day 0 (D0, before treatment), day 5 (D5), day 10 (D10) and day 15 (D15) upon treatment. The average amount of faeces collected from each mouse was around 0.3 g. 0.1 g faecal sample from each mouse was mixed well and used for bacterial DNA extraction. The treatment scheme is shown in FIG. 16A.

Bacterial Genomic DNA Extraction from Faecal Samples

Total genomic DNA was isolated from faecal samples. In brief, 0.1 g faeces were vortexed in 4 ml sterile PBS (pH7.4)

for 5 min, then centrifuged at 40×g for 8 min to collect the upper phase containing the bacteria. After repeating this procedure once, the supernatants were combined and centrifuged at 2000×g for 8 min. The supernatant was discarded. The bacterial pellets were washed twice with PBS, then resuspended in 200 µl lysing buffer I (150 mM NaCl; 100 mM EDTA (ethylenediaminetetraacetic acid); pH 8.0) and 66.7 µl proteinase K (4 mg/ml) was then added. After incubation at 55° C. for 2 h, 200 µl lysing buffer II (100 mM NaCl, 500 mM Tris-HCl, pH 8.0), plus 66.7 µl 10% SDS were then added and incubated at room temperature for 5 min. The mixture was extracted sequentially by phenol, phenol/chloroform/isoamyl (25:24:1, v/v/v), chloroform/isoamyl (24:1, v/v), followed by two volumes of cold ethanol and 1/10 volume of sodium acetate (3 M, pH 5.2) for the precipitation of DNA. The solution was kept overnight at −20° C. Genomic DNA pellets were collected by centrifuging at 15000×g for 15 min, and then washed twice with cold 70% ethanol, dried, then dissolved in PCR H$_2$O with 1.0 mg/ml RNase A. The DNA concentration was determined by NanoDrop 1000 spectrophotometry.

ERIC (Enterobacterial Repetitive Intergenic Consensus)-PCR

ERIC sequences are non-coding, highly conserved intergenic repeated sequences that reside in the genome of various bacterial species in addition to enterobacteria. ERIC-PCR was used to detect the gut microbiome using faecal genomic DNA as the template and a pair of ERIC specific primer sequences: ERIC 1R (SEQ ID No. 1) (5'-ATGTAAGCTCCTGGGGATTCAC-3') and ERIC 2 (SEQ ID No. 2) (5'-AAGTAAGTGACTGGGGTGAGCG-3'). The 25 µl reaction mixture contained 5 µl 5×PCR reaction buffer, 200 µM dNTP, 2.5 mM Mg$^{2+}$, 0.4 µM primers, 1 unit Hotstart Taq polymerase, and 50 ng faecal genomic DNA. PCR was performed using the following protocol: 94° C. for 5 min, followed by 35 cycles of 95° C. for 50 s, 49° C. for 30 s, 46° C. for 30 s and 72° C. for 3 min, and then a final extension at 72° C. for 9 min. 10 µl of each PCR product was loaded onto a 2% (w/v) agarose gel containing 0.5 µg/ml ethidium bromide and run for 40 min at 100 V in 1×TAE buffer. A DNA ladder (0.1-10.0 kb) was used as the DNA marker (NEB, N3200). The agarose gels were photographed using a Gel Doc™ XR+ System (Bio-Rad, Hercules, Calif., USA).

Application of PLS-DA for ERIC-PCR Data Analysis

Partial least squares discriminant analysis (PLS-DA) is one of the most widely used methods in multivariate classification. In this embodiment of the present invention, the inventors applied PLS-DA to evaluate the similarity of microbial composition between the control and treatment groups based on the ERIC-PCR data. The banding patterns of the ERIC-PCR products (see FIG. 2B to FIG. 2F) were photographed and digitized using the Image Lab 3.0 system (Bio-Rad) to generate the data based on the sum of the distance and the intensity of each DNA band within each sample lane. The scores were subjected to PLS-DA plot using the SIMCA-P 12.0 tool (Umetrics, Umea, Sweden).

Quantitative Real Time PCR (qPCR)

The abundance of specific bacteria was measured by qPCR using Applied Biosystems ViiA™ 7 PCR system (Carlsbad, Calif., USA) with taxon-specific 16S rRNA gene primers (Invitrogen, Carlsbad, Calif., USA). A universal primer set was used to detect the 16S rRNA gene of total bacteria, and used to calculate the relative abundance of specific bacteria group. The sequences of the primers used were listed in Table 1. Briefly, the qPCR was carried out using Power SYBR® Green PCR Maser Mix (Applied Biosystems Inc.) with 5 ng faecal genomic DNA and 200 nM of each primer. The amplification conditions were as follow: 95° C. for 10 min, followed by 40 cycles of 95° C. for 15 s and 60° C. for 1 min. Using the same batch of genomic DNA from each faecal sample, qPCR was performed to determine the amount of the following bacteria: Firmicutes, Bacteroidetes, *Bacteroides, Lactobacillus, Bifidobacterium, Clostridium* Cluster IV and *Faecalibacterium prausnitzii*. Ten samples were used for each experimental group. The comparative Ct method ($2^{-\Delta\Delta Ct}$ method) was applied to determine the relative change of specific bacteria in the faeces of individual mouse before (D0) and after treatment. $\Delta\Delta Ct = (Ct_{treatment\_specific\ bacteria} - Ct_{treatment\_total\ bacteria}) - (Ct_{D0\_specific\ bacteria} - Ct_{D0\_total\ bacteria})$.

Statistical Analysis

The data obtained from two independent experiments, a total of ten mice per group were analyzed and presented as mean±SEM. Statistical comparisons were performed using repeated measures ANOVA followed by Dunnett's post test with the GraphPad Prism version 5.00 (GraphPad Software, San Diego, Calif., USA) at P values of <0.001(*), <0.01 () or <0.05(*).

Results

Herbal Saponins Altered the Profiles of Faecal Microbiota

Figure 16B:
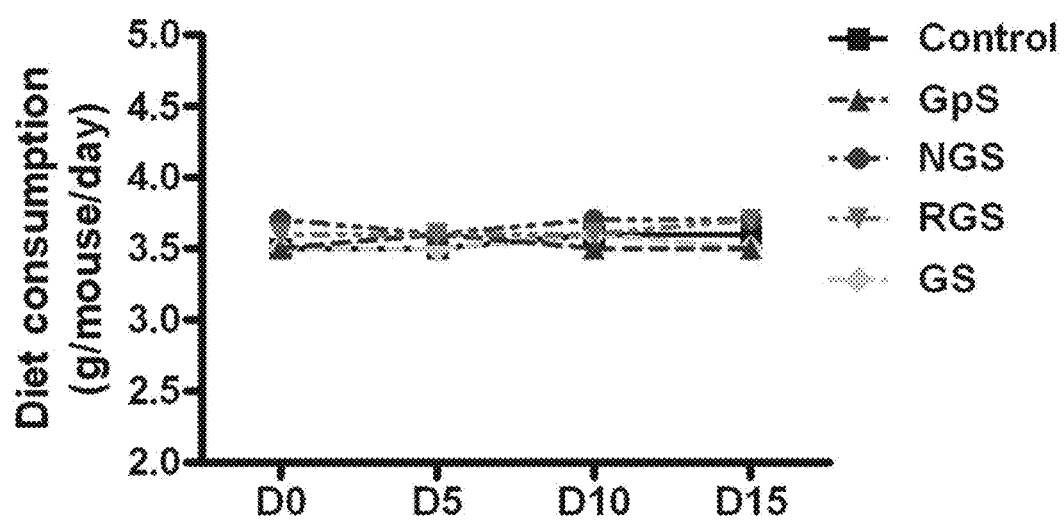
FIG. 16B shows diet consumption of a time course study of the faecal microbiota of mice from different herbal saponins treatment groups.
Figure 16C:
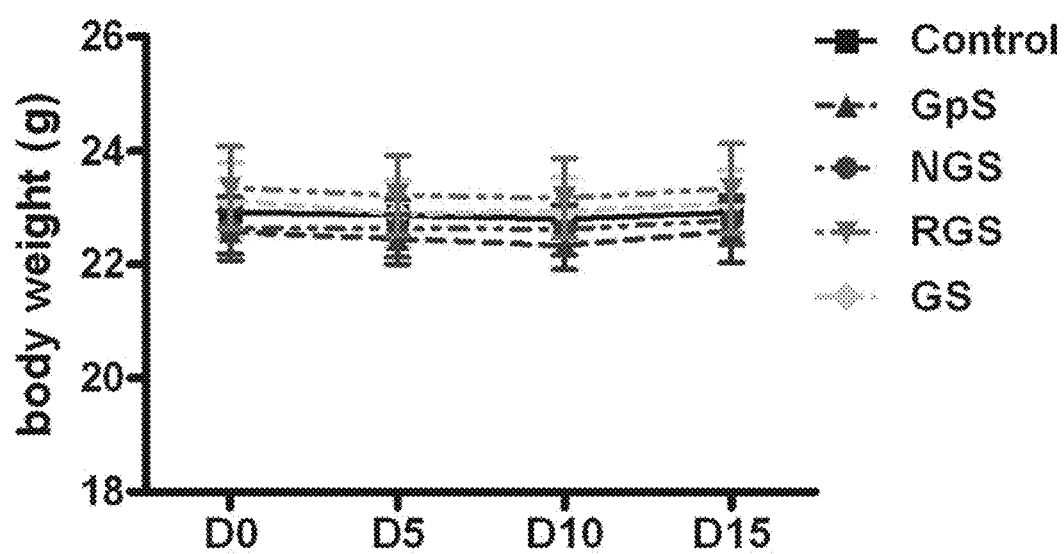
FIG. 16C shows body weight of a time course study of the faecal microbiota of mice from different herbal saponins treatment groups.
Figure 17A:
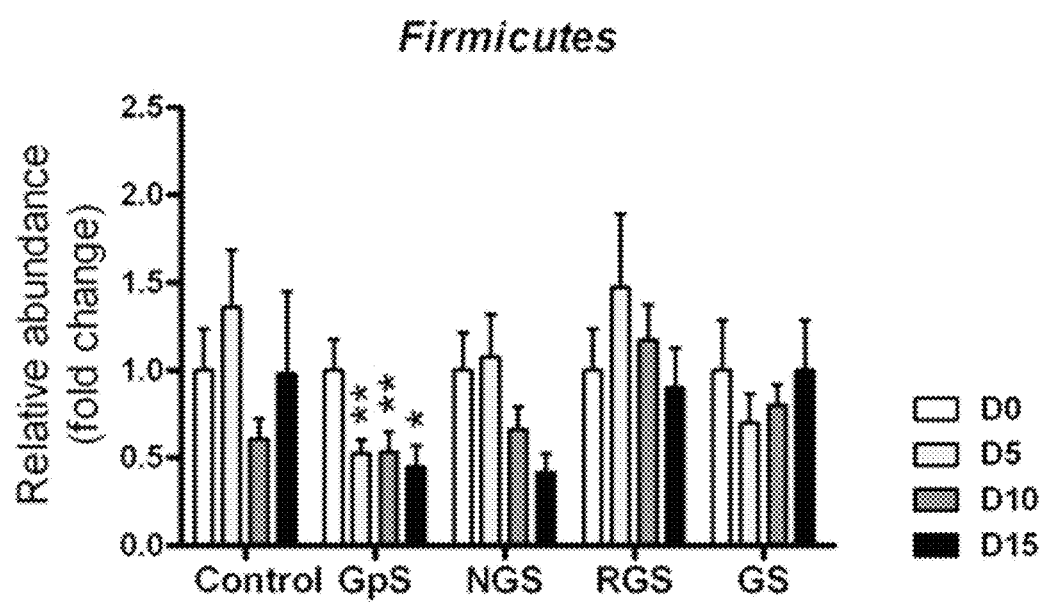
FIG. 17A shows the relative abundance of Firmicutes.
Figure 17B:
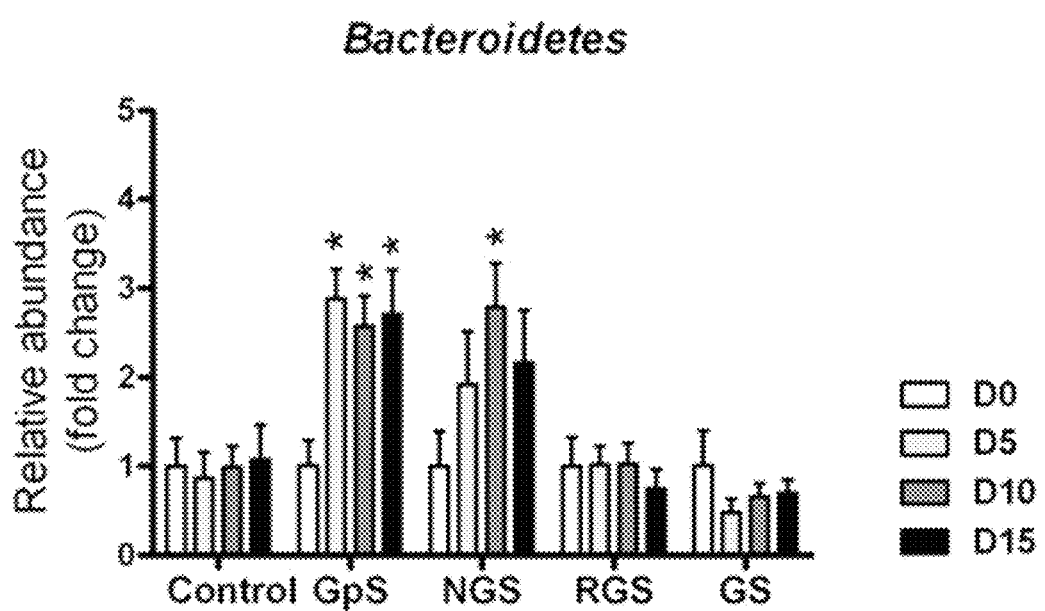
FIG. 17B shows the relative abundance of Bacteroidetes.
Figure 17C:
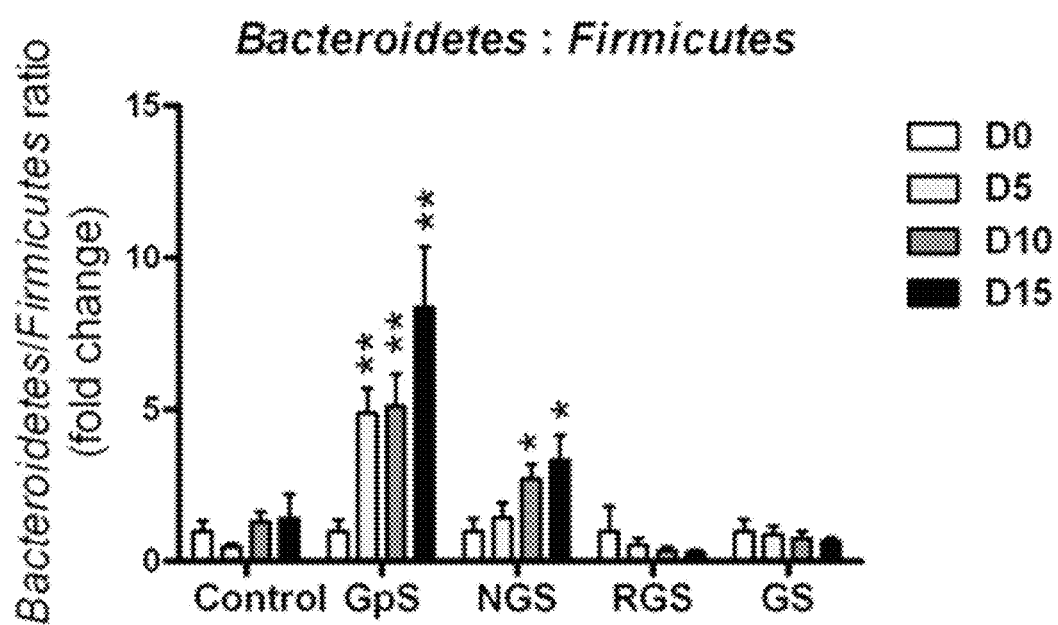
FIG. 17C shows Bacteroidetes/Firmicutes ratio in the faeces of control and herbal saponins-treated mice. Bacterial genomic DNA is extracted from the faecal samples of mice at Day 0, 5, 10 and 15, and the abundance of Firmicutes and Bacteroidetes is determined by qPCR with each phylum-specific 16S rRNA gene primers. The relative abundance of the specific bacteria is normalized to that of the total faecal bacteria, and expressed as fold change over the D0 sample of each mouse. All of the data are presented as the mean±SEM (*P<0.05, **P<0.01 versus D0 samples); n=10/group.

To investigate the impact of herbal saponins on the gut microbiota, faecal samples were collected from the control and four experimental groups at Day 0, Day 5, Day 10 and Day 15 (FIG. 16A). The food intake, body weight and faeces production of mice in all five groups were monitored throughout the experimental period. No significant changes in either food intake or body weight were observed in any of the groups (FIG. 16B and FIG. 16C). As for faecal samples, the faecal microbial fingerprints of ERIC-PCR showed an average of 19 bands per sample, ranging from approximately 100 to 3000 bp with various intensities (FIG. 2B to FIG. 2F). The resulting PCR gel images were converted to digitized profiles and analyzed using PLS-DA tool. Each data point represented faecal microbiota from an individual mouse, 10 mice for each group. The data showed that all treatment groups formed distinct clusters compared to the non-treatment control group (FIG. 3A to FIG. 3D).

qPCR Analysis of the Effect of Saponins on the Relative Abundance of Bacteroidetes and Firmicutes in Faecal Microbiota Firmicutes and Bacteroidetes are the two bacterial phyla dominated in the gut microbiota of healthy mice. To learn more about the compositions of the faecal microbiota upon saponins treatment, the inventors carried out qPCR with 16S rRNA gene specific primers to identify the presence of Firmicutes and Bacteroidetes in the faecal samples. In contrast to the control group, the relative abundance of Firmicutes was significantly decreased in the GpS treatment group (FIG. 17A), whereas the relative abundance of Bacteroidetes was significantly enriched in the GpS and NGS treatment groups (FIG. 17B). In addition, GpS- and NGS-treated mice showed a time-dependent shift in the faecal Bacteroidetes/Firmicutes ratio in favour of Bacteroidetes in the course of 15-day treatment (FIG. 17C).

qPCR Analysis of the Effect of Saponins on the Levels of Common Commensal Bacteria

Figure 18A:
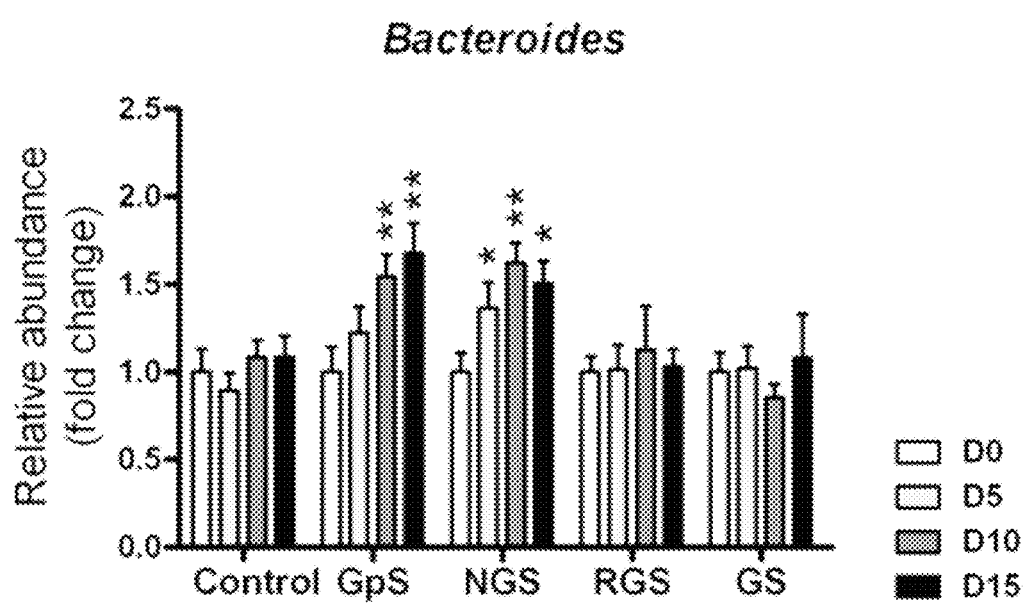
FIG. 18B (*Lactobacillus*)
FIG. 18C (*Bifidobacterium*)
FIG. 18D (*Clostridium* Cluster IV)
FIG. 18E (*Faecalibacterium prausnitzii*). qPCR is used to determine the number of bacteria with each taxon-specific 16S rRNA gene primers and normalized to that of the total faecal bacteria, and expressed as fold change over the D0 sample of each mouse. All of the data are presented as the mean±SEM (*P<0.05, **P<0.01 versus D0 samples); n=10/group.
Figure 18B:
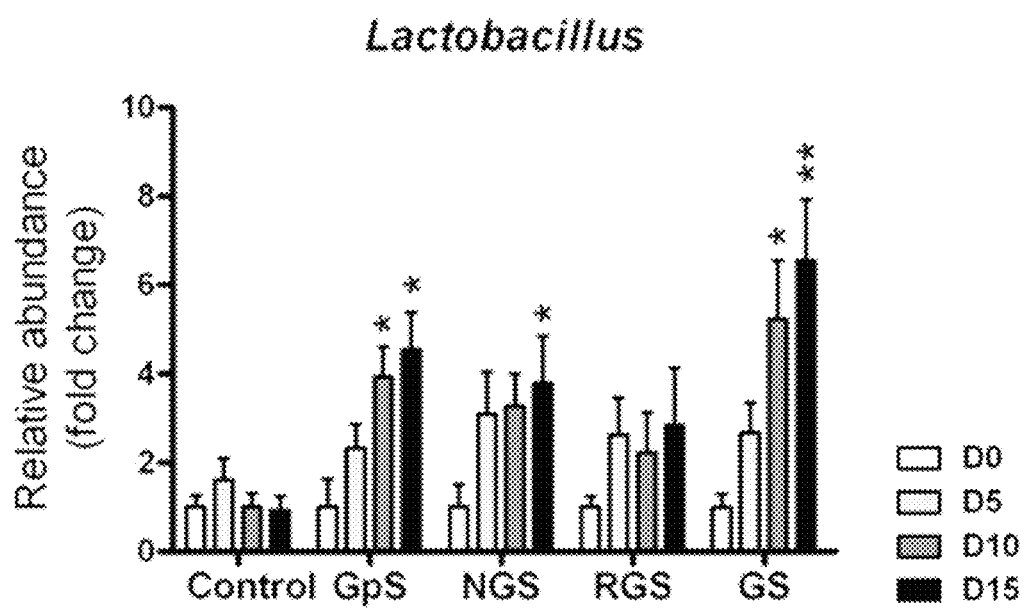
Figure 18C:
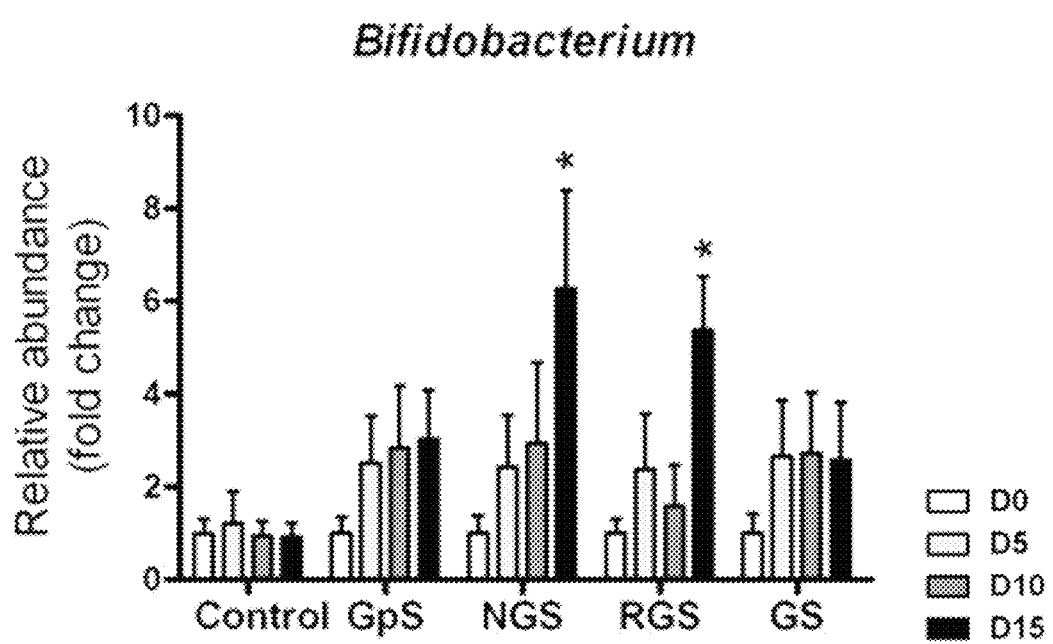
Figure 18D:
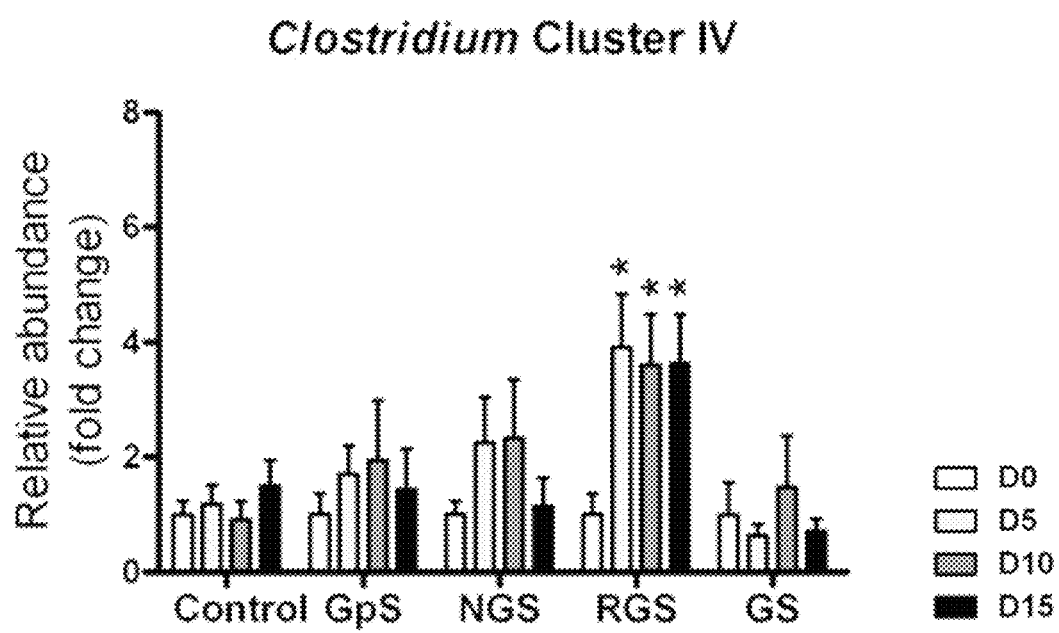
Figure 18E:
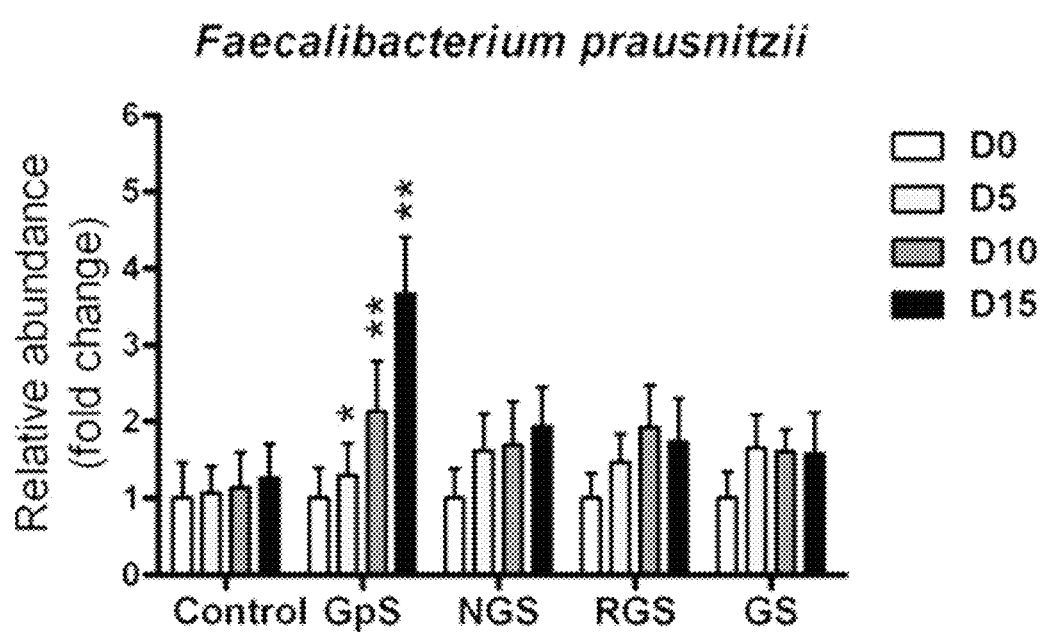

*Bacteroides*, consisting well-known beneficial bacteria, is a predominant genus within Bacteroidetes phylum in the intestinal tract. Both GpS- and NGS-fed mice showed an increased level of *Bacteroides* (FIG. 18A), which was in line with the enrichment of Bacteroidetes in the GpS and NGS groups showed in FIG. 17. Two common beneficial genera, *Bifidobacterium* and *Lactobacillus* were also assessed. The qPCR results showed that GpS, NGS and GS effectively increased *Lactobacillus* (FIG. 18B), whereas NGS and RGS significantly enhanced the level of *Bifidobacterium* (FIG. 18C). In addition, the level of *Clostridium* Cluster IV, which is one of the major clusters of butyrate-producing bacteria, was markedly higher in RGS-treated mice than any other treatment groups (FIG. 18D). Furthermore, within the *Clostridium* Cluster IV, an anti-inflammatory commensal bacterial species, *Faecalibacterium prausnitzii* was significantly enhanced in the GpS-group (FIG. 18E). The above results indicated that the ingested herbal saponins can indeed modulate beneficial bacteria in the gut of the host.

Discussion

Triterpene saponins have been recognized as the main constituents contributing to the health benefits of many dietary and medicinal plants. Ginseng, both raw and processed, *notoginseng* and jiaogulan are among the most common saponin-rich herbal tea used in China and Southeastern Asia. These four herbs share some common saponins, however, they have their own unique profile of saponins. This can somehow explain the overlapping biological activities of the four herbs, as well as the specific health benefits and pharmacological functions of each herb.

Prebiotics are considered as nondigestible food ingredients that can stimulate the growth of beneficial intestinal bacteria, including bifidobacteria and lactic acid bacteria to the benefit of the host health. Synergism between prebiotics and probiotics also reveals impact on health promotion and immunomodulation. In the past ten years, prebiotic research has mainly focused on fibre and polyphenolic compounds. The potential role of triterpenoid saponins has been overlooked.

The results presented here are to address the interaction between the gut microbiota and dietary herbal saponins, and determine whether herbal triterpenoid saponins can act as prebiotics by influencing the host intestinal microbiota. In this embodiment of the present invention, the inventors reported the changes of the faecal microbiota obtained from mice receiving daily oral administration of 500 mg/kg of herbal saponins over a period of 15 days. The dosage used in the present embodiment seems to be at the high side, however, it caused no advert effect to the animals (FIG. 16B to FIG. 16C). One of the known traits of saponins is the poor bioavailability and they are hard to be absorbed through the intestinal wall. This might be one of the reasons that the mice can tolerate oral dosage of saponins up to 1000 mg/kg for long duration of treatment without advert effect. It is known that some dietary phytochemicals are poorly absorbed and the bioavailability of ingested bioactive food compounds is a complex and challenging process. Interestingly, some studies showed that the bioavailability of a single bioactive compound is much poorer than it is consumed with the whole plant extract, suggesting that the consumption of whole herbal tea may show a greater bioavailability than that of saponins alone. The potential synergistic effects of saponins and other phytonutrients on gut microbiota would be of interest for further investigation.

Figure 3A:
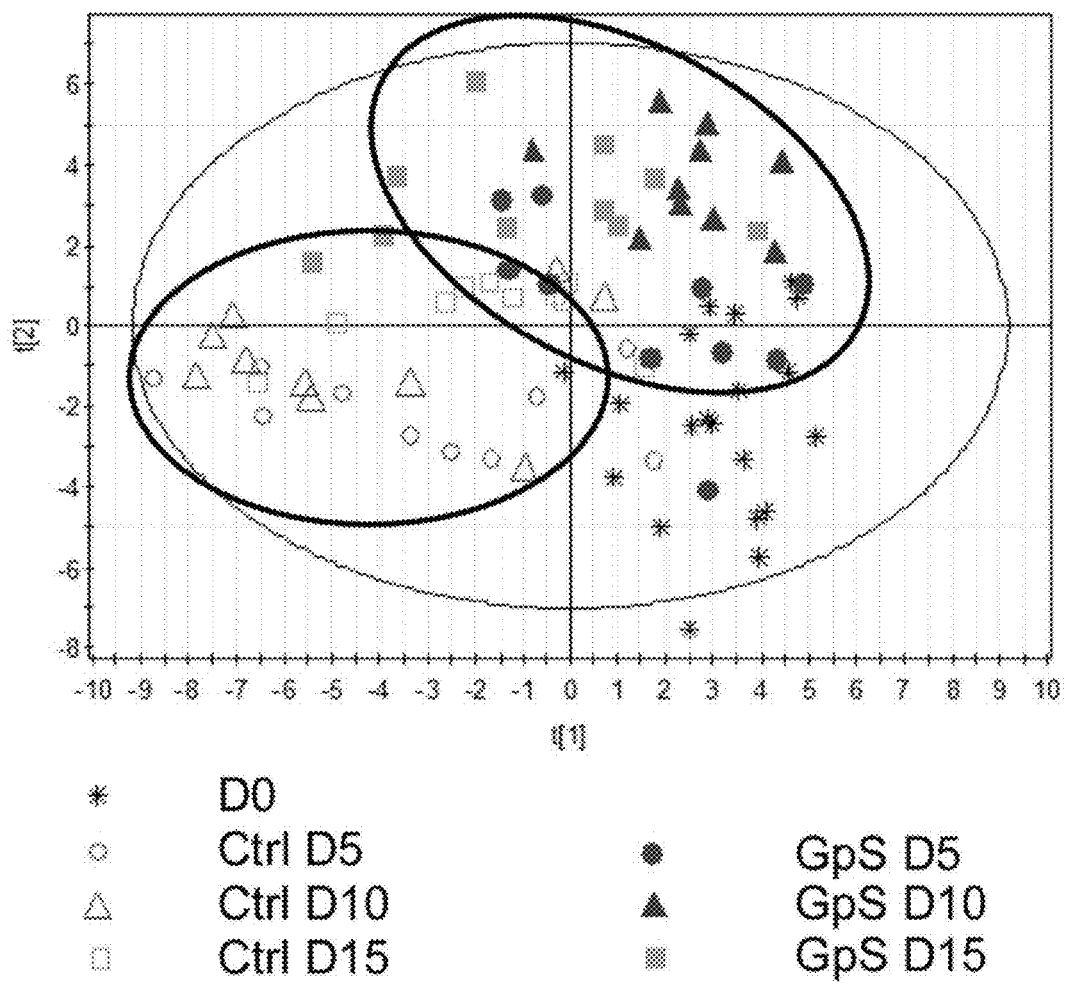
FIG. 3A shows the PLS-DA score plots of ERIC-PCR detail illustrating the comparison of fecal microbial composition between control versus Gp saponins (GpS) treated mice.
Figure 3B:
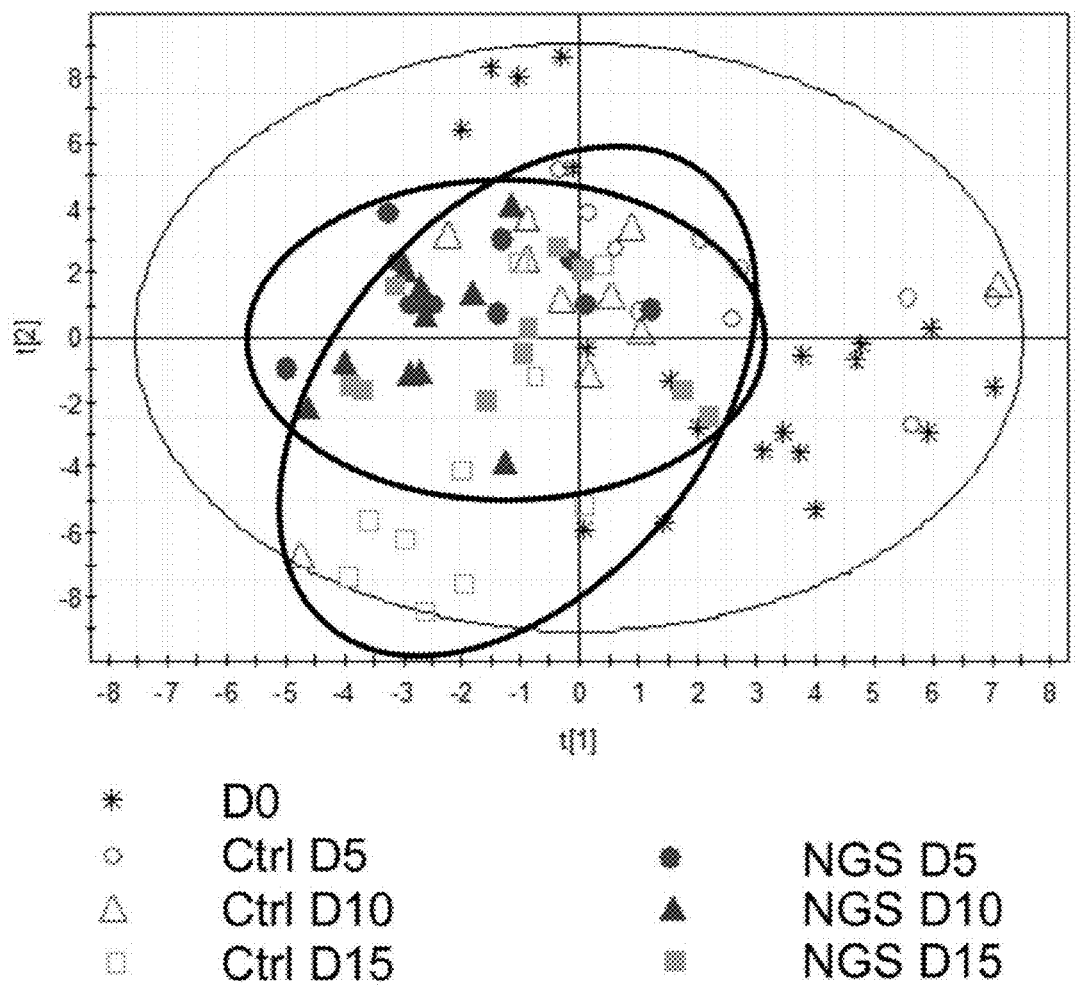
FIG. 3B shows PLS-DA score plots of ERIC-PCR detail illustrating the comparison of fecal microbial composition between control versus *notoginseng* saponins (NGS) treated mice.
Figure 3C:
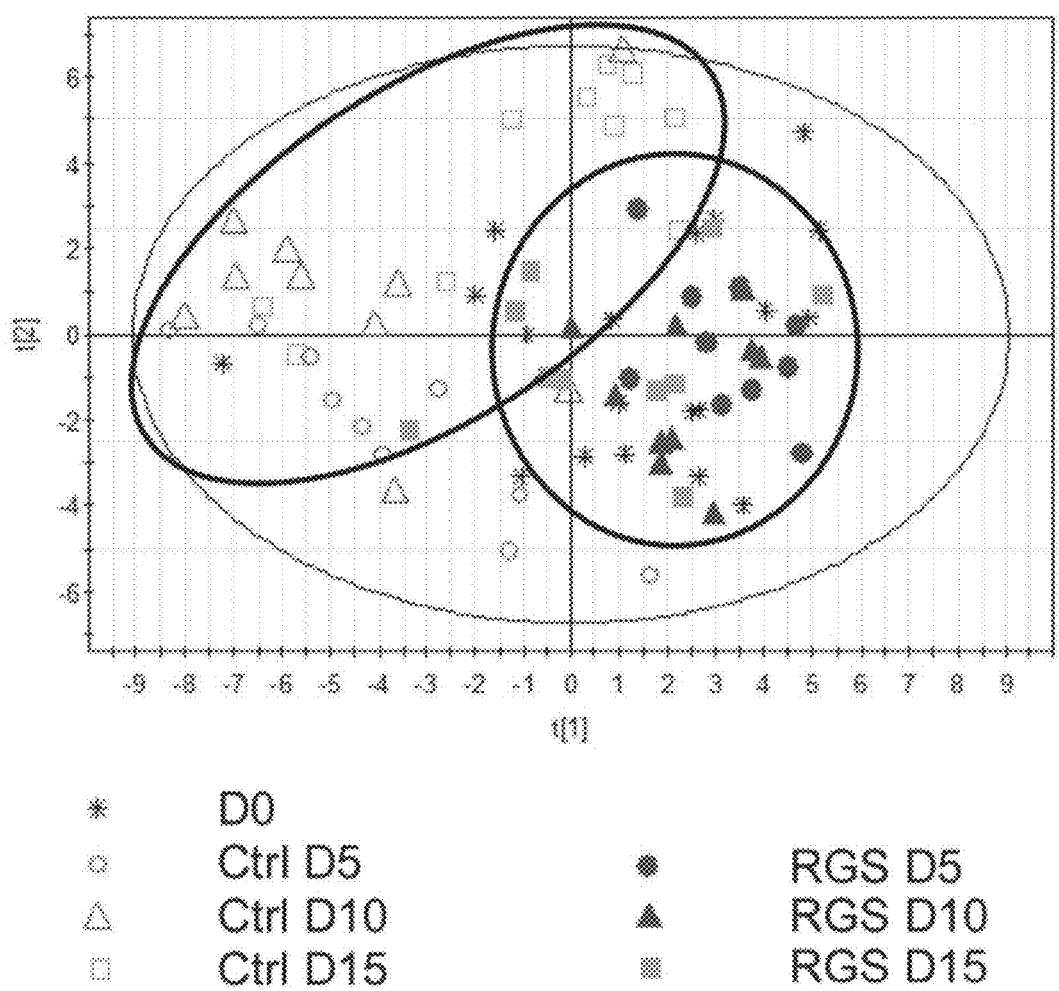
FIG. 3C shows PLS-DA score plots of ERIC-PCR detail illustrating the comparison of fecal microbial composition between control versus red *ginseng* saponins (RGS) treated mice.
Figure 3D:
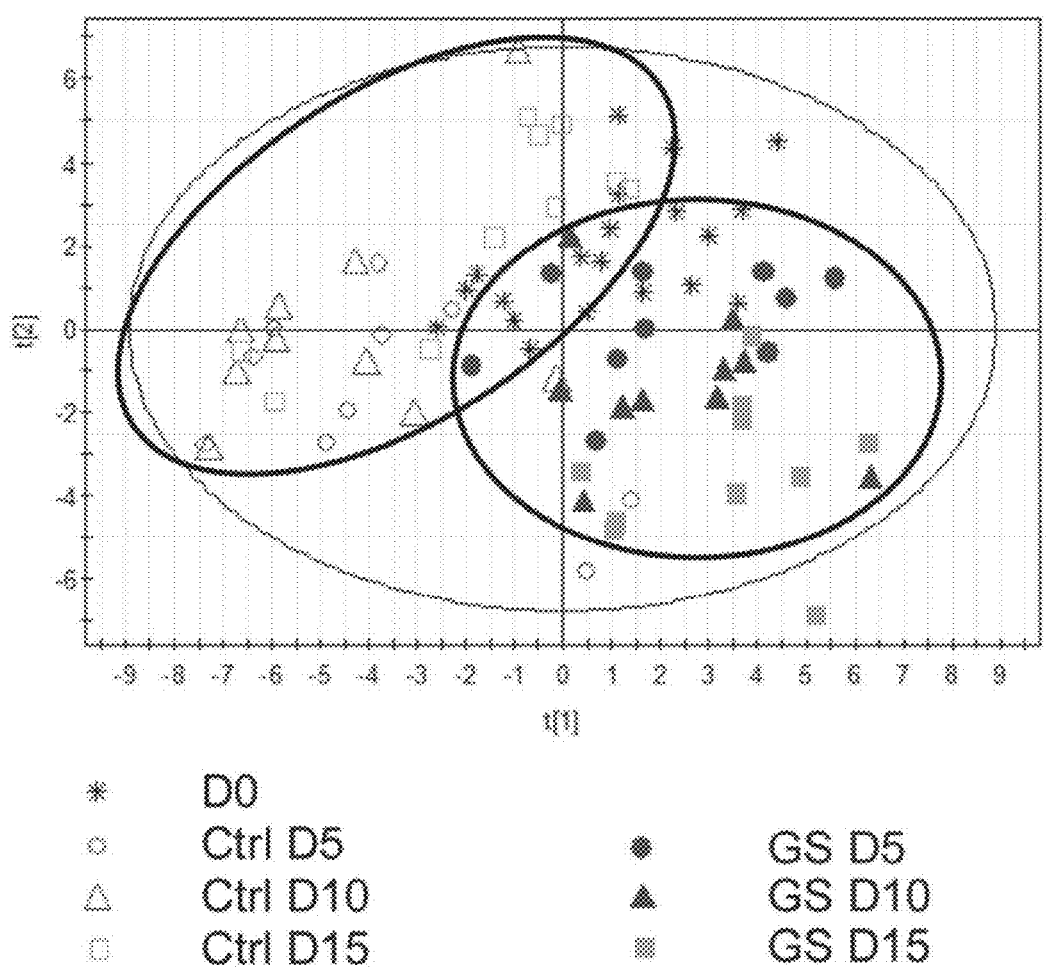
FIG. 3D shows the results of PLS-DA score plots of ERIC-PCR detail illustrating the comparison of fecal microbial composition between control versus *ginseng* saponins (GS) treated mice.
Figure 4A:
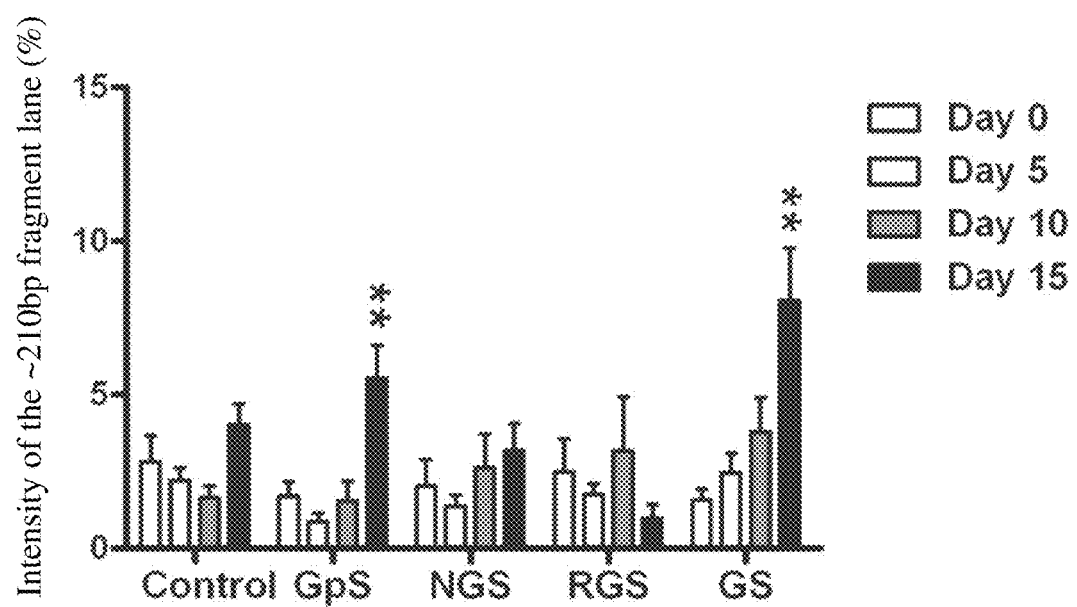
FIG. 4A shows the intensity of the 210 bp fragment among control group.
Figure 4B:
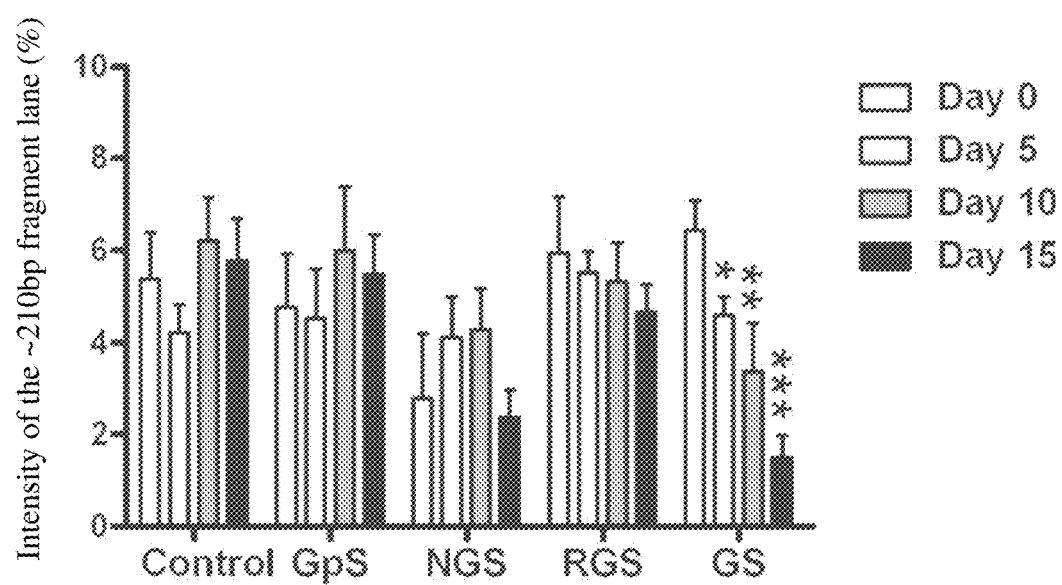
FIG. 4B shows the intensity of the 210 bp fragment among GpS treatment group.
Figure 4C:
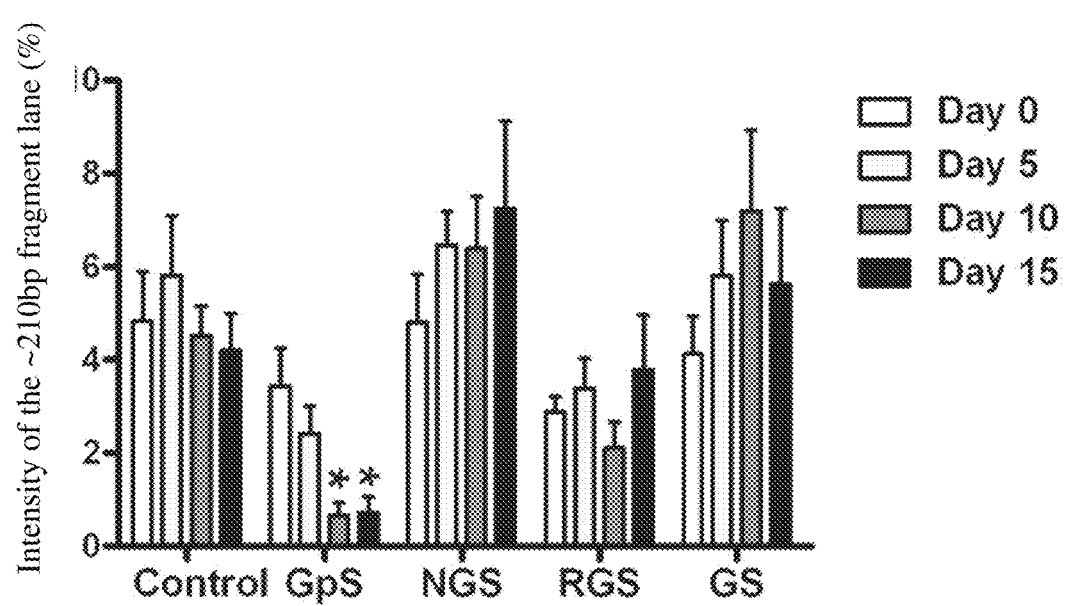
FIG. 4C shows the intensity of the 210 bp fragment among NGS treatment group.
Figure 4D:
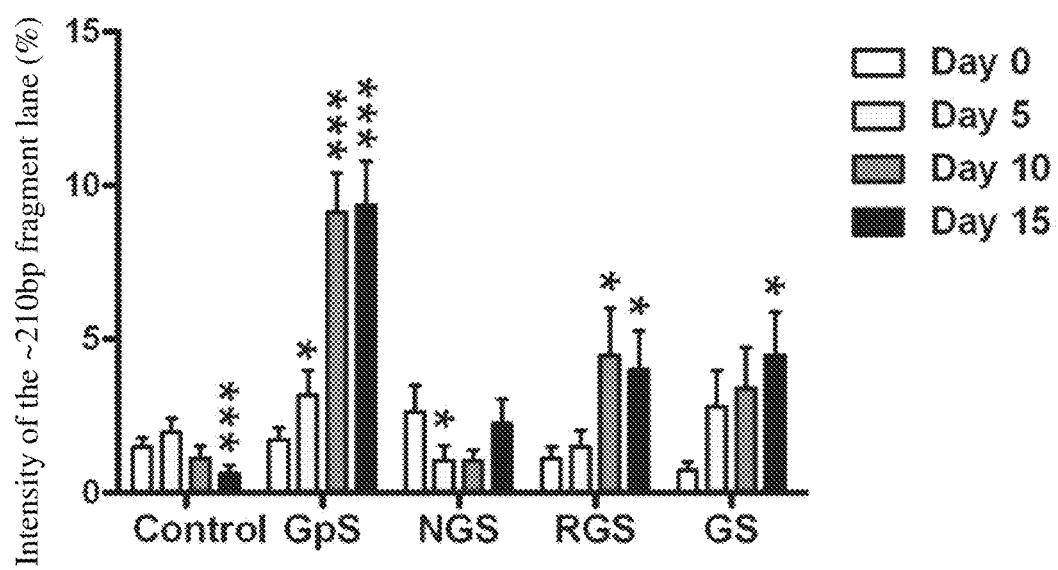
FIG. 4D shows that intensity of the 210 bp fragment among RGS treatment group.

In order to evaluate the changes of microbial profile responding to saponins administration, PLS-DA was applied based on the ERIC-PCR fingerprints of the faecal DNA samples between the treatment and the control groups. The data showed that all treatment groups formed distinct clusters compared to the non-treatment control group. Furthermore, the gut microbiota responded differently to each herbal saponins (FIG. 3A to FIG. 3D). Interestingly, RGS and GS, which share similar chemical profiles, displayed similar profiles in the microbial composition in the relationship to the control group (FIG. 3C and FIG. 3D).

The increased ratio of Firmicutes to Bacteroidetes has been reported to positively correlate with several diseases and symptoms, such as obesity and irritable syndrome. In the present embodiment, the Bacteroidetes/Firmicutes ratio was elevated after the administration of GpS and NGS, indicating that GpS and NGS play a role to revert the aberrant shift of Bacteroidetes to Firmicutes. Certain gut *Bacteroides* has been linked to various health benefits. For example, *Bacteroides* alleviates obesity-associated metabolic syndromes. Certain species of *Bacteroides* such as *B. acidifaciens* can promote IgA production. In the present embodiment, the level of *Bacteroides* was significantly enhanced in mice feeding with GpS or NGS. *Bifidobacterium* and *Lactobacillus* are commonly consumed as probiotics, and were stimulated after administration of the tested saponins. The stimulation of *Lactobacillus* was more prominent with GpS and GS, while the enhancement of *Bifidobacterium* was stronger with NGS and RGS treatments. One of the beneficial effects of *Bacteroides* and *Bifidobacterium*, as revealed in recent reports, is the ability to metabolize ginsenoside Rb1 to compound K, which exhibits potent pharmacological effects in antitumor, anti-inflammatory, and anti-allergic activities. In addition, the present invention echoes the results of studies on the effects of polyphenol-rich green and black tea extracts on enhancing the *Bifidobacterium* species and the associated bifidogenic effects. This similar effect suggests that the dietary herbal saponins may possess prebiotic potential.

Another interesting finding was the enhancement effect of GpS on a butyrate producing bacterium, *Faecalibacterium prausnitzii*. Butyrate is a short chain fatty acid (SCFA) derived from the microbial metabolites of dietary fibre in the gut. Butyrate exhibits a wide range of health effects from anti-inflammatory properties to enhancement of intestinal barrier function. Due to its multiple epigenetic effects, butyrate has been well documented for various diseases prevention and treatment. *Faecalibacterium prausnitzii* is the most important butyrate-producing bacterium. It belongs to the *Clostridium* cluster IV, one of the main sources of butyrate-producing microbes, which was also found significantly elevated in the RGS-treated mice. *F. prausnitzii* has been reported to ameliorate dysbiosis and mediate protective effects in Crohn's disease (CD) patients. The presence of *F. prausnitzii* is directly associated with the reduction of low-grade inflammation in obesity and diabetes independently of calorie intake. Thus, modulation of *F. prausnitzii* by exogenous substances may have preventive or therapeutic applications to human health. Accordingly, saponins of GS, RGS, NGS and Gp of the present invention modulate beneficial gut commensal microbiota and leads to health-promoting effects.

Conclusion

The impact of the four herbal saponins on common commensal bacteria in a mammalian gut of the present invention is clearly demonstrated. The tested dietary saponins exerted prebiotic-like effects, enhancing bacteria known to be beneficial to the host. The present invention shows the long-recognized beneficial effects of dietary herbal saponins in gut microbiota. The present invention provides the use of dietary saponins as prebiotics. The present invention also provides the use of dietary saponins in combination with other prebiotics to modulate beneficial bacteria in the gut.

Further Embodiment of the Present Invention

Preventive Treatment of GpS Reduced the Intestinal Polyps in Apc$^{Min/+}$ Mice

Figure 19A:
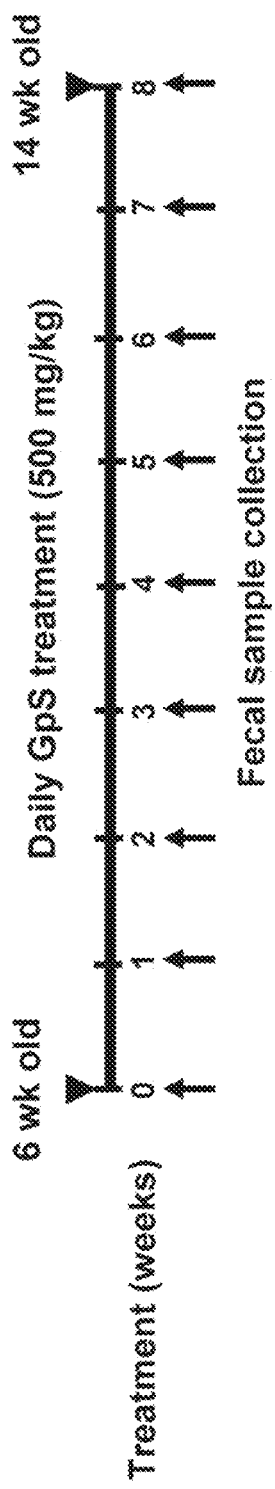
FIG. 19A is the schematic diagram of the experiment design to test the effect of GpS on the intestinal polyp formation in the Apc$^{Min/+}$ mice.
Figure 19B:
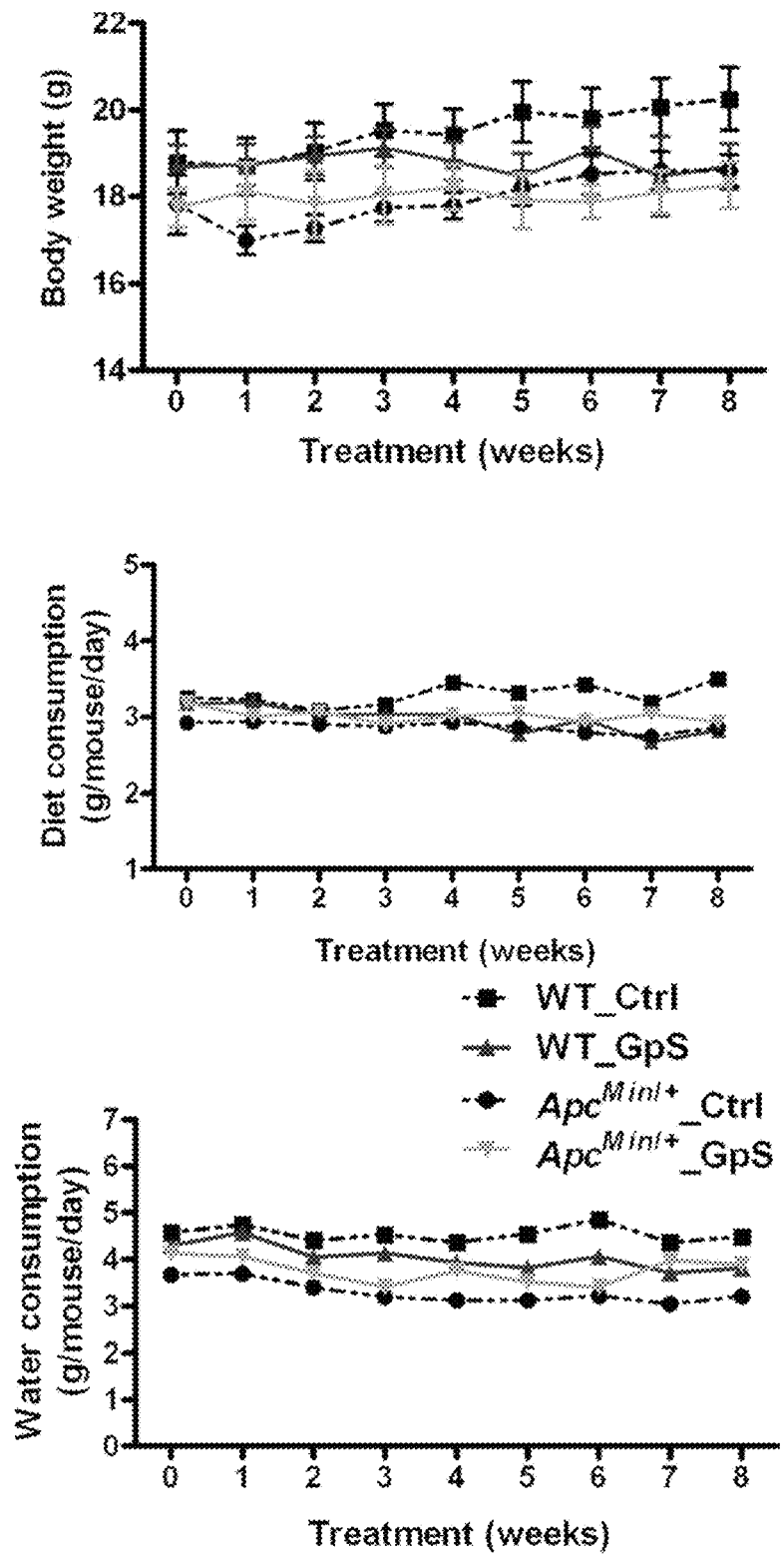
FIG. 19B shows the profiles of body weight, diet and water consumption.
Figure 19C:
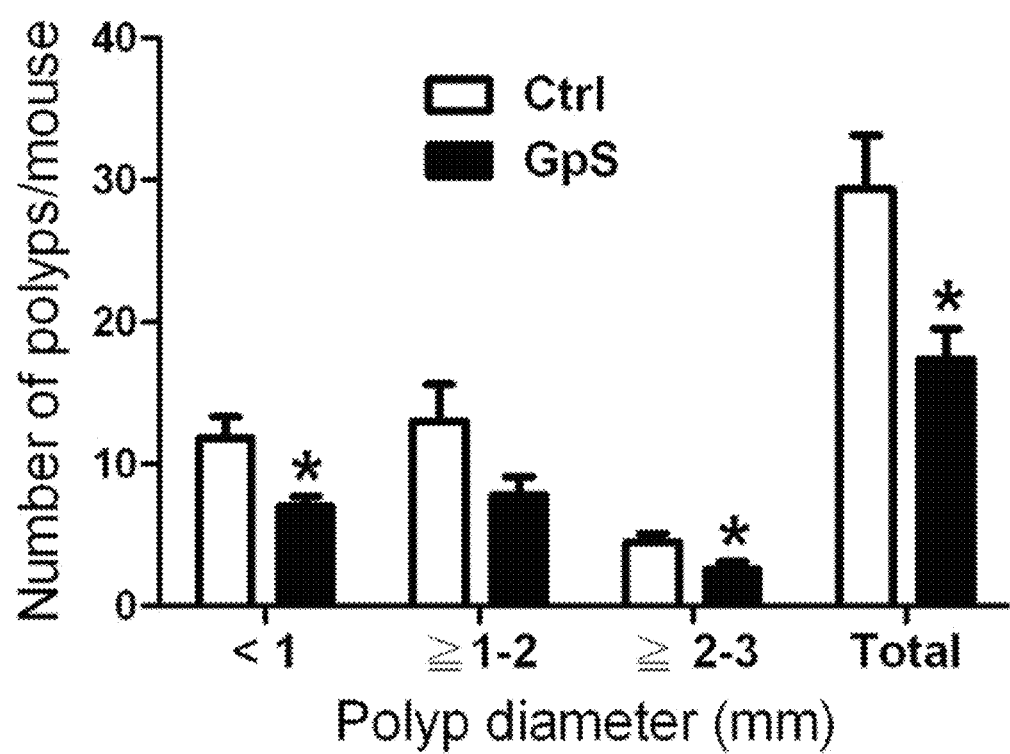
FIG. 19C shows effect of GpS on the size distribution of polyps. Data is presented as the mean±SEM (*P<0.05 versus control); n=6/group.
Figure 19D:
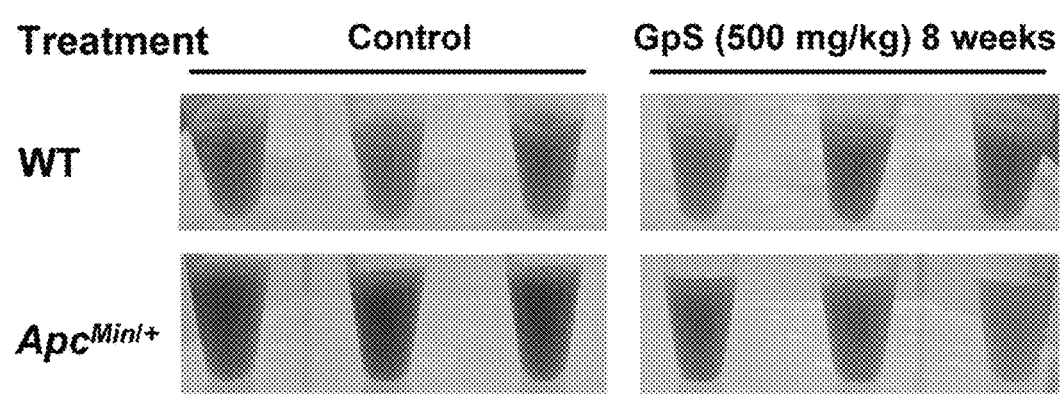
FIG. 19D shows the fecal extracts of the WT and Apc$^{Min/+}$ mice with or without GpS treatment for 8 weeks.

Normally, the intestinal polyps can be found in Apc$^{Min/+}$ mice at the age of 8-week. To investigate the preventive effects of GpS on polyp formation, the treatment was started on 6 weeks old mice. Single dose of GpS at 500 mg/kg or solvent control (0.5% CMC) was given daily by gavage for 8 weeks. The treatment scheme is illustrated in FIG. 19A. Throughout the experimental period, none of the treated animals showed weight loss and abnormal food or water intake (FIG. 19B). (FIG. 19C) showed that administration of GpS significantly reduced the number of polyps by 40.68% (P<0.05) when compared with the untreated controls. In the study, we found that the polyp formation in Apc$^{Min/+}$ mice was often accompanied with blood feces and darker color of the fecal extracts compared with their WT littermates. Interestingly, in the later stage of the treatment scheme, the fecal extracts again appeared in darker color in the untreated, but not in the treated Apc$^{Min/+}$ mice (FIG. 19D).

Figure 20A:
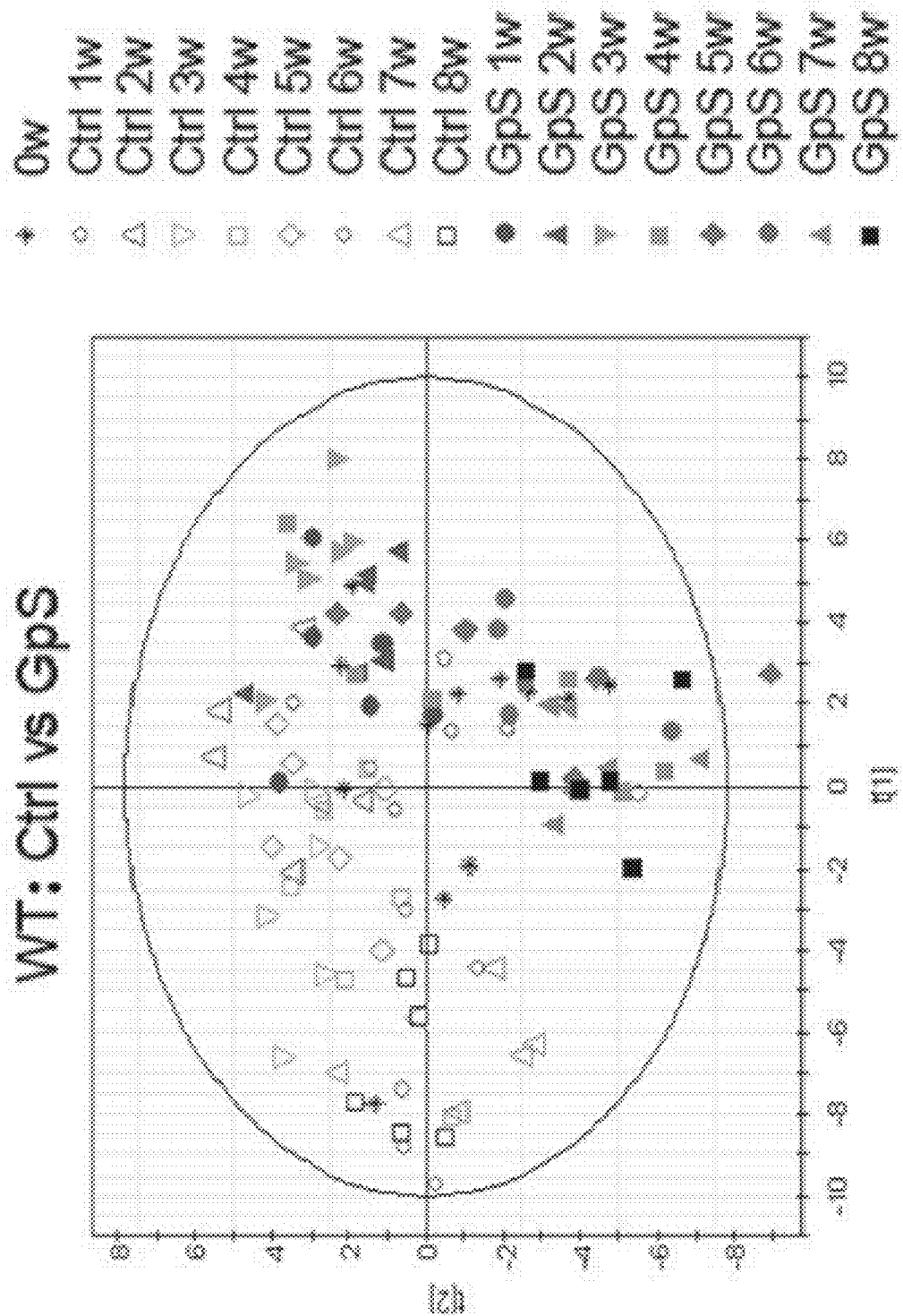
FIG. 20A shows the time course PLS-DA plots of ERIC-PCR DNA profile of WT and FIG. 20B shows the time course PLS-DA plots of ERIC-PCR DNA profile of Apc$^{Min/+}$ mice treated and untreated with GpS. Open symbols: control mice; Solid symbols: GpS-treated mice (n=6/group). Fecal genomic DNA is subjected to ERIC-PCR, and the gel pictures are digitized by Image Lab 3.0 system (Bio-Rad). Based on the distance and the intensity of each DNA bands, SIMCA-P 12.0 tool is applied to obtain the PLS-DA score plots.
Figure 20B:
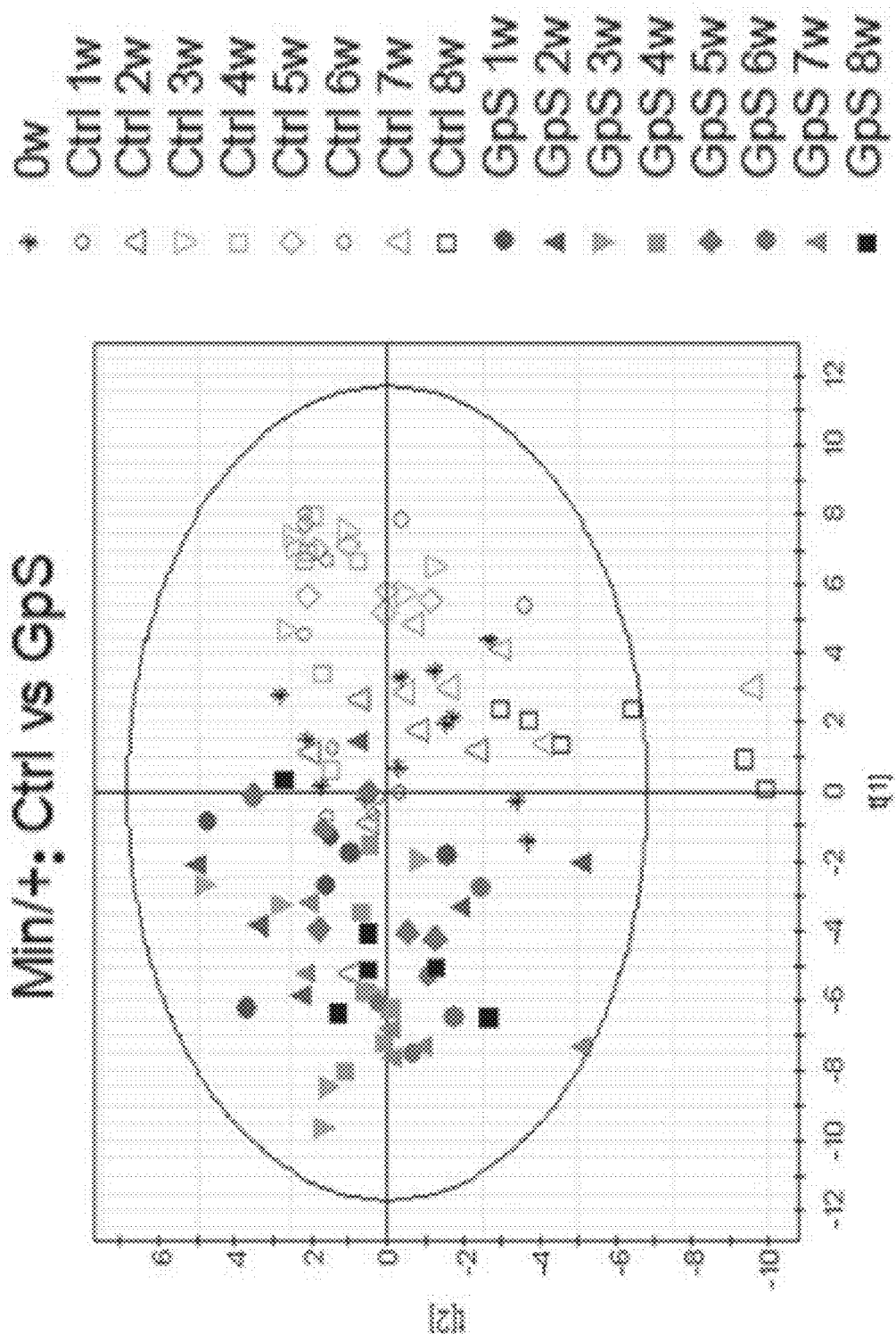

GpS Treatment Significantly Altered the Fecal Microbiome of WT and Apc$^{Min/+}$ Mice In order to understand the gut microbiota composition upon GpS treatment in Apc$^{Min/+}$ mice and their wild-type littermates, fecal samples were collected before the treatment, and weekly after the treatment for eight consecutive weeks (FIG. 19A). The comparative study of microbial profiles between GpS-treated and untreated mice was conducted using ERIC-PCR analysis of the collected fecal samples. The resulting digitized data of ERIC-PCR fingerprints was analyzed by PLS-DA. Results showed a clear segregation of the microbial communities between the controls and GpS treated mice. This phenomenon existed in both the WT (FIG. 20A) and Apc$^{Min/+}$ mice (FIG. 20B).

Figure 20C:
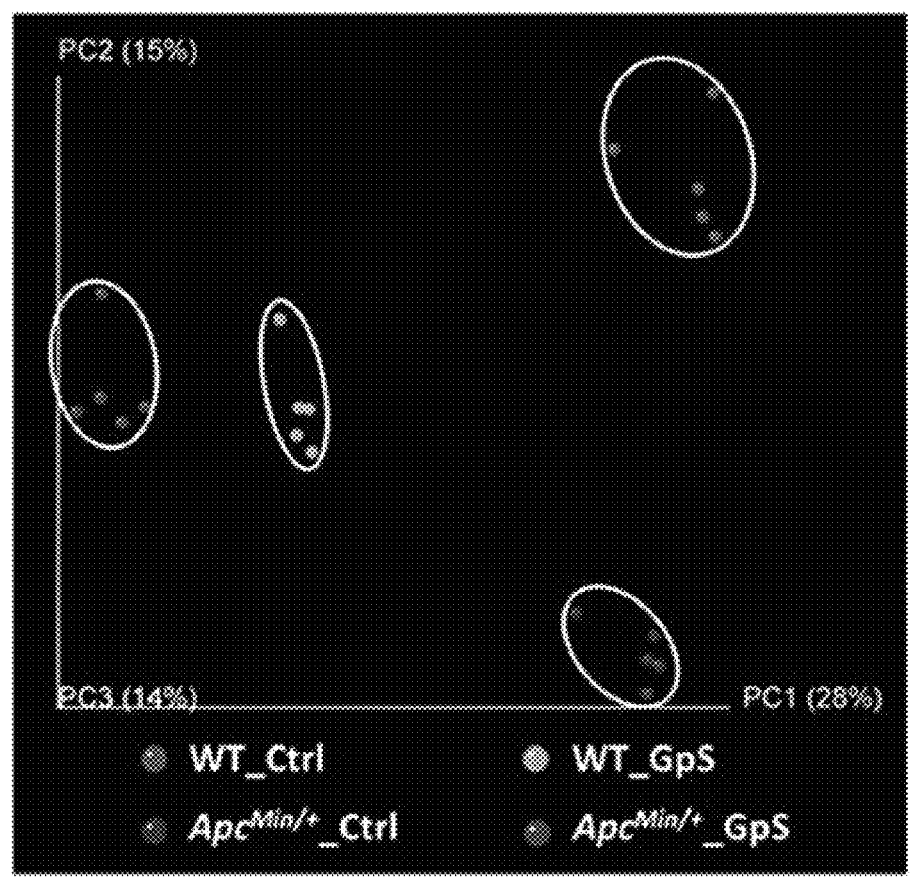
Figure 20E:
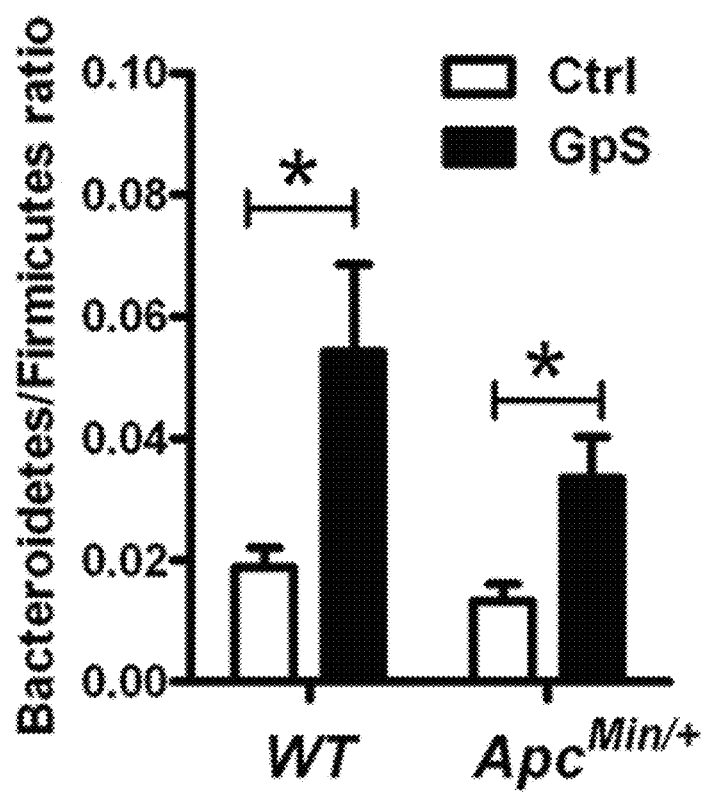
Figure 21:
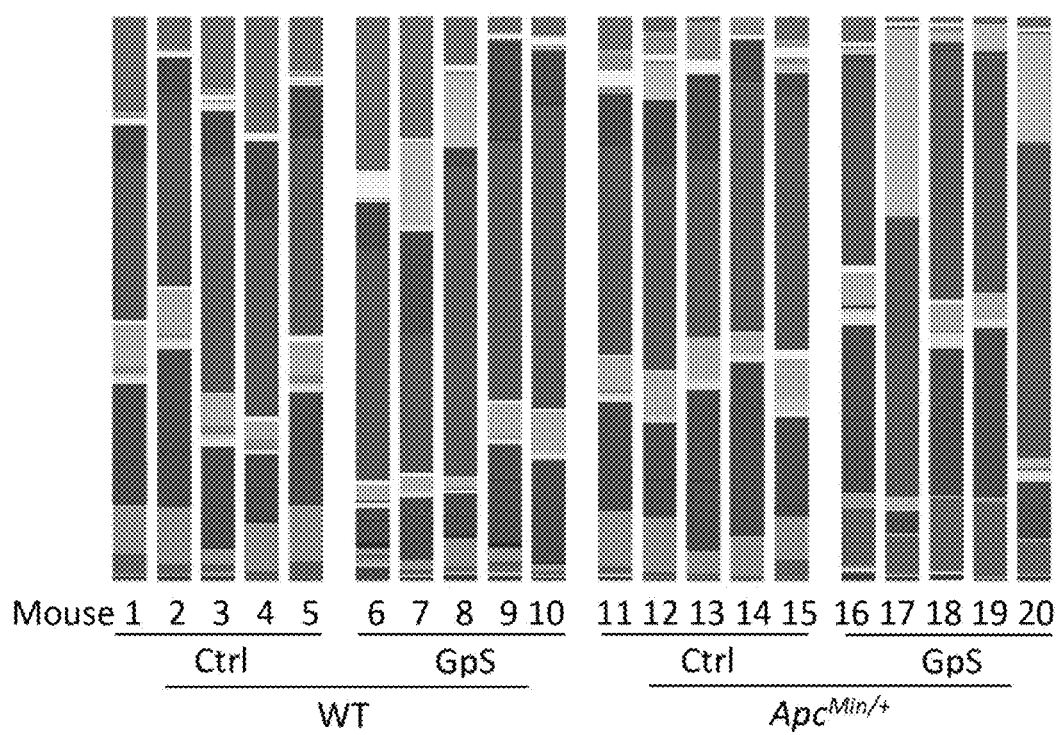
FIG. 21 shows a bar chart of the relative abundance of bacterial genera in the individual mice of different treatment groups.

To further examine the detailed composition of the fecal microbiome, 16S rRNA gene pyrosequencing was performed on the fecal DNA obtained from the WT and Apc$^{Min/+}$ mice at the W8 time point. Five fecal samples per group and a total of 20 samples were subjected for pyrosequencing. A total of 591,640 reads that passed quality control were produced with an average of 29,582 sequences per sample. PCoA plots showed a clear separation among the fecal microbiome of the four experiment groups (FIG. 20C). The relative abundance of dominant phylum in the fecal microbiota also altered upon GpS treatment (FIG. 20D). In the WT mice, GpS treatment markedly reduced the abundance of Firmicutes (from 39.42% down to 21.58%). In the meantime, it substantially increased the relative abundance of Proteobacteria (from 44.95 to 62.24%). In Apc$^{Min/+}$ mice, compared with the controls, mice treated with GpS exhibited relatively lower abundance of Tenericutes (from 6.10 down to 1.08%). In addition, in contrast to the untreated mice, the increased Bacteroidetes/Firmicutes ratio can be observed in both the GpS-treated Apc$^{Min/+}$ and WT mice (FIG. 20E). Furthermore, the pyrosequencing data also revealed that GpS altered the microbial communities at genus level (FIG. 21).

Figure 22A:
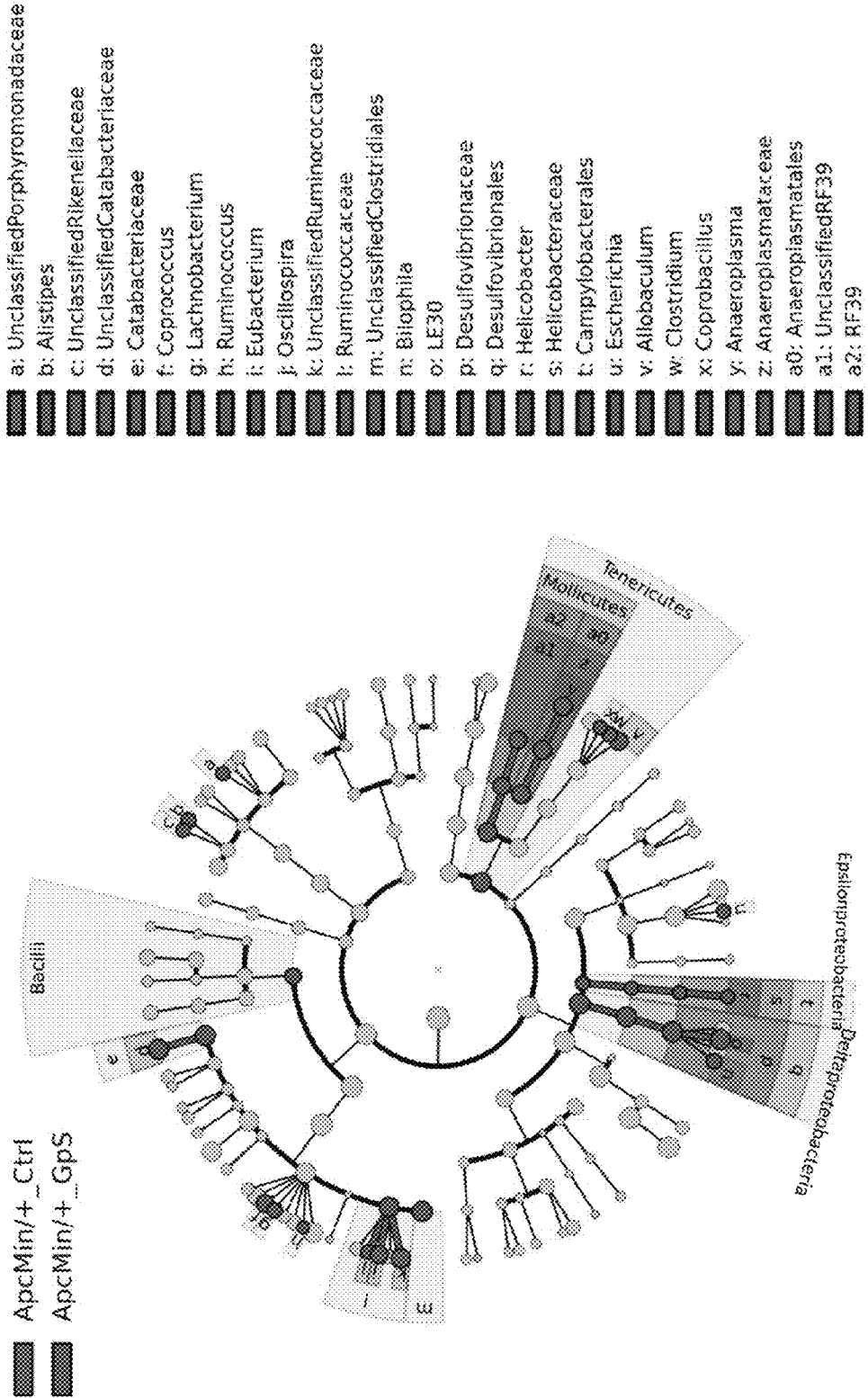
FIG. 22A-F shows the identification of the key phylotypes in the fecal microbiome of GpS-treated and untreated Apc$^{Min/+}$ mice.
Figure 22B:
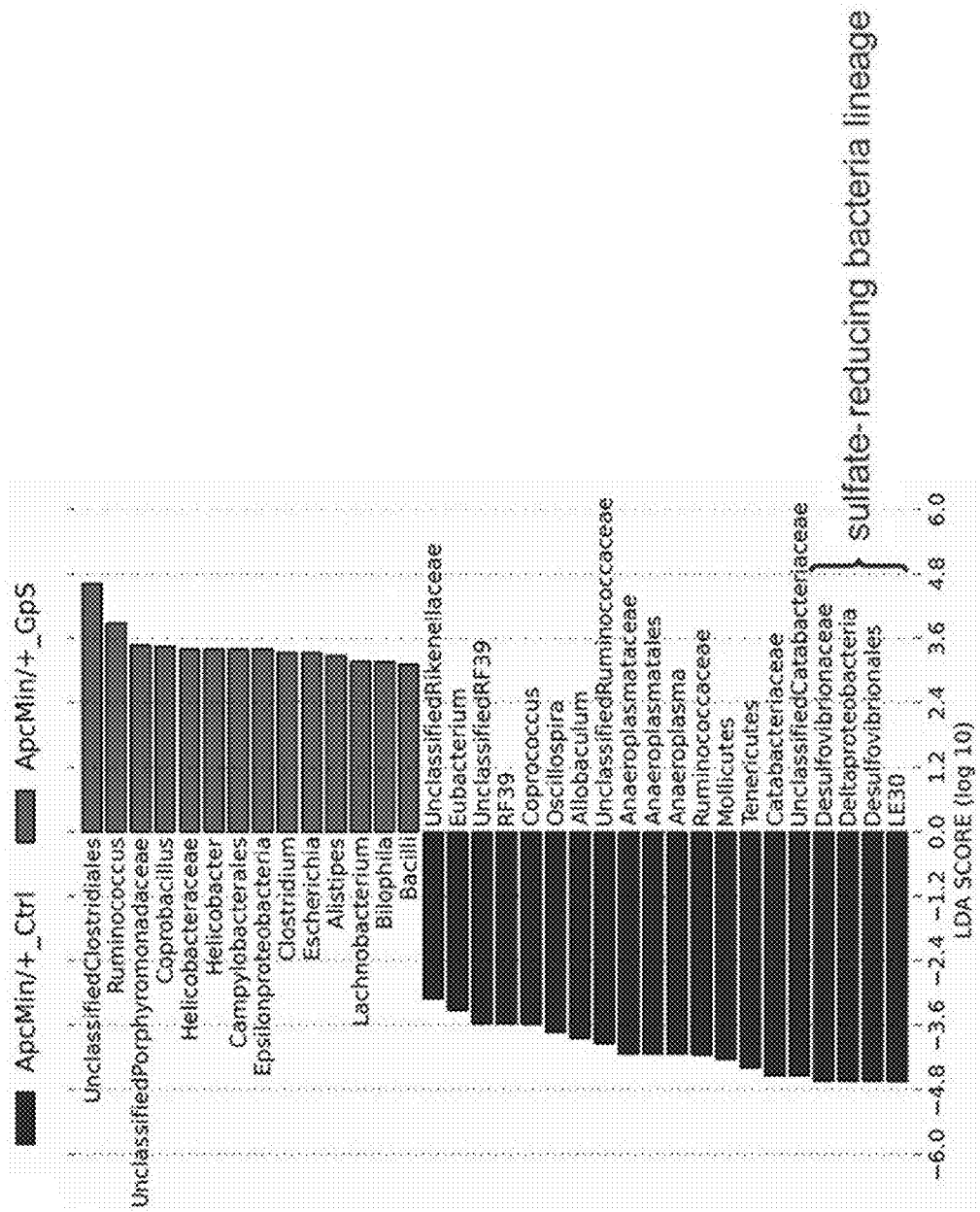
Figure 22C:
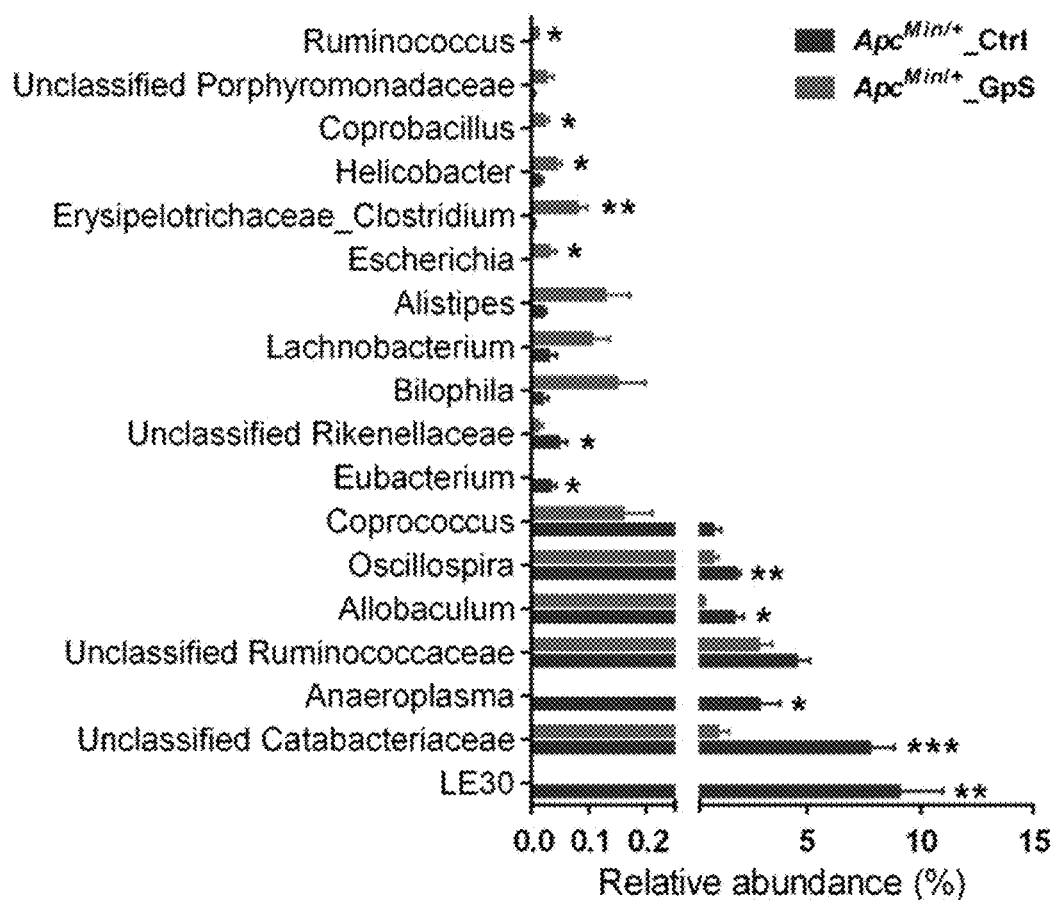

GpS Treatment Significantly Reduced Sulfate-Reducing Bacteria in Apc$^{Min/+}$ Mice The inventors then further investigated the key phylotypes responsible for the differences of fecal microbiome by LefSe tool. Within the Apc$^{Min/+}$ mice group, four lineages were identified as the main contributors to the differences in the fecal microbiome structure between GpS-treated and untreated Apc$^{Min/+}$ mice. Three lineages, including Deltaproteobacteria-Desulfovibrionales-Desulfovibrionaceae-LE30, Tenericutes-Mollicutes-RF39-Unclassified RF39, and Tenericutes-Mollicutes-Anaeroplasmatales-Anaeroplasmataceae-*Anaeroplasma*, were overrepresented in the untreated Apc$^{Min/+}$ mice, whereas Epsilonproteobacteria-Campylobacterales-Helicobacteraceae-*Helicobacter* lineage was relatively enriched in the GpS-treated Apc$^{Min/+}$ mice (FIG. 22A). It was noteworthy that genus LE30, affiliated with the sulfate-reducing bacteria (SRB) family Desulfovibrionacea, was identified with a very high LDA score (FIG. 22B), reflecting marked abundance in Apc$^{Min/+}$ control mice. Interestingly, LE30 was completely depleted in the GpS-treated Apc$^{Min/+}$ mice. Likewise, *Anaeroplasma* and *Eubacterium* were also absent from the GpS-treated individuals. Conversely, *Ruminococcus, Coprobacillus* and *Escherichia* were unique to the GpS-treated Apc$^{Min/+}$ mice. All these unique genera showed statistically significant difference in the relative abundance between the GpS-treated and untreated Apc$^{Min/+}$ mice (FIG. 22C).

Figure 22D:
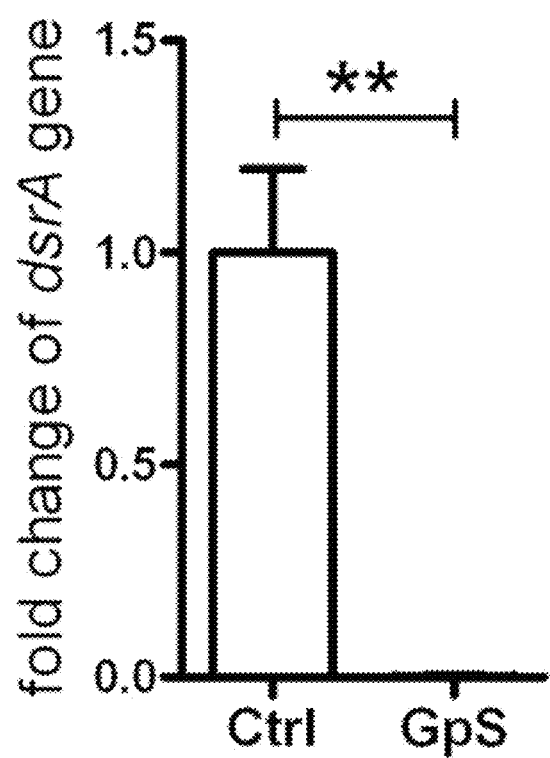
Figure 22E:
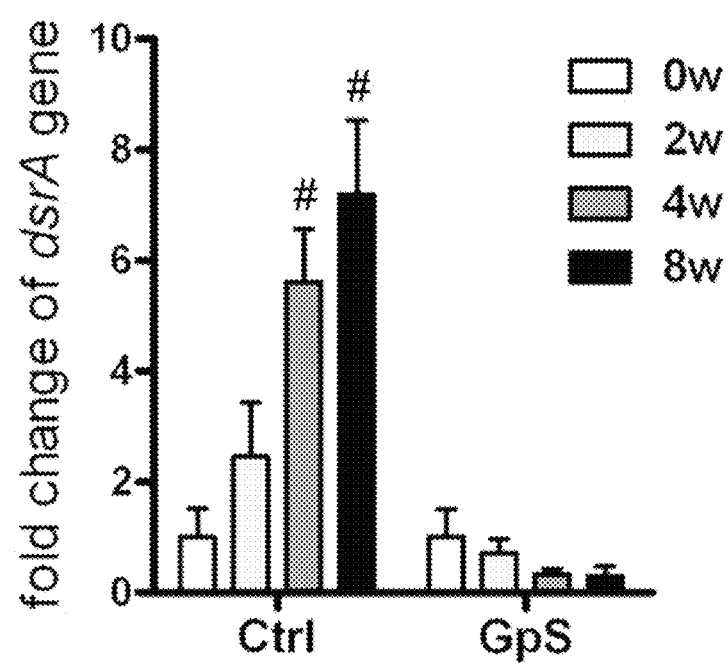
Figure 22F:
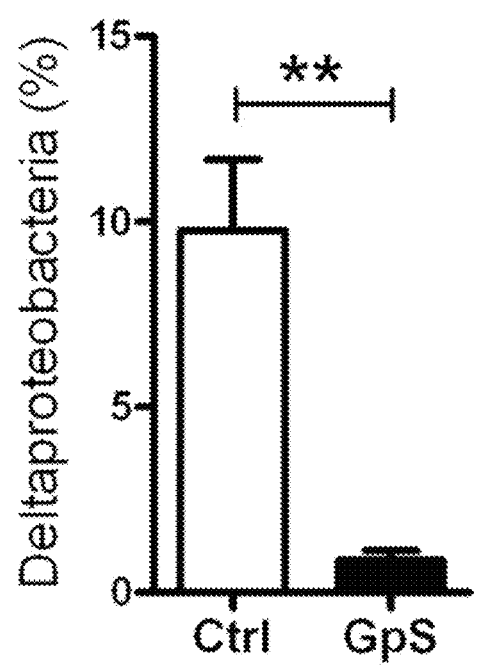

SRB are able to reduce sulfate to hydrogen sulfide ($H_2S$) through a process termed "dissimilatory sulfate reduction". Hydrogen sulfide can damage the intestinal epithelium leading to chronic inflammation and imbalance between cellular proliferation and apoptosis, indicating a possible association of SRB with CRC. The dissimilatory (bi)sulfite reductase (dsrA) gene, a crucial gene of SRB, is involved in the energy metabolism of SRB and have been employed as a reliable marker for the presence of SRB. The inventors then performed real-time qRT-PCR of the dsrA gene to quantify SRB in the W8-fecal samples. Compared with the controls, significant down-regulation of dsrA was observed in the fecal DNA samples of GpS-treated Apc$^{Min/+}$ mice (FIG. 22D), which is in line with the data of decreased SRB lineage obtained by pyrosequencing analysis (FIG. 22B). The inventors also performed qRT-PCR of dsrA in fecal samples collected at different experimental time points. The level of dsrA increased in the control, while decreased in the GpS-treated Apc$^{Min/+}$ in a time-dependent manner. These finding indicates a correlation between polyp development and SRB abundancy (FIG. 22E). Deltaproteobacteria is one of the major phylogenetic lineages of SRB. Compared with the controls, GpS-treated Apc$^{Min/+}$ mice showed a substantial reduction in the relative abundance of Deltaproteobacteria as validated by pyrosequencing analysis (FIG. 22F). GpS effectively suppresses SRB, for which the polyp formation was reduced.

GpS Treatment Affected Beneficial Bacteria in Treated Mice

Figure 23A:
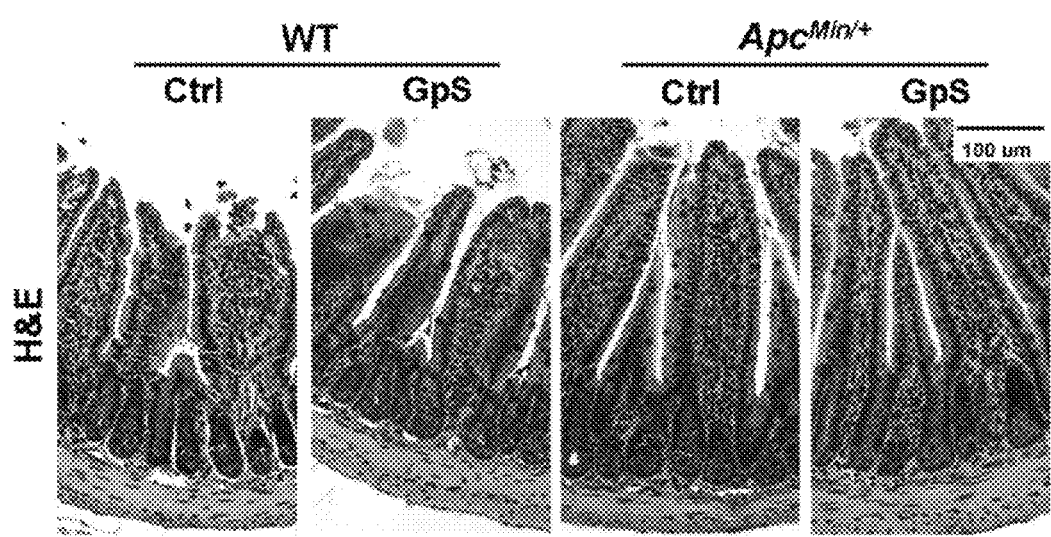
FIG. 23A-F shows the effect of GpS on the intestinal epithelium. Intestinal tissues are collected after 8 weeks of treatment with or without GpS from the WT and Apc$^{Min/+}$ mice.
Figure 23B:
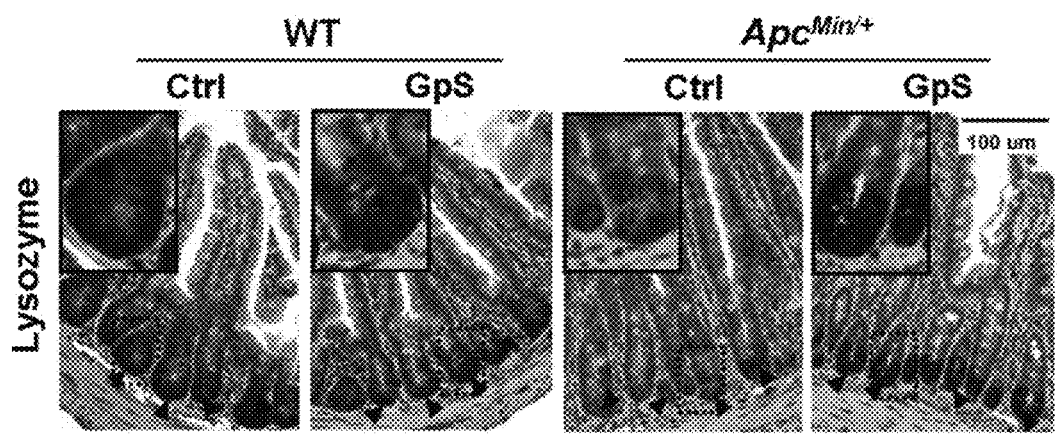
Figure 23C:
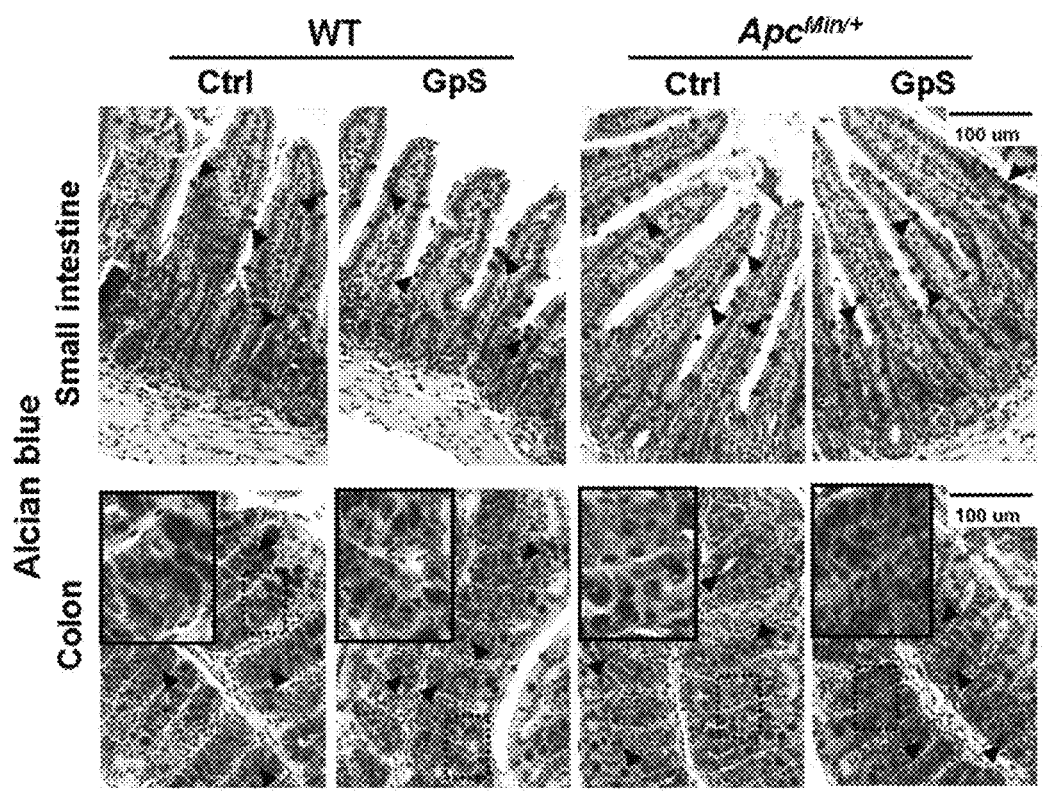
Figure 23D:
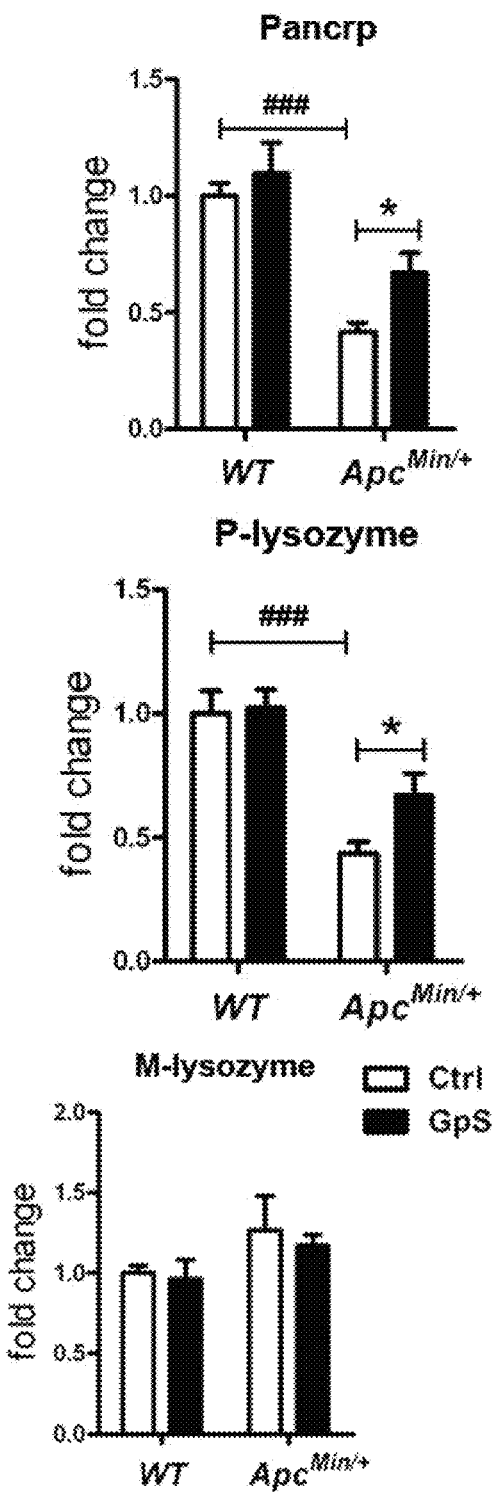
Figure 23E:
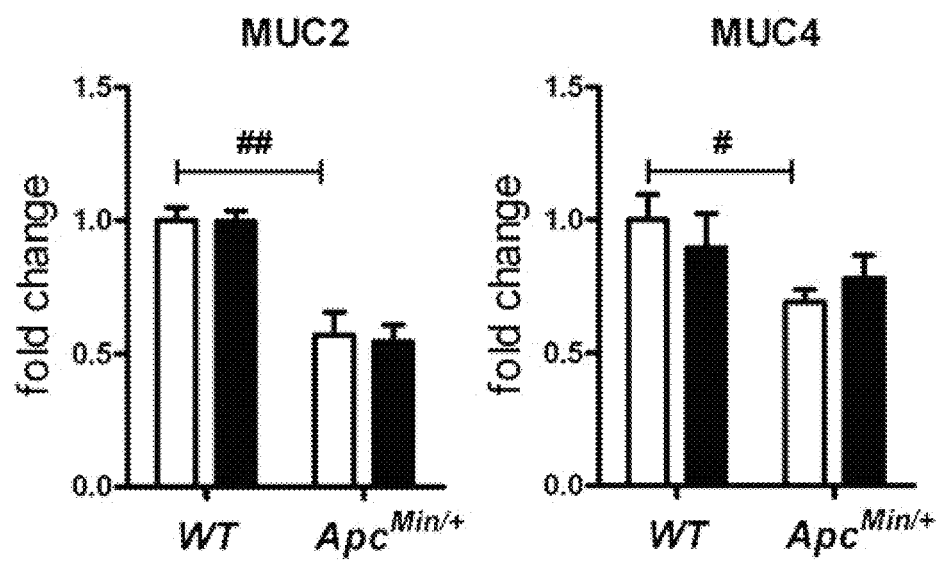
Figure 23E:
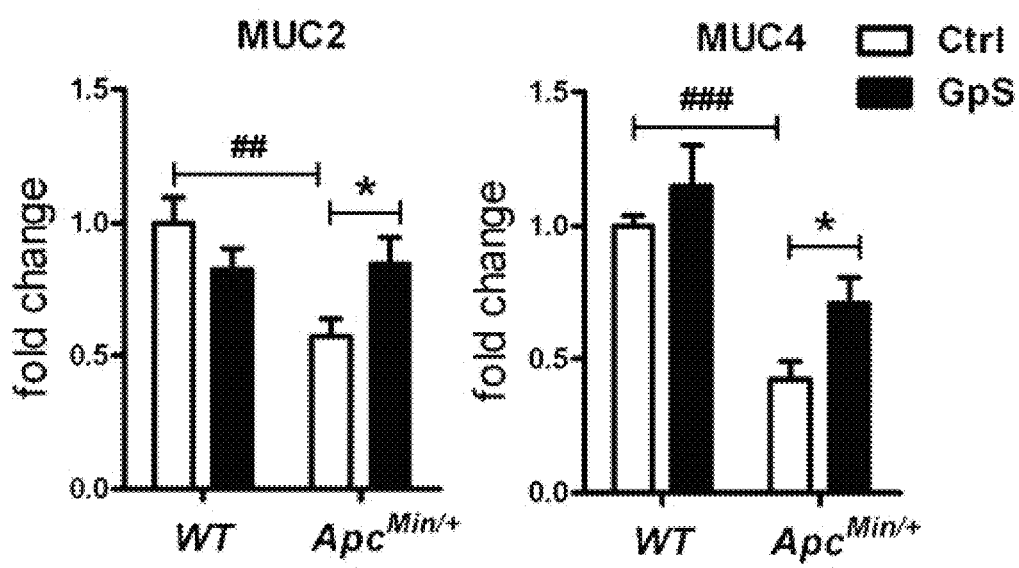

Pyrosequencing data also identified several well-known beneficial bacteria. As shown in Table 2, compared with the WT, Apc$^{Min/+}$ mice showed a significant increase in the relative abundance of *Bacteroides uniformis* but a substantial decrease in *Bifidobacterium pseudolongum*. However, GpS treatment restored the level of these two species to certain extent. Additionally, *Lactobacillus* intestinalis was unique to the GpS-treated WT mice. Compared with the Apc$^{Min/+}$ control mice, *Allobaculum* spID4, *Clostridium cocleatum* and *Streptococcus thermophilus* were significantly elevated upon GpS feeding. In addition, *Streptococcus thermophilus* and *Parabacteroides distasonis* were only detected in the GpS-treated Apc$^{Min/+}$ mice, and the relative abundance of *Bacteroides acidifaciens* was increased by 212.00% compared with the untreated Apc$^{Min/+}$ controls. GpS treatment increases the levels of several bacterial species showing various beneficial effects to the host. In addition, certain opportunistic pathogen like *Acinetobacter lwoffii* was only observed in the Apc$^{Min/+}$ mice and exhibited a 93.10% decrease upon GpS treatment. Most *Helicobacter* and *Escherichia* are commensal gut microbiota, while particular strains are pathogenic. In the present embodiment, none of the known pathogenic microbes were observed in either treated or untreated mice, although GpS-fed Apc$^{Min/+}$ mice showed higher relative abundance of *Helicobacter* and *Escherichia* at the genus level (FIG. 22C).

to restore the mRNA levels of α-defensins and P-lysozyme. In mice, there are two common forms of lysozyme. The P-lysozyme is expressed in intestinal epithelium, especially in the Paneth cells. The M lysozyme is expressed mainly in myeloid cells. In this embodiment, no differences were observed in M-lysozyme expression among different experimental groups (FIG. 23D). Likewise, the mRNA levels of MUC2 and MUC4 in the colon tissue were highly expressed in the GpS-treated Apc$^{Min/+}$ mice than the controls (FIG. 23E). These data show that GpS treatment improve the

TABLE 2

Changes in relative abundance of the bacterial species in the microbial communities of feces

| | WT | | | Apc$^{Min/+}$ | | |
|---|---|---|---|---|---|---|
| Species | Ctrl (%) | GpS (%) | Percent change | Ctrl (%) | GpS (%) | Percent change |
| *Acinetobacter lwoffii* | — | — | — | 0.0087 ± 0.0087 | 0.0006 ± 0.0006 | ↓ 93.10% |
| *Allobaculum* spID4 | 0.0561 ± 0.0093 | 0.1868 ± 0.0732 | ↑ 232.98% | 0.0492 ± 0.0100 | 0.1584 ± 0.0267 ** | ↑ 221.95% |
| *Bacteroides acidifaciens* | 0.0865 ± 0.0329 | 0.1193 ± 0.0547 | ↑ 37.92% | 0.0400 ± 0.0117 | 0.1248 ± 0.0459 | ↑ 212.00% |
| *Bacteroides uniformis* | 0.0015 ± 0.0009 | 0.0147 ± 0.0091 | ↑ 880.00% | 0.0367 ± 0.0057 ## | 0.0109 ± 0.0057 * | ↓ 70.30% |
| *Bifidobacterium pseudolongum* | 0.1226 ± 0.0190 | 0.3978 ± 0.2824 | ↑ 224.47% | 0.0368 ± 0.0082 ## | 0.0604 ± 0.0156 | ↑ 64.13% |
| *Clostridium cocleatum* | 0.0376 ± 0.0220 | 0.0929 ± 0.0497 | ↑ 147.07% | 0.0044 ± 0.0017 | 0.0807 ± 0.0162 ** | ↑ 1734.09% |
| *Lactobacillus intestinalis* | — | 0.0172 ± 0.0066 * | — | — | — | — |
| *Parabacteroides distasonis* | — | — | — | — | 0.0081 ± 0.0040 | — |
| *Streptococcus thennophilus* | — | — | — | — | 0.0031 ± 0.0013 * | — |

Data are shown as mean ± SEM (n = 5).
* $p < 0.05$,
** $p < 0.01$,
GpS versus Control;
$p < 0.01$,
Apc$^{Min/+}$ versus WT.

GpS Treatment Improved the Intestinal Epithelial Barrier of Apc$^{Min/+}$ Mice

Gut epithelial barrier dysfunction of Apc$^{Min/+}$ mice has been reported in several studies, and such defective epithelial barrier can facilitate the translocation of inflammatory cytokines, resulting in the promotion of tumor growth. After revealing the impact of GpS on the gut microbiota of WT and Apc$^{Min/+}$ mice, the inventors investigated any corresponding changes of the epithelium under GpS treatment. Paneth cells, along with goblet cells, enterocytes, and enteroendocrine cells, are the principal cell types of the intestinal epithelium. The inventors first examined the general intestinal morphology by H&E staining and observed no obvious difference between the control and GpS treatment groups (FIG. 23A). Paneth cells, which are normally located at the bottom of the crypts in the small intestine, are a principal source of antimicrobial substances, including lysozyme and α-defensins. Immunohistochemistry (IHC) staining for lysozyme, which is used as the marker for the presence of Paneth cells, demonstrated a reduction of Paneth cells in the Apc$^{Min/+}$ mice compared with their WT littermates (FIG. 23B). Goblet cells take responsibility for generating mucus, which constitutes the first line of immune defense. The result indicated a decrease of goblet cells in the Apc$^{Min/+}$ mice compared to the WT mice, particularly in the colonic region (FIG. 23C). Interestingly, the lysozyme-expressing Paneth cells and Alcian blue positive goblet cells in the GpS-treated Apc$^{Min/+}$ mice was comparable to the WT mice. Consistent results were obtained by examining the mRNA expressions of microbicidal peptide and mucins secreted by Paneth cells and goblet cell using qRT-PCR. The mRNA of α-defensins (Pancrp), P-lysozyme, MUC2 and MUC4 were significantly reduced in the Apc$^{Min/+}$ mice relative to the WT controls. However, GpS treatment tended intestinal epithelial barrier in the Apc$^{Min/+}$ mice by increasing the number and secretions of Paneth and goblet cells.

Figure 23F:
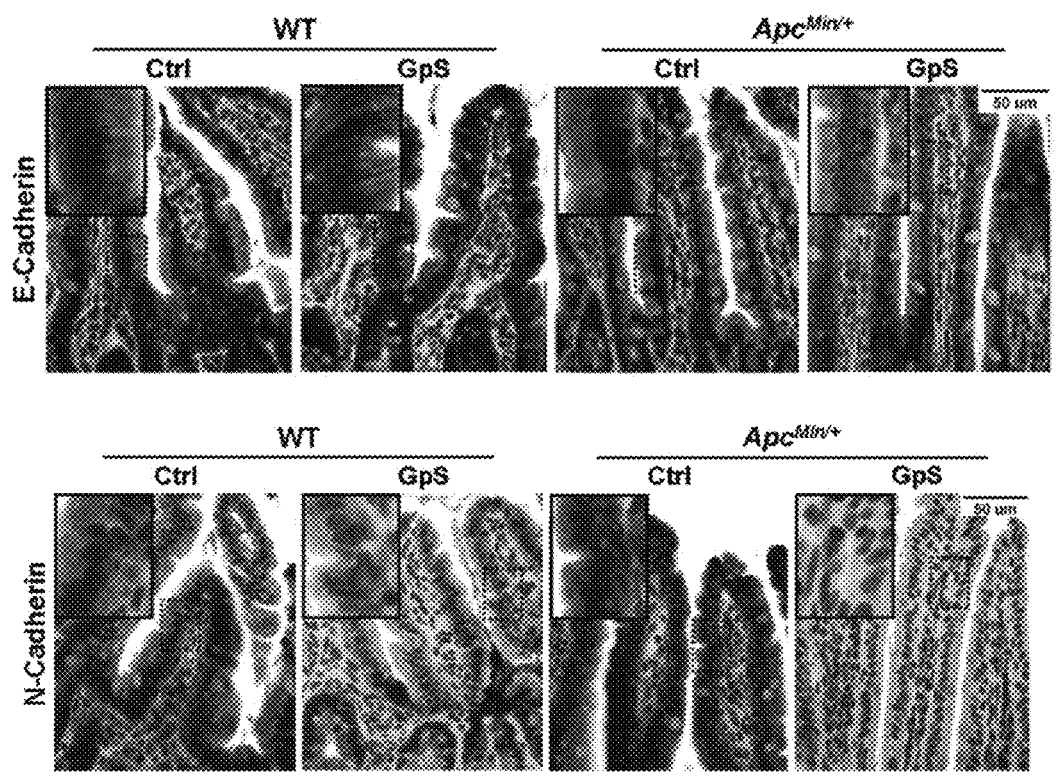

E-cadherin is not only a key adherens junction molecule, it is also required for intestinal morphogenesis, and Paneth cell maturation among other functions. Impaired expression of E-cadherin has been linked to defective gut barrier function, and switching expression from E-cadherin to N-cadherin was found to be associated with CRC progression. The inventors therefore examined the expressions of E-cadherin and N-cadherin in the small intestines by IHC staining. In comparison to the WT mice, an obvious decrease in E-cadherin and increase in N-cadherin were observed in the small intestines of the Apc$^{Min/+}$ mice. GpS treatment effectively reversed the trend, for which the level of E-cadherin was up-regulated and N-cadherin was significantly down-regulated (FIG. 23F), showing an improvement of the pathological condition of the intestinal epithelium.

Figure 24A:
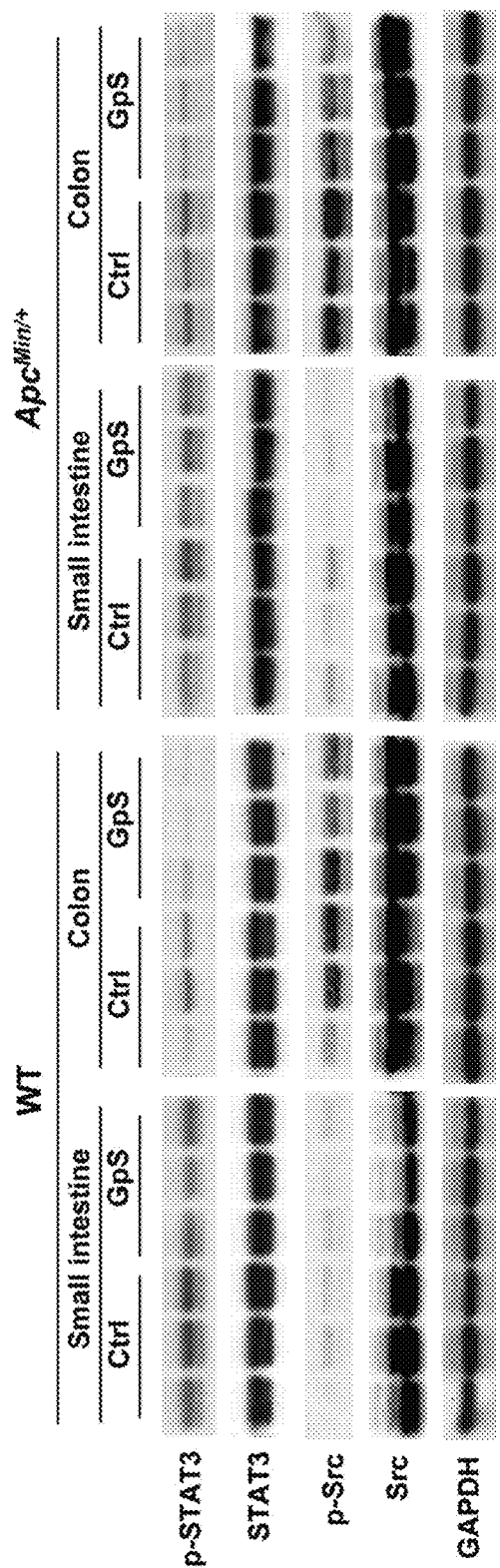
FIG. 24A-C shows the effect of GpS on the protein expression of STAT3 and beta-catenin.
Figure 24B:
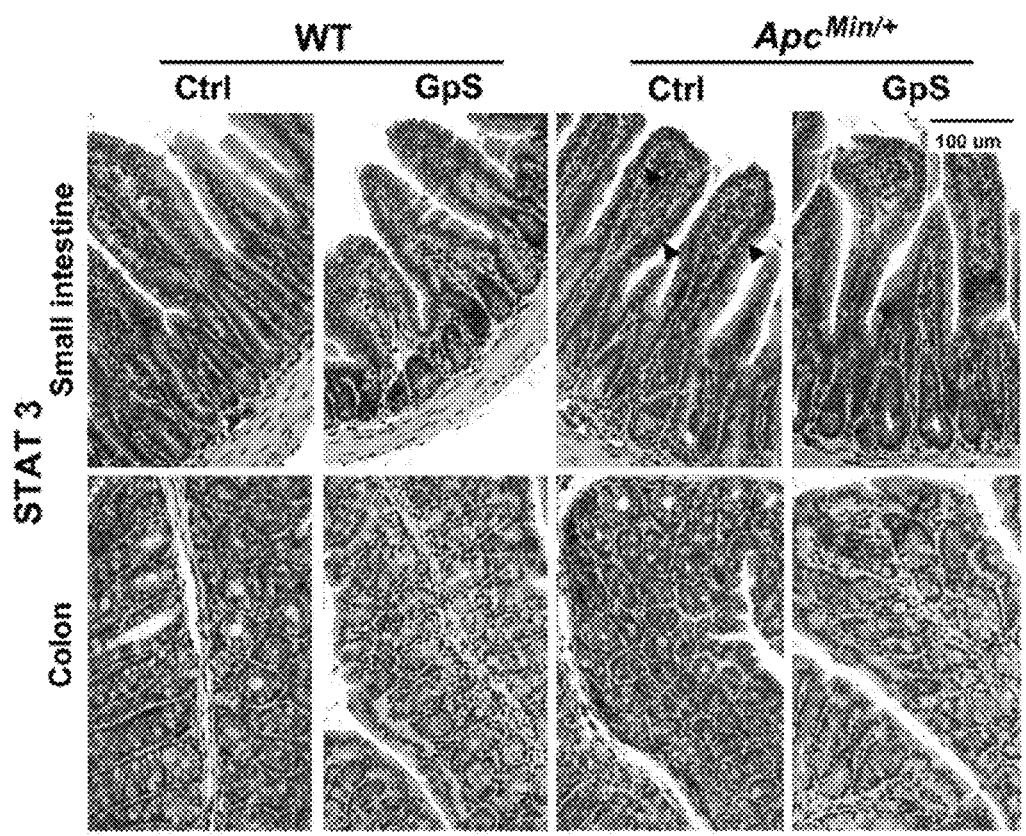
Figure 24C:
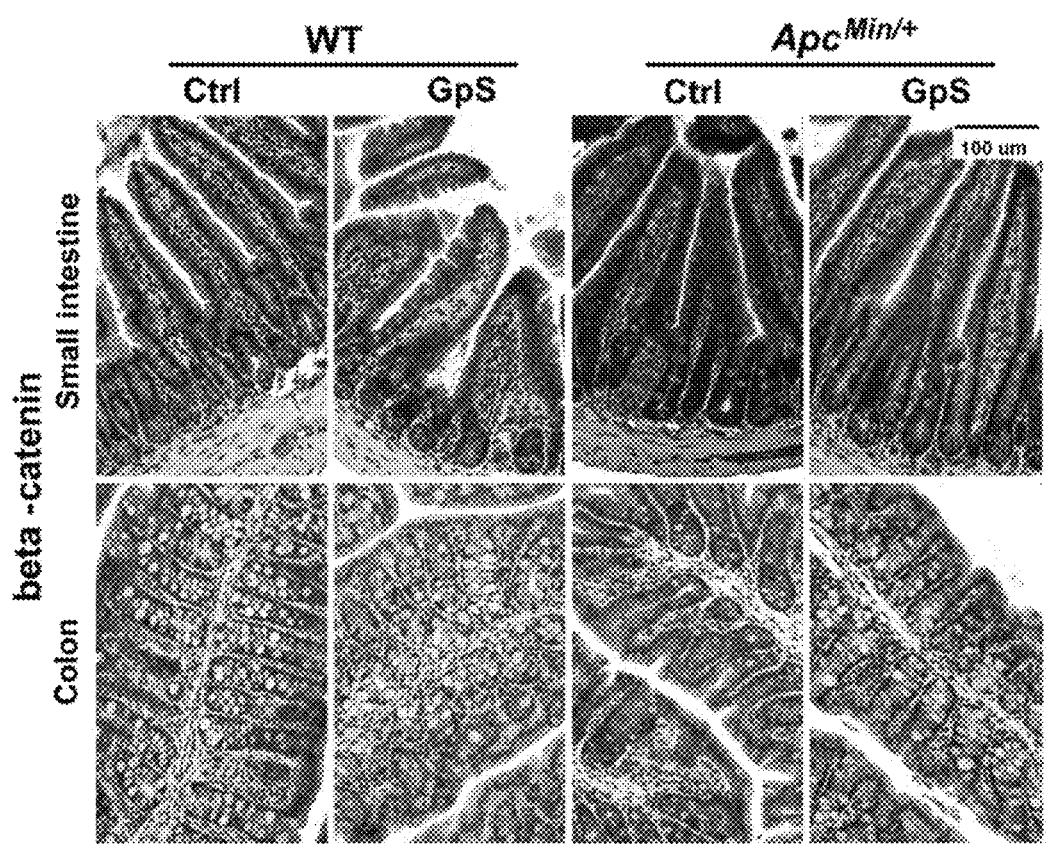

GpS Down-Regulated Protein Expressions of p-SRC, p-STAT3 and β-Catenin in Intestinal Mucosa Signal transducer and activator of transcription 3 (STAT3) can negatively regulate E-cadherin and positively modulate N-cadherin and has become a promising target for cancer immunotherapy. The gut microbiota has also been shown to enhance tumor burden in Apc$^{Min/+}$ mice partially via STAT3 phosphorylation. Aberrant β-catenin expression is known to be involved in CRC development, and the resident intestinal bacteria is associated with the stability of β-catenin in intestinal epithelial cells. The inventors thus investigated the impact of GpS on β-catenin, phosphorylation of STAT3 (p-STAT3) and the STAT3 activator, phosphorylated SRC (p-SRC) proteins in the intestine. GpS treatment down-regulated p-STAT3 and p-SRC, in particular in the colonic mucosa in the western blotting analysis (FIG. 24A). As shown in FIG. 24B, nuclear STAT3 was observed in the small intestine of the Apc$^{Min/+}$ mice, but hardly appeared in the nuclei of the GpS-treated epithelial cells. These results are consistent with the down-regulated effect of GpS on the p-STAT3 that is required for nuclear translocation of the protein. IHC staining also further revealed the down-regulated effect of GpS on the expression of β-catenin (FIG. 24C). Altogether, GpS treatment increased E-cadherin but decreased N-cadherin in the Apc$^{Min/+}$ mice, and the down-regulation of p-STAT3 might account for such results.

GpS Modulated the Mucosal Cytokine Profiles in Apc$^{Min/+}$ Mice

Figure 25B:
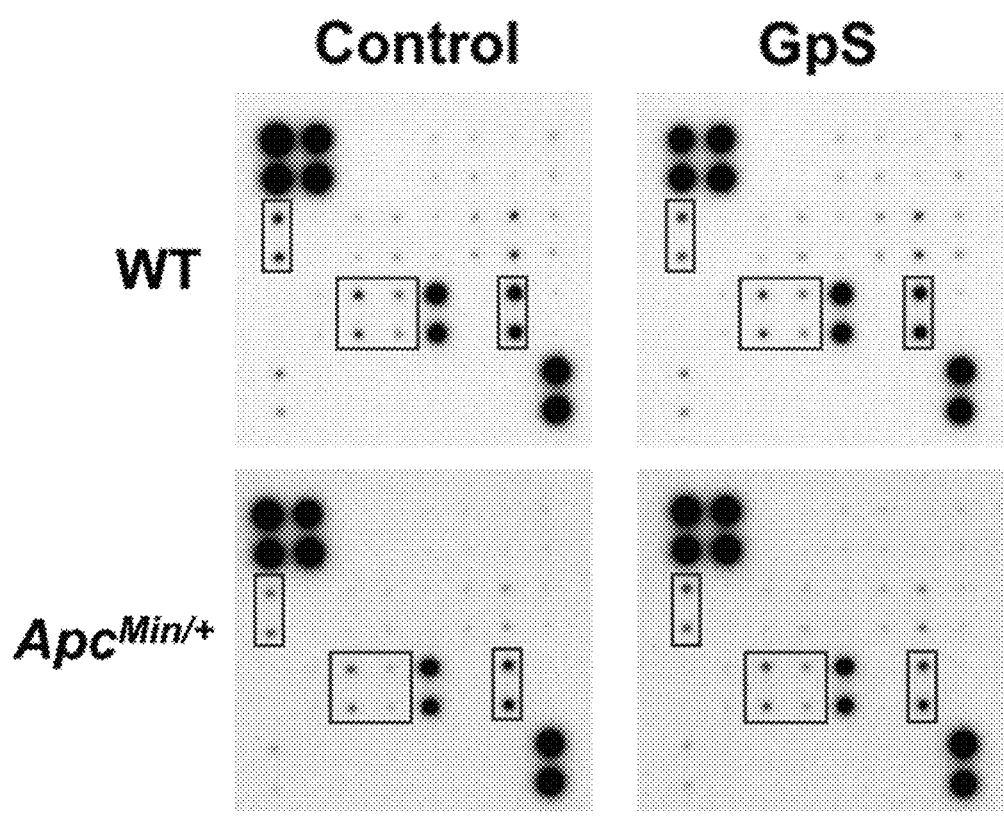
Figure 25C:
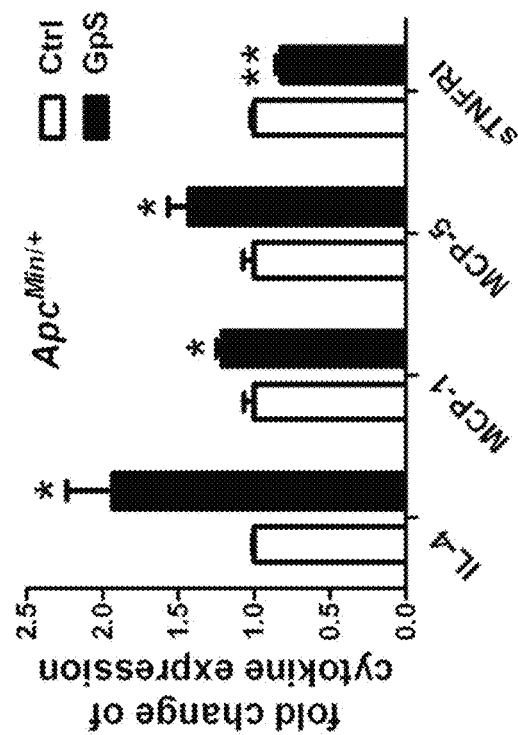
Figure 25C:
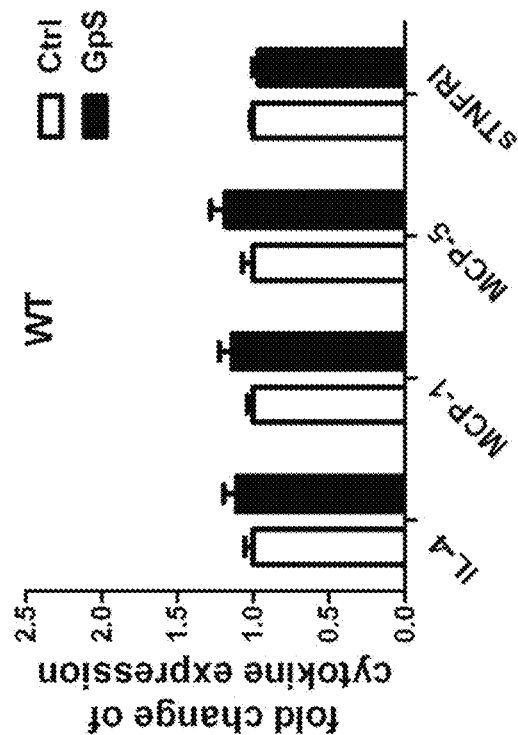
Figure 25D:
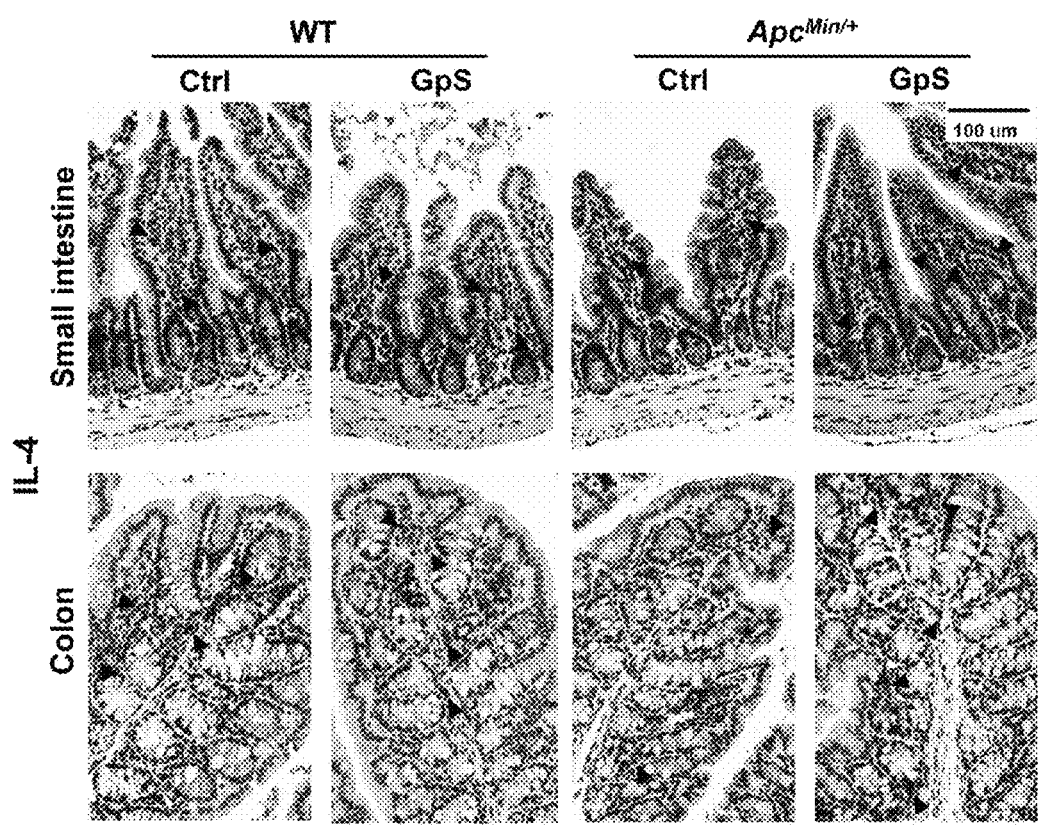

Cytokines have been suggested to play a crucial role in regulating immune response between the mucosal barrier and the commensal microbiota. To investigate the effect of GpS treatment on cytokine profiles, RayBiotech mouse cytokine array containing 22 main cytokines (FIG. 25A) was used to detect the cytokines in the intestinal mucosal protein from experimental groups (FIG. 25B). It is shown that the levels of IL-4, MCP-1 and MCP-5 were significantly increased, whereas sTNFRI was significantly decreased in the intestinal mucosa from GpS-treated Apc$^{Min/+}$ mice compared with the controls. However, the effect of GpS treatment was not apparent in the WT (FIG. 25C). IHC staining of IL-4 further confirmed the finding in the cytokine array (FIG. 25D). IL-4 has been reported to induce mucin secretion in goblet cells, which echoed the inventors' earlier results showing concurrent elevations of IL-4 and mucins were observed in the GpS-treated Apc$^{Min/+}$ mice in contrast to the controls.

Figure 26A:
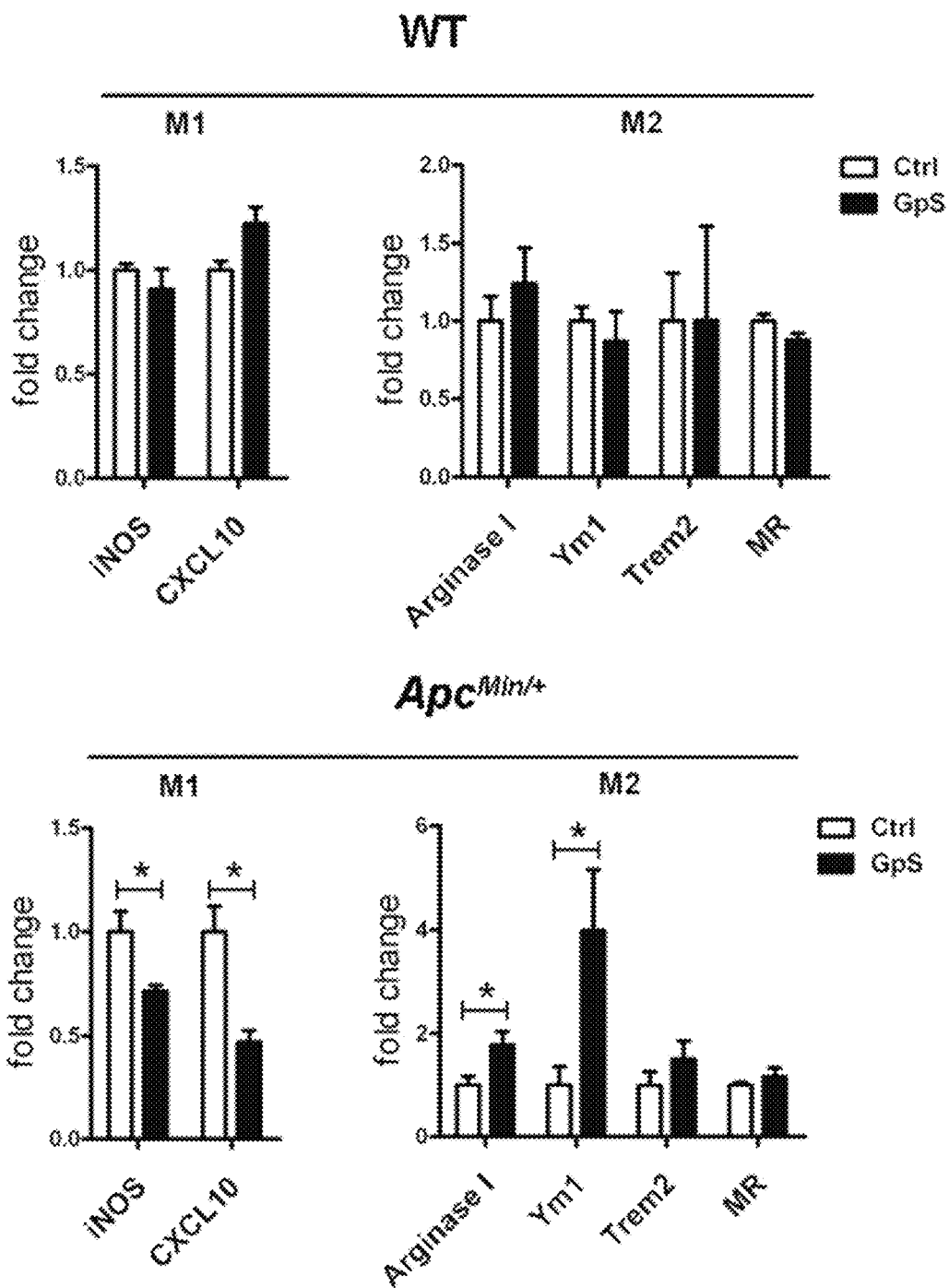
FIG. 26A-D shows the effect of GpS on the macrophage phenotypic polarization.

GpS Might Facilitate Polarization of M2 Macrophage and Improve the Intestinal Barrier IL-4 is the stimulus for alternatively activated M2 macrophages whose primary roles are in tissue repair and anti-inflammation. To evaluate the phenotype of macrophages in the intestine, the inventors next investigated the mRNA expressions of several M1 and M2 markers by qRT-PCR. In the Apc$^{Min/+}$ mice, mRNA of iNOS and CXCL10, which are the key effector molecules produced by pro-inflammatory M1 phenotype, were significantly lower in the normal mucosa of the GpS-treated mice compared with the controls. On the other hand, expressions of arginase 1, Ym1, Trem2 and MR, which are the typical anti-inflammatory M2 phenotypes markers, were higher in the GpS-treated Apc$^{Min/+}$ mice than the untreated controls. Differences were not observed between the GpS-treated and untreated WT mice (FIG. 26A).

Figure 26B:
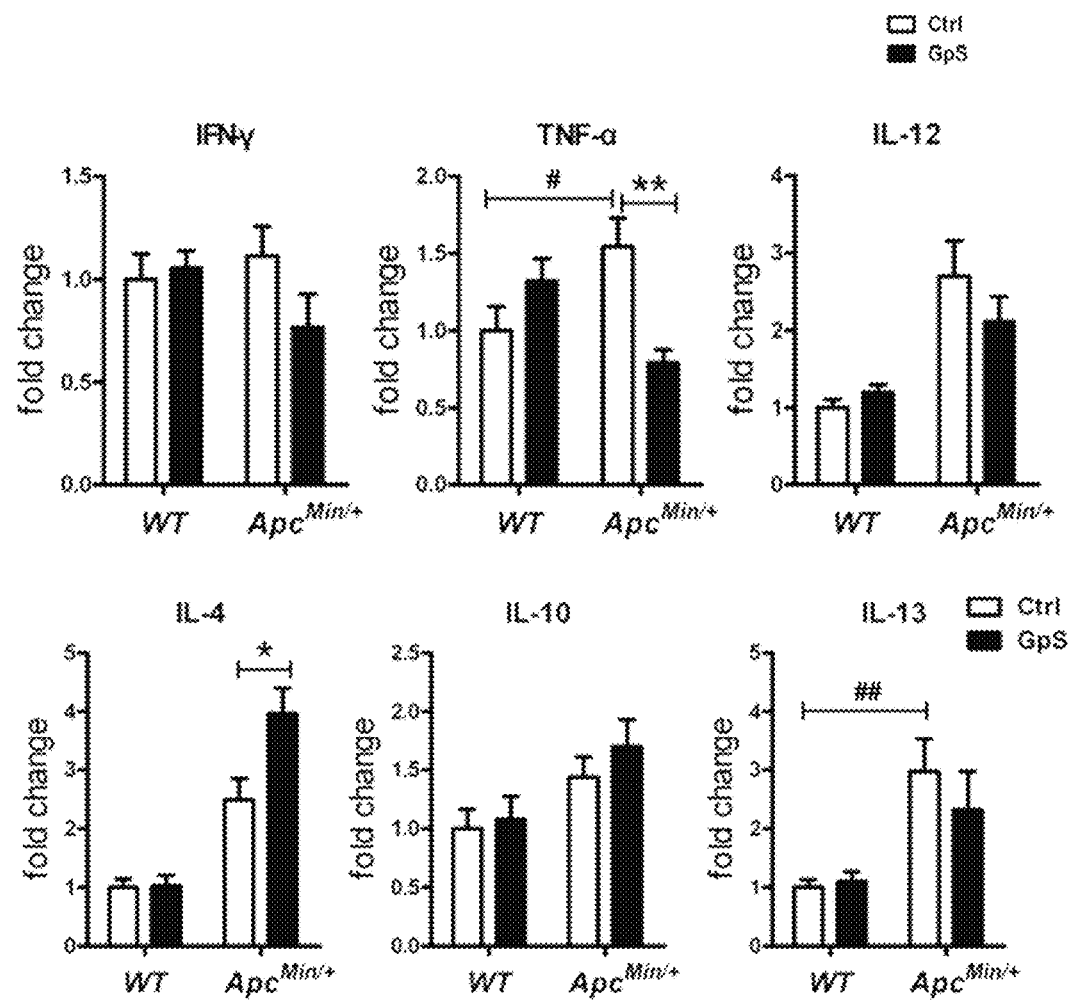
Figure 26C:
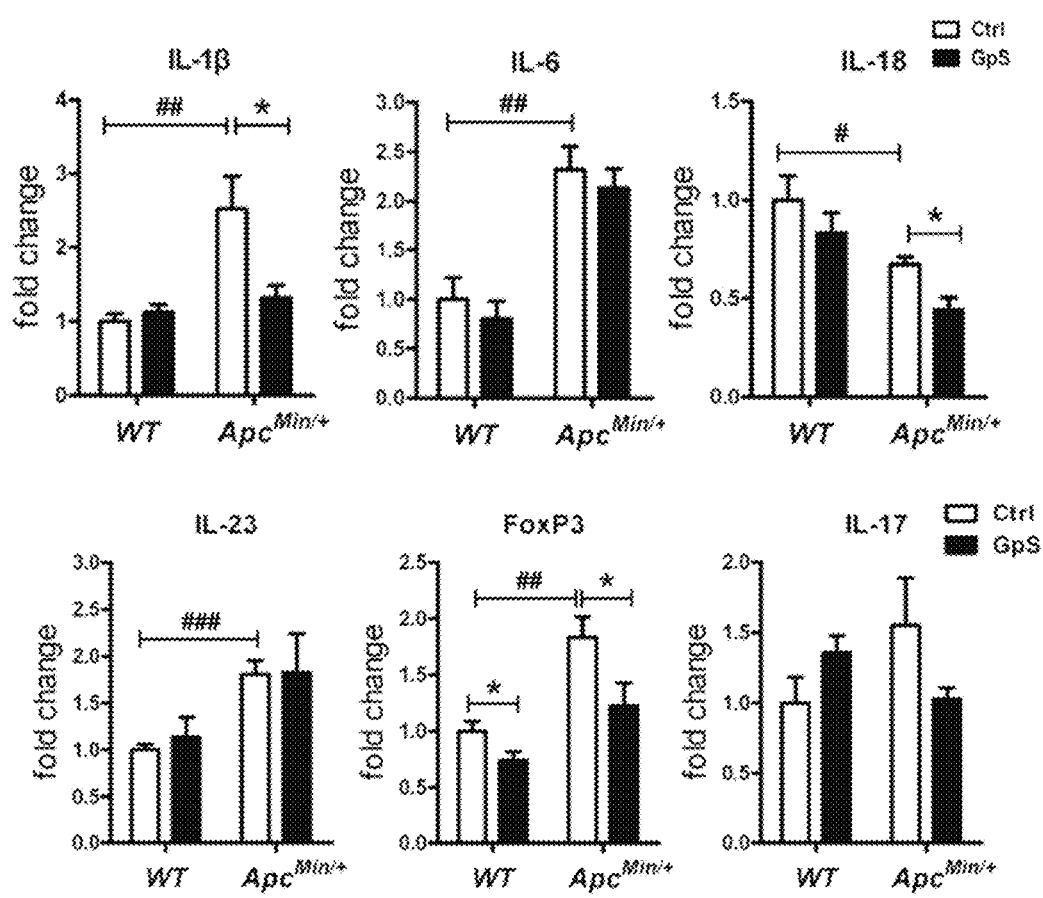

IFN-γ, TNF-α and IL-12 are responsible for inducing M1 phenotype, while IL-4, IL-10 and IL-13 are M2-polarizing cytokines. Since macrophages can alter their phenotype in response to the microenvironment where they exist, the inventors further investigated those factors that can affect the polarization of macrophages. Compared with the WT mice, the mRNA expression of TNF-α and IL-13 were elevated in the Apc$^{Min/+}$ mice. Interestingly, the mRNA expression of TNF-α was lower, while IL-4 was higher in the intestinal mucosa of the GpS-treated Apc$^{Min/+}$ mice relative to the untreated controls (FIG. 26B). Thus, the cytokine expression profile of intestinal microenvironment was consistent with the increased M2 macrophage phenotype. Subsequent evaluation of molecules in relation to inflammatory response revealed that the mRNA levels of IL-1β, IL-6, IL-23, FoxP3 and IL-17 were significantly elevated or showed an increasing trend in the Apc$^{Min/+}$ mice compared with the WT, but IL-18 was significantly down-regulated (FIG. 26C). These findings demonstrated a high inflammatory status in the intestinal mucosa of the Apc$^{Min/+}$ mice. Remarkably, after GpS feeding, the Apc$^{Min/+}$ mice showed a significant decrease in the mRNA expression of IL-1β, IL-18 and FoxP3 without obviously affecting IL-6, IL-23 and IL-17. Chronic inflammation of the intestinal mucosa is associated with an increased risk of developing CRC. These data supported the role of GpS in the process of inflammation during intestinal tumorigenesis.

Figure 26D:
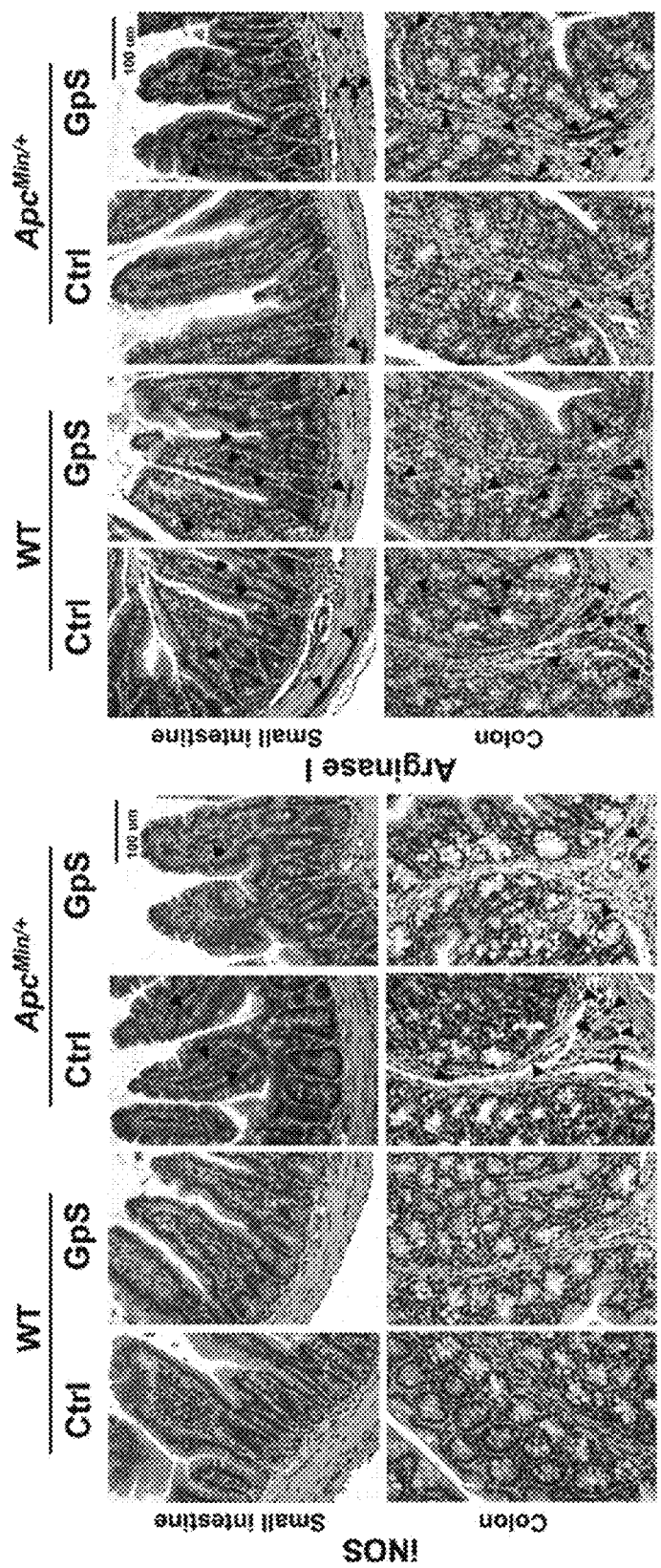

To further substantiate the inventors' findings regarding repairing effects of GpS on the intestinal epithelium, the inventors next applied IHC staining to examine the expression of macrophage subtype markers in the intestinal mucosa to further confirm the polarizing effects of GpS treatment on macrophages. iNOS and Arginase I are the common markers for M1 and M2 macrophages, respectively. In contrast to the WT mice, the Apc$^{Min/+}$ mice exhibited relatively higher expression of iNOS and lower expression of Arginase I. Meanwhile, GpS-treated Apc$^{Min/+}$ mice demonstrated increased Arginase I and decreased iNOS immunoreactivity compared with the controls (FIG. 26D). Collectively, these findings indicated that GpS treatment alters cytokine profile by enhancing IL-4 and thus skewed M1 macrophages to M2 phenotype in the intestinal mucosa microenvironment, contributing to the intestinal tissue repair.

Discussion

Currently, little is known about the function of herbal saponins in the homeostasis of the intestinal microenvironment. The present application demonstrates the cancer preventive function of Gp saponins by alteration of intestinal microbiota and mucosal barrier of the host. In this embodiment employing a colonic carcinogenic Apc$^{Min/+}$ mouse model, the inventors demonstrate the GpS effects on the growth of tumor in the gut; the composition of fecal microbiota; the host's intestinal mucosal barrier; and the intestinal inflammation status of host. To the best knowledge of the inventors, the present application is the first to demonstrate the novel role of botanical saponins in the homeostasis of gut microbiota and mucosal environment.

Figure 27A:
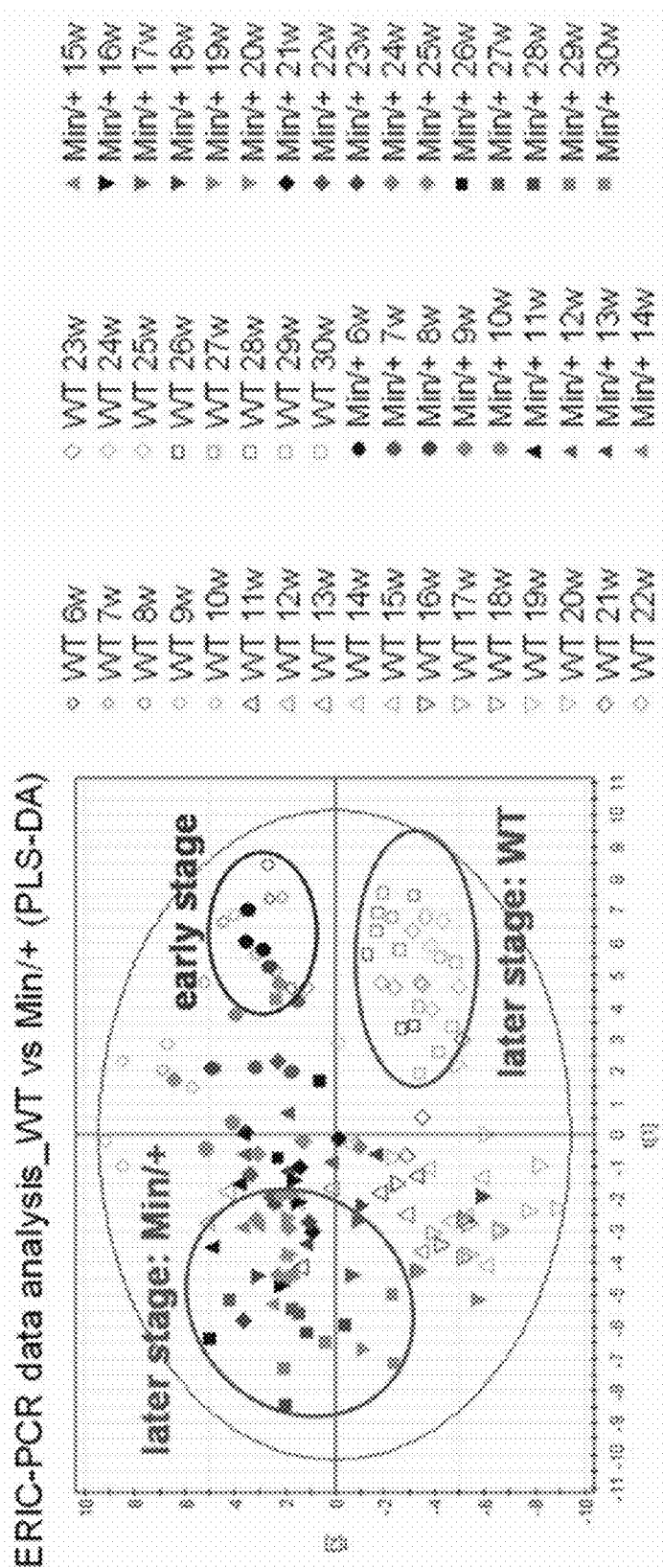
FIG. 27A shows the time course PLS-DA plots of ERIC-PCR DNA profile of $Apc^{Min/+}$ mice versus WT. Open symbols: WT; Solid symbols: $Apc^{Min/+}$ mice.
Figure 27B:
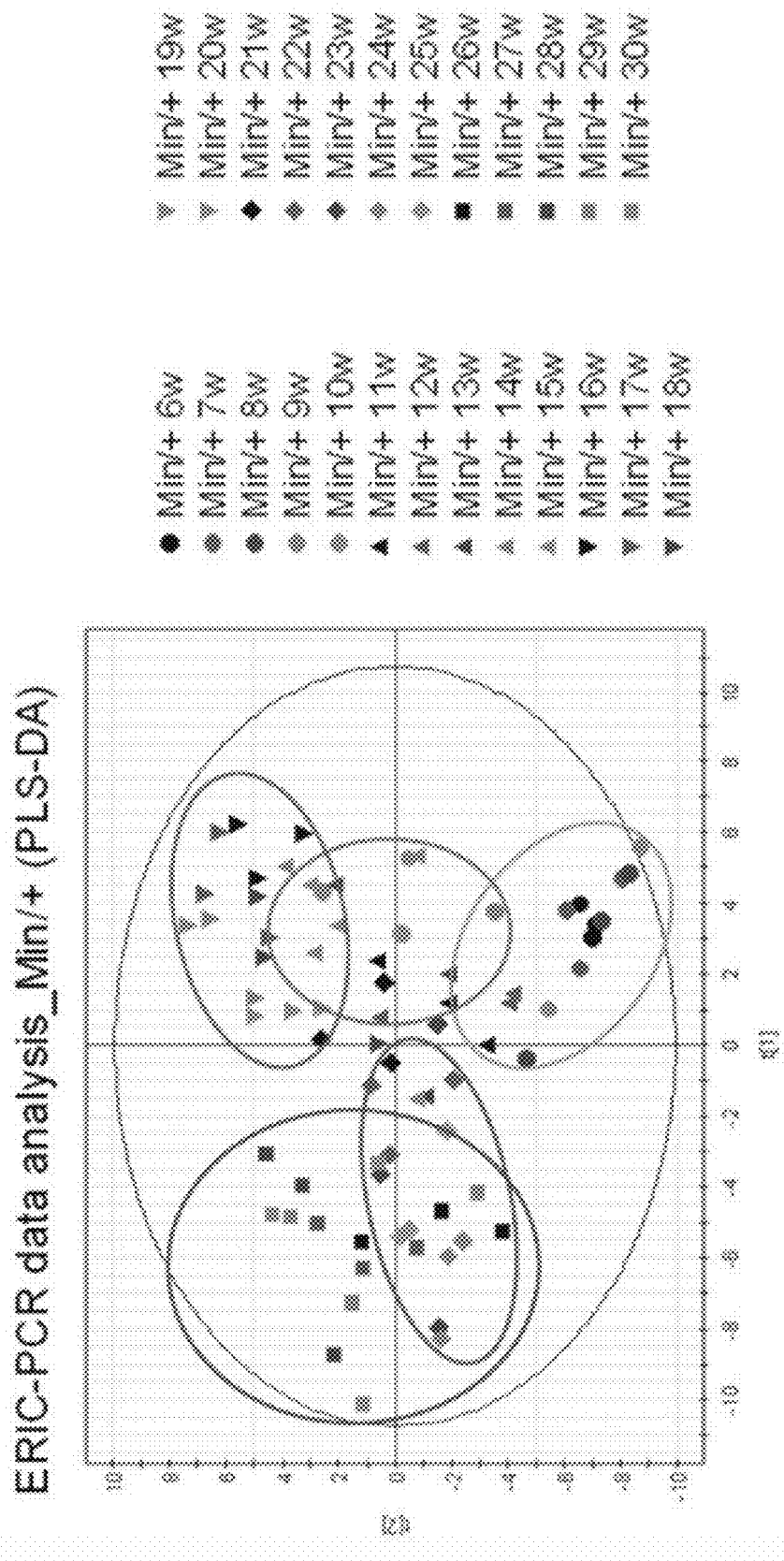
FIG. 27B is the time course PLS-DA plots of ERIC-PCR DNA profile of $Apc^{Min/+}$ mice at different disease stages. Different symbol shapes represented for different disease stages. The microbial profiles of $Apc^{Min/+}$ mice and their WT littermates are characterized from 6 weeks to 30 weeks of age for 25 consecutive weeks. The fecal samples were prepared for genomic DNA and subjected for ERIC-PCR. Gel pictures were digitized by Image Lab 3.0 system (Bio-Rad). Based on the distance and the intensity of each DNA band, SIMCA-P 12.0 tool was applied to obtain the PLS-DA score plots. WT: n=3; $Apc^{Min/+}$ mice: n=3.

In this embodiment, the inventors found that the WT and Apc$^{Min/+}$ mice exhibited similar profile of fecal microbiome at 6 wk of age. As the mice grew older, disparity of microbial profiles between the WT and their Min/+ littermates become apparent (FIG. 27A to FIG. 27B). This is coincided with the timing of onset of intestinal polyps which usually starts in 8 to 10 wk of age. The present application also demonstrates that tumor grafting can significantly alter the composition of gut microbiota in nude mice. Based on these observations, tumor growth impacts the gut microbiota, regardless the tumors develop in the gut or distant from the gut. Asides from the above, the present application shows the prebiotic-like effect of GpS by which a favorable growth environment was tuned for the propagation of beneficial microbes, with the decreased proportion of Furmicutes and the increased proportion of Bacteroidetes (FIG. 20D & FIG. 20E). At the species level, increased beneficial bacteria were revealed by pyrosequencing upon GpS treatment (Table 2). For instance, GpS increased the abundance of *Bifidobacterium pseudolongum*, which is a beneficial inhabitant in the intestine and known as probiotics. *Streptococcus thermophilus* is an essential lactic acid bacterium, and commonly used in the production of yogurt. Oral administration of bacterial components derived from *Parabacteroides distasonis* was reported to reduce chronic intestinal inflammation. Interestingly, both *Streptococcus thermophilus* and *Parabacteroides distasonis* can only be detected in the GpS-treated Apc$^{Min/+}$ mice. GpS treatment stimulated *Clostridium cocleatum*, for which the colonization of harmful bacteria *C. difficile* was prevented and decrease of intestinal diseases was reported.

Figure 28:
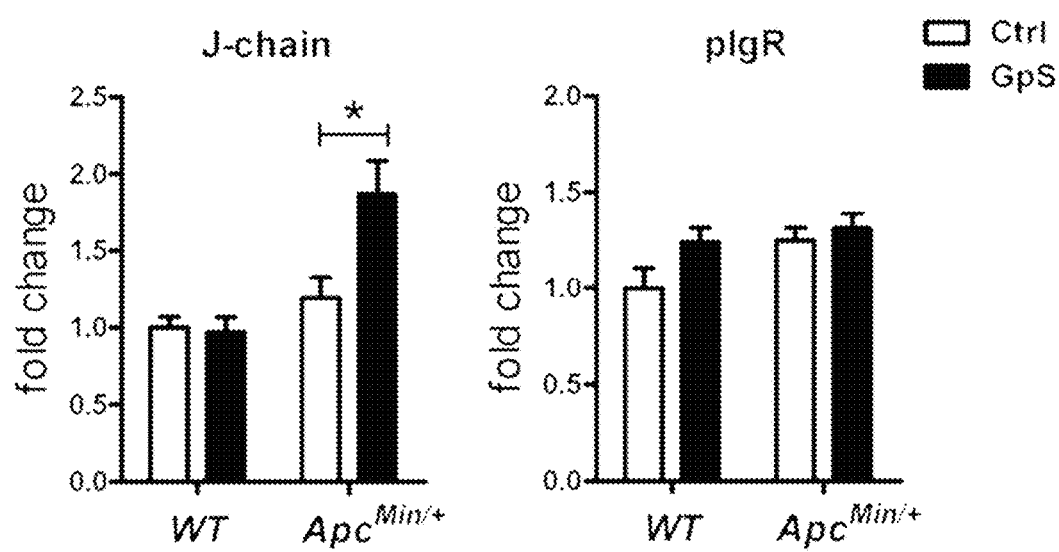
FIG. 28 shows the relative mRNA expression of J-chain and pIgR. J-chain is known to be critical for polymeric immunoglobulin receptor (pIgR)-mediated epithelial transport of IgA. Data are normalized to the expression of reference gene, and expressed as fold change of the WT control group. Data is presented as the mean±SEM (*$P<0.05$, GpS versus control samples); n=6/group.

Additionally, an increasing trend of *Bacteroides acidifaciens* and elevated transcripts of IgA transport related J-chain gene (FIG. 28) were observed in the GpS-fed mice, which coincided with previous reports showing that *Bacteroides acidifaciens* can promote IgA production, which may contribute to maintain the intestinal homeostasis.

More importantly, besides upregulating the beneficial bacteria, the inventors also demonstrate that the abundance of SRB linkage as well as the critical enzyme dsrA for the sulfur cycle in SRB decreased significantly in the Apc$^{Min/+}$ mice fed with dietary Gp saponins. SRB, such as *Desulfovibrio* and *Bilophila*, are common colonic inhabitants found both in humans and mice. They produce and use $H_2S$ for energy harvesting in the gastrointestinal track and have been found to be associated with gastrointestinal diseases and cancer. Expansion of SRB, such as *Bilophila wadsworthia*, has been found in hosts that are genetically susceptible or have impaired function of mucosal barrier. The presence of $H_2S$ has been suggested as a potential etiological agent in gastrointestinal disease due to its genotoxic, cytotoxic and inflammatory effects. Study also showed that $H_2S$ can contribute to the cancer progression trigged by the genotoxic insult to the colonic epithelium. Higher level of $H_2S$ has been reported in the stool of individuals with high risk of CRC. Moreover, hydrogen sulfide-producer *Fusobacterium nucleatum* has been found to be associated with colorectal cancer. Interestingly, recent report showed that the prebiotics treatment in mice was able to decrease the population of a group of SRB which was significantly elevated in mice under treatment of high fat diet. Their findings are in line with GpS treatment of the present invention. The present invention demonstrates that Gp saponins along with few other saponins from edible plants exhibit prebiotic-like properties. The profound effect of GpS on the reduction of SRB lineage alleviates the deleterious effects evolved by the growth of intestinal tumor in the Apc$^{Min/+}$ mice and improve the host gut barrier. Considering the fact that colonic mucosa is persistently colonized by SRB, the beneficial versus toxic effects of $H_2S$ need to be elucidated.

Intestinal epithelial cells consist of different cell types, including the anti-microbial peptides-secreted Paneth and mucin-secreted goblet cells. Paneth cells play an important role in maintenance of host-microorganism homeostasis in small intestine, while goblet cells contribute to innate immune defense. The inventors' histological data showed that the number of Paneth cells and goblets were low in Apc$^{Min/+}$ compared to the WT, but markedly increased under GpS treatment. These findings were further supported by the qRT-PCR analysis of mRNA expressions of Pancrp, P-lysozyme, MUC2 & 4 (FIG. 23A to FIG. 23F). Lack of mucin can lead to a defective mucus barrier and result in increased pathogenic bacterial adhesion and penetration into surface epithelial cells, and increase intestinal permeability. Study showed that Paneth cell dysfunction can affect the secretion of α-defensins and cause the microbial imbalance, predisposing the host to intestinal inflammation. α-defensin deficiency can also cause a decrease in the relative abundance of Bacteroidetes but an increase in Firmicutes. In the present embodiment, compared with the control mice, GpS-treated Apc$^{Min/+}$ mice showed increased population of Paneth cells in the small intestine and also displayed increased ratio of Bacteroidetes/Firmicutes. Furthermore, E-cadherin, which was found strikingly upregulated in GpS-treated Apc$^{Min/+}$, is also playing a key role in the maturation of Paneth and goblet cells. Overexpression of STAT3 has been shown to dramatically downregulate E-cadherin and upregulate N-cadherin in CRC cells and to lead to CRC cells invasion and resist to apoptosis. Here, the inventors found daily feeding of GpS supplements effectively downregulated p-STAT3 in the treated Min/+ mice. In the same group of mice, the inventors detected a marked increase in E-cadherin and decrease in N-cadherin. Before GpS treatment, the Apc$^{Min/+}$ mice showed a different profile with low expression of E-cadherin and high expression of N-cadherin. Collectively, the cancer preventive property of GpS is shown.

The present cytokine arrays study also showed that IL-4, along with MCP-1 and -5 were upregulated in the mucosa of the GpS treated Apc$^{Min/+}$ mice. IL-4 is known as an anti-inflammatory and as an immunoregulator cytokine. Early reports showed that defect in IL-4 expression in the colonic mucosa was closely associated with patients suffered from inflammatory bowel disease (IBD) and the risk of CRC. IL-4 was suggested to inhibit colon cancer cell growth. Thus, a continuous expression of IL-4 may provide an effective therapy for various diseases, including cancers and immunologic disorders. IL-4 has been reported to induce mucin secretion in goblet cells. It can also promote alternative activation of macrophages into M2 cells, and increase of M2 cells can contribute to an enhanced tissue repair and reduce pathological inflammation. Therefore, the GpS on the protective effects in the gut mucosal barrier is partially based on the induction of IL-4 secretion, as well as the polarization of M2 macrophages. The function of the macrophage subtypes in normal tissue is known to be quite different from that of tumor associated macrophages (TAMs).

In addition to IL-4, GpS significantly increased MCP-1 and MCP-5 that possess tumoricidal activity of macrophages in vivo. MCP-1 can recruit monocytes, T-lymphocytes and dendritic cells to the inflammatory sites of tissue injury or infection, and IL-4 functions as a potent stimulator for MCP-1 expression. Recent studies have revealed that MCP-1 is mainly produced by goblet and Paneth cells. The present application shows increased IL-4 and the increase population of Paneth cells and goblet cells induced by GpS are account for the elevation of MCP-1 and/or MCP-5. In a recent investigation on the stress effect on gut microbiota, the relative abundance of bacteria in the genus of *Coprococcus* is in the negatively correlation with the MCP-1 expression. This study coincided with the present application in which in contrast to the controls, the GpS-treated Apc$^{Min/+}$ mice showed a reduction in *Coprococcus* and an increase of mucosal MCP-1, as increased MCP-1 has been reported to be negatively correlated with the abundance of *Coprococcus*.

Human Equivalent Dosage (HED)

Examples of the present invention demonstrate a dosage of 500 mg/kg of saponins is effective to stimulate beneficial commensal bacteria in mice. Base on a dose translation formula in the art, human equivalent dose (mg/kg) is animal dose (mg/kg)×animal Km/human Km (Reagan-Shaw at al. Dose translation from animal to human studies revisited, The FASEB Journal, 22, 659-661. 2007). Adult human Km is 37; mouse Km is 3. Therefore, the human equivalent dosage of the present invention is about 40 mg of saponins per kg of the human subject (500×3/37).

Figure 29:
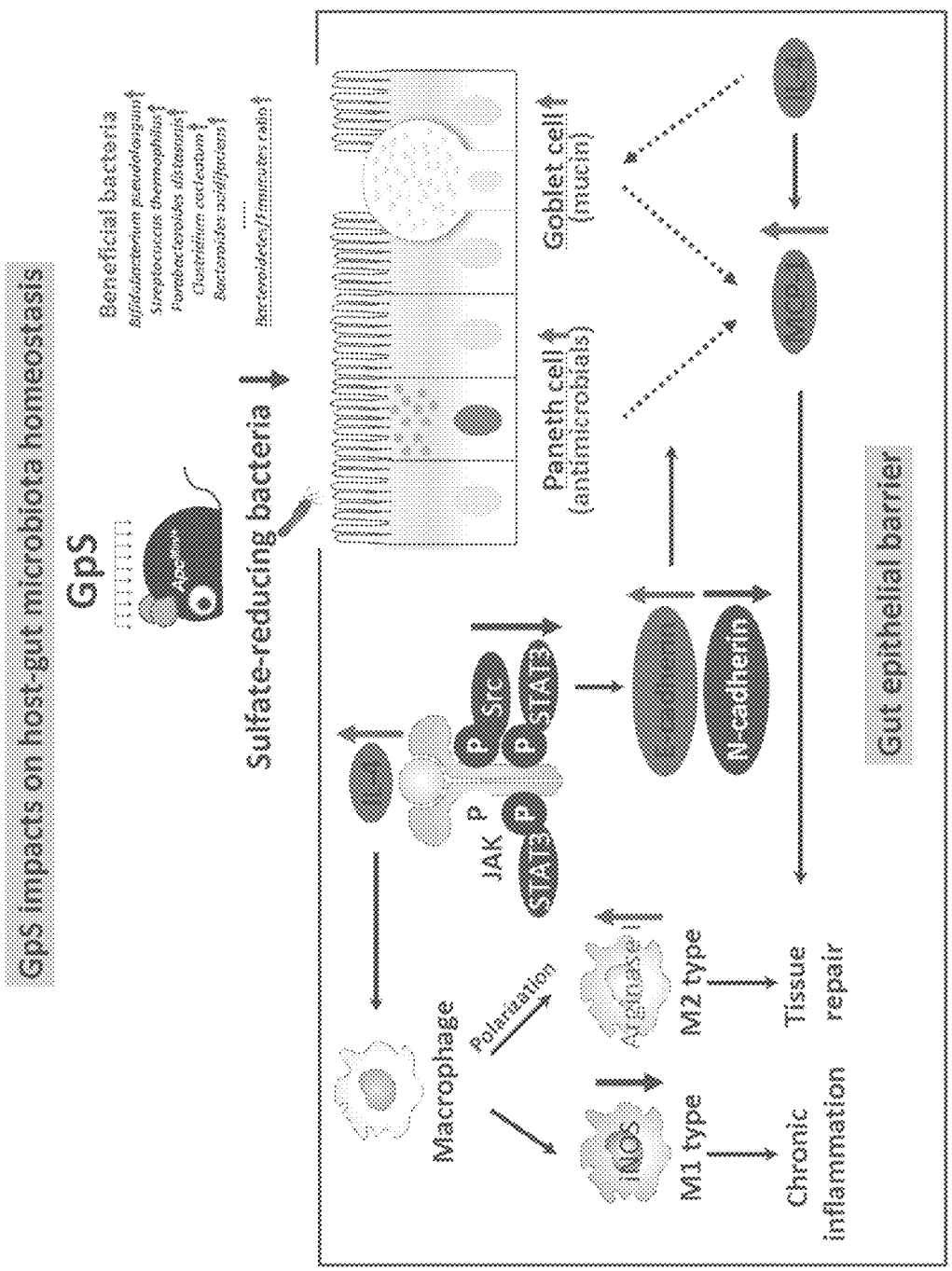
FIG. 29 shows the summary of the impacts of GpS in $Apc^{Min/+}$ mice.

In summary, an unique insight into the intricate interplay between the host and gut microbiota upon dietary herbal saponins administration is shown in the present application. Here the inventors show that GpS effectively enhance beneficial commensal bacteria, and substantially reduce the sulfate-reducing bacteria. To the host intestinal epithelial barrier, GpS remarkably suppress a repertoire of pro-inflammatory, and pro-oncogenic cytokines and signaling molecules, and present an overall anti-inflammatory, and anti-oncogenic epithelial microenvironment in the gut of $Apc^{Min/+}$ mice. Thus, the present invention provides the use of GpS to prevent colorectal cancer by bringing the disease state of the host to a balance and healthy state through the modulation of the interaction between host and gut microbiota (FIG. 29). The impact of herbal saponins on the gut microbial ecosystem and mechanisms for their cancer preventive effects are illustrated in the present invention. Such health beneficial effects of GpS apply to alleviate other chronic elements associated with inflammatory intestinal environment.

Materials and Methods

Animals and Treatments

Experimental procedures were conducted according to the guidelines for the care and use of laboratory animals. All procedures were approved by the Baptist University Ethics Review Committee for animal research. Heterozygous male $Apc^{Min/+}$ (C57BL/6J-$Apc^{Min/+}$) and female wild-type (WT) C57BL/6J mice were purchased from Jackson Laboratory. An in-house breeding colony has been maintained by breeding C57BL/6J-$Apc^{Min/+}$ male to WT female C57BL/6J mice. The $Apc^{Min/+}$ genotype of offspring is confirmed by polymerase chain reaction analysis. Mice were fed with Pico-Lab® Rodent Diet 20-5053 (LabDiet, USA), and housed in a 12-h light/12-h dark cycle facility with free access to food and water. GpS was purchased from Hauduo Natural Products (Guangzhou, China). According to the procedures outlined by Wu et al., each batch of GpS was authenticated and chemically profiled. GpS was dissolved in 0.5% carboxymethyl cellulose (CMC) at 50 mg/ml. Single dose of GpS at 500 mg/kg or solvent control was given daily by gavage, started at 6 weeks of age before the appearance of spontaneous intestinal polyps of the animals. The treatment was carried out for 8 weeks. Total twelve female mice were used for each experimental group, including WT-control, WT-GpS, $Apc^{Min/+}$ control, and $Apc^{Min/+}$-GpS groups. Six mice per group were used in the first batch of experiment, followed by three mice per group were used in the second and third batches of experiment, respectively. The second and third batches of experiment were applied to collect more intestinal mucosa from the experimental mice for the subsequent experiments. The mice with the same genotype and the same treatment were housed in the same cage for the first batch of experiment, while mice with the same genotype but different treatment (GpS-treated or untreated) were co-housed in the same cage for the second and third batches of experiment. Euthanasia of animals was carried out according to the guidance of the American Veterinary Medical Association (AVMA). Total 48 mice were used in this study, and carbon dioxide ($CO_2$) inhalation was used for euthanasia of mice.

Fecal Samples Collection and Bacterial Genomic DNA Extraction

Fecal samples were collected from each mouse for two consecutive hours from 8:00 to 10:00 A.M. before treatment and weekly after treatment. All fecal samples were immediately stored at $-20°$ C. for later DNA extraction. Total genomic DNA was isolated from fecal samples as described and kept for later time-course study. QIAamp DNA Stool Mini Kit (QIAGEN) was used to extract the fecal genomic DNA from experimental mice and kept for later pyrosequencing.

Enterobacterial Repetitive Intergenic Consensus (ERIC)-PCR and Data Analysis

ERIC sequences reside in the genome of various bacterial species in addition to enterobacteria. ERIC-PCR was performed to profile the gut microbiota by using fecal genomic DNA from different treatment groups. Partial least squares discriminant analysis (PLS-DA) was applied to visualize the changes of microbial composition before and after treatments using SIMCA-P 12.0 tool (Umetrics, Umea, Sweden) for which the confidence level was set at 95% (P<0.05).

16S rRNA Gene Pyrosequencing of Fecal DNA Samples and Data Analysis

Five fecal samples randomly picked from each experimental group on week 8 were subjected to further analysis by using 16S rRNA gene pyrosequencing as described above with slight modification. Briefly, 0.1 µg/µl BSA was added to enhance the PCR efficiency, and PCR was performed for each sample in a final reaction volume of 20 ul comprising 100 ng extracted DNA. Amplicon libraries were quantified, emulsion-PCR and pyrosequencing using titanium chemistry on the GS Junior System (454 Life Sciences Corp., Branford, Conn., USA) was carried out as detailed by the manufacturer. Pyrosequencing data were processed and analyzed using the Quantitative Insights Into Microbial Ecology software (QIIME version 1.5.0). The raw 454 pyrosequencing data were deposited in NCBI's Sequence Read Archive (SRA) database under accession number of SRP057080. The differences in overall microbiota composition between compared samples were determined using the unweighted UniFrac metric. A matrix of pairwise distances between communities was constructed and used to generate Principal Coordinates Analysis (PCoA) plots. Linear discriminant analysis (LDA) effect size (LEfSe) method was used to evaluate the key phylotypes responsible for the observed differences between microbial communities. The alpha value used for the algorithm of LEfSe was internally set at 0.05, which corresponded to 95% confidence level (P<0.05) to detect features with significant differential abundance and to test the biological consistency.

Gut Samples Collection and Polyp Counting

At the end of the experiment, all mice were sacrificed and the intestinal tract was removed. Small intestine and colon were divided at cecal junction. 2 cm of small intestine and colon were cut from the adjacent cecum, rinsed with PBS and then fixed in 10% formalin for later histological sections. The remaining part of colon and 8 cm of distal small intestine were used for mucosal scrapings. Other part of the intestinal tract was opened longitudinally and rinsed with PBS and then fixed in 10% formalin. The number and sizes of polyps in the intestine were determined with a dissecting microscope after methyl blue staining.

Quantitative Reverse Transcription Polymerase Chain Reaction (qRT-PCR)

RNA was isolated from mucosal scrapings samples using TRIzol reagent (Invitrogen, Carlsbad, Calif., USA) according to the manufacturer's instructions. First-strand cDNA was synthesized from 5 µg of total RNA using random primers and SuperScript II reverse transcriptase (Invitrogen, Carlsbad, Calif., USA). qRT-PCR was performed to measure changes in mRNA expression using Applied Biosystems ViiA™ 7 PCR system (Carlsbad, Calif., USA). The sequences of the primers used were listed in Table 3. Briefly, the qRT-PCR was carried out using Power SYBR® Green PCR Maser Mix (Applied Biosystems Inc., Carlsbad, Calif., USA). The amplification conditions were as follow: 95° C. for 10 min, followed by 40 cycles of 95° C. for 15 s and 60° C. for 1 min. Six samples were used for each experimental group. Hypoxanthine-guanine phosphoribosyl transferase 1 (Hprt1) was used as an internal control. Before the inventors applied Hprt1 to qRT-PCR data analysis, the inventors compared the expression stability of Hprt1 and β-actin, and the two reference genes showed a similar expression pattern among different samples. On the other hand, the expression of dsrA gene was also carried out by qRT-PCR using 5 ng fecal genomic DNA, and normalized to that of the total fecal bacteria, which was detected by 16S rRNA gene. The $2^{-\Delta\Delta Ct}$ method was applied to calculate the fold change of relative gene expression. $\Delta\Delta Ct=(Ct_{treatment\_target\ gene}-Ct_{treatment\_reference\ gene})-(Ct_{control\_target\ gene}-Ct_{control\_reference\ gene})$.

TABLE 3

Primers for Quantitative Real-Time PCR

| Target gene | Forward (5' to 3') | Reverse (5' to 3') |
|---|---|---|
| β-actin | TGTTACCAACTGGGACGACA (SEQ ID No. 22) | CTGGGTCATCTTTTCACGGT (SEQ ID No. 23) |
| Hprt1 | TCAGTCAACGGGGGACATAAA (SEQ ID No. 24) | GGGGCTGTACTGCTTAACCAG (SEQ ID No. 25) |
| dsrA | CTGCGAATATGCCTGCTACA (SEQ ID No. 26) | TGGTCGARCTTGATGTCGTC (SEQ ID No. 27) |
| Pan Crp | GGTGATCATCAGACCCCAGCATCAGT (SEQ ID No. 28) | AAGAGACTAAAACTGAGGAGCAGC (SEQ ID No. 29) |
| Lyz 1 (P-lyso-zyme) | GCCAAGGTCTACAATCGTTGTGAGTTG (SEQ ID No. 30) | CAGTCAGCCAGCTTGACACCACG (SEQ ID No. 31) |
| Lyz 2 (M-lyso-zyme) | GGCTGGCTACTATGGAGTCAGCCTG (SEQ ID No. 32) | GCATTCACAGCTCTTGGGGTTTTG (SEQ ID No. 33) |
| MUC2 | CCCAGAAGGGACTGTGTATG (SEQ ID No. 34) | TTGTGTTCGCTCTTGGTCAG (SEQ ID No. 35) |
| MUC4 | GTCTCCCATCACGGTTCAGT (SEQ ID No. 36) | TGTCATTCCACACTCCCAGA (SEQ ID No. 37) |
| J-chain | GAACTTTGTATACCATTTGTCAGACG (SEQ ID No. 38) | CTGGGTGGCAGTAACAACCT (SEQ ID No. 39) |
| pIgR | AGTAACCGAGGCCTGTCCTT (SEQ ID No. 40) | GTCACTCGGCAACTCAGGA (SEQ ID No. 41) |
| iNOS | GTTCTCAGCCCAACAATACAAGA (SEQ ID No. 42) | GTGGACGGGTCGATGTCAC (SEQ ID No. 43) |
| CXCL10 | CCAAGTGCTGCCGTCATTTTC (SEQ ID No. 44) | GGCTCGCAGGGATGATTTCAA (SEQ ID No. 45) |
| Arginase1 | TGGCTTGCGAGACGTAGAC (SEQ ID No. 46) | GCTCAGGTGAATCGGCCTT (SEQ ID No. 47) |
| Ym1 | TTATCCTGAGTGACCCTTCTAAG (SEQ ID No. 48) | TCATTACCCTGATAGGCATAGG (SEQ ID No. 49) |
| Trem2 | CTGGAACCGTCACCATCACTC (SEQ ID No. 50) | CGAAACTCGATGACTCCTCGG (SEQ ID No. 51) |
| MR | GCTGAATCCCAGAAATTCCGC (SEQ ID No. 52) | ATCACAGGCATACAGGGTGAC (SEQ ID No. 53) |
| IFN-γ | ATGAACGCTACACACTGCATC (SEQ ID No. 54) | CCATCCTTTTGCCAGTTCCTC (SEQ ID No. 55) |
| TNF-α | CAAATGGCCTCCCTCTCAT (SEQ ID No. 56) | CTCCTCCACTTGGTGGTTTG (SEQ ID No. 57) |
| IL-12 | ACTCTGCGCCAGAAACCTC (SEQ ID No. 58) | CACCCTGTTGATGGTCACGAC (SEQ ID No. 59) |
| IL-4 | GGTCTCAACCCCCAGCTAGT (SEQ ID No. 60) | GCCGATGATCTCTCTCAAGTGAT (SEQ ID No. 61) |
| IL-10 | GCTCTTACTGACTGGCATGAG (SEQ ID No. 62) | CGCAGCTCTAGGAGCATGTG (SEQ ID No. 63) |
| IL-13 | GGATATTGCATGGCCTCTGTAAC (SEQ ID No. 64) | AACAGTTGCTTTGTGTAGCTGA (SEQ ID No. 65) |
| IL-1β | GCTGAAAGCTCTCCACCTCA (SEQ ID No. 66) | GGCCACAGGTATTTTGTCGT (SEQ ID No. 67) |
| IL-6 | CTTCCATCCAGTTGCCTTCTTG (SEQ ID No. 68) | AATTAAGCCTCCGACTTGTGAAG (SEQ ID No. 69) |
| IL-18 | CCTGACATCTTCTGCAACCT (SEQ ID No. 70) | TTCCGTATTACTGCGGTTGT (SEQ ID No. 71) |
| IL-23 | GCACCTGCTTGACTCTGACA (SEQ ID No. 72) | ATCCTCTGGCTGGAGGAGTT (SEQ ID No. 73) |
| Foxp3 | CCCATCCCCAGGAGTCTTG (SEQ ID No. 74) | ACCATGACTAGGGGCACTGTA (SEQ ID No. 75) |
| IL-17 | TTTAACTCCCTTGGCGCAAAA (SEQ ID No. 76) | CTTTCCCTCCGCATTGACAC (SEQ ID No. 77) |

Mucosal Protein Extraction

The protein of mucosal scraping samples from small intestine of colon were extracted by homogenization, and followed by sonication in Raybiotech cell lysis buffer with protease inhibitors. Protein concentration was determined by DC Protein Assay (Bio-Rad, Hercules, Calif.).

Cytokine Array

Mucosal lysates from the same experimental group were pooled together and applied to a mouse cytokine array (RayBiotech, Inc.). Each cytokine was represented in duplicate on the membrane. Two independent experiments were performed to evaluate the expression level of various cytokines. The intensity of signal was quantified by densitometry (ImageJ, NIH). The positive control was used to normalize the results from different membranes being compared.

Western Blot

Western blot analysis was performed using standard methods on the mucosal protein lysates from individual experimental mice. Immunodetection was performed using specific antibodies against beta-catenin (1:2000, sc-7963), c-Myc (1:500, sc-789), TLR4 (1:1000, sc-293072) and GAPDH (1:1000, sc-20357) purchased from Santa Cruz Biotechnology (Santa Cruz, Calif.), and p-Stat3 (1:1000, cell signaling #9138), Stat3 (1:1000, cell signaling #9132), p-Src (1:1000, cell signaling #6943) and Src (1:1000, cell signaling #2123) purchased from Cell Signaling Technology (Beverly, Mass.).

Histology and Immunohistochemistry

5 μm thick paraffin sections were used for hematoxylin and eosin (H&E) staining, Alcian blue-staining, and immunohistochemical staining using standard procedures. Immunohistochemistry was performed using antibodies against Lysozyme (1:200, A0099, DAKO), E-Cadherin (1:200, #3195S, Cell Signaling), N-Cadherin (1:100, 610920, BD), Stat3 (1:200, #9139, Cell Signaling), beta-catenin (1:50, sc-7963, Santa Cruz), IL-4 (1:100, PAB16160, Abnova), iNOS (1:200, ab129372, Abcam), Arginase I (1:100, 610708, BD), and LSAB+System-HRP kit (K0679, DAKO). The slides were mounted and viewed on a Nikon Eclipse 80i microscope. Images were photographed with a SPOT RT3 CCD camera and SPOT Advanced software (Diagnostic Instruments, Sterling Heights, Mich., USA).

Statistical Analysis

The data is presented as mean±SEM, and statistical comparisons were performed using one-way ANOVA followed by Dunnett's post test with the GraphPad Prism version 5.00 (GraphPad Software, San Diego, Calif., USA) or Student's t-test at $P<0.001(*)$, $P<0.01()$ or $P<0.05(*)$.

Abbreviations

APC: adenomatous polyposis *coli*; BLAST: basic local alignment search tool; CMC: carboxymethyl cellulose; CRC: colorectal cancer; dsrA: dissimilatory (bi)sulfite reductase; ERIC: enterobacterial repetitive intergenic consensus; Gp: *Gynostemma pentaphyllum*; GpS: *Gynostemma pentaphyllum* saponins; $H_2S$: hydrogen sulfide; H&E: hematoxylin and eosin; Hprt1: hypoxanthine-guanine phosphoribosyl transferase 1; IgA: immunoglobulin A; IHC: immunohistochemistry; ISC: intestinal stem cell; LDA: linear discriminant analysis; LEfSe: linear discriminant analysis effect size; MCP: monocyte chemoattractant protein; PCoA: principal coordinates analysis; pIgR: polymeric immunoglobulin receptor; PLS-DA: partial least squares discriminant analysis; QIIME: quantitative insights into microbial ecology; qRT-PCR: quantitative reverse transcription polymerase chain reaction; SRA: sequence read archive; SRB: sulfate-reducing bacteria; STAT3: signal transducer and activator of transcription 3; sTNFRI: soluble tumor necrosis factor receptor I; TAM: tumor associated macrophage; WT: wild-type.

Those skilled in the art will appreciate that the invention described herein is susceptible to variations and modifications other than those specifically described. If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

The invention claimed is:

1. A method of altering bacterial abundance of microbiota in digestive organs of a subject in need thereof, comprising administering to said subject a composition comprising saponins extracted from *Gynostemma pentaphyllum* at a dose of 40 mg of said saponins per kg of said subject daily.

2. The method according to claim 1 wherein said digestive organs comprising the gut, intestines and digestive track of said subject.

3. The method according to claim 1 wherein said composition is administered orally to said subject.

4. The method according to claim 1 wherein said subject in need thereof is a mammal with $Apc^{Min/+}$.

5. The method according to claim 4, wherein said altering bacterial abundance of microbiota comprises depleting a sulfate-reducing bacteria lineage.

6. The method according to claim 5, wherein said sulfate-reducing bacteria lineage comprises Desulfovibrionaceae, Deltaproteobacteria, Desulfovibrionales, and LE30.

7. The method according to claim 1, wherein the subject in need thereof is human with $Apc^{Min/+}$.

8. The method according to claim 1, wherein said microbiota comprises Actinobacteria, Bacteroidetes, Cyanobacteria, Firmicutes, Proteobacteria, Tenericutes, Verrucomicrobia, Ruminococcus, Coprobacillus, Helicobacteraceae, *Helicobacter*, Campylobacterales, Epsilonproteobacteria, *Clostridium, Escherichia*, Alistipes, Lachnobacterium, *Bilophila*, Bacilli, *Eubacterium*, RF39, *Coprococcus*, Oscillospira, *Allobaculum*, Anaeroplasmataceae, Anaeroplasmatales, *Anaeroplasma*, Ruminococcaceae, Mollicutes, Catabacteriaceae, Desulfovibrionaceae, Deltaproteobacteria, Desulfovibrionales, and LE30.

9. The method according to claim 1, wherein said altering bacterial abundance of microbiota comprises increasing the abundance of short chain fatty acid producing bacteria.

10. The method according to claim 1, wherein said short chain fatty acid producing bacteria comprises *Faecalibacterium prausnitzii*.

* * * * *

SEQUENCE LISTING

```
<160> NUMBER OF SEQ ID NOS: 77

<210> SEQ ID NO 1
<211> LENGTH: 22
<212> TYPE: DNA
<213> ORGANISM: artificial sequence
<220> FEATURE:
<223> OTHER INFORMATION: enterobacteria

<400> SEQUENCE: 1
atgtaagctc tgggattc ac                                              22

<210> SEQ ID NO 2
<211> LENGTH: 22
<212> TYPE: DNA
<213> ORGANISM: artificial sequence
<220> FEATURE:
<223> OTHER INFORMATION: enterobacteria

<400> SEQUENCE: 2
aagtaagtga ctggggtgag cg                                            22
```

```
<210> SEQ ID NO 3
<211> LENGTH: 21
<212> TYPE: DNA
<213> ORGANISM: artificial sequence
<220> FEATURE:
<223> OTHER INFORMATION: primer sequence

<400> SEQUENCE: 3
actcctacgg gaggcagcag t                                              21

<210> SEQ ID NO 4
<211> LENGTH: 18
<212> TYPE: DNA
<213> ORGANISM: artificial sequence
<220> FEATURE:
<223> OTHER INFORMATION: primer sequence

<400> SEQUENCE: 4
attaccgcgg ctgctggc                                                  18

<210> SEQ ID NO 5
<211> LENGTH: 21
<212> TYPE: DNA
<213> ORGANISM: artificial sequence
<220> FEATURE:
<223> OTHER INFORMATION: primer sequence

<400> SEQUENCE: 5
tgaaactyaa aggaattgac g                                              21

<210> SEQ ID NO 6
<211> LENGTH: 21
<212> TYPE: DNA
<213> ORGANISM: artificial sequence
<220> FEATURE:
<223> OTHER INFORMATION: primer sequence

<400> SEQUENCE: 6
tgaaaccyaa aggaattgac g                                              21

<210> SEQ ID NO 7
<211> LENGTH: 17
<212> TYPE: DNA
<213> ORGANISM: artificial sequence
<220> FEATURE:
<223> OTHER INFORMATION: primer sequence

<400> SEQUENCE: 7
accatgcacc acctgtc                                                   17

<210> SEQ ID NO 8
<211> LENGTH: 20
<212> TYPE: DNA
<213> ORGANISM: artificial sequence
<220> FEATURE:
<223> OTHER INFORMATION: primer sequence

<400> SEQUENCE: 8
caaacaggat tagataccct                                                20

<210> SEQ ID NO 9
<211> LENGTH: 20
<212> TYPE: DNA
<213> ORGANISM: artificial sequence
<220> FEATURE:
<223> OTHER INFORMATION: primer sequence
```

<400> SEQUENCE: 9
cgaacaggat tagataccct                                          20

<210> SEQ ID NO 10
<211> LENGTH: 19
<212> TYPE: DNA
<213> ORGANISM: artificial sequence
<220> FEATURE:
<223> OTHER INFORMATION: primer sequence

<400> SEQUENCE: 10
ggtaaggttc ctcgcgtat                                           19

<210> SEQ ID NO 11
<211> LENGTH: 18
<212> TYPE: DNA
<213> ORGANISM: artificial sequence
<220> FEATURE:
<223> OTHER INFORMATION: primer sequence

<400> SEQUENCE: 11
gagaggaagg tcccccac                                            18

<210> SEQ ID NO 12
<211> LENGTH: 19
<212> TYPE: DNA
<213> ORGANISM: artificial sequence
<220> FEATURE:
<223> OTHER INFORMATION: primer sequence

<400> SEQUENCE: 12
cgctacttgg ctggttcag                                           19

<210> SEQ ID NO 13
<211> LENGTH: 19
<212> TYPE: DNA
<213> ORGANISM: artificial sequence
<220> FEATURE:
<223> OTHER INFORMATION: primer sequence

<400> SEQUENCE: 13
agcagtaggg aatcttcca                                           19

<210> SEQ ID NO 14
<211> LENGTH: 17
<212> TYPE: DNA
<213> ORGANISM: artificial sequence
<220> FEATURE:
<223> OTHER INFORMATION: primer sequence

<400> SEQUENCE: 14
caccgctaca catggag                                             17

<210> SEQ ID NO 15
<211> LENGTH: 22
<212> TYPE: DNA
<213> ORGANISM: artificial sequence
<220> FEATURE:
<223> OTHER INFORMATION: primer sequence

<400> SEQUENCE: 15
gcgtgcttaa cacatgcaag tc                                       22

<210> SEQ ID NO 16

```
<211> LENGTH: 21
<212> TYPE: DNA
<213> ORGANISM: artificial sequence
<220> FEATURE:
<223> OTHER INFORMATION: primer sequence

<400> SEQUENCE: 16
cacccgtttc caggagctat t                                      21

<210> SEQ ID NO 17
<211> LENGTH: 25
<212> TYPE: DNA
<213> ORGANISM: artificial sequence
<220> FEATURE:
<223> OTHER INFORMATION: primer sequence

<400> SEQUENCE: 17
ttaacacaat aagtaatcca cctgg                                  25

<210> SEQ ID NO 18
<211> LENGTH: 25
<212> TYPE: DNA
<213> ORGANISM: artificial sequence
<220> FEATURE:
<223> OTHER INFORMATION: primer sequence

<400> SEQUENCE: 18
ttaacacaat aagttatcca cctgg                                  25

<210> SEQ ID NO 19
<211> LENGTH: 21
<212> TYPE: DNA
<213> ORGANISM: artificial sequence
<220> FEATURE:
<223> OTHER INFORMATION: primer sequence

<400> SEQUENCE: 19
accttcctcc gttttgtcaa c                                      21

<210> SEQ ID NO 20
<211> LENGTH: 21
<212> TYPE: DNA
<213> ORGANISM: artificial sequence
<220> FEATURE:
<223> OTHER INFORMATION: primer sequence

<400> SEQUENCE: 20
gatggcctcg cgtccgatta g                                      21

<210> SEQ ID NO 21
<211> LENGTH: 19
<212> TYPE: DNA
<213> ORGANISM: artificial sequence
<220> FEATURE:
<223> OTHER INFORMATION: primer sequence

<400> SEQUENCE: 21
ccgaagacct tcttcctcc                                         19

<210> SEQ ID NO 22
<211> LENGTH: 20
<212> TYPE: DNA
<213> ORGANISM: artificial sequence
<220> FEATURE:
<223> OTHER INFORMATION: primer sequence

<400> SEQUENCE: 22
```
tgttaccaac tgggacgaca  20

<210> SEQ ID NO 23
<211> LENGTH: 20
<212> TYPE: DNA
<213> ORGANISM: artificial sequence
<220> FEATURE:
<223> OTHER INFORMATION: primer sequence

<400> SEQUENCE: 23
ctgggtcatc ttttcacggt  20

<210> SEQ ID NO 24
<211> LENGTH: 21
<212> TYPE: DNA
<213> ORGANISM: artificial sequence
<220> FEATURE:
<223> OTHER INFORMATION: primer sequence

<400> SEQUENCE: 24
tcagtcaacg ggggacataa a  21

<210> SEQ ID NO 25
<211> LENGTH: 21
<212> TYPE: DNA
<213> ORGANISM: artificial sequence
<220> FEATURE:
<223> OTHER INFORMATION: primer sequence

<400> SEQUENCE: 25
ggggctgtac tgcttaacca g  21

<210> SEQ ID NO 26
<211> LENGTH: 20
<212> TYPE: DNA
<213> ORGANISM: artificial sequence
<220> FEATURE:
<223> OTHER INFORMATION: primer sequence

<400> SEQUENCE: 26
ctgcgaatat gcctgctaca  20

<210> SEQ ID NO 27
<211> LENGTH: 20
<212> TYPE: DNA
<213> ORGANISM: artificial sequence
<220> FEATURE:
<223> OTHER INFORMATION: primer sequence

<400> SEQUENCE: 27
tggtcgarct tgatgtcgtc  20

<210> SEQ ID NO 28
<211> LENGTH: 26
<212> TYPE: DNA
<213> ORGANISM: artificial sequence
<220> FEATURE:
<223> OTHER INFORMATION: primer sequence

<400> SEQUENCE: 28
ggtgatcatc agacccagc atcagt  26

<210> SEQ ID NO 29
<211> LENGTH: 24
<212> TYPE: DNA

```
<213> ORGANISM: artificial sequence
<220> FEATURE:
<223> OTHER INFORMATION: primer sequence

<400> SEQUENCE: 29
aagagactaa aactgaggag cagc                                              24

<210> SEQ ID NO 30
<211> LENGTH: 27
<212> TYPE: DNA
<213> ORGANISM: artificial sequence
<220> FEATURE:
<223> OTHER INFORMATION: primer sequence

<400> SEQUENCE: 30
gccaaggtct acaatcgttg tgagttg                                           27

<210> SEQ ID NO 31
<211> LENGTH: 23
<212> TYPE: DNA
<213> ORGANISM: artificial sequence
<220> FEATURE:
<223> OTHER INFORMATION: primer sequence

<400> SEQUENCE: 31
cagtcagcca gcttgacacc acg                                               23

<210> SEQ ID NO 32
<211> LENGTH: 25
<212> TYPE: DNA
<213> ORGANISM: artificial sequence
<220> FEATURE:
<223> OTHER INFORMATION: primer sequence

<400> SEQUENCE: 32
ggctggctac tatggagtca gcctg                                             25

<210> SEQ ID NO 33
<211> LENGTH: 24
<212> TYPE: DNA
<213> ORGANISM: artificial sequence
<220> FEATURE:
<223> OTHER INFORMATION: primer sequence

<400> SEQUENCE: 33
gcattcacag ctcttggggt tttg                                              24

<210> SEQ ID NO 34
<211> LENGTH: 20
<212> TYPE: DNA
<213> ORGANISM: artificial sequence
<220> FEATURE:
<223> OTHER INFORMATION: primer sequence

<400> SEQUENCE: 34
cccagaaggg actgtgtatg                                                   20

<210> SEQ ID NO 35
<211> LENGTH: 20
<212> TYPE: DNA
<213> ORGANISM: artificial sequence
<220> FEATURE:
<223> OTHER INFORMATION: primer sequence

<400> SEQUENCE: 35
ttgtgttcgc tcttggtcag                                                   20
```

<210> SEQ ID NO 36
<211> LENGTH: 20
<212> TYPE: DNA
<213> ORGANISM: artificial sequence
<220> FEATURE:
<223> OTHER INFORMATION: primer sequence

<400> SEQUENCE: 36
gtctcccatc acggttcagt                                                  20

<210> SEQ ID NO 37
<211> LENGTH: 20
<212> TYPE: DNA
<213> ORGANISM: artificial sequence
<220> FEATURE:
<223> OTHER INFORMATION: primer sequence

<400> SEQUENCE: 37
tgtcattcca cactcccaga                                                  20

<210> SEQ ID NO 38
<211> LENGTH: 26
<212> TYPE: DNA
<213> ORGANISM: artificial sequence
<220> FEATURE:
<223> OTHER INFORMATION: primer sequence

<400> SEQUENCE: 38
gaactttgta taccatttgt cagacg                                           26

<210> SEQ ID NO 39
<211> LENGTH: 20
<212> TYPE: DNA
<213> ORGANISM: artificial sequence
<220> FEATURE:
<223> OTHER INFORMATION: primer sequence

<400> SEQUENCE: 39
ctgggtggca gtaacaacct                                                  20

<210> SEQ ID NO 40
<211> LENGTH: 20
<212> TYPE: DNA
<213> ORGANISM: artificial sequence
<220> FEATURE:
<223> OTHER INFORMATION: primer sequence

<400> SEQUENCE: 40
agtaaccgag gcctgtcctt                                                  20

<210> SEQ ID NO 41
<211> LENGTH: 19
<212> TYPE: DNA
<213> ORGANISM: artificial sequence
<220> FEATURE:
<223> OTHER INFORMATION: primer sequence

<400> SEQUENCE: 41
gtcactcggc aactcagga                                                   19

<210> SEQ ID NO 42
<211> LENGTH: 23
<212> TYPE: DNA
<213> ORGANISM: artificial sequence
<220> FEATURE:

```
<223> OTHER INFORMATION: primer sequence

<400> SEQUENCE: 42
gttctcagcc caacaataca aga                                          23

<210> SEQ ID NO 43
<211> LENGTH: 19
<212> TYPE: DNA
<213> ORGANISM: artificial sequence
<220> FEATURE:
<223> OTHER INFORMATION: primer sequence

<400> SEQUENCE: 43
gtggacgggt cgatgtcac                                               19

<210> SEQ ID NO 44
<211> LENGTH: 21
<212> TYPE: DNA
<213> ORGANISM: artificial sequence
<220> FEATURE:
<223> OTHER INFORMATION: primer sequence

<400> SEQUENCE: 44
ccaagtgctg ccgtcatttt c                                            21

<210> SEQ ID NO 45
<211> LENGTH: 21
<212> TYPE: DNA
<213> ORGANISM: artificial sequence
<220> FEATURE:
<223> OTHER INFORMATION: primer sequence

<400> SEQUENCE: 45
ggctcgcagg gatgatttca a                                            21

<210> SEQ ID NO 46
<211> LENGTH: 19
<212> TYPE: DNA
<213> ORGANISM: artificial sequence
<220> FEATURE:
<223> OTHER INFORMATION: primer sequence

<400> SEQUENCE: 46
tggcttgcga gacgtagac                                               19

<210> SEQ ID NO 47
<211> LENGTH: 21
<212> TYPE: DNA
<213> ORGANISM: artificial sequence
<220> FEATURE:
<223> OTHER INFORMATION: primer sequence

<400> SEQUENCE: 47
gctcaggtga atcggccttt t                                            21

<210> SEQ ID NO 48
<211> LENGTH: 23
<212> TYPE: DNA
<213> ORGANISM: artificial sequence
<220> FEATURE:
<223> OTHER INFORMATION: primer sequence

<400> SEQUENCE: 48
ttatcctgag tgacccttct aag                                          23
```

```
<210> SEQ ID NO 49
<211> LENGTH: 22
<212> TYPE: DNA
<213> ORGANISM: artificial sequence
<220> FEATURE:
<223> OTHER INFORMATION: primer sequence

<400> SEQUENCE: 49
tcattaccct gataggcata gg                                              22

<210> SEQ ID NO 50
<211> LENGTH: 21
<212> TYPE: DNA
<213> ORGANISM: artificial sequence
<220> FEATURE:
<223> OTHER INFORMATION: primer sequence

<400> SEQUENCE: 50
ctggaaccgt caccatcact c                                               21

<210> SEQ ID NO 51
<211> LENGTH: 21
<212> TYPE: DNA
<213> ORGANISM: artificial sequence
<220> FEATURE:
<223> OTHER INFORMATION: primer sequence

<400> SEQUENCE: 51
cgaaactcga tgactcctcg g                                               21

<210> SEQ ID NO 52
<211> LENGTH: 21
<212> TYPE: DNA
<213> ORGANISM: artificial sequence
<220> FEATURE:
<223> OTHER INFORMATION: primer sequence

<400> SEQUENCE: 52
gctgaatccc agaaattccg c                                               21

<210> SEQ ID NO 53
<211> LENGTH: 21
<212> TYPE: DNA
<213> ORGANISM: artificial sequence
<220> FEATURE:
<223> OTHER INFORMATION: primer sequence

<400> SEQUENCE: 53
atcacaggca tacagggtga c                                               21

<210> SEQ ID NO 54
<211> LENGTH: 21
<212> TYPE: DNA
<213> ORGANISM: artificial sequence
<220> FEATURE:
<223> OTHER INFORMATION: primer sequence

<400> SEQUENCE: 54
atgaacgcta cacactgcat c                                               21

<210> SEQ ID NO 55
<211> LENGTH: 21
<212> TYPE: DNA
<213> ORGANISM: artificial sequence
<220> FEATURE:
<223> OTHER INFORMATION: primer sequence
```

<400> SEQUENCE: 55
ccatcctttt gccagttcct c                                              21

<210> SEQ ID NO 56
<211> LENGTH: 19
<212> TYPE: DNA
<213> ORGANISM: artificial sequence
<220> FEATURE:
<223> OTHER INFORMATION: primer sequence

<400> SEQUENCE: 56
caaatggcct ccctctcat                                                 19

<210> SEQ ID NO 57
<211> LENGTH: 20
<212> TYPE: DNA
<213> ORGANISM: artificial sequence
<220> FEATURE:
<223> OTHER INFORMATION: primer sequence

<400> SEQUENCE: 57
ctcctccact tggtggtttg                                                20

<210> SEQ ID NO 58
<211> LENGTH: 19
<212> TYPE: DNA
<213> ORGANISM: artificial sequence
<220> FEATURE:
<223> OTHER INFORMATION: primer sequence

<400> SEQUENCE: 58
actctgcgcc agaaacctc                                                 19

<210> SEQ ID NO 59
<211> LENGTH: 21
<212> TYPE: DNA
<213> ORGANISM: artificial sequence
<220> FEATURE:
<223> OTHER INFORMATION: primer sequence

<400> SEQUENCE: 59
caccctgttg atggtcacga c                                              21

<210> SEQ ID NO 60
<211> LENGTH: 20
<212> TYPE: DNA
<213> ORGANISM: artificial sequence
<220> FEATURE:
<223> OTHER INFORMATION: primer sequence

<400> SEQUENCE: 60
ggtctcaacc cccagctagt                                                20

<210> SEQ ID NO 61
<211> LENGTH: 23
<212> TYPE: DNA
<213> ORGANISM: artificial sequence
<220> FEATURE:
<223> OTHER INFORMATION: primer sequence

<400> SEQUENCE: 61
gccgatgatc tctctcaagt gat                                            23

<210> SEQ ID NO 62
<211> LENGTH: 21

```
<212> TYPE: DNA
<213> ORGANISM: artificial sequence
<220> FEATURE:
<223> OTHER INFORMATION: primer sequence

<400> SEQUENCE: 62
gctcttactg actggcatga g                                              21

<210> SEQ ID NO 63
<211> LENGTH: 20
<212> TYPE: DNA
<213> ORGANISM: artificial sequence
<220> FEATURE:
<223> OTHER INFORMATION: primer sequence

<400> SEQUENCE: 63
cgcagctcta ggagcatgtg                                                20

<210> SEQ ID NO 64
<211> LENGTH: 23
<212> TYPE: DNA
<213> ORGANISM: artificial sequence
<220> FEATURE:
<223> OTHER INFORMATION: primer sequence

<400> SEQUENCE: 64
ggatattgca tggcctctgt aac                                            23

<210> SEQ ID NO 65
<211> LENGTH: 22
<212> TYPE: DNA
<213> ORGANISM: artificial sequence
<220> FEATURE:
<223> OTHER INFORMATION: primer sequence

<400> SEQUENCE: 65
aacagttgct ttgtgtagct ga                                             22

<210> SEQ ID NO 66
<211> LENGTH: 20
<212> TYPE: DNA
<213> ORGANISM: artificial sequence
<220> FEATURE:
<223> OTHER INFORMATION: primer sequence

<400> SEQUENCE: 66
gctgaaagct ctccacctca                                                20

<210> SEQ ID NO 67
<211> LENGTH: 20
<212> TYPE: DNA
<213> ORGANISM: artificial sequence
<220> FEATURE:
<223> OTHER INFORMATION: primer sequence

<400> SEQUENCE: 67
ggccacaggt attttgtcgt                                                20

<210> SEQ ID NO 68
<211> LENGTH: 22
<212> TYPE: DNA
<213> ORGANISM: artificial sequence
<220> FEATURE:
<223> OTHER INFORMATION: primer sequence

<400> SEQUENCE: 68
```
cttccatcca gttgccttct tg                                                    22

<210> SEQ ID NO 69
<211> LENGTH: 23
<212> TYPE: DNA
<213> ORGANISM: artificial sequence
<220> FEATURE:
<223> OTHER INFORMATION: primer sequence

<400> SEQUENCE: 69
aattaagcct ccgacttgtg aag                                                   23

<210> SEQ ID NO 70
<211> LENGTH: 20
<212> TYPE: DNA
<213> ORGANISM: artificial sequence
<220> FEATURE:
<223> OTHER INFORMATION: primer sequence

<400> SEQUENCE: 70
cctgacatct tctgcaacct                                                       20

<210> SEQ ID NO 71
<211> LENGTH: 20
<212> TYPE: DNA
<213> ORGANISM: artificial sequence
<220> FEATURE:
<223> OTHER INFORMATION: primer sequence

<400> SEQUENCE: 71
ttccgtatta ctgcggttgt                                                       20

<210> SEQ ID NO 72
<211> LENGTH: 20
<212> TYPE: DNA
<213> ORGANISM: artificial sequence
<220> FEATURE:
<223> OTHER INFORMATION: primer sequence

<400> SEQUENCE: 72
gcacctgctt gactctgaca                                                       20

<210> SEQ ID NO 73
<211> LENGTH: 20
<212> TYPE: DNA
<213> ORGANISM: artificial sequence
<220> FEATURE:
<223> OTHER INFORMATION: primer sequence

<400> SEQUENCE: 73
atcctctggc tggaggagtt                                                       20

<210> SEQ ID NO 74
<211> LENGTH: 19
<212> TYPE: DNA
<213> ORGANISM: artificial sequence
<220> FEATURE:
<223> OTHER INFORMATION: primer sequence

<400> SEQUENCE: 74
cccatcccca ggagtcttg                                                        19

<210> SEQ ID NO 75
<211> LENGTH: 21
<212> TYPE: DNA
<213> ORGANISM: artificial sequence -continued

```
<220> FEATURE:
<223> OTHER INFORMATION: primer sequence

<400> SEQUENCE: 75
accatgacta ggggcactgt a                                                 21

<210> SEQ ID NO 76
<211> LENGTH: 21
<212> TYPE: DNA
<213> ORGANISM: artificial sequence
<220> FEATURE:
<223> OTHER INFORMATION: primer sequence

<400> SEQUENCE: 76
tttaactccc ttggcgcaaa a                                                 21

<210> SEQ ID NO 77
<211> LENGTH: 20
<212> TYPE: DNA
<213> ORGANISM: artificial sequence
<220> FEATURE:
<223> OTHER INFORMATION: primer sequence

<400> SEQUENCE: 77
ctttccctcc gcattgacac                                                   20
```